United States Patent
Vassilatis et al.

(10) Patent No.: US 10,946,019 B2
(45) Date of Patent: Mar. 16, 2021

(54) NURR1:RXR ACTIVATING COMPOUNDS FOR SIMULTANEOUS TREATMENT OF SYMPTOMS AND PATHOLOGY OF PARKINSON'S DISEASE

(71) Applicant: Demetrios K. Vassilatis, Cholargos (GR)

(72) Inventors: Demetrios K. Vassilatis, Cholargos (GR); Athanasios D. Spathis, Volos (GR); Demostenes Fokas, Ioannina (GR)

( * ) Notice: Subject to any disclaimer, the term of this patent is extended or adjusted under 35 U.S.C. 154(b) by 0 days.

(21) Appl. No.: 15/770,162

(22) PCT Filed: Oct. 20, 2016

(86) PCT No.: PCT/EP2016/075279
§ 371 (c)(1),
(2) Date: Apr. 20, 2018

(87) PCT Pub. No.: WO2017/068070
PCT Pub. Date: Apr. 27, 2017

(65) Prior Publication Data
US 2018/0311243 A1    Nov. 1, 2018

(30) Foreign Application Priority Data
Oct. 20, 2015 (LU) .......................................... 92852

(51) Int. Cl.
| | | |
|---|---|---|
| *C07D 239/42* | (2006.01) | |
| *A61K 31/505* | (2006.01) | |
| *A61P 25/18* | (2006.01) | |
| *A61K 31/519* | (2006.01) | |
| *C07D 487/04* | (2006.01) | |
| *A61P 25/16* | (2006.01) | |

(52) U.S. Cl.
CPC ............ *A61K 31/519* (2013.01); *A61P 25/16* (2018.01); *C07D 239/42* (2013.01); *C07D 487/04* (2013.01)

(58) Field of Classification Search
CPC ............................... A61K 31/505; A61P 25/18
USPC ......... 544/309, 315, 269, 275; 514/269, 275
See application file for complete search history.

(56) References Cited

U.S. PATENT DOCUMENTS

| | | | |
|---|---|---|---|
| 3,361,749 A | 1/1968 | Matter et al. | |
| 8,865,723 B2 * | 10/2014 | Gurney ................ | A61K 31/506 514/256 |
| 2006/0293343 A1 * | 12/2006 | Naganuma ........... | C07D 405/04 514/256 |

FOREIGN PATENT DOCUMENTS

| | | |
|---|---|---|
| FR | 2244459 A1 | 4/1975 |
| WO | 2005/047268 A2 | 5/2005 |
| WO | 2007/048064 A2 | 4/2007 |

OTHER PUBLICATIONS

Del Rey et al. Frontiers in Neuroanatomy, Dec. 2018, vol. 12, Article 113, pp. 1-14.*
International Search Report and Written Opinion for PCT/EP2016/075279, dated Mar. 20, 2017 (14 pages).

* cited by examiner

*Primary Examiner* — Venkataraman Balasubramanian
(74) *Attorney, Agent, or Firm* — FisherBroyles, LLP; Cara L. Crowley-Weber

(57) ABSTRACT

The invention provides a series of substituted aryl pyrimidine compounds and the use of these compounds as therapeutics to treat or prevent neurodegenerative disorders, including Parkinson's disease. Compounds of the invention are also able to treat the symptoms of such diseases and therefore represent a new treatment modality for ameliorating chronic and acute conditions. The compounds of the invention are capable of selectively potentiating the activity of the Nurr1:RXRα heterodimer, and are able to treat diseases or conditions associated with aberrant Nurr1:RXRα function. The invention further provides methods for treating neurodegenerative disorders by administration of Nurr1:RXRα activating agents.

15 Claims, 95 Drawing Sheets

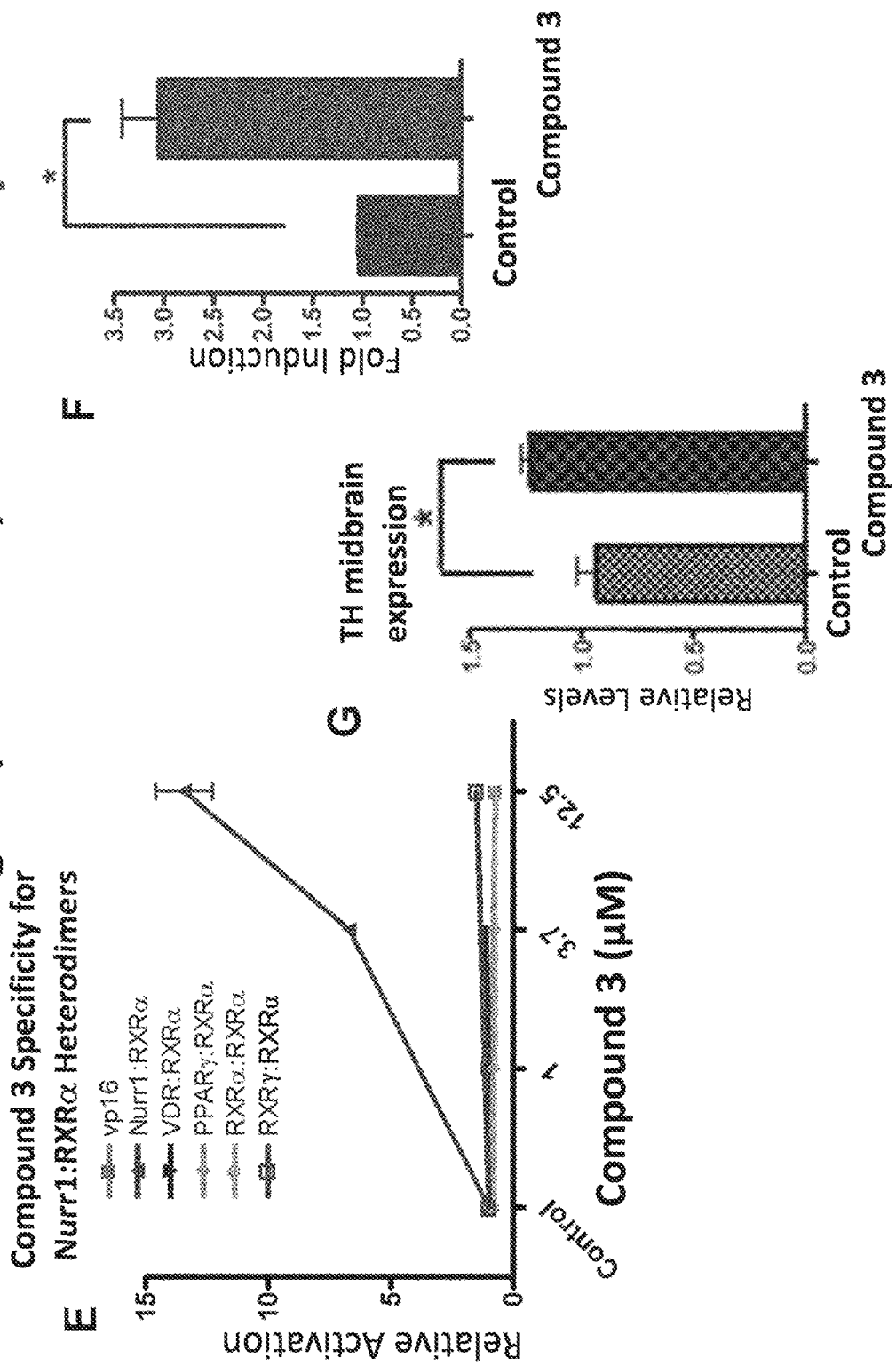

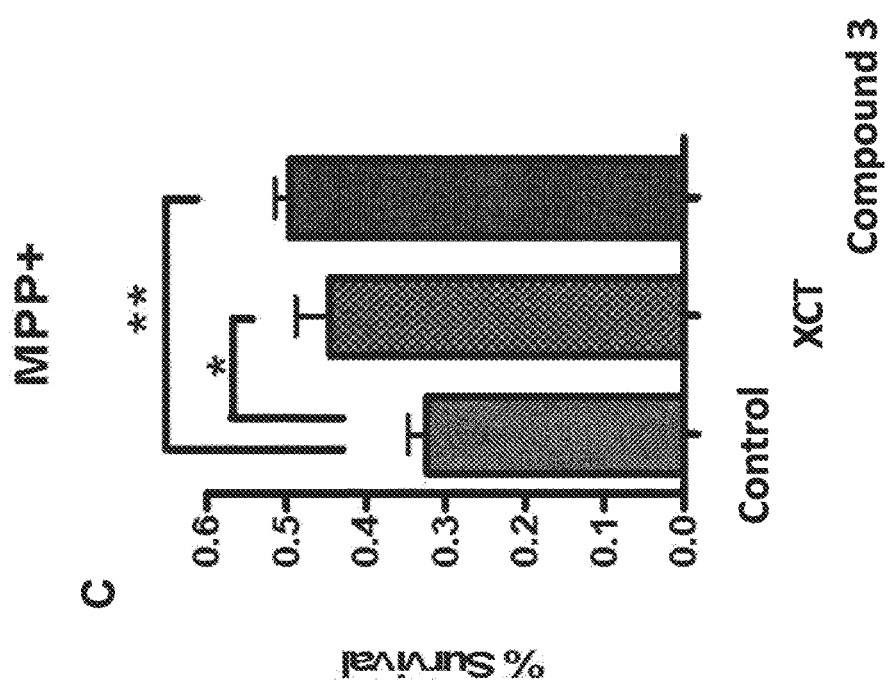
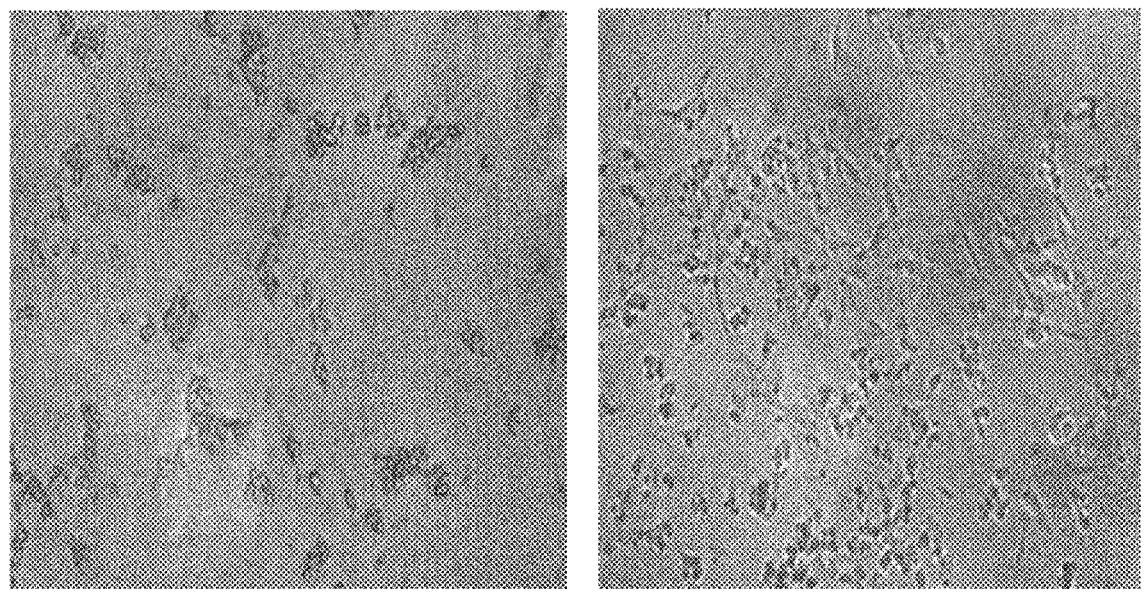
Fig. 2 (Continued)

Fig. 5 (Continued)
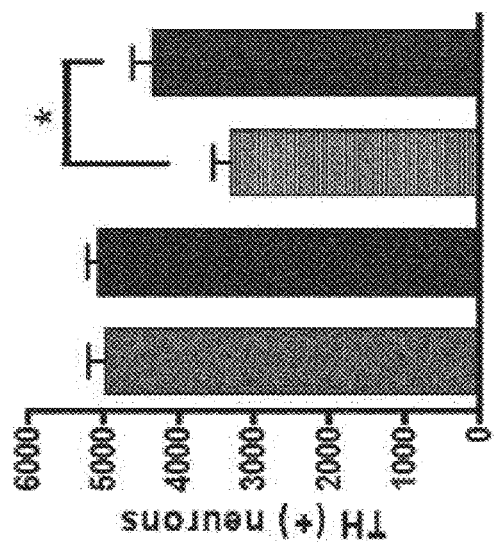

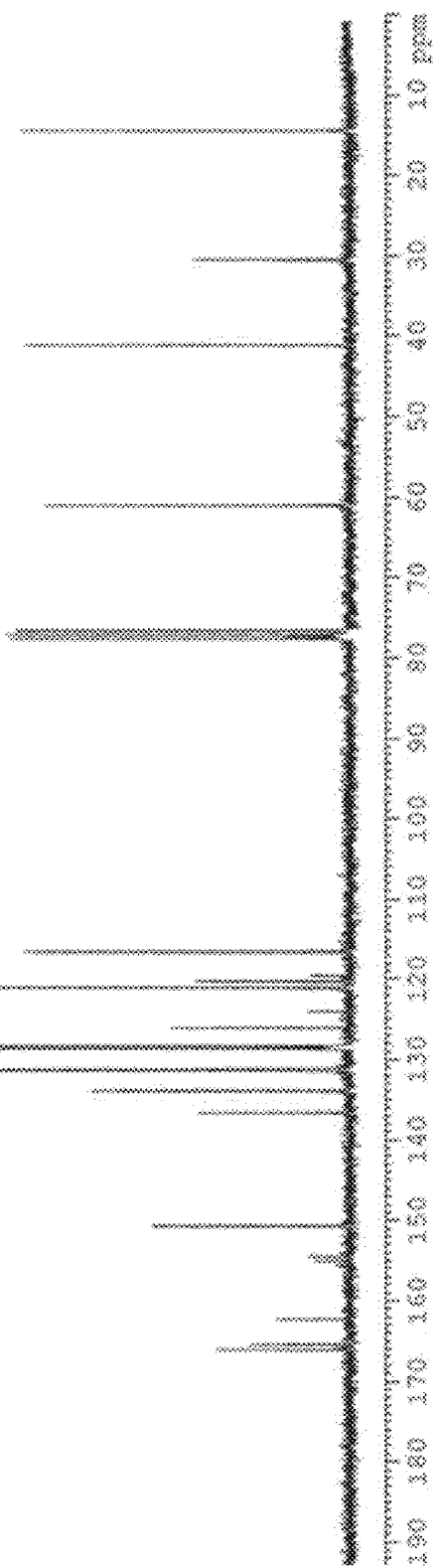
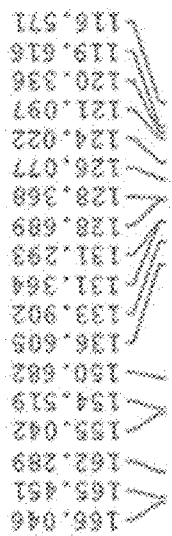
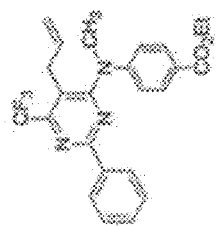
Fig. 9

Fig. 31 EXAMPLE 19 and 20 -¹H NMR

NURR1:RXR ACTIVATING COMPOUNDS FOR SIMULTANEOUS TREATMENT OF SYMPTOMS AND PATHOLOGY OF PARKINSON'S DISEASE

CROSS-REFERENCE TO RELATED APPLICATIONS

This application is a US 371 National Stage Application of PCT/EP2016/075279, filed Oct. 20, 2016, which claims the benefit of LU 92 852, filed Oct. 20, 2015, each of which are incorporated herein by reference. To the extent appropriate, a claim of priority is made to each of the above-disclosed applications.

BACKGROUND OF THE INVENTION

Neurodegenerative Diseases

Neurodegenerative diseases are characterized by progressive dysfunction of the nervous system and frequently are associated with gradual deterioration and death of affected neurons. Generally, these diseases are associated with aging and include Alzheimer's disease, Huntington's disease, Parkinson's disease, Steele-Richardson-Olszewski syndrome, Multiple-system atrophy, and amyotrophic lateral sclerosis. Considering that overall life expectancy is rising, age-associated neurodegenerative diseases, such as Parkinson's and Alzheimer's disease, constitute the fastest growing group of diseases worldwide and represent an enormous societal and financial burden on the western world. Among the neurodegenerative diseases, Alzheimer's disease is the most common, and Parkinson's disease affects nearly seven to ten million people worldwide of any age, but it is most common in people older than 65 years.

Parkinson's disease affects movement, leading to progressive loss of muscle control, leading to trembling of the limbs and head while at rest, stiffness, slowness, and impaired balance. As symptoms worsen, it may become difficult to walk, talk, and complete simple tasks. The disease is accompanied or even preceded by non-motor symptoms that include autonomic dysfunction, neuropsychiatric symptoms affecting mood and cognition, as well as sensory and sleep disturbances.

The symptoms of Parkinson's disease are associated with the greatly reduced activity and number of dopaminergic neurons of the substantia nigra in the midbrain. Lack of dopamine and loss of dopaminergic neuron projections to the striatum lead to activity alterations in the basal ganglia that regulate movement. Dopamine depletion in other non-striatal dopamine pathways is thought to explain some of the neuropsychiatric pathology associated with the disease.

The current treatment for PD is symptomatic and is based on replenishing the dopamine deficiency through the administration of the dopamine metabolic precursor L-3,4-dihydroxyphenylalanine (L-DOPA), which was discovered in the 1960's. L-DOPA restores temporarily DA levels and alleviates DA dependent motor and some non-motor symptoms. Prolonged L-DOPA treatment leads to dyskinesias (abnormal involuntary movements), which abolishes its beneficial effect (Prashanth 2011). Additionally, L-DOPA treatment does not stop the neuron degeneration, and, on the contrary it might be toxic, increasing neuronal degeneration.

Only a limited number of compounds have been tested for neuroprotection in clinical trials of PD patients because it is not possible to measure the number of dopaminergic neurons in vivo (Henchcliffe 2011). Thus, it has been thought that a realistic goal for Parkinson's therapies is to minimize symptoms, rather than to see if we can extend the life of brain cells. In addition, the effects of PD medications that patients are receiving complicate the evaluation of the extent of nerve cell loss. Ideally, a compound that improves both the symptoms of PD but also prevents or diminishes neuronal loss could become a way to cure the disease.

Nurr1

Nurr1 (NR4A2), an orphan nuclear receptor that is required for midbrain dopaminergic neuron development, regulates the expression of genes involved in dopamine biosynthesis, Neuropilin1, VIP, BDNF and in resistance to oxidative stress (Hermanson 2006, Luo 2007, Volpicelli 2007, Sousa 2007). While Nurr1−/− mice die shortly after birth and fail to develop midbrain dopaminergic neurons, Nurr1+/− mice appear normal but with reduced striatal dopamine levels. Nurr1 expression in midbrain dopaminergic neurons continues throughout life. During aging, Nurr1 expression levels decrease and decrease even further in the substantia nigra of PD patients. Importantly, six Nurr1 mutations have been found in familial (2) and sporadic (4) PD cases linking the function of the gene with PD. The two familial mutations were detected in all affected individuals of each family in ten different families. Five of the mutations have been mapped to the first untranslated exon of Nurr1 and result in decreased steady state mRNA levels (Le 2003, Hering 2004, Healy 2006, Grimes 2006, Sleiman 2009). The sixth mutation is in the coding region affecting a phosphorylation site and results in decreased transcriptional activity of the protein.

As a transcription factor Nurr1 binds to DNA as monomer, as a homodimer or as a heterodimer with RXR (Retinoid X Receptor) α and γ, nuclear receptors that form heterodimers with several other members of the nuclear receptor family. RXRα expression is ubiquitous, while expression of RXRγ is detected primarily in the brain and particularly in the striatum, the hypothalamus and the pituitary.

Retinoid X Receptors (RXRs)

RXRs are nuclear receptors that are activated by 9-cis retinoic acid. RXRs have been shown to be important in development and differentiation and to be involved in many processes, including metabolism. There are three retinoic X receptors (RXR): RXR-α, RXR-β, and RXR-γ. All three are capable of forming heterodimers with a variety of nuclear receptors including RAR, CAR, FXR, LXR, PPAR, PXR, RAR, TR, NR4A2 (nurr1), NR4A1 and VDR. The activity of these heterodimers can be modulated by RXR ligands.

SUMMARY OF THE INVENTION

In one aspect, the present invention relates to a compound of formula (I):

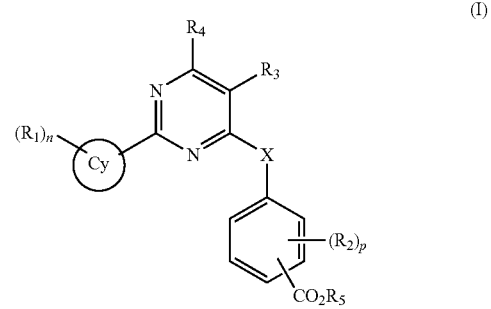

or a pharmaceutical acceptable salt thereof, where n is 0 to 2, p is 0 to 2, X is $N(R_6)$ or O;

Cy is a phenyl ring or a heteroaromatic 5- or 6-membered ring containing between 1 and 4 heteroatoms;

each $R_1$ is independently selected from the group consisting of halogen, cyanate, isocyanate, thiocyanate, isothiocyanate, selenocyanate, isoselenocyanate, alkoxy, trifluoromethoxy, azido, cyano, nitro, hydroxy, acyl, mercapto, carboxyl, optionally substituted alkyl, optionally substituted cycloalkyl, optionally substituted heterocyclyl, optionally substituted aryl, optionally substituted heteroaryl, $-OR_7$, $-SR_7$, and $-N(R_8)R_7$;

each $R_2$ is independently selected from the group consisting of halogen, cyanate, isocyanate, thiocyanate, isothiocyanate, selenocyanate, isoselenocyanate, alkoxy, trifluoromethoxy, azido, cyano, nitro, hydroxy, acyl, mercapto, carboxyl, optionally substituted alkyl, optionally substituted cycloalkyl, optionally substituted heterocyclyl, optionally substituted aryl, optionally substituted heteroaryl, $-OR_7$, $-SR_7$, and $-N(R_8)R_7$;

$R_3$ is selected from the group consisting of hydrogen, halogen, cyanate, isocyanate, thiocyanate, isothiocyanate, selenocyanate, isoselenocyanate, alkoxy, trifluoromethoxy, azido, cyano, nitro, hydroxy, acyl, mercapto, optionally substituted alkyl, optionally substituted alkenyl, optionally substituted alkynyl, $OR_7$, $-SR_7$, $-N(R_8)R_7$, optionally substituted aryl, optionally substituted heteroaryl, optionally substituted cycloalkyl and optionally substituted heterocyclyl, or $R_3$ and $R_6$, when present, combine with the atoms to which they are bound to form an optionally substituted 5-membered heteroaryl or heterocyclyl;

$R_4$ is selected from the group consisting of hydrogen, halogen, optionally substituted alkyl, optionally substituted cycloalkyl, optionally substituted aryl, optionally substituted aryl-alkyl, optionally substituted heterocyclyl, optionally substituted heteroaryl, optionally substituted heteroaryl-alkyl, optionally substituted heterocyclolalkyl, $OR_7$, and $-N(R_8)R_7$;

$R_5$ is selected from the group consisting of hydrogen, optionally substituted alkyl, optionally substituted alkenyl, and optionally substituted aryl;

$R_6$ is selected from the group consisting of hydrogen and optionally substituted alkyl;

each $R_7$ is independently selected from the group consisting of hydrogen, optionally substituted alkyl, optionally substituted alkenyl, optionally substituted aryl, optionally substituted aryl-alkyl, and optionally substituted heterocyclyl; and each $R_8$ is independently selected from the group consisting of hydrogen and optionally substituted alkyl.

In certain embodiments, the compound is not a compound selected from the group consisting of:

i. ethyl 4-(5-allyl-6-methyl-2-phenylpyrimidin-4-ylamino)benzoate;
ii. methyl 4-(5-allyl-6-methyl-2-phenylpyrimidin-4-ylamino)benzoate;
iii. 4-(6-methyl-2-phenyl-5-propylpyrimidin-4-ylamino)benzoic acid;
iv. 4-(5-isopropyl-6-methyl-2-phenylpyrimidin-4-ylamino)benzoic acid;
v. 4-(5-ethyl-6-methyl-2-phenylpyrimidin-4-ylamino)benzoic acid;
vi. 4-(2-(4-chlorophenyl)-5-ethyl-6-methylpyrimidin-4-ylamino)benzoic acid;
vii. 4-(6-methyl-2-phenylpyrimidin-4-ylamino)benzoic acid;
viii. 4-(5-ethyl-6-methyl-2-phenylpyrimidin-4-yloxy)benzoic acid;
ix. 4-(2-(4-chlorophenyl)-5-ethyl-6-methylpyrimidin-4-yloxy)benzoic acid;
x. 4-(5-allyl-6-methyl-2-phenylpyrimidin-4-ylamino)benzoic acid;
xi. ethyl 4-(6-methyl-2-phenylpyrimidin-4-ylamino)benzoate;
xii. methyl 4-(2,6-diphenylpyrimidin-4-yloxy)benzoate;
xiii. 3-(6-methyl-2-phenylpyrimidin-4-ylamino)benzoic acid;
xiv. ethyl 4-(2,6-diphenylpyrimidin-4-ylamino)benzoate;
xv. methyl 4-(2-(4-bromophenyl)-6-methylpyrimidin-4-yloxy)benzoate;
xvi. 4-(2-(2-hydroxyphenyl)-6-methylpyrimidin-4-yloxy)benzoic acid;
xvii. ethyl 4-(2-(2-hydroxyphenyl)-6-methylpyrimidin-4-ylamino)benzoate;
xviii. methyl 4-(2-(2-hydroxyphenyl)-6-methylpyrimidin-4-ylamino)benzoate;
xix. methyl 3-(2-(2-hydroxyphenyl)-6-methylpyrimidin-4-ylamino)benzoate;
xx. 4-(5-carboxy-2-methoxyanilino)-2-(pyrazin-2-yl)-6-trifluoromethylpyrimidine;
xxi. 4-(5-carboxy-2-hydroxyanilino)-2-(pyridin-3-yl)-6-(trifluoromethyl)pyrimidine;
xxii. 4-[2-methyl-5-(carboxymethylester)anilino]-2-(pyridin-3-yl)-6-(trifluoromethyl)pyrimidine;
xxiii. 4-(5-carboxy-2-methoxyanilino)-2-(pyridin-3-yl)-6-(trifluoromethyl)pyrimidine; and
xxiv. 2-(6-methyl-2-phenylpyrimidin-4-ylamino)benzoic acid.

In certain embodiments, the compound is not a compound selected from the group consisting of:

i. ethyl 4-(5-allyl-6-methyl-2-phenylpyrimidin-4-ylamino)benzoate;
ii. methyl 4-(5-allyl-6-methyl-2-phenylpyrimidin-4-ylamino)benzoate;
iii. 4-(6-methyl-2-phenyl-5-propylpyrimidin-4-ylamino)benzoic acid;
iv. 4-(5-isopropyl-6-methyl-2-phenylpyrimidin-4-ylamino)benzoic acid;
v. 4-(5-ethyl-6-methyl-2-phenylpyrimidin-4-ylamino)benzoic acid;
vi. 4-(2-(4-chlorophenyl)-5-ethyl-6-methylpyrimidin-4-ylamino)benzoic acid;
vii. 4-(6-methyl-2-phenylpyrimidin-4-ylamino)benzoic acid;
viii. 4-(5-ethyl-6-methyl-2-phenylpyrimidin-4-yloxy)benzoic acid;
ix. 4-(2-(4-chlorophenyl)-5-ethyl-6-methylpyrimidin-4-yloxy)benzoic acid;
x. 4-(5-allyl-6-methyl-2-phenylpyrimidin-4-ylamino)benzoic acid;
xi. ethyl 4-(6-methyl-2-phenylpyrimidin-4-ylamino)benzoate;
xii. methyl 4-(2,6-diphenylpyrimidin-4-yloxy)benzoate;
xiii. 3-(6-methyl-2-phenylpyrimidin-4-ylamino)benzoic acid;
xiv. ethyl 4-(2,6-diphenylpyrimidin-4-ylamino)benzoate;
xv. methyl 4-(2-(4-bromophenyl)-6-methylpyrimidin-4-yloxy)benzoate;
xvi. 4-(2-(2-hydroxyphenyl)-6-methylpyrimidin-4-yloxy)benzoic acid;
xvii. ethyl 4-(2-(2-hydroxyphenyl)-6-methylpyrimidin-4-ylamino)benzoate;
xviii. methyl 4-(2-(2-hydroxyphenyl)-6-methylpyrimidin-4-ylamino)benzoate;

xix. methyl 3-(2-(2-hydroxyphenyl)-6-methylpyrimidin-4-ylamino)benzoate;
xx. 4-(5-carboxy-2-methoxyanilino)-2-(pyrazin-2-yl)-6-trifluoromethylpyrimidine;
xxi. 4-(5-carboxy-2-hydroxyanilino)-2-(pyridin-3-yl)-6-(trifluoromethyl)pyrimidine;
xxii. 4-[2-methyl-5-(carboxymethylester)anilino]-2-(pyridin-3-yl)-6-(trifluoromethyl)pyrimidine;
xxiii. 4-(5-carboxy-2-methoxyanilino)-2-(pyridin-3-yl)-6-(trifluoromethyl)pyrimidine;
xxiv. 2-(6-methyl-2-phenylpyrimidin-4-ylamino)benzoic acid;
xxv. 2',3'-dihydroxypropyl 2-(6-methyl-2-(3-trifluoromethylphenyl)pyrimidin-4-ylamino)benzoate;
xxvi. methyl 2-(6-methyl-2-(3-trifluoromethylphenyl)pyrimidin-4-ylamino)benzoate;
xxvii. 2',2'-dimethyl-1',3'-dioxolan-4'-ylmethyl 2-(6-methyl-2-(3-trifluoromethylphenyl)pyrimidin-4-ylamino)benzoate;
xxviii. ethyl 4-(2-(4-chlorophenyl)-6-methylpyrimidin-4-ylamino)benzoate;
xxix. methyl 2-(2-(4-chlorophenyl)-6-methylpyrimidin-4-ylamino)benzoate;
xxx. 2',2'-dimethyl-1',3'-dioxolan-4'-ylmethyl 2-(2-(4-chlorophenyl)-6-methylpyrimidin-4-ylamino)benzoate;
xxxi. 2',3'-dihydroxypropyl 2-(2-(4-chlorophenyl)-6-methylpyrimidin-4-ylamino)benzoate;
xxxii. ethyl 4-(2-(3-fluorophenyl)-6-methylpyrimidin-4-ylamino)benzoate;
xxxiii. methyl 2-(2-(3-fluorophenyl)-6-methylpyrimidin-4-ylamino)benzoate;
xxxiv. 2',2'-dimethyl-1',3'-dioxolan-4'-ylmethyl 2-(2-(3-fluorophenyl)-6-methylpyrimidin-4-ylamino)benzoate;
xxxv. 2',3'-dihydroxypropyl 2-(2-(3-fluorophenyl)-6-methylpyrimidin-4-ylamino)benzoate;
xxxvi. ethyl 4-(6-methyl-2-(3-trifluoromethylphenyl)pyrimidin-4-ylamino)benzoate;
xxxvii. ethyl 4-(6-methyl-2-(3,4-methylenedioxyphenyl)pyrimidin-4-ylamino)benzoate;
xxxviii. methyl 2-(6-methyl-2-(3,4-methylenedioxyphenyl)pyrimidin-4-ylamino)benzoate;
xxxix. 2',2'-dimethyl-1',3'-dioxolan-4'-ylmethyl 2-(6-methyl-2-(3,4-methylenedioxyphenyl)pyrimidin-4-ylamino)benzoate;
xl. 2',3'-dihydroxypropyl 2-(6-methyl-2-(3,4-methylenedioxyphenyl)pyrimidin-4-ylamino)benzoate;
xli. ethyl 4-(6-methyl-2-(3,4,5-trimethoxyphenyl)pyrimidin-4-ylamino)benzoate;
xlii. methyl 2-(6-methyl-2-(3,4,5-trimethoxyphenyl)pyrimidin-4-ylamino)benzoate;
xliii. 2',2'-dimethyl-1',3'-dioxolan-4'-ylmethyl 2-(6-methyl-2-(3,4,5-trimethoxyphenyl)pyrimidin-4-ylamino)benzoate;
xliv. 2-[(6-methyl-2-morpholin-4-ylpyrimidin-4-yl)amino]benzoic acid;
xlv. 2-{[6-methyl-2-(4-methylpiperazin-1-yl)pyrimidin-4-yl]amino}benzoic acid; and
xlvi. 2-(6-chloro-2-phenylpyrimidin-4-ylamino)benzoic acid.

In some embodiments, $R_3$ is not hydrogen. In some embodiments, Cy is a phenyl ring, $R_3$ is optionally substituted alkyl or optionally substituted alkenyl, $R_4$ is optionally substituted methyl (e.g., halomethyl), and $R_5$ is hydrogen or optionally substituted alkyl. For instance, in some embodiments, Cy is a phenyl ring, $R_3$ is alkyl or alkenyl, $R_4$ is methyl or trifluoromethyl, and $R_5$ is hydrogen or alkyl.

In particular embodiments of this aspect, n in formula (I) above is 0. In alternative embodiments, n is 0 or 1, and p is 0 or 1. In certain embodiments, X is $NR_6$, optionally wherein $R_4$ is haloalkyl, such as trifluoromethyl.

In other embodiments, $R_3$ and $R_6$ combine with the atoms to which they are bound to form an optionally substituted 5-membered heteroaryl or heterocyclyl. For example, the compound is a compound of the formula (1e):

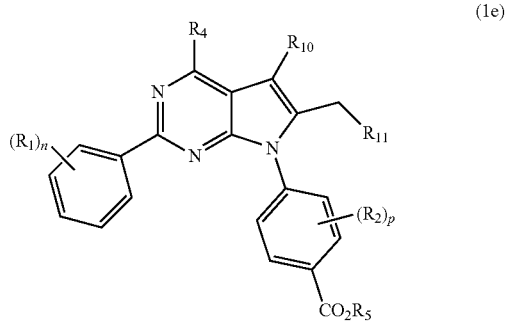

(1e)

where $R_{10}$ is selected from the group consisting of hydrogen, optionally substituted alkyl, optionally substituted aryl, optionally substituted aryl-alkyl, optionally substituted heteroaryl, optionally substituted cycloalkyl, and optionally substituted heterocyclyl; and $R_{11}$ is selected from the group consisting of optionally substituted alkyl, optionally substituted aryl, optionally substituted aryl-alkyl, optionally substituted heteroaryl, optionally substituted cycloalkyl, and optionally substituted heterocyclyl.

Additional embodiments of the invention include compounds of formula (1b):

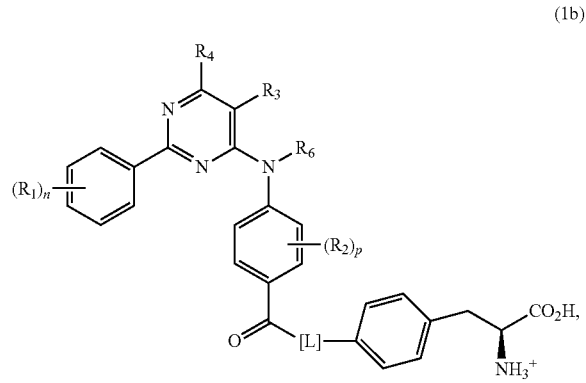

(1b)

or a free base thereof, where L is selected from the group consisting of —O—, —O—$R_9$—O—, and —O—$R_9$—, wherein $R_9$ is an optionally substituted alkylene, optionally substituted alkenylene, or optionally substituted alkynylene chain.

In other embodiments, the compound is a compound of formula (1f):

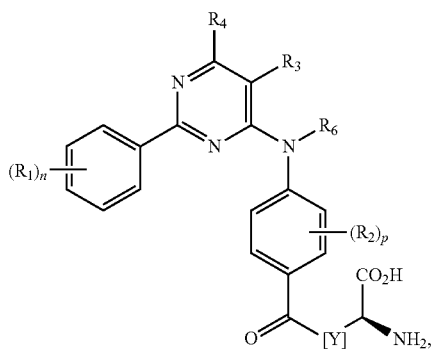

(1f)

or a salt thereof,
where Y is —O—R$_9$—, wherein R$_9$ is an optionally substituted alkylene, optionally substituted alkenylene, or optionally substituted alkynylene chain.

Embodiments of the invention further include compounds of formula (1g):

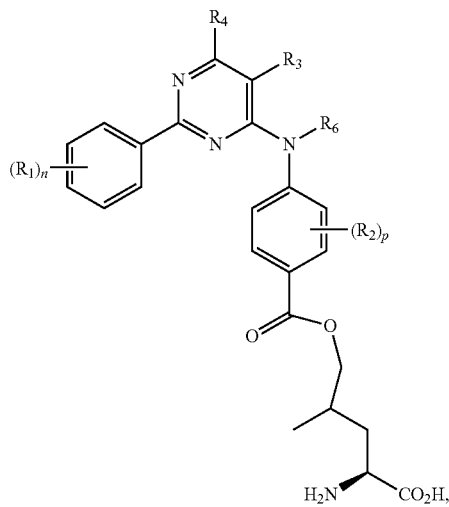

(1g)

or a salt thereof,

Additional embodiments of the above aspects of the invention include compounds of formula (1h):

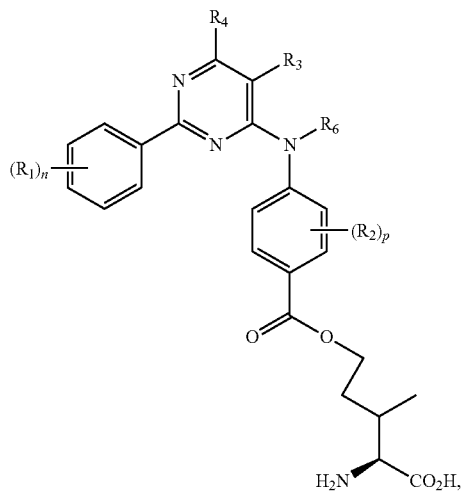

(1h)

or a salt thereof,

In particular embodiments of the invention, X in the above formulas is O.

In an additional aspect, the compound is selected from the group consisting of:

a) 4-((5-allyl-2-phenyl-6-(trifluoromethyl)pyrimidin-4-yl)(methyl)amino)benzoic acid;
b) 4-(4,6-dimethyl-2-phenyl-7H-pyrrolo[2,3-d]pyrimidin-7-yl)benzoic acid;
c) 3-bromo-4-(4,6-dimethyl-2-phenyl-7H-pyrrolo[2,3-d]pyrimidin-7-yl)benzoic acid;
d) 4-(5-allyl-2-(4-chlorophenyl)-6-methylpyrimidin-4-ylamino)benzoic acid;
e) 4-((5-allyl-6-methyl-2-phenylpyrimidin-4-yl)(methyl)amino)-2-fluorobenzoic acid;
f) 4-(5-allyl-2-(4-chlorophenyl)-6-(trifluoromethyl)pyrimidin-4-ylamino)benzoic acid;
g) (E)-4-(2-(4-chlorophenyl)-5-(prop-1-enyl)-6-(trifluoromethyl)pyrimidin-4-ylamino)benzoic acid;
h) 4-((5-allyl-2-(4-chlorophenyl)-6-methylpyrimidin-4-yl)(methyl)amino)benzoic acid;
i) 4-(5-allyl-2-phenyl-6-(trifluoromethyl)pyrimidin-4-ylamino)benzoic acid;
j) (E)-4-(2-phenyl-5-(prop-1-enyl)-6-(trifluoromethyl)pyrimidin-4-ylamino)benzoic acid;
k) 4-((2-(4-chlorophenyl)-5-ethyl-6-methylpyrimidin-4-yl)(methyl)amino)benzoic acid;
l) pivaloyloxymethyl 4-(5-allyl-6-methyl-2-phenylpyrimidin-4-ylamino)benzoate;
m) 4-((6-methyl-2-phenylpyrimidin-4-yl)(propyl)amino)benzoic acid;
n) (S)-2-(4-(4-(5-allyl-6-methyl-2-phenylpyrimidin-4-ylamino)benzoyloxy)phenyl)-1-carboxyethanaminium chloride; and
o) (S)-2-(4-(3-(4-(5-allyl-6-methyl-2-phenylpyrimidin-4-ylamino)benzoyloxy)propoxy)phenyl)-1-carboxyethanaminium chloride;
or a salt or free base thereof.

In embodiments of any of the above described aspects of the invention, the compound may be incorporated into a pharmaceutical composition in combination with a pharmaceutically acceptable excipient. In particular embodiments, the pharmaceutical composition may contain an additional therapeutically active compound. For example, in certain cases, the additional therapeutically active compound is selected from the group consisting of levodopa (L-dihydroxyphenylalanine), L-aromatic amino acid decarboxylase (AADC) inhibitors, and catechol O-methyl transferase (COMT) inhibitors.

In addition, the present invention provides a method of treating a neurodegenerative disorder in a human by administration to the human of an effective amount of a compound or pharmaceutical composition described above. The invention further provides a method of alleviating or preventing one or more symptoms of a neurodegenerative disorder in a human by administration to the human of an effective amount of a compound or pharmaceutical composition described above. In particular cases, the symptom is selected from the group consisting of bradykinesia and dyskinesias. In other embodiments, the symptom is selected from the group consisting of anxiety and depression. The symptom may alternatively be selected from the group consisting of learning difficulties, memory disorders, and attention deficit disorder. In other cases, the symptom may be selected from the group consisting of insomnia and katalepsy.

The present invention additional relates to a method of treating a disorder in a human patient in which Nurr1 activity is reduced or impaired relative to a healthy human by administration to the human of an effective amount of a compound or pharmaceutical composition described above.

In embodiments of any of the above-described methods of the invention, the disorder that can be treated by administration to the human of an effective amount of a compound or pharmaceutical composition described herein is Parkinson's disease.

In particular embodiments of the methods described above, the effective amount is sufficient to halt or prevent degeneration of neurons. In certain cases, these neurons are dopaminergic midbrain neurons. Additionally or alternatively, the effective amount is sufficient to increase the rate of dopamine biosynthesis. In certain cases, the effective amount is sufficient to increases the rate of transcription or translation of a polynucleotide encoding an enzyme involved in dopamine biosynthesis. For example, in particular embodiment, the enzyme is selected from the group consisting of tyrosine hydroxylase (TH), aromatic amino acid decarboxylase (AADC), and phenylalanine hydroxylase (PheOH). In alternative embodiments, the effective amount is sufficient to increases the rate of tetrahydrobiopterin (BH4) biosynthesis. In certain cases, the effective amount is sufficient to increase the rate of transcription or translation of a polynucleotide encoding an enzyme involved in BH4 biosynthesis. For instance, in particular embodiments, the enzyme is GTP cyclohydrolase 1 (GCH1). In alternative embodiments, the effective amount is sufficient to increase the rate of serotonin (5-HT) biosynthesis. In particular cases, the effective amount is sufficient to increases the rate of transcription or translation of a polynucleotide encoding an enzyme involved in 5-HT biosynthesis. For instance, in certain embodiments, the enzyme is selected from the group consisting of tryptophan hydroxylase (TPH) and amino acid decarboxylase (DDC).

In certain embodiments of the above-described methods, the compound selectively activates a Nurr1:RXRα heterodimer over one or more other RXRα-containing dimers. Additionally or alternatively, the compound may increase the rate of dopamine biosynthesis and serotonin biosynthesis.

The present invention additionally provides a method of increasing the rate of dopamine biosynthesis in a human by administration to the human of an effective amount of a compound or pharmaceutical composition described above. In certain cases, the administration increases the rate of serotonin biosynthesis.

The invention further relates to a method of treating a neurodegenerative disorder in a human by administration to the human of an effective amount of a compound capable of activating Nurr1.

The invention additionally features the compound of any of the aspects or embodiments described above for use in treating a neurodegenerative disorder (e.g., Parkinson's disease) in a human patient. Compounds of any of the aspects or embodiments described above can be used for alleviating or preventing one or more symptoms of a neurodegenerative disorder in a human patient, such as bradykinesia, dyskinesias, anxiety, depression, learning difficulties, memory disorders, attention deficit disorder, insomnia, and katalepsy. The invention also features the compound of any of the aspects or embodiments described above for use in treating a disorder in a human patient in which Nurr1 activity is reduced or impaired relative to a healthy human. The invention additionally features the compound of any of the aspects or embodiments described above for use in increasing the rate of dopamine biosynthesis and/or serotonin biosynthesis in a human.

In another aspect, the invention features a kit containing a compound or pharmaceutical composition as described herein. The kit may contain a package insert, for example, instructing a user of the kit to perform a method described herein, such as to administer a compound or pharmaceutical composition of the invention to a patient (e.g., a human patient) to treat a neurodegenerative disorder, such as Parkinson's disease, to alleviate or prevent one or more symptoms of a neurodegenerative disorder, such as bradykinesia, dyskinesias, anxiety, depression, learning difficulties, memory disorders, attention deficit disorder, insomnia, and katalepsy, to treat a disorder in a human patient in which Nurr1 activity is reduced or impaired relative to a healthy human, and/or to increase the rate of dopamine biosynthesis and/or serotonin biosynthesis in a human patient.

Definitions

As used herein, "acyl" refers to an —C(O)R moiety, wherein R is hydrogen, optionally substituted alkyl, optionally substituted alkenyl, or optional substituted alkynyl.

As used herein, "alkoxy" refers to a —O—R moiety, where R is optionally substituted alkyl, optionally substituted alkenyl, or optionally substituted alkynyl group.

As used herein, alkyl, alkenyl, and alkynyl carbon chains, unless otherwise specified, contain 1 to 6 carbons and can be straight or branched. Unless otherwise specified, alkenyl carbon chains of 2 to 6 carbons contain 1 to 2 double bonds. Unless otherwise specified, alkynyl carbon chains of 2 to 6 carbons contain 1 to 2 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl(propynyl).

As used herein, "alkylamino" refers to a —N($R_1$)$R_2$ moiety, where $R_1$ and $R_2$ are, independently, optionally substituted alkyl, optionally substituted alkenyl, or optionally substituted alkynyl groups.

As used herein, the "amelioration" of a symptom of a particular disorder by administration of a particular compound or pharmaceutical composition refers to any lessening of the symptom, whether permanent or temporary, that can be attributed to or associated with administration of the compound or pharmaceutical composition.

As used herein, the term "amino acid" refers to α-amino acids that are racemic or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. Amino acids may be of either the L- or D-form. The configuration for naturally occurring amino acid residues is generally L. When not specified, the residue is the L form.

As used herein, "aryl" refers to aromatic monocyclic or multicyclic groups containing from 6 to 19 carbon atoms. Aryl groups include, but are not limited to, unsubstituted or substituted fluorenyl, unsubstituted or substituted phenyl, and unsubstituted or substituted naphthyl.

As used herein, "aryl-alkyl" refers to an alkyl group in which one of the hydrogen atoms of the alkyl is replaced by an aryl group.

As used herein, "azido" refers to a —N=N=N moiety.

As used herein, the term "carboxyl" refers to a —COOH moiety.

As used herein, "cyanate" refers to a —O—C≡N moiety.

As used herein, "cyano" refers to a —C≡N moiety.

As used herein, the term "cycloalkyl" refers to a saturated mono- or multi-cyclic ring system of from 3 to 6 carbon atoms. The ring systems of the cycloalkyl groups may be composed of one ring or two or more rings which may be joined together in a fused, bridged or spiro-connected fashion.

As used herein, "$EC_{50}$" refers to a dosage, concentration, or amount of a particular test compound that elicits a dose-dependent response at 50% of maximal expression of a particular response that is induced, provoked, or potentiated by the particular test compound.

As used herein, the suffix "-ene" refers to a divalent version of the parent group.

As used herein, the term "halogen" refers to fluorine, chlorine, bromine, and/or iodine moieties.

As used herein, "haloalkyl" refers to an alkyl group in which one or more of the hydrogen atoms are replaced by one or more halogen atoms. Such groups include, but are not limited to, chloromethyl, trifluoromethyl, and 1-chloro-2-fluoroethyl.

As used herein, "heteroaryl-alkyl" refers to an alkyl group in which one of the hydrogen atoms of the alkyl is replaced by a heteroaryl group.

As used herein, the term "heteroaryl" refers to a monocyclic or multicyclic aromatic ring system, in certain embodiments, of 5 to 15 members where one or more (e.g., from 1 to 4) of the atoms in the ring system is a heteroatom (O, N, or S). A heteroaryl group may be optionally fused to another ring, such as an optionally substituted phenyl ring. Heteroaryl groups include, without limitation, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl, and isoquinolinyl.

As used herein, the term "heteroatom" refers to an element other than carbon, including, without limitation, nitrogen, oxygen, or sulfur.

As used herein, the terms "heterocyclyl" refer to a monocyclic or multicyclic non-aromatic ring system, in one embodiment of 3 to 10 members, in another embodiment of 4 to 7 members, in a further embodiment of 5 to 6 members, where one or more (e.g., from 1 to 4) of the atoms in the ring system is a heteroatom (e.g., O, N, or S). In embodiments where the heteroatom(s) is(are) nitrogen, the nitrogen may be optionally substituted with alkyl, alkenyl, alkynyl, aryl, heteroaryl, aryl-alkyl, heteroaryl-alkyl, cycloalkyl, heterocyclyl, cycloalkylalkyl, heterocyclylalkyl, acyl, or guanidino moieties, or the nitrogen may be quaternized to form an ammonium group containing substituents selected from those listed above.

As used herein, heterocyclyl-alkyl refers to an alkyl group in which one of the hydrogen atoms of the alkyl is replaced by a heterocyclyl group As used herein, "hydroxy" refers to a —OH moiety.

As used herein, "isocyanate" refers to a —N=C=O moiety.

As used herein, "isoselenocyanate" refers to a —N=C=Se moiety.

As used herein, "isothiocyanate" refers to a —N=C=S moiety.

As used herein, "mercapto" refers to a —SR moiety in which R is selected from the group consisting of hydrogen, alkyl, alkenyl, alkynyl, and aryl.

As used herein, "nitro" refers to a —$NO_2$ moiety.

As used herein, "optionally substituted alkyl," "optionally substituted alkenyl," "optionally substituted alkynyl," "optionally substituted cycloalkyl," "optionally substituted cycloalkenyl," "optionally substituted cycloalkynyl," "optionally substituted aryl," "optionally substituted heteroaryl" and "optionally substituted heterocyclyl" refer to alkyl, alkenyl, alkynyl, cycloalkyl, cycloalkenyl, cycloalkynyl, aryl, heteroaryl, and heterocyclyl groups, respectively, that, when substituted, are independently substituted with one or more substituents selected from the group consisting of a halogen, cyanate, isocyanate, thiocyanate, isothiocyanate, selenocyanate, isoselenocyanate, alkoxy, trifluoromethoxy, haloalkyl, alkylamino, azido, cyano, nitro, hydroxy, acyl, mercapto, carboxyl, ester, alkyl group, alkenyl group, alkynyl group, aryl group, aryl-alkyl group, heteroaryl group, heteroaryl-alkyl group, cycloalkyl group, heterocyclyl group, —$OR_7$, —$SR_7$, and —$N(R_8)R_7$, where $R_7$ is selected from the group consisting of hydrogen, alkyl, alkenyl, alkynyl, aryl, aryl-alkyl, heteroaryl, heteroaryl-alkyl, cycloalkyl, and heterocyclyl, or R7 and R8, when present, may combine with the atom to which they are bound to form a heteroaryl or heterocyclyl ring; and $R_8$ is selected from the group consisting of hydrogen and alkyl.

As used herein, the term "prevention" refers to the prophylactic treatment of a subject who is at risk of developing a condition (e.g., a neurodegenerative disorder) resulting in a decrease in the probability that the subject will develop the condition.

As used herein, "selenocyanate" refers to a —Se—C≡N moiety.

As used herein, "thiocyanate" refers to a —S—C≡N moiety.

As used herein, the term "treatment" refers to any manner in which one or more of the symptoms of a disease or disorder are ameliorated or otherwise beneficially altered. Treatment also encompasses any pharmaceutical use of the compositions herein, such as a use for treating a disease or disorder as described herein.

As used herein, the term "trifluoromethoxy" refers to a —$OCF_3$ moiety.

Where the number of any given substituent is not specified (e.g., haloalkyl), there may be one or more substituents present. For example, "haloalkyl" may include one or more of the same or different halogens. As another example, "$C_{1-3}$ alkoxyphenyl" may include one or more of the same or different alkoxy groups independently containing one, two, or three carbons.

When the compounds described herein contain olefinic double bonds or other centers of geometric asymmetry, and unless specified otherwise, it is intended that the compounds include both E and Z geometric isomers. Likewise, all tautomeric forms of carbonyl-containing compounds are also intended to be included.

It is to be understood that the compounds provided herein may contain chiral centers. Such chiral centers may be of either the (R) or (S) configuration, or may be a mixture thereof. Thus, the compounds provided herein may be enantiomerically pure, or may be stereoisomeric or diastereomeric mixtures. As such, one of skill in the art will recognize that administration of a compound in its (R) form is equivalent, for compounds that undergo epimerization in vivo, to administration of the compound in its (S) form.

BRIEF DESCRIPTION OF THE FIGURES

FIG. 1A shows a schematic representation of the components used in a luciferase assay as described herein. FIG. 1B shows the results of a screen of select compounds of the invention in a luciferase reporter assay to evaluate the Nurr1-activating properties of these compounds. XCT, a known Nurr1 activator, is used as a positive control. FIG. 1C shows the results of a luciferase assay to assess the capacity of compound 3 (as listed in Table 1) to activate Nurr1:RXR heterodimers. FIG. 1D shows the results of a luciferase assay to assess the specificity of a compound 3 for Nurr1:RXRα heterodimers over other RXRα-containing heterodimers. FIG. 1E demonstrates that compound 3 selectively potentiates Nurr1:RXRα activity over other heterodimers containing the RXRα subunit. Gal4 DNA binding domain fusions with various RXRa and PPARg, VDR RXRa, RXRγ and Nurr1 ligand binding domains activated with compound 3 show that only Nurr1:RXRa heterodimers are activated by compound 3. FIG. 1F demonstrates that compound 3 administration in mice activates cjun expression as assessed by qPCR. FIG. 1G shows that compound 3 administration in mice activates tyrosine hydroxylase expression as assessed by qPCR.

FIG. 2A demonstrates that compound 3 protects Neuro2A cells from MPP+ induced toxicity. FIG. 2B shows that compound 3 protects SHSY-5Y cells from low MPP+ (0.5 mM) induced toxicity. The graph in FIG. 2B shows, from left to right, control, XCT, and compound 3. FIGS. 2C and 2D show that compound 3 protects SHSY-5Y cells from high MPP+ (4 mM) induced toxicity. The graph in FIG. 2C shows, from left to right, control, XCT, and compound 3. FIG. 2E demonstrates that a retrovirus carrying shNurr1 is capable of infecting SHSY-5Y cells and lowering endogenous Nurr1 mRNA levels by ~60% assessed by qPCR. FIG. 2F shows that a retrovirus carrying shNurr1 is capable of infecting SHSY-5Y cells, lowering endogenous Nurr1 mRNA levels, and in turn attenuating the response of Nurr1:RXRα heterodimers to compound 3, indicating activity is based on Nurr1. The graph in FIG. 2F shows, from left to right, control, shNurr1, control compound 3, and shNurr1 compound 3. FIG. 2G shows that a retrovirus carrying shNurr1 infected SHSY-5Y cells lowers endogenous Nurr1 mRNA levels and lowers neuroprotective effect of compound 3, indicating activity is based on Nurr1. The graph in FIG. 2G shows, from left to right, control, control+compound 3, shNurr1, and shNurr1+compound 3.

FIG. 3A shows that C57/BL6 mice injected IP with 20 mg/kg compound 3 exhibit increased TH expression levels in comparison with vehicle IP injections as determined by qPCR. FIG. 3B shows that C57/BL6 mice injected IP with 20 mg/kg compound 3 exhibit increased striatum DA levels and DA metabolite (DOPAC, HVA) levels in comparison with vehicle IP injections as determined by HPLC. FIG. 3C shows that C57/BL6 mice injected IP with 20 mg/kg compound 3 exhibit increased striatum 5HT levels and 5HT metabolite 5HIAA levels in comparison with vehicle IP injections as determined by HPLC. FIG. 3D shows that C57/BL6 mice injected with 20 mg/kg compound 3 do not exhibit increased striatum noradrenaline levels in comparison with vehicle IP injections as determined by HPLC.

FIG. 4A shows C57/BL6 1-methyl-4-phenyl-1,2,3,6-tetrahydropyridine (MPTP)-treated mice injected once IP with 20 mg/kg compound 3 7 days after MPTP treatment increase movement coordination as compared to vehicle IP injections as determined by rotarod experiments done on a Columbus Instruments apparatus. FIG. 4B shows C57/BL6 6OHDA-treated mice injected once IP with 20 mg/kg compound 3 20 days after 6OHDA treatment increase movement coordination vs. vehicle IP injections as determined by rotarod experiments done on a Columbus Instruments apparatus. FIG. 4C shows C57/BL6 6OHDA-treated mice injected daily for 14 days IP with 20 mg/kg compound 3 starting 20 days after 6OHDA treatment do not induce abnormal involuntary movements (AIMS) vs. daily L-DOPA IP injections. FIG. 4D shows C57/BL6 wt mice injected once IP with 20 mg/kg compound 3 starting 20 days after CMS treatment increase swim times vs. vehicle IP injections in the Porsolt forced swim test. FIG. 4E shows C57/BL6 wt mice injected once IP with 20 mg/kg compound 3 starting 20 days after CMS treatment decrease floating times vs. vehicle IP injections in the Porsolt forced swim test.

FIGS. 5A and 5B show C57/BL6 6OHDA-treated mice injected daily IP with 20 mg/kg compound 3 for 20 days after MPTP treatment increase midbrain dopaminergic neuron numbers vs. C57/BL6 6OHDA-treated mice injected daily IP with vehicle as determined by computer-assisted image analysis system. The graph in FIG. 5A shows, from left to right, control, control compound 3, 6-OHDA, and 6-OHDA compound 3. FIGS. 5C and 5D show C57/BL6 MPTP-treated mice injected daily IP with 20 mg/kg compound 3 for 7 days after MPTP treatment increase midbrain dopaminergic neuron numbers vs. C57/BL6 MPTP-treated mice injected daily IP with vehicle as determined by computer-assisted image analysis system. The graph in FIG. 5C shows, from left to right, control, control compound 3, MPTP, and MPTP compound 3. FIG. 5E shows Nurr1 heterozygote 129/SV MPTP-treated mice injected daily IP with 20 mg/kg compound 3 for 7 days after MPTP treatment do not exhibit increased midbrain dopaminergic neuron numbers in comparison with C57/BL6 MPTP-treated mice injected daily IP with vehicle and in comparison with 120/SV control mice as determined by computer-assisted image analysis system. The graph in FIG. 5E shows, from left to right, wt vehicle, wt MPTP, wt MPTP compound 3, Nurr1 het vehicle, Nurr1 het MPTP, and Nurr1 het MPTP compound 3.

FIG. 69A shows the detection of compound 3 in plasma 1, 2, 4, 8 and 24 hours after IP administration (n=5) to mice. FIG. 69B shows that IP administration of compound 3 resulted in appreciable penetration of the compound in the brain. Mice (n=5) were sacrificed 1, 2, 4, 8 and 24 hours after IP administration and brains were dissected 1, 2, 4, 8 and 24 hours post administration. The concentrations of the parent compound in plasma and brain were determined by LC/MSMS. FIG. 69C shows c-jun transcriptional activation in the midbrain as determined by qPCR 2 hours after IP administration of compound 3.

FIG. 70A shows that administration by IP injection to mice revealed significant c-jun transcriptional activation in the midbrain as determined by qPCR 2 hours after administration. FIG. 70B shows the results of experiments conducted to assess whether compound 46 possesses neuroprotective properties. Compound 46 (12.5 µM) was added to human origin SHSY-5Y dopaminergic cells in which death was induced by the mitochondria complex I inhibitor MPP+ (1-methyl-4-phenylpyridinium), the active metabolite of MPTP (1-methyl-4-phenyl-1,2,3,6-tetrahydropyridine). Pretreatment of the cells with compound 46 for 12 to 24 hours prior to incubation with MPP+ significantly increased the survival of cells against varying concentrations of the toxic stimulus. Most of the MPP+-treated cells receiving vehicle died, while the few surviving cells remained attached to the plate but were rounded and had lost all projections. These morphological changes indicated impaired neuronal function. On the contrary, cells treated with compound 46 appeared healthy, flattened, and well-attached, and their projections remained intact.

FIGS. 72A-72R show the ability of compound 3 to induce the expression of genes involved in dopamine biosynthesis as well as the neuroprotective effects of compound 3 in cell lines and patient iPCs-derived dopaminergic neurons. FIG. 72A shows coordinated expression levels of the three dopamine biosynthesis genes (TH, AADC and GCH1) mediated by activation of Nurr1:RXRα by compound 3 (12.5 µM), as assessed by qPCR (n=8). FIG. 72B shows SHSY-5Y cell viability increases with compound 3 treatment, as measured by MTT assay, after exposure to varying concentrations (0-16 µM) of hydrogen peroxide. FIG. 72C shows compound 3 concentration-dependent SHSY-5Y cell viability, measured by MTT assay, after exposure to varying concentrations (0-4 mM) of MPP+. FIG. 72D shows compound 3-mediated SHSY-5Y cell viability against MPP+ (2 mM) is dependent on Nurr1 levels, as determined by retroviral knockdown of Nurr1. FIG. 72E shows that compound 3 treatment of primary rat cortical neurons reduces apoptotic death induced by co-transfecting a LRRK2 G2019S or wild-type LRRK2 cDNA with CMV GFP, as measured by DAPI staining. FIGS. 72F, 72G, 72H, and 72I show representative confocal microscopy images of the compound 3-treated primary rat cortical neurons. FIG. 72J shows the survival of human iPS cell-derived dopaminergic neurons exposed to MPP+ (0.5 and 1.0 mM) and receiving either vehicle or compound 3 treatment. FIGS. 73K and 72L show that compound 3 treatment preserves dopaminergic neuron projections as determined by TH immunofluorescence of surviving iPS cell-derived DAergic neurons after exposure to MPP+. FIG. 72M-72R show the effects of compound 3 on PD patient iPS cell-derived dopaminergic neurons with the LRRK2-G2019S mutation or corrected mutation (GC). Compound 3 treatment rescues neurite length (M, expressed in nm), number (N) and branching (O) phenotypes. Representative images show staining with TuJ, TH and DAPI (FIGS. 72P, 72Q, and 72R).

FIGS. 73A-73F show the ability of compound 3 to protect dopaminergic neurons against MPTP toxicity. FIG. 73A shows the results of a Rotarod test. Increased motor coordination was observed for C57BL/6 mice exposed to MPTP and receiving compound 3 treatment for 7 days. FIG. 73C shows stereological counts of substantia nigra TH(+) neurons of control C57BL/6 mice or mice exposed to MPTP and receiving either vehicle or compound 3 treatment. FIG. 73D shows images of TH ICH of substantia nigra dopaminergic projections to the striatum in C57BL/6 mice exposed to MPTP and receiving either vehicle or compound 3 treatment. FIG. 73E shows the quantification of TH ICH dopaminergic projections to the striatum of C57BL/6 mice exposed to MPTP and receiving either vehicle or compound 3 treatment. FIG. 73F shows stereological counts of substantia nigra TH(+) neurons of control wild-type 129SV mice or mice exposed to MPTP and receiving either vehicle or compound 3 treatment (first three bars) and of Nurr1+/− 129SV mice exposed to MPTP and receiving either vehicle or compound 3 treatment (last three bars).

FIG. 74A shows a decreased number of apomorphine-induced contralateral turns in C57BL/6 mice injected unilaterally with 6-OHDA and treated daily with either vehicle or compound 3 for 13 days, showing over 8-fold improvement (n=5). FIG. 74B shows the results of a Rotarod test of mice subjected to unilateral injection of 6-OHDA and receiving either vehicle or compound 3, showing 12-fold improvement with compound 3 treatment (n=5). FIG. 74C shows SN TH ICH images of mice that received unilateral injection of 6-OHDA and were treated with either vehicle or compound 3. FIG. 74D shows stereological counts of SN TH(+) neurons of mice receiving unilateral injections of 6-OHDA and treated daily either vehicle or compound 3. Compound 3 treatment increased the number of TH(+) neurons by 47% (n=5). FIG. 74E shows striatum TH ICH of mice that received 6-OHDA injections and were treated with either vehicle or compound 3, showing 10-fold increased innervation (FIG. 74F) (n=5). FIG. 74G shows SN TH ICH images of mice that received unilateral injections of AAV-ASYN and contra-lateral injections of AAV-GFP and were treated with either vehicle or compound 3. FIG. 74H shows stereological counts of SN TH(+) neurons of mice that received unilateral injections of AAV-ASYN and were treated daily either with vehicle or compound 3. Compound 3 increased the number of TH(+) neurons by 48% (n=7). FIG. 74I shows the striatum TH ICH of mice that received injections of AAV-ASYN or AAV-GFP and were treated with either vehicle or compound 3, showing 10-fold increased innervation (FIG. 74J) (n=7).

FIG. 75A shows the results of qPCR assays conducted to assess TH expression levels in mouse midbrain 4 hours after vehicle or compound 3 (10 mg/kg) IP administration. FIG. 75B shows dopamine and dopamine metabolite levels 4 hours after IP administration of vehicle or compound 3 (10 mg/kg) in wild-type mice as assessed by HPLC. FIG. 75C shows dopamine and dopamine metabolite levels 4 hours after IP administration of vehicle or compound 3 (10 mg/kg) in alpha synuclein transgenic mice as assessed by HPLC (n=4). FIG. 75D shows noradrenaline levels 4 hours after IP administration of vehicle or compound 3 (10 mg/kg) as assessed by HPLC. FIGS. 75E and 75F show schematic representations of the compound 3 treatment regimens. FIG. 75G shows the accelerating rotarod latency times of MPTP-treated mice (4-40 rpm over 5 min) 4 hours after IP administration of vehicle or compound 3 (10 mg/kg). FIG. 75H shows the accelerating rotarod latency times of 6-OHD-treated mice (4-40 rpm over 5 min) 4 hours after IP administration of vehicle or compound 3 (10 mg/kg). FIG. 75I shows spontaneous contralateral turns per minute of 6-OHDA-treated mice 4 hours after IP administration of vehicle, compound 3 (10 mg/kg) or L-DOPA. FIG. 75J shows a schematic representation of the compound 3/L-DOPA treatment regimen.

DETAILED DESCRIPTION

Figure 1:
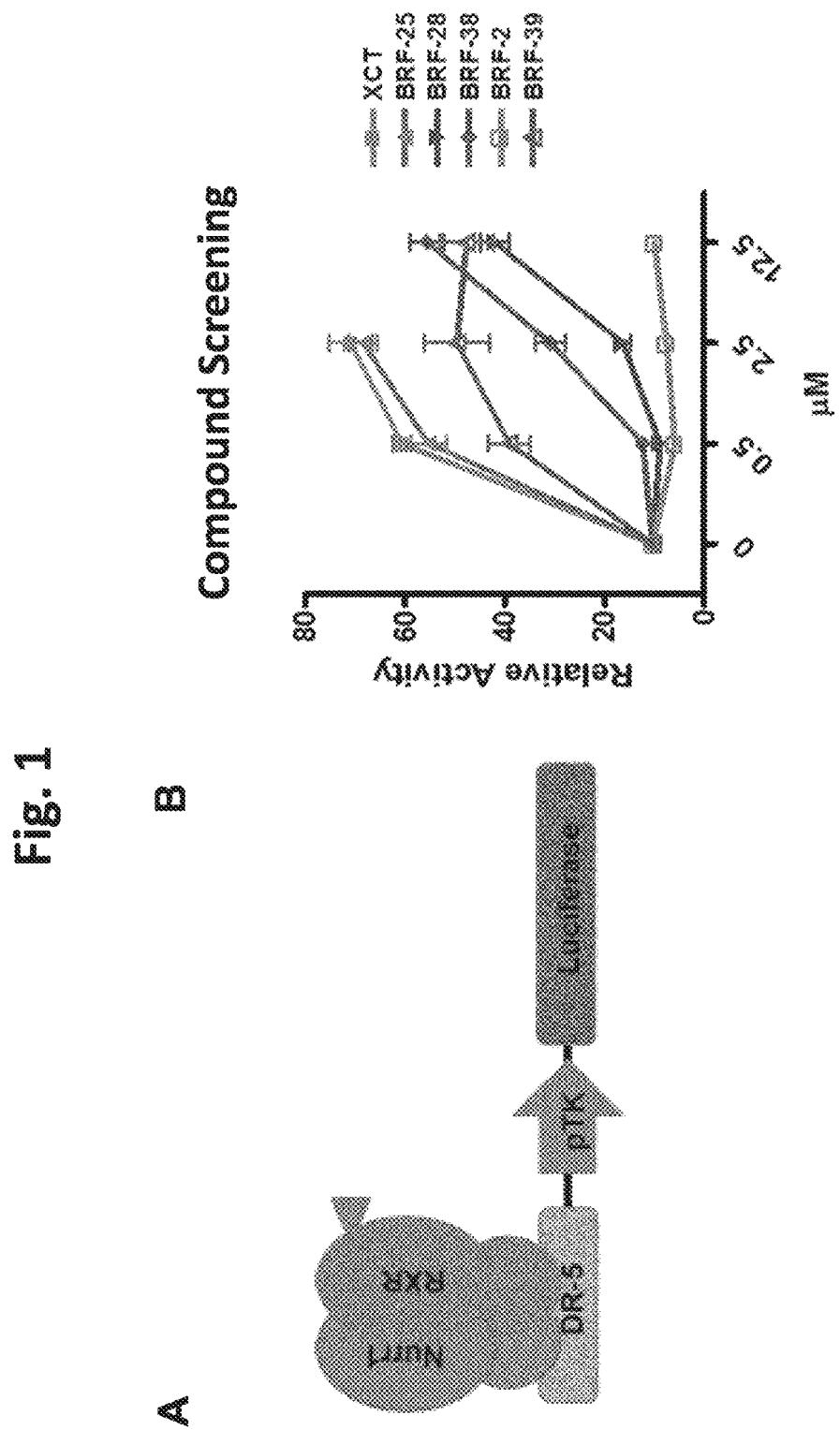
FIG. 1A-1G show various biochemical properties of compound 3.
Figure 1:
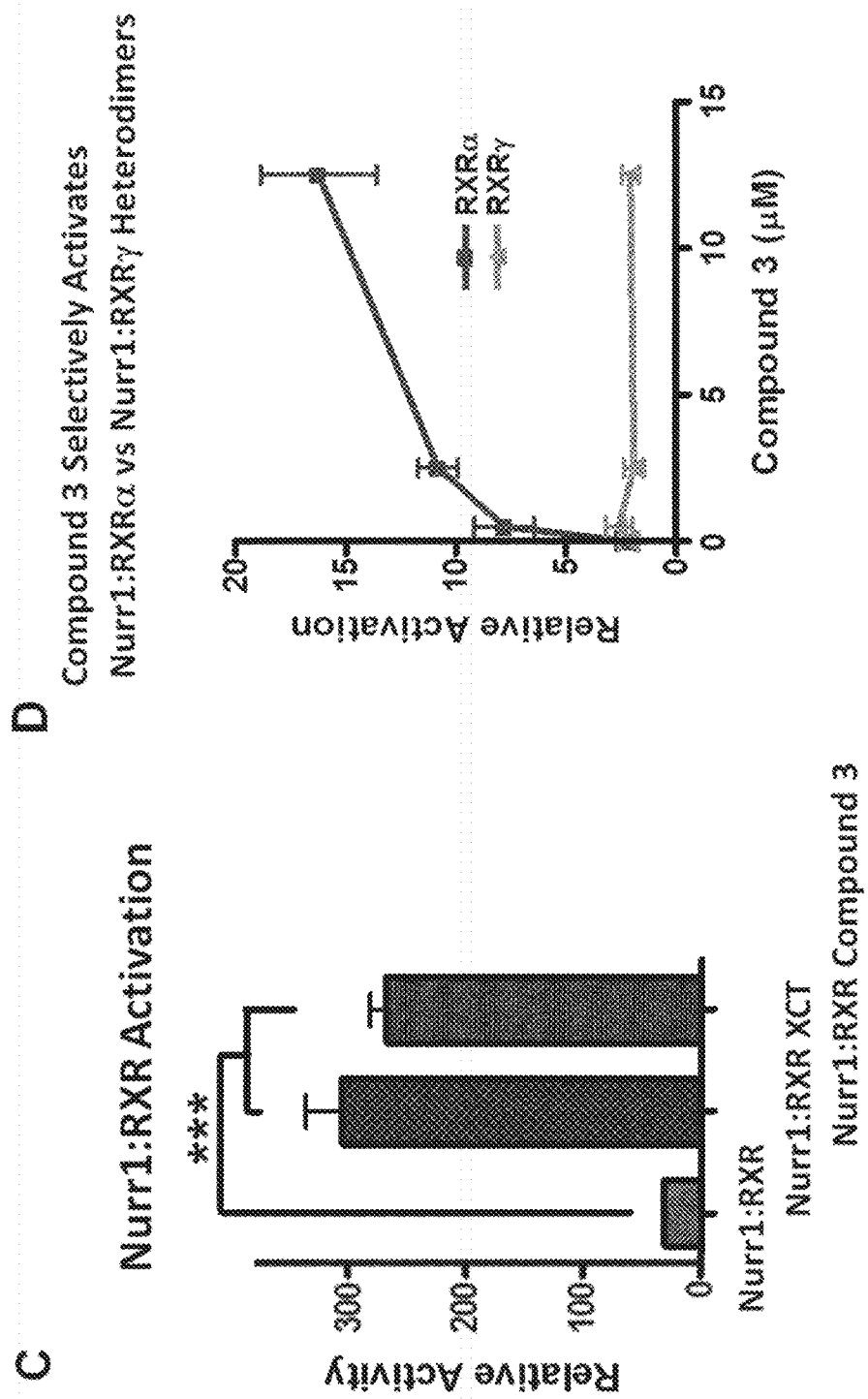

The present invention provides substituted pyrimidines that are, for example, effective as activators of the Nurr1:RXRα heterodimer. Substituted pyrimidines of formula (I) are selective agonists of the Nurr1:RXRα heterodimer and can inhibit neuronal degeneration and symptoms usually observed in Parkinson's disease:

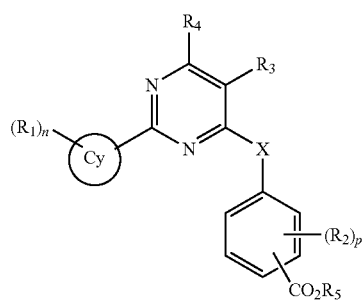

(I)

wherein n is 0 to 2, p is 0 to 2, X is N($R_6$), or O;
Cy is a phenyl ring or a heteroaromatic 5- or 6-membered ring containing between 1 and 4 heteroatoms (e.g., selected from O, N, and S);
each $R_1$ is independently selected from the group consisting of halogen, cyanate, isocyanate, thiocyanate, isothiocyanate, selenocyanate, isoselenocyanate, alkoxy, trifluoromethoxy, azido, cyano, nitro, hydroxy, acyl, mercapto, carboxyl, optionally substituted alkyl, optionally substituted cycloalkyl, optionally substituted heterocyclyl, optionally substituted aryl, optionally substituted heteroaryl, —$OR_7$, —$SR_7$, and —N($R_8$)$R_7$;
each $R_2$ is independently selected from the group consisting of halogen, cyanate, isocyanate, thiocyanate, isothiocyanate, selenocyanate, isoselenocyanate, alkoxy, trifluoromethoxy, azido, cyano, nitro, hydroxy, acyl, mercapto, carboxyl, optionally substituted alkyl, optionally substituted cycloalkyl, optionally substituted heterocyclyl, optionally substituted aryl, optionally substituted heteroaryl, —$OR_7$, —$SR_7$, and —N($R_8$)$R_7$;
$R_3$ is selected from the group consisting of hydrogen, halogen, cyanate, isocyanate, thiocyanate, isothiocyanate, selenocyanate, isoselenocyanate, alkoxy, trifluoromethoxy, azido, cyano, nitro, hydroxy, acyl, mercapto, optionally substituted alkyl, optionally substituted alkenyl, optionally substituted alkynyl, $OR_7$, —$SR_7$, —N($R_8$)$R_7$, optionally substituted aryl, optionally substituted heteroaryl, optionally substituted cycloalkyl and optionally substituted heterocyclyl, or $R_3$ and $R_6$, when present, combine with the atoms to which they are bound to form an optionally substituted 5-membered heteroaryl or heterocyclyl;
$R_4$ is selected from the group consisting of hydrogen, halogen, optionally substituted alkyl, optionally substituted cycloalkyl, optionally substituted aryl, optionally substituted aryl-alkyl, optionally substituted heterocyclyl, optionally substituted heteroaryl, optionally substituted heteroaryl-alkyl, optionally substituted heterocyclylalkyl, $OR_7$, and —N($R_8$)$R_7$;
$R_5$ is selected from the group consisting of hydrogen, optionally substituted alkyl, optionally substituted alkenyl, and optionally substituted aryl;
$R_6$ is selected from the group consisting of hydrogen and optionally substituted alkyl;
each $R_7$ is independently selected from the group consisting of hydrogen, optionally substituted alkyl, optionally substituted alkenyl, optionally substituted aryl, optionally substituted aryl-alkyl, and optionally substituted heterocyclyl; and
each $R_8$ is independently selected from the group consisting of hydrogen and optionally substituted alkyl.

The compounds of formula (I), wherein $R_5$ is H, are carboxylic acids that can be used in the form of free acids or in the form of salts, which can result from the combination of the acid with an inorganic base, or preferably with a pharmaceutically acceptable, non-toxic organic base. Inorganic bases that can be used to produce an addition salt of the invention include, without limitation, the hydroxides of sodium, potassium, magnesium, and calcium. Organic bases that can be used to produce an addition salt of the invention include, without limitation, amines, amino alcohols, basic amino acids such as lysine or arginine, or compounds bearing a tertiary amine function, such as betaine or choline. Salts of formula (I) with an inorganic or organic base can be obtained in conventional manner using well known methods to those skilled in the art, e.g., by mixing stoichiometric amounts of an acid of formula (I) (wherein $R_5$ is H) and a base in a solvent such as water or a hydroalcoholic mixture and then lyophilizing the resulting solution.

Esterified compounds of formula (I) that can be used in the form of a prodrug are pharmaceutically acceptable esters that can be produced by the derivatization of the carboxylic acid with an appropriately substituted aliphatic or aromatic alcohol or an alkyl halide.

Preferred embodiments of substituted pyrimidines include, for example, compounds in which $R_3$ is not hydrogen, such as compounds in which Cy is a phenyl ring, $R_3$ is optionally substituted alkyl or optionally substituted alkenyl, $R_4$ is optionally substituted methyl (e.g., halomethyl), and $R_5$ is hydrogen or optionally substituted alkyl. For instance, in some preferred embodiments, Cy is a phenyl ring, $R_3$ is alkyl or alkenyl, $R_4$ is methyl or trifluoromethyl, and $R_5$ is hydrogen or alkyl.

Preferred embodiments of substituted pyrimidines also include compounds of formula (1a):

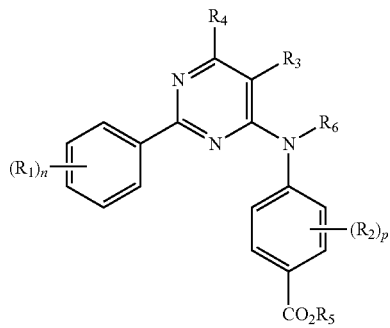

(1a)

wherein each of n, p, and $R_1$-$R_6$ are as defined above.

Preferred embodiments of substituted pyrimidines additionally include compounds of formula (1b):

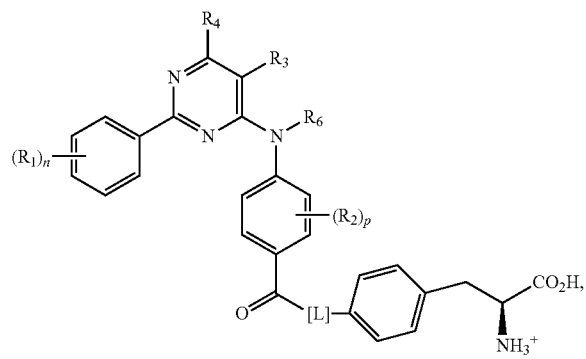

(1b)

or a free base thereof,
wherein each of n, p, and $R_1$-$R_4$ and $R_6$ are as defined above; and L is selected from the group consisting of —O—, —O—$R_9$—O—, and —O—$R_9$—, wherein $R_9$ is an optionally substituted alkyl, optionally substituted alkenyl, or optionally substituted alkynyl moiety.

Preferred embodiments of substituted pyrimidines further include compounds of formula (1a) in which $R_4$ is haloalkyl, e.g., $CF_3$. For example, preferred embodiments of substituted pyrimidines include compounds of formula (1c):

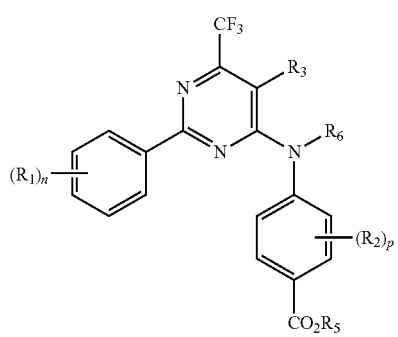

(1c)

wherein each of n, p, and $R_1$-$R_3$, $R_5$, and $R_6$ are as defined above.

Preferred embodiments of substituted pyrimidines also include compounds of formula (1d):

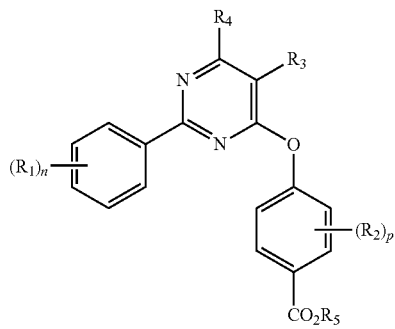

(1d)

wherein each of n, p, and $R_1$-$R_5$ are as defined above.

Preferred embodiments of substituted pyrimidines also include compounds of formula (1e):

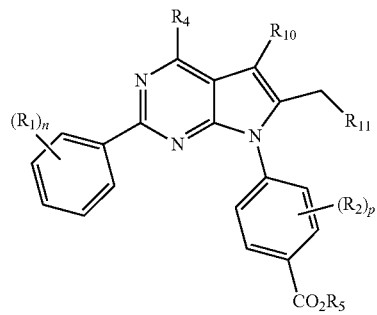

(1e)

wherein each of n, p, $R_1$, $R_2$, $R_4$, and $R_5$ are as defined above;

$R_{10}$ is selected from the group consisting of hydrogen, optionally substituted alkyl, optionally substituted aryl, optionally substituted aryl-alkyl, optionally substituted heteroaryl, optionally substituted cycloalkyl, and optionally substituted heterocyclyl; and $R_{11}$ is selected from the group consisting of optionally substituted alkyl, optionally substituted aryl, optionally substituted aryl-alkyl, optionally substituted heteroaryl, optionally substituted cycloalkyl, and optionally substituted heterocyclyl.

Preferred embodiments of substituted pyrimidines further include compounds of formula (1f):

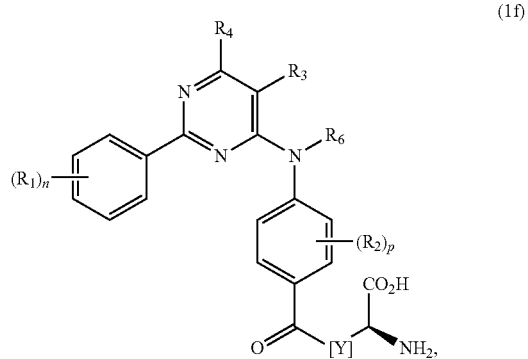

(1f)

or a salt thereof, where each of n, p, and $R_1$-$R_4$ and $R_6$ are as defined above; and Y is —$R_9$—, wherein $R_9$ is an optionally substituted alkylene, optionally substituted alkenylene, or optionally substituted alkynylene chain.

For instance, preferred embodiments of substituted pyrimidines include compounds of formula (1g):

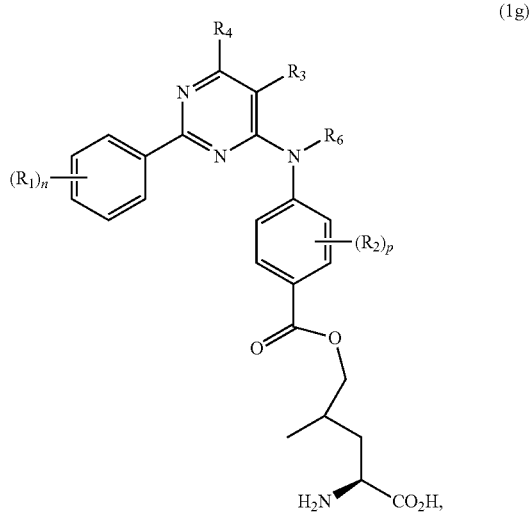

(1g)

or a salt thereof, where each of n, p, and $R_1$-$R_4$ and $R_6$ are as defined above.

Additional preferred embodiments of substituted pyrimidines include compounds of formula (1 h):

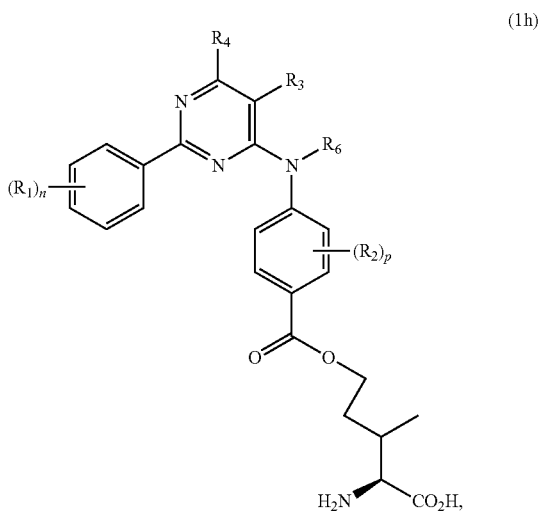

(1h)

or a salt thereof, where each of n, p, and $R_1$-$R_4$ and $R_6$ are as defined above.

Methods of Treatment
Neurodegenerative Disorders and Nurr1

Parkinson's disease is a common neurodegenerative disease, and its pathology is characterized by the progressive loss of the dopaminergic (DAergic) neurons of the substantia nigra (SN), leading to striatal dopamine (DA) deficiency (Meissner, Rev. Neurol. 168:809-814, 2012). Current medications replenish dopamine, and offer temporary symptomatic relief to patients. However, chronic treatments cause serious side effects in almost all patients, including abnormal involuntary movements (AIMs) and dyskinesias, limiting their efficacy (Athauda et al. Nature Reviews Neurology 11:25-40, 2015). Moreover, DA replacement does not impede neurodegeneration, and PD pathology progresses (Fahn. J. Neural Transm. Suppl. 70:419-426, 2006). Despite considerable progress in our understanding of PD pathophysiology, pharmacological strategies to prevent neurodegeneration remain elusive, and the disease remains incurable. Therefore, validation of novel targets that diminish DA replacement side-effects and halt or slow disease progression is an urgent unmet clinical need (Meissner et al. Nat. Rev. Drug Discov. 10:377-393, 2011).

Nurr1 (NR4A2), a nuclear receptor, has been a promising target candidate for therapy, as it is implicated in both DA biosynthesis and DAergic neuron survival. Nurr1 is expressed in developing and mature dopaminergic neurons, and it is required for both survival and final complete dopaminergic differentiation (Zetterstrom et al. Science 276: 248-250, 1997 and Saucedo-Cardenas et al. Proc. Natl. Acad. Sci. U S A. 95:4013-4018, 1998). Nurr1 enhances in vitro and in vivo transcription of tyrosine hydroxylase (TH), the rate-limiting enzyme of DA biosynthesis, and of GTP cyclohydrolase I (GCH1), the first enzyme in the biosynthesis of tetrahydrobiopterin (BH4), an essential cofactor for TH activity (Kim et al. J. Neurochem. 85:622-634, 2003 and Gil et al. J Neurochem 101:142-150, 2007). Decreased Nurr1 levels have been strongly associated with PD and reduced DAergic neuron survival. Nurr1 ablation in adult mice leads to dystrophic dopaminergic axons (Kadkhodaei et al. J. Neurosci. 29:5923-5932, 2009), loss of striatal DA (Kadkhodaei et al. Proc. Natl. Acad. Sci. U S A. 110:2360-2365, 2013) and behavioral features of parkinsonism during aging (Zhang et al. Neurobiol. Aging 33:7-16, 2012). Nurr1 mutations decreasing its mRNA have been found in familial and sporadic PD patients (Le et al. Nat. Genet. 33:85-89, 2003 and Sleiman et al. Neurosci. Lett. 457:75-79, 2009). Given the role of Nurr1 in PD, we demonstrate that selective activation of Nurr1 by compounds of the invention represents a monotherapeutic treatment paradigm for PD that offers both disease modification and symptomatic relief.

Nurr1 binds to DNA as a monomer, homodimer or heterodimer with RXRα or RXRγ. Since in midbrain dopaminergic neurons Nurr1 heterodimerizes with RXRα (Wallen-Mackenzie et al. Genes Dev. 17:3036-3047, 2003), synthetic ligands that bind to the RXRα binding pocket are the preferred approach to neurodegenerative disease therapy described herein. RXRα is a heterodimer partner of several nuclear receptors, and existing synthetic RXRα ligands activate several RXRα heterodimers (Pérez et al. Biochim. Biophys. Acta 1821:57-69, 2012). Two such ligands, XCT0135908 and bexarotene (Wallen-Mackenzie et al. Genes Dev. 17:3036-3047, 2003 and Cramer et al. Science 335:1503-1506, 2012) have been shown to activate Nurr1: RXRα but also other RXRα heterodimers. Bexarotene, an approved antineoplastic activating RXRα heterodimers with LXR, PPARγ and Nurr1, had promising results in animal models of Alzheimer's disease and PD (Cramer et al. Science 335:1503-1506, 2012 and McFarland et al. ACS Chem. Neurosci. 4:1430-1438, 2013) however, failed to be replicated (Landreth et al. Science 340:924-g, 2013 and Volakakis et al. J. Neurosci. 35:14370-14385, 2015). In vitro, XCT0135908 (Wallen-Mackenzie et al. Genes Dev. 17:3036-3047, 2003), activates Nurr1:RXRα heterodimers and RXRα:RXRα homodimers (McFarland et al. ACS Chem. Neurosci. 4:1430-1438, 2013), but its bioavailability has not been reported.

As described herein, compounds of the invention meet an important unmet clinical need, as compounds of the invention are highly bioavailable, blood-brain barrier penetrant, and selectively potentiate the activity of the Nurr1:RXRα heterodimer, thereby modulating dopamine biosynthesis and other important gene expression profiles while minimizing potentially undesirable off-target effects.

Gene Modulating Effects and Neuroprotective Effects of Compounds of the Invention Compounds of the invention can be used to treat or inhibit the progression of a disease or condition that involves the activity of the transcription co-activator Nurr1. Nurr1 forms a heterodimeric protein complex with RXRα, and this ensemble modulates the expression of a variety of genes that collectively regulate dopaminergic neuron activity and differentiation in the brain. Attenuated activity of the Nurr1 transcription co-activator has been correlated with the onset of Parkinson's disease as well as symptoms associated with Parkinson's disease that are not limited to patients presenting with this ailment, such as bradykinesia, dyskinesia, learning difficulties, memory disorders, attention deficit disorder, insomnia, and katalepsy. Compounds of the present invention can thus be used to treat any or all of these symptoms, either in a patient suffering from Parkinson's disease or in a patient presenting with a different neurodegenerative disorder. Compounds of the invention can also be used to treat or inhibit the progression of a disease characterized by aberrant biosynthesis of one or more products of Nurr1 signalling, such as L-dopamine, as well as diseases and conditions in which the activity of Nurr1 is impaired or aberrant relative to a healthy subject, such as those characterized by a reduction in the quantity and activity of dopaminergic neurons. By promoting L-dopamine biosynthesis and release, compounds of the invention are capable of halting neurodegeneration of significant neurons, such as dopamine midbrain neurons and other neurons of the dopaminergic system. For instance, a lack of dopamine and loss of dopaminergic neuron projections to the striatum is manifested in activity alterations in the basal ganglia that regulate movement. Moreover, dopamine depletion from non-striatal dopamine pathways may underlie neuropsychiatric pathology associated with Parkinson's disease. Compounds of the invention can be administered to a patient in order to induce neuroprotection in any or all of these areas.

Due to their Nurr1-stimulating activity, compounds of the invention are capable of increasing the rate of transcription of polynucleotides (e.g., genes) encoding enzymes involved in dopamine biosynthesis, such as tyrosine hydroxylase (TH), aromatic amino acid decarboxylase (AADC), and phenylalanine hydroxylase (PheOH, alternatively PheH or PAH). Compounds of the instant invention are also capable of enhancing the rate of transcription of polynucleotides (e.g., genes) encoding enzymes involved in tetrahydrobiopterin (BH4) biosynthesis, such as GTP cyclohydrolase (GCH1). Compounds of the invention are also capable of increasing the rate of translation of the RNA resulting from the above-described transcription processes and thus increasing the amount of functional protein produced.

The compounds of the invention are unique in that they can selectively potentiate the activity of the Nurr1:RXRα heterodimer over a series of related transcription co-activator complexes that include RXRα. Known binding partners of RXRα include Nurr1, vitamin D receptor (VDR), peroxisome proliferator-activated receptor γ (PPARγ), RXRα, and RXRγ. The compounds of the invention thus represent an improvement over previously reported therapeutics, as the compounds of the present invention are capable of discriminating among these transcription co-activator complexes and selectively modulating Nurr1:RXRα activity. Additionally, compounds of the present invention are uniquely suitable for administration to a subject in vivo, as these compounds are readily bioavailable and are capable of inducing Nurr1-dependent neuroprotection in subjects.

Besides the dopaminergic system, the serotoninergic (5-HT) system and raphe nucleus (Braak et al., 2003) is also thought to be involved in the non motor PD symptoms. In the normal brain, there is a dense serotonergic innervation of the basal ganglia from the raphe nuclei. Indeed, in early postmortem studies of patients with PD, there is depletion of serotonin in the caudate as well. Imaging studies in vivo have also suggested depletion of 5-HT innervation to the striatum as measured via decreased serotonin transporter binding. The loss of striatal 5-HT in PD may be secondary to neurodegeneration as Lewy bodies are seen in the raphe nuclei and there is associated cell loss.

Surprisingly, compounds of the invention are also capable of potentiating the biosynthesis and release of serotonin by exerting activating effects on the serotoninergic (5-HT) system and raphe nucleus of the brain. This region is thought to be involved in the propagation of non-motor Parkinson's disease symptoms. Compounds of the invention can thus be used to treat symptoms mediated by the release and activity of serotonin, such as anxiety and depression that are often observed in patients suffering from Parkinson's disease. Significantly, the compounds of the present invention represent the first reported examples of therapeutics that are capable of treating symptoms that occur due to Nurr1 and 5-HT-mediated signaling.

Due to their serotoninergic system-stimulating activity, compounds of the invention are capable of increasing the rate of transcription of polynucleotides (e.g., genes) encoding enzymes involved in serotonin biosynthesis, such as tryptophan hydroxylase (TPH) and amino acid decarboxylase. Compounds of the invention are also capable of increasing the rate of translation of the RNA resulting from these transcription processes and thus increasing the amount of functional protein produced.

The current paradigm for treating Parkinson's disease primarily focuses on treating the symptoms associated with Parkinson's disease. To date, drug discovery efforts for PD have traditionally aimed either on symptomatic DA replacement treatments and alleviating dyskinesias or on neuroprotection. Existing DA replacement therapies may improve PD symptoms; however, they do not offer disease modification, and chronic use causes severe side effects such as dyskinesias (Rascol et al. Mov. Disord. 30:1451-1460, 2015 and Schapira. CNS Drugs 25:1061-1071, 2011). For instance, L-DOPA, has traditionally been administered to patients with Parkinson's disease in order to promote an increase in dopamine biosynthesis and release. Neuroprotective approaches, while they aim at the core of PD pathology, so far have not delivered the expected results (Stocchi. Neurotherapeutics 11:24-33, 2014). The compounds of the instant invention are unique in that they not only provide a symptomatic treatment modality but can also be administered to a patient with Parkinson's disease in order to induce a sustained neuroprotective effect in the dopaminergic and serotoninergic systems of the brain. These compounds can therefore be administered to a patient, e.g., at the onset of one or more symptom of the disease, such as bradykinesia, dyskinesia, insomnia, or katalepsy, among others, in order to alleviate these symptoms. Additionally or alternatively, compounds of the invention may be administered to a patient over the course of a prolonged treatment regimen in order to provide long-term relief from the disease by inducing neuroprotection in dopaminergic and serotoninergic systems of the brain.

Target Specificity

Compounds of the invention surprisingly exhibit an important biological benefit, as these compounds are capable of selectively activating the Nurr1:RXRα heterodimer over a series of closely related RXRα-containing transcription factors. In this way, compounds of the invention may modulate dopamine and serotonin biosynthesis and induce neuroprotection without promoting potentially undesirable off-target effects. Compounds of the invention therefore satisfy an unmet clinical need, as previous Nurr1 agonists lack this target selectivity. For example, XCT0135908 (also referred to herein as "XCT") is a known Nurr1 activator described in, e.g., WO 2005/047268. This compound has the structure shown below:

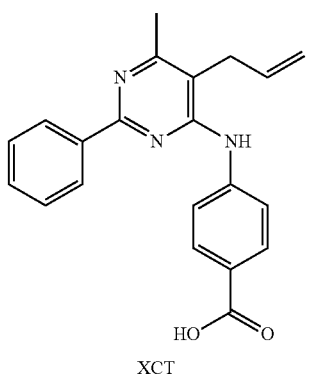 [SMILES: C=CCc1c(C)nc(-c2ccccc2)nc1Nc1ccc(C(=O)O)cc1]

XCT

Figure 67:
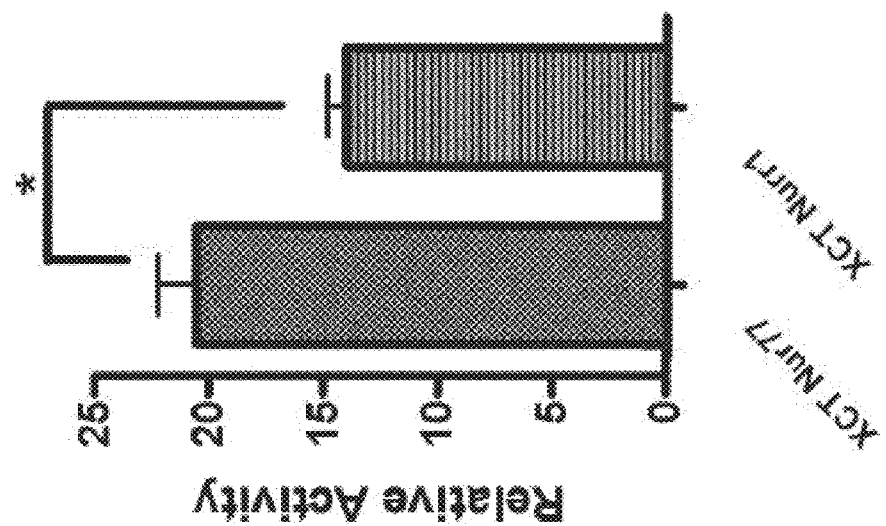
FIG. 67 shows the relative activation of Nurr1 and Nur77 by XCT0135908 as assessed using a luciferase reporter assay.

XCT activates Nurr1:RXRα heterodimers as well as RXRα:RXRα homodimers (McFarland et al. ACS Chem. Neurosci. 4:1430-1438, 2013). Additionally, present data show that XCT preferentially activates Nur77:RXRα heterodimers and not Nurr1:RXRα heterodimers. Thus, XCT does not selectively activate the Nurr1:RXRα heterodimer (FIG. 67). In contrast, compounds described herein, such as compound 3, selectively potentiate the activity of the Nurr1:RXRα homodimer.

As described herein, compounds of the invention, such as compound 3, are capable of specifically activating the Nurr1:RXRα complex over closely related potential targets, including other RXRα-containing heterodimers. As reported below, the ligand binding domains of Nurr1, RXRα and a variety of other nuclear receptors were cloned to create GAL4 chimeras, and the ligand binding domain of RXRα was fused with VP16. These molecular chimeras were co-transfected in pairs with the RXRα:VP16 along with a GAL4-responsive luciferase reporter into SHSY-5Y dopaminergic cells and were assayed for their ability to be activated by compounds of the invention. Compounds described herein readily activate Nurr1 GAL4:RXRαVP16 heterodimer chimeras without activating RXRαGAL4 homodimer chimeras, indicating again that these compounds are Nurr1:RXRα-selective agonists. For example, RXRαVP16 heterodimer chimeras with VDRGAL4, RXRγGAL4 or PPARγGAL4 were not activated by compound 3, as this compound was capable of selectively activating the Nurr1:RXRα heterodimer. These data indicate the high degree of selectivity of compounds of the invention for Nurr1 GAL4:RXRαVP16 heterodimers and the lack of activity towards other closely related molecular targets. The selectivity of compounds of the invention for the Nurr1:RXRα heterodimer is attributed to the fact that the ligand binding pocket of RXRα varies slightly depending on the heterodimer partner (Lionta et al. Curr. Top. Med. Chem. 14:1923-1938, 2014). Compounds of the invention are therefore capable of discriminating among transcriptional activators and selectively potentiating the activity of the Nurr1:RXRα complex (see, e.g., FIG. 1E).

Bioavailability

Figure 68:
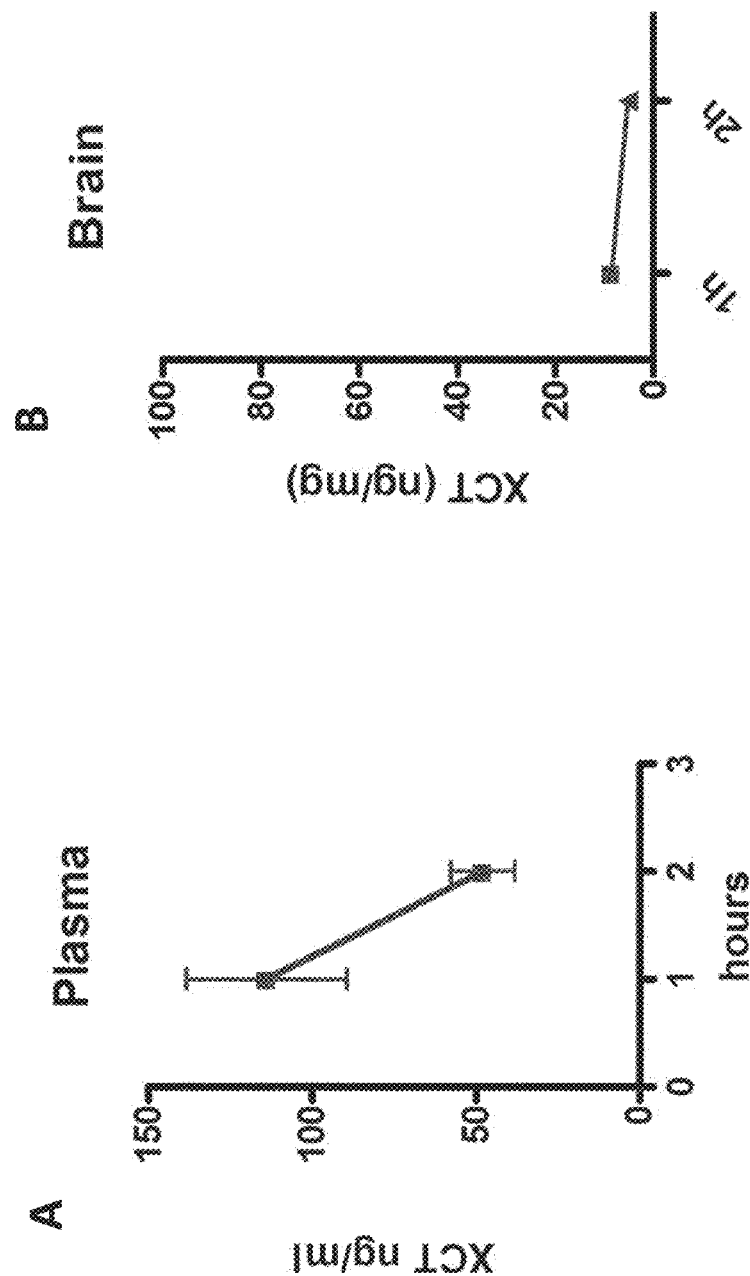
FIGS. 68A and 68B show the pharmacokinetic profile of XCT in blood plasma and in the brain of mice injected with this compound. Intraperitoneal (IP) or intracerebroventricular (ICV) XCT0135908 (1 and 10 mg/kg) injections did not achieve any downstream effect in the midbrain, failing to upregulate the expression of c-jun or of tyrosine hydroxylase (TH). IP administration of XCT0135908 in mice (1 mg/kg) resulted in minimal penetration of the compound in the brain. Serial tail bleeds (n=3) were used for detection of the compound in plasma 1 and 2 hours after IP administration. Similarly, mice (n=3) were sacrificed 1 and 2 hours after IP administration and brains were dissected. The concentrations of the parent compound in plasma and brain were determined by LC-MS/MS.

In addition to selectively activating the Nurr1:RXRα heterodimer, compounds of the invention exhibit high bioavailability and are readily brain-penetrant. The beneficial absorption and distribution profiles of the compounds of the invention represent an innovative solution to an unmet clinical problem, as previous Nurr1 agonists, such as XCT, lack the ability to persist in vivo and to cross the blood-brain barrier. For instance, as reported in the examples below, XCT was administered to mice to test its bioactivity in vivo. Intraperitoneal (IP) or intracerebroventricular XCT (1 and 10 mg/kg) injections did not result in any expression alterations of midbrain genes such c-jun or tyrosine hydroxylase at different time points after administration. LC-MS/MS analysis of blood plasma or brain homogenates and targeted searching of the parent compound at 1 and 2 hours after IP XCT (1 μg/kg) administration indicated low compound stability and minimal brain penetration (brain/blood<0.03; FIGS. 68A-B).

Figure 69:
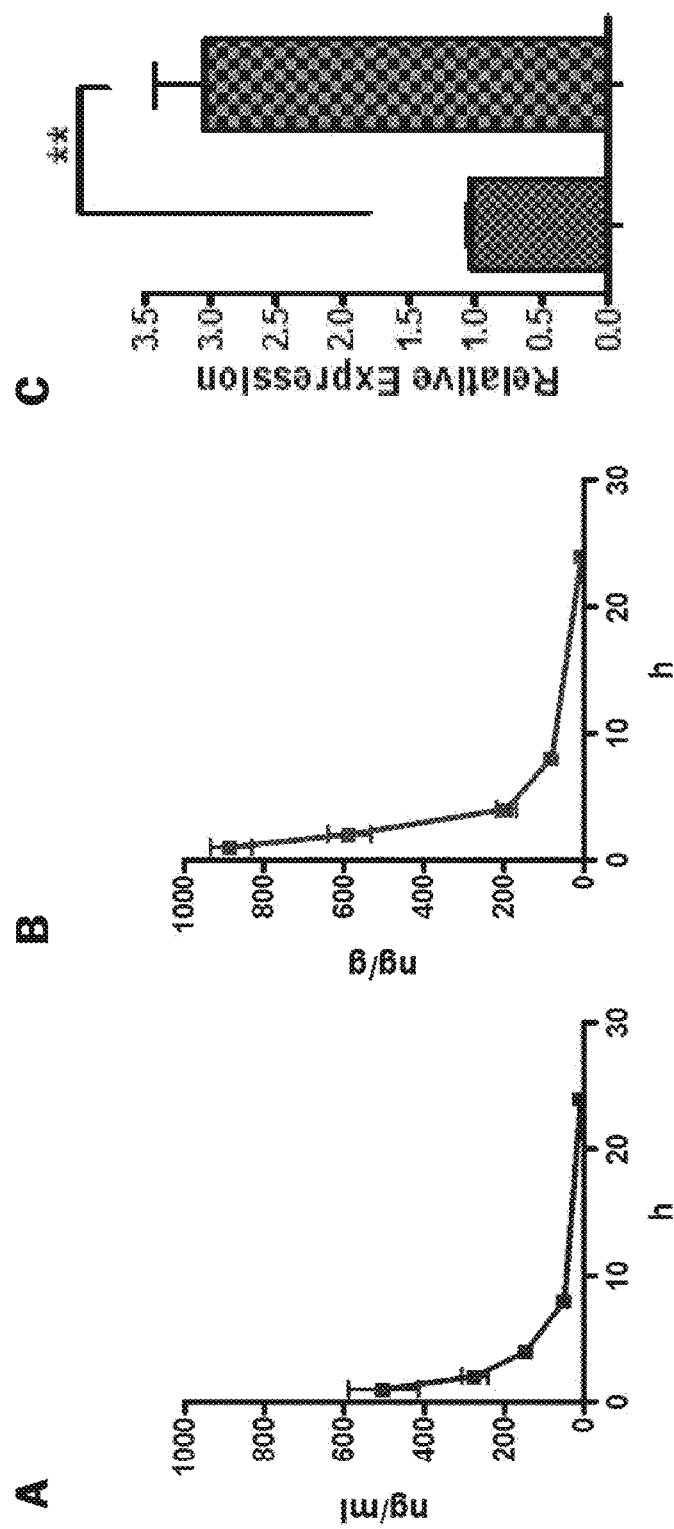
FIGS. 69A-69C show the brain penetration, half-life, and c-jun transcriptional activation of compound 3.
Figure 70:
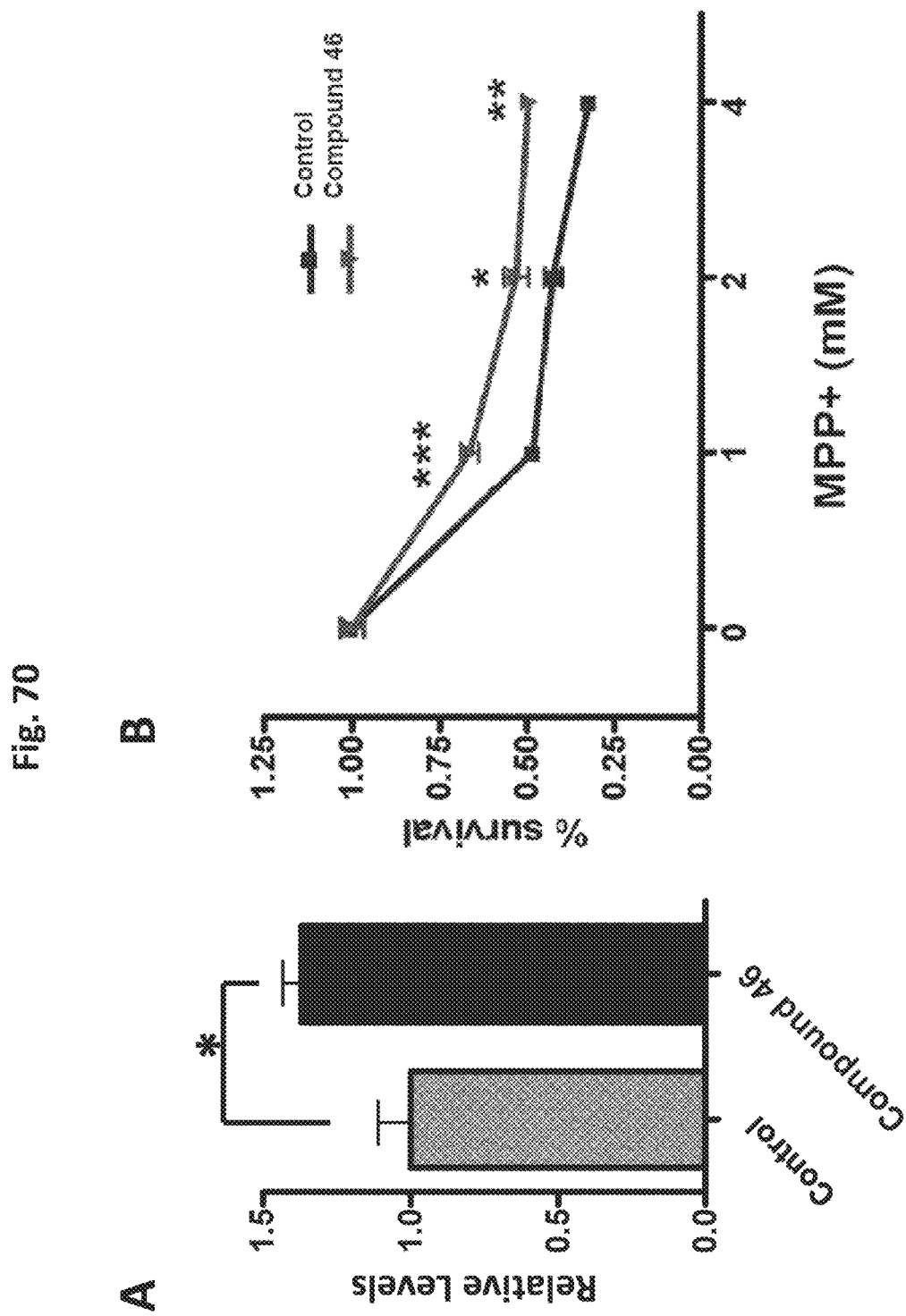
FIGS. 70A and 70B show the c-jun activating effects and neuroprotective properties of compound 46.

In contrast to XCT, compounds of the invention exhibit a high bioavailability and are readily blood-brain barrier penetrant. For example, IP administration of compound 3 (1 mg/kg) in mice revealed that this compound reaches the brain and exhibits an approximate half-life of about 2 hours in both blood and brain as assessed by LC-MS/MS (brain/blood concentration AUC ratio 1.7, FIGS. 69A-C). Additionally, compound 3 was biologically active in the brain, as administration of this compound resulted in increased midbrain c-jun expression (FIGS. 1F and 69C). Similarly, compound 46 is highly bioavailable and capable of crossing the blood brain barrier. Administration by IP injection to mice revealed significant c-jun transcriptional activation in the midbrain as determined by qPCR 2 hours after administration (FIG. 70A). This compound additionally exhibits a strong neuroprotective effect (FIG. 70B).

Since specific Nurr1:RXRα activators have not been reported previously (Vaz B et al. Expert Opin. Drug Discov. 7:1003-1016, 2012), compounds of the invention represent a first-in-class approach to targeted neurodegenerative disease therapy. The compounds described herein are specific for Nurr1:RXRα heterodimers, stable in vivo, and brain-penetrant. These compounds exhibit combinatorial neuroprotective and symptomatic benefits in preclinical animal models, validating selective Nurr1:RXRα heterodimer activation as a therapeutic paradigm for the treatment of neurodegenerative disorders, such as Parkinson's disease.

Nurr1:RXRα is a Validated Target for Neurodegenerative Disease Therapy

Our experiments demonstrate that activation of Nurr1:RXRα by compounds of the invention, such as compound 3 and compound 46, provide neuroprotection that can halt neuronal loss associated with neurodegenerative disorders, such as Parkinson's disease, in both toxin-based and genetic preclinical mouse models of Parkinson's disease. In addition, we demonstrate that the effects of compounds of the invention, such as compound 3, both in vitro and in vivo depend on Nurr1 expression. Compounds of the invention, such as compound 3, also increase DA levels in vivo and offer symptomatic relief in two post-degeneration PD animal models at the same dose. This dual activity indicates that, unlike most efforts for developing therapeutic approaches for the treatment of Parkinson's disease, Nurr1:RXRα activation offers a unique combined efficacy distinct from that of other targets. Because of the divergent toxin and genetic insults we have used in our PD models, our data indicate that various pathways leading to the demise of dopaminergic neurons can be overcome using compounds of the invention, such as compound 3 and compound 46. This implies coordinated control of a complex neuroprotective network by Nurr1:RXRα. Moreover, as opposed to the dopamine-excessive bursts induced by dopamine replacement therapies, compounds of the invention, such as compound 3, finely regulate dopamine production in a more physiological manner via the transcriptional activation of the dopamine biosynthesis genes (TH, GCH1 and AADC), without affecting dopamine catabolism and without eliciting dyskinesias.

Therapeutic uses of the compounds of the invention are unique in that they represent the first instances in which a single compound that activates a specific target achieves a dual therapeutic advantage for treating neurodegenerative disorders, such as Parkinson's disease. Since the neuroprotective effects of compounds of the invention, such as compound 3, extend to induced pluripotent stem cell (iPSc)-derived dopaminergic neurons of Parkinson's disease patients, selective Nurr1:RXRα activation provides a clear therapeutic benefit to patients suffering from this condition.

Pharmaceutical Compositions

The compounds of the invention can be formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts or as prodrugs. All forms are within the scope of the invention. In accordance with the methods of the invention, the described compounds or salts, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy (2012, $22^{nd}$ ed.) and in The United States Pharmacopeia: The National Formulary (2015, USP 38 NF 33).

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions containing a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the effective dose of a compound of the invention can range, e.g., from about 0.0001 to about 100 mg/kg of body weight per single (e.g., bolus) administration, multiple administrations or continuous administration. Alternatively, a compound of the invention may be administered in an appropriate dose to achieve a suitable serum concentration, e.g., a serum concentration of 0.0001-5000 µg/mL per single (e.g., bolus) administration, multiple administrations or continuous administration, or any effective range or value therein depending on the condition being treated, the route of administration and the age, weight, and condition of the subject. The dose may be administered one or more times (e.g., 2-10 times) per day, week, month, or year to a patient (e.g., a human) in need thereof.

Compositions for Combination Therapy

A compound of the invention can be used alone or in combination with other agents that can be used to treat neurodegenerative disorders, such as Parkinson's disease. A compound of the invention can be admixed with an additional active agent and administered to a patient in a single composition (e.g., a tablet or capsule), or a compound of the invention can be administered to a patient separately from an additional active agent. A compound of the invention and an additional active agent can be sequentially administered to a patient as part of a dosing regimen described herein. For instance, a compound of the invention may be admixed or formulated for co-administration with Levodopa (L-dihydroxyphenylalanine), L-aromatic amino acid decarboxylase (AADC) inhibitors, and/or catechol O-methyltransferase (COMT) inhibitors. Exemplary AADC inhibitors that may be included in a pharmaceutical composition of the invention include Carbidopa ((2S)-3-(3,4-dihydroxyphenyl)-2-hydrazinyl-2-methylpropanoic acid) and Benserazide (2-amino-3-hydroxy-N'-[(2,3,4-trihydroxyphenyl)methyl] propanehydrazide). Exemplary COMT inhibitors that may be included in a pharmaceutical composition of the invention include Entacapone ((E)-2-cyano-3-(3,4-dihydroxy-5-nitrophenyl)-N,N-diethylprop-2-enamide), Tolcapone ((3,4-dihydroxy-5-nitrophenyl)-(4-methylphenyl)methanone), and Nitecapone (3-[(3,4-dihydroxy-5-nitrophenyl)methylidene]pentane-2,4-dione).

In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined may provide a therapeutic effect.

EXAMPLES

The following examples are put forth so as to provide those of ordinary skill in the art with a description of how the compositions and methods claimed herein are performed, made, and evaluated, and are intended to be purely exemplary of the invention and are not intended to limit the scope of what the inventors regard as their invention.

I. General Synthetic Methods

The compounds of formula (I) in which X is $N(R_6)$, $R_6$=H, and $R_5$=alkyl, H may be prepared as described in Scheme 1. For example, alkylation of β-ketoester of formula (II) with an alkyl halide under standard conditions (i.e., NaOEt/EtOH) will result in an alkylated β-ketoester of formula (III). A compound of formula (III) can undergo a cyclization reaction with an amidine of formula (IV) to afford a pyrimidinol of formula (V) (J. Org. Chem. 2007, 72, 5835-5838). Treatment of compound of formula (V) with neat $POCl_3$ will generate a chloropyrimidine of formula (VI) (Chem. Pharm. Bull. 1982, 30, 4314-4324), which, upon coupling with aminobenzoate of formula (VII) under acidic conditions (Bioorg. Med. Chem. 2006, 14, 7761-7773), will generate a compound of formula (I) in which $R_6$=H, $R_5$=alkyl. Ester hydrolysis under standard basic conditions will produce an acid compound of formula (I) in which $R_5$, $R_6$=H.

In another embodiment, the compounds of formula (I) in which X is $N(R_6)$, $R_6$=alkyl, and $R_5$=alkyl, H may be prepared according to Scheme 1. For example, alkylation of the secondary nitrogen of compound of formula (I) in which $R_6$=H and $R_5$=alkyl with an alkyl halide (R—X) in the presence of a base such as $Cs_2CO_3$ will generate an N-alkylated compound of formula (I) in which $R_6$=alkyl and $R_5$=alkyl, which can undergo an ester hydrolysis under standard basic conditions to afford an acid compound of formula (I) in which $R_6$=alkyl and $R_5$=H.

Scheme 1

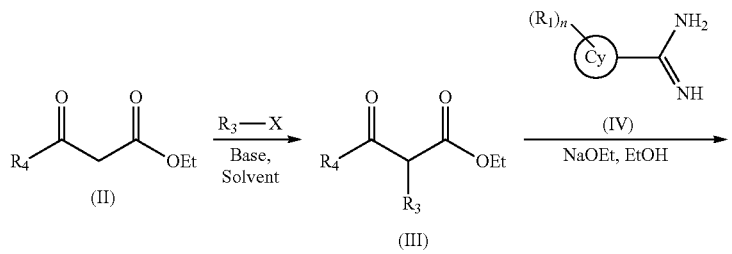

-continued

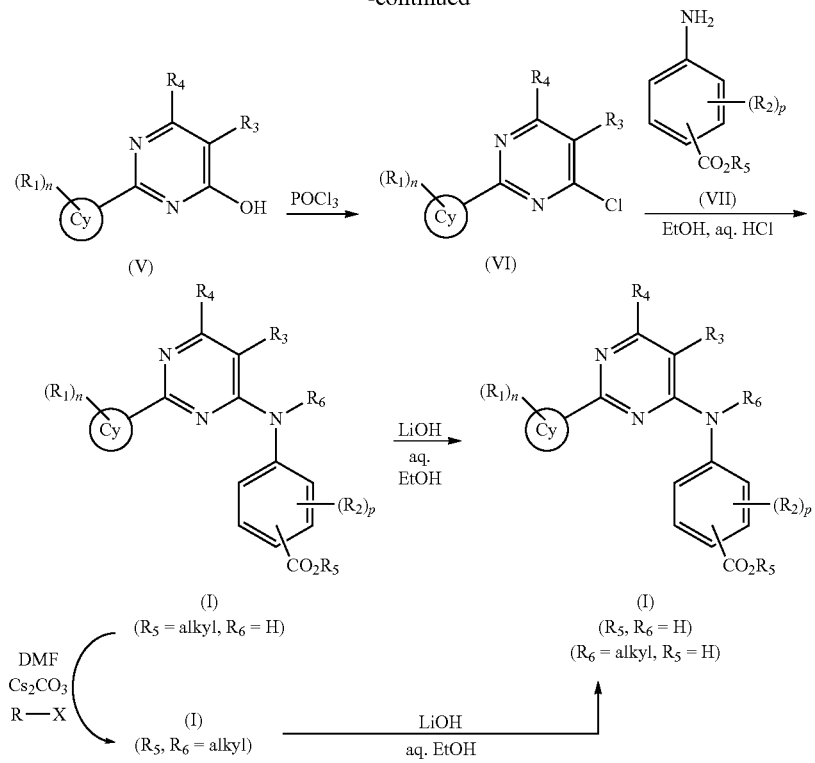

Preparation of a compound of formula (II): A compound of formula (II) was added to a solution of NaOEt in EtOH at room temperature under stirring for 15 min. Then addition of an alkyl halide as a solution in EtOH followed, and the reaction mixture was refluxed for 4-5 h. When TLC indicated the consumption of compound of formula (II), the reaction mixture was concentrated under reduced pressure, and the resulting residue was diluted with water and extracted with $CH_2Cl_2$. The combined organic layer was washed with water, dried over $MgSO_4$, filtered, and concentrated under reduced pressure to give the crude product. Purification by flash chromatography on silica gel with Hex:EtOAc or vacuum distillation afforded the compound of formula (III).

Preparation of a compound of formula (V): A ketoester of formula (II) was added to a solution of NaOEt (21% w/w solution in EtOH) and an amidine hydrochloride of formula (IV) in EtOH. The reaction mixture was stirred overnight under reflux and concentrated under reduced pressure. The resulting residue was treated with 1 N HCl and then extracted with $CH_2Cl_2$. The combined organic layer was washed with 1 N HCl, brine, dried over $MgSO_4$, filtered, and concentrated under reduced pressure to give the crude product. Purification by crystallization or flash column chromatography on silica gel with Hex:EtOAc afforded the compound of formula (V).

Preparation of a compound of formula (VI): A compound of formula (V) was dissolved in neat $POCl_3$, and the resulting solution was stirred for 6 h under reflux. The solvent was evaporated under reduced pressure, and the resulting residue was dissolved in EtOAc and then washed with saturated $Na_2CO_3$ and brine. The organic layer was dried over $MgSO_4$, filtered, and concentrated under reduced pressure to give the crude product. Purification by flash chromatography on silica gel with Hex:EtOAc afforded the compound of formula (VI).

Preparation of a compound of formula (I) in which $R_6$=H, $R_5$=alkyl: A solution of a compound of formula (VI), an aminobenzoate of formula (VI), and a catalytic amount of concentrated HCl in EtOH was stirred under reflux. The reaction progress was monitored by TLC, and catalytic amounts of concentrated HCl were gradually added to the reaction mixture in order to drive the reaction to completion. When TLC indicated the consumption of compound of formula (VI), the solvent was evaporated under reduced pressure. The resulting residue was treated with water followed by extraction with EtOAc. The combined organic layer was washed with water, dried over $MgSO_4$, filtered, and concentrated under reduced pressure to give the crude product. Purification by flash chromatography on silica gel with Hex:EtOAc afforded the compound of formula (I) in which $R_5$=alkyl, $R_6$=H.

Preparation of compound of formula (I) in which $R_5$, $R_6$=H: A solution of compound of formula (I) in which $R_5$=alkyl, $R_6$=H in EtOH was treated with 1 N LiOH and then stirred at room temperature overnight. The solvent was evaporated under reduced pressure, and the resulting residue was treated with 1 N NaOH and then extracted with $Et_2O$. The remaining aqueous layer was acidified with 1 N HCl to pH~2-3 and then extracted with EtOAc. The combined organic layer was washed with 0.1 N HCl, dried over $MgSO_4$, filtered, and concentrated under reduced pressure to afford carboxylic acid compound of formula (I) in which $R_5$, $R_6$=H.

Preparation of a compound of formula (I) in which $R_5$, $R_6$=alkyl: A solution of a compound of formula (I) in which $R_6$=H, $R_5$=alkyl in DMF was treated with $Cs_2CO_3$, and then an alkyl halide was added. The reaction mixture was stirred at room temperature overnight and then diluted with water followed by extraction with EtOAc. The combined organic layer was washed with water, dried over $MgSO_4$, filtered, and concentrated under reduced pressure to give the crude product. Purification by flash chromatography on silica gel with Hex:EtOAc afforded the ester compound of formula (I) in which $R_5$, $R_6$=alkyl.

Preparation of a compound of formula (I) in which $R_6$=alkyl, $R_5$=H: A solution of an ester compound of formula (I) in which $R_5$, $R_6$=alkyl in EtOH was treated with 1 N LiOH and then stirred at room temperature overnight. The solvent was evaporated under reduced pressure, and the resulting residue was treated with 1 N NaOH and then extracted with $Et_2O$. The remaining aqueous layer was acidified with 1 N HCl to pH~2-3 and then extracted with EtOAc. The combined organic layer was washed with 0.1 N HCl, dried over $MgSO_4$, filtered, and concentrated under reduced pressure to afford carboxylic acid compound of formula (I) in which $R_6$=alkyl, $R_5$=H.

Compounds of formula (I) in which X is $N(R_6)$ as ester prodrugs of L-tyrosine, a LAT1 (large neutral amino acid transport system) substrate, that penetrate the brain via a transporter mechanism (*J. Med. Chem.* 2008, 51, 932-936), may be prepared as described in Scheme 2. For example, EDCI-mediated esterification of acid compound of formula (I, $R_5$, $R_6$=H) with diprotected tyrosine compound of formula (VIII), the product of the N-tert-butoxycarbonylation of the commercially available L-Tyrosine tert-butyl ester (*Nucl. Med. Biol.* 2011, 38, 53-62), will give a tyrosine ester compound of formula (IX). Subsequent cleavage of the Boc and t-butyl ester groups of compound of formula (IX) upon treatment of with acid such as trifluoroacetic acid or HCl (Greene & Wuts (1999) *Protective Groups in Organic Synthesis*, pp404, 617, $3^{rd}$ Ed.; John Wiley, New York) will afford a tyrosine ester prodrug compound of formula (I). Similarly, esterification of an acid compound of formula (I) in which $R_5$, $R_6$=H with a tyrosine compound of formula (X), the product of the $Cs_2CO_3$ mediated O-alkylation of a diprotected tyrosine compound of formula (VIII) with 3-bromopropanol in DMF, will produce a tyrosine ester compound of formula (XI) which can be converted accordingly to a tyrosine ester prodrug compound of formula (I).

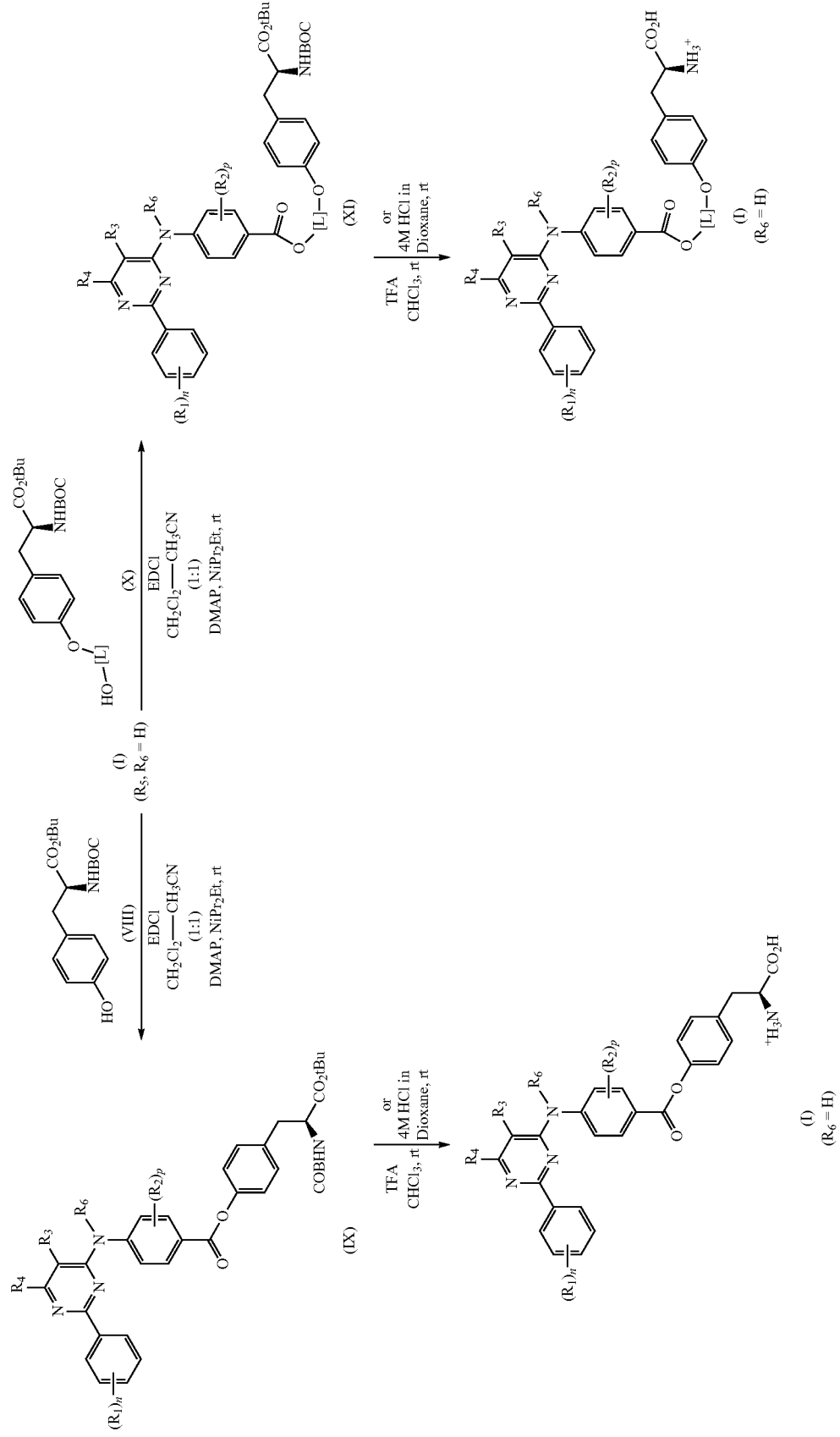

Preparation of a compound of formula (XI) in which $R_6$=H, L=—(CH$_2$)$_3$—: A solution of a carboxylic acid of formula (I, R$_5$, R$_6$=H), NiPr$_2$Et, DMAP, and EDCI in CH$_2$Cl$_2$—CHCN (1:1) was treated with a tyrosine compound of formula (X) and then stirred at room temperature overnight. The reaction mixture was then concentrated under reduced pressure, and the resulting residue was diluted with water and extracted with CH$_2$Cl$_2$. The combined organic layer was washed with aq. NaHCO$_3$, brine, dried over Na$_2$SO$_4$, filtered, and concentrated under reduced pressure to give the crude product. Purification by flash chromatography on silica gel with Hex:EtOAc afforded a tyrosine ester compound of formula (XI) in which $R_6$=H, L=—(CH$_2$)$_3$—.

Preparation of a compound of formula (IX) in which $R_6$=H: A compound of formula (IX) in which $R_6$=H can be prepared according to the method described above for the synthesis of a compound of formula (XI) in which $R_6$=H, L=—(CH$_2$)$_3$—, starting from a carboxylic acid of formula (I) in which R$_5$, $R_6$=H and a diprotected tyrosine compound of formula (VIII).

Preparation of a tyrosine ester prodrug compound of formula (I) in which $R_6$=H, L=—(CH$_2$)$_3$—: A solution of tyrosine ester compound of formula (XI) in which $R_6$=H, L=—(CH$_2$)$_3$— in CHCl$_3$ (or Dioxane) was treated with trifluoroacetic acid (or 4 M HCl in Dioxane). The reaction mixture was stirred at room temperature until TLC indicated the consumption of compound of formula (XI), and the solvent was then evaporated under reduced pressure to give the crude product. Purification by reverse phase preparative HPLC with an CH$_3$CN—H$_2$O (0.1% TFA) solution as the eluent afforded the tyrosine ester compound of formula (I) in which $R_6$=H, L=—(CH$_2$)$_3$—.

Preparation of a tyrosine ester prodrug compound of formula (I) in which $R_6$=H: A tyrosine ester prodrug compound of formula (I) in which $R_6$=H can be prepared according to the method described above for the synthesis of compound of formula (I) in which $R_6$=H, L=—(CH$_2$)$_3$—, starting from a compound of formula (IX, $R_6$=H).

Compounds of formula (I) in which X is N(R$_6$), R$_4$=CF$_3$, $R_6$=H, CH$_3$, and R$_5$=alkyl, H may be prepared as described in Scheme 3. A series of trifluoromethylated pyrimidine compounds of formula (I) can result as well from the β-ketoester compound of formula (XII) in a similar manner.

Scheme 3

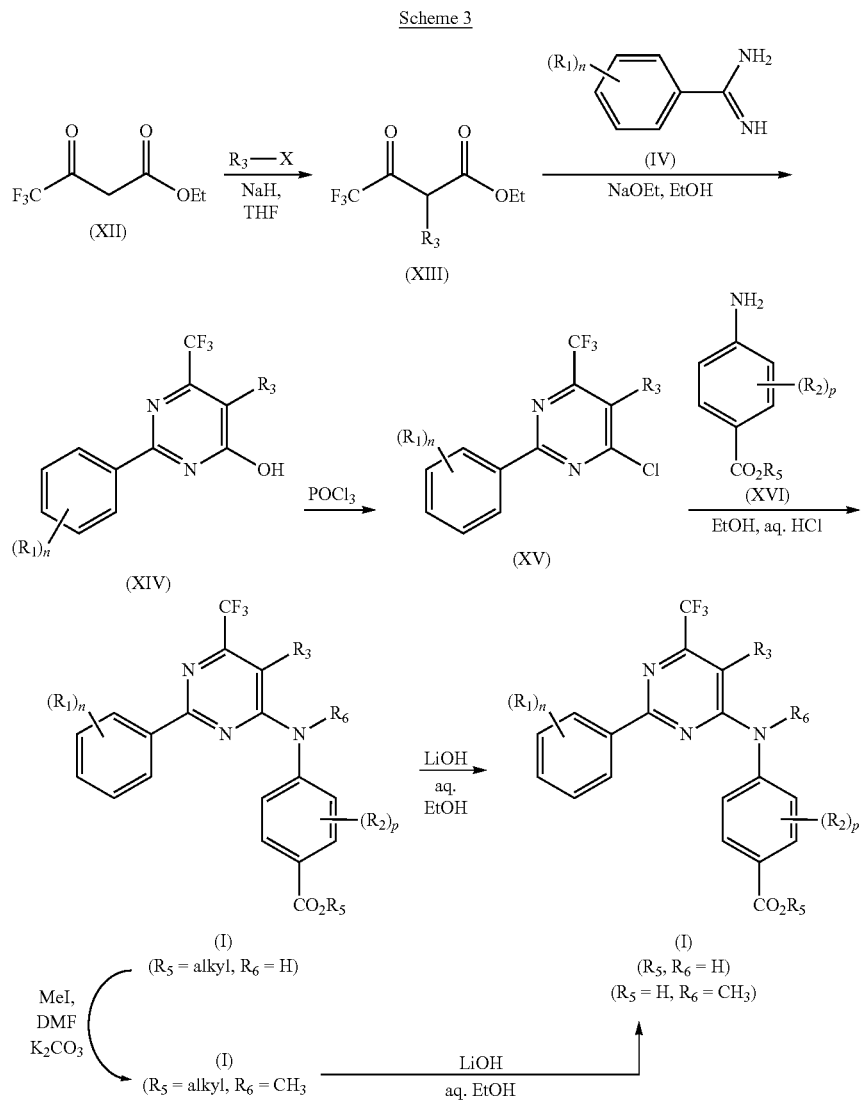

A compound of formula (XIII) can be prepared by alkylation of a commercially available β-ketoester of formula (XII) with a suitable base and solvent such as NaH and THF, according to: Aubert, C.; Bégué, J.-P.; Charpentier-Morize, M.; Nee, G.; Langlois. B. *J. Fluorine Chem.* 1989, 44, 3, 361-376.

A compound of formula (XIV) can be prepared according to the method described for the preparation of a compound of formula (V) as described in Scheme 1.

A compound of formula (XV) can be prepared according to the method described for the preparation of a compound of formula (VI) as described in Scheme 1.

A compound of formula (I) in which $R_4$=$CF_3$, $R_6$=H, and $R_5$=alkyl can be prepared according to the method described for the preparation of an ester compound of formula (I) in which $R_6$=H, $R_5$=alkyl as described in Scheme 1.

A compound of formula (I) in which $R_4$=$CF_3$, $R_5$, $R_6$=H can be prepared according to the method described for the preparation of a carboxylic acid compound of formula (I) in which $R_5$, $R_6$=H as described in Scheme 1.

A compound of formula (I) in which $R_4$=$CF_3$, $R_6$=$CH_3$, $R_5$=alkyl can be prepared according to the method described for the preparation of an ester compound of formula (I) in which $R_6$=alkyl, $R_5$=alkyl as described in Scheme 1.

A compound of formula (I) in which $R_4$=$CF_3$, $R_6$=$CH_3$, $R_5$=H can be prepared according to the method described for the preparation of a carboxylic acid compound of formula (I) in which $R_6$=alkyl, $R_5$=H as described in Scheme 1.

Preferred compounds of formula (I) in which X is O and $R_5$=alkyl, H may be prepared as described in Scheme 4. For example, treatment of a chloropyrimidine compound of formula (VI) with hydroxybenzoate compound of formula (XVII) in the presence of a base such as $Cs_2CO_3$ will give phenoxypyrimidine compound of formula (I, $R_5$=alkyl), which can undergo an ester hydrolysis under basic conditions to give phenoxypyrimidine acid compound of formula (I) in which $R_5$=H.

Scheme 4

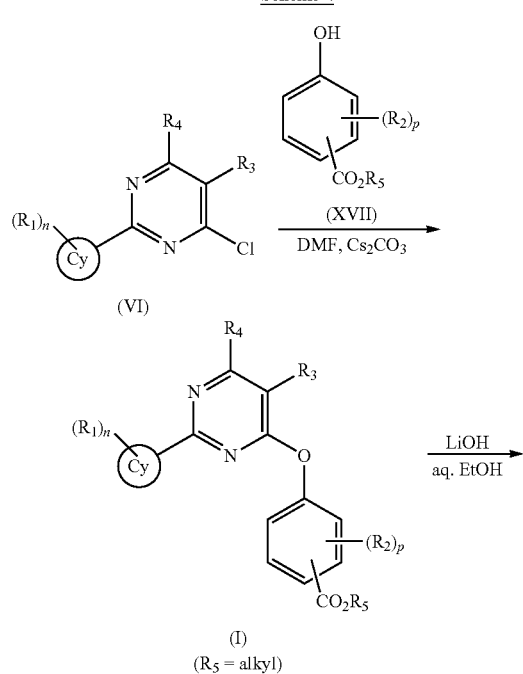

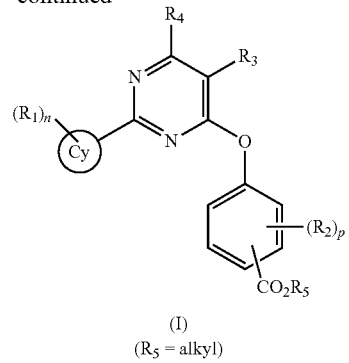

(I)
($R_5$ = alkyl)

A compound of formula (I) in which $R_5$=alkyl) can be prepared according to the following exemplary procedure: A solution of a compound of formula (VI) and a compound of formula (XVII) in DMF was treated with $Cs_2CO_3$. The reaction mixture was stirred at room temperature overnight and then diluted with water and extracted with EtOAc. The aqueous phase was extracted with EtOAc, and the combined organic layer was washed with brine, dried over $Na_2SO_4$, and concentrated under reduced pressure to give the crude product. Purification by flash chromatography on silica gel with Hex:EtOAc afforded the ester compound of formula (I) in which $R_5$=alkyl.

A compound of formula (I) in which $R_5$=H can be prepared according to the following exemplary procedure: A solution of an ester of formula (I) in which $R_5$=alkyl in EtOH was treated with 1 N LiOH and then stirred at room temperature overnight. The solvent was evaporated under reduced pressure, and the resulting residue was treated with 1 N NaOH and then extracted with $Et_2O$. The remaining aqueous layer was acidified with 1 N HCl to pH~2-3 and then extracted with EtOAc. The combined organic layer was washed with 0.1 N HCl, dried over $Na_2SO_4$, filtered, and concentrated under reduced pressure to afford carboxylic acid compound of formula (I) in which $R_5$=H.

Preferred pyrrolopyrimidine compounds of formula (I), wherein $R_5$=H, alkyl, $R_{10}$, $R_{11}$=H, alkyl, aryl, may be prepared as described in Scheme 5. For example, bromination of the double bond of a pyrimidine compound of formula (I) in which X is NH and $R_3$ is an optionally substituted allyl group will result in dibromo compound of formula (XVIII) which upon treatment with base can undergo an intramolecular cyclization to afford a pyrrolopyrimidine compound of formula (I) (*Khim. Geterotsikl.* 1982, 1686-1689; *J. Org. Chem.* 1991, 56, 980-983).

Scheme 5

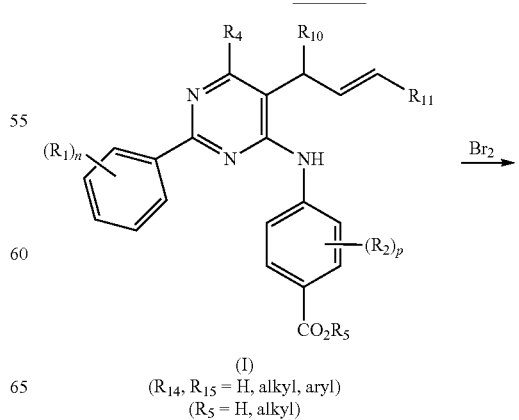

(I)
($R_{14}$, $R_{15}$ = H, alkyl, aryl)
($R_5$ = H, alkyl)

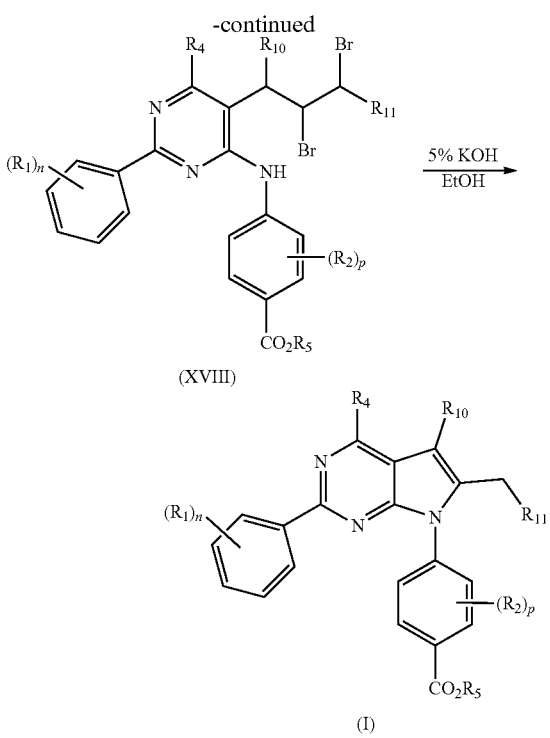

Preparation of a compound of formula (XVIII): To a solution of an appropriately substituted compound of formula (I) in a solvent such as CHCl$_3$ (or AcOH), wherein R$_5$=H, alkyl and R$_3$ is an optionally substituted allyl group (R$_{10}$, R$_{11}$=H, alkyl, aryl), bromine was added dropwise as a solution in CHCl$_3$ (or AcOH). The reaction mixture was stirred at room temperature for 30 minutes, and the solvent was then evaporated to give the crude dibromo compound of formula (XVIII).

Preparation of a pyrrolopyrimidine compound of formula (I): To a solution of a crude compound of formula (XVIII) in EtOH, a solution of 5% KOH in EtOH was added, and the reaction mixture was set up to reflux for 5 h. The solvent was then evaporated under reduced pressure, and the resulting residue was diluted with water and extracted with EtOAc. The combined organic layer was washed with brine, dried over Na$_2$SO$_4$, filtered, and concentrated under reduced pressure to give the crude product. Purification by flash chromatography on silica gel with Hex:EtOAc or reverse phase preparative HPLC with an CH$_3$CN—H$_2$O (0.1% TFA) solution as the eluent afforded the pyrrolopyrimidine compound of formula (I) in which R$_5$=H.

Preparation of Individual Compounds

The following examples illustrate methods for the preparation of individual compounds of formula (I).

Preparation 1: ethyl 2-(2,2,2-trifluoroacetyl)pent-4-enoate

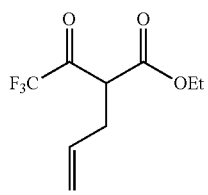

Ethyl 2-(2,2,2-trifluoroacetyl)pent-4-enoate was prepared according to Aubert, C.; Bégué, J.-P.; Charpentier-Morize, M.; Nee, G.; Langlois. B. *J. Fluorine Chem.* 1989, 44, 3, 361-376. To a suspension of 60% w/w NaH in mineral oil (1.08 g, 27.1 mmol) in 20 mL of dry THF under argon atmosphere at 0° C., a solution of ethyl 4,4,4-trifluoro-3-oxobutanoate (5.0 g, 27.1 mmol) in THF (10 mL) was added dropwise. The mixture was stirred at 0° C. for 1 h, and the solvent was then evaporated under reduced pressure to give a white solid which was suspended in acetone (15 mL) followed by treatment with KI (449 mg, 2.7 mmol). The resulting suspension was stirred at room temperature for 15 min followed by dropwise addition of a solution of allyl bromide (3.3 g, 27.2 mmol) in acetone (10 mL). The reaction mixture was heated at 60° C. for 48 h, and the solvent was then evaporated under reduced pressure. The resulting residue was treated with 1 N HCl (50 mL) and then extracted with CH$_2$Cl$_2$ (2×30 mL). The combined organic layer was washed with water, dried over MgSO$_4$, filtered, and concentrated under reduced pressure to give the title compound (3.3 g, 54%) as an orange liquid, which was used in the next step without any further purification.

Preparation 2:
5-allyl-2-phenyl-6-(trifluoromethyl)pyrimidin-4-ol

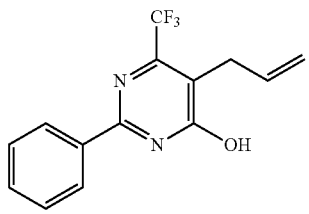 [SMILES: C=CCc1c(O)nc(-c2ccccc2)nc1C(F)(F)F]

Ethyl 2-(2,2,2-trifluoroacetyl)pent-4-enoate (Preparation 1) (3.3 g, 14.7 mmol) was added to a solution of NaOEt (5.5 mL of 21% w/w solution in EtOH, 16.7 mmol) and benzamidine hydrochloride hydrate (2.3 g, 14.7 mmol) in EtOH (15 mL). The reaction mixture was stirred overnight under reflux and concentrated under reduced pressure. The resulting residue was treated with 1 N HCl (40 mL) and then extracted with CH$_2$Cl$_2$ (2×30 mL). The combined organic layer was washed with 1 N HCl, brine, dried over MgSO$_4$, filtered, and concentrated under reduced pressure to give the crude product. Purification by fractional recrystallization in ethanol afforded the title compound (2.7 g, 66%) as white needle crystals. $^1$H NMR (250 MHz, CDCl$_3$) δ 8.27 (d, 2 H, J=8.0 Hz), 7.58 (m, 3 H), 5.92 (m, 1 H), 5.21 (dd, 1 H, J=1.3, 17.0 Hz), 5.10 (dd, 1 H, J=1.5, 10.0 Hz), 3.51 (m, 2 H). $^{13}$C NMR (62.9 MHz, CDCl$_3$) δ 165.3, 155.1, 149.7 (q, $J_{C-F}$=34.3 Hz), 133.5, 132.8, 131.2, 129.3, 127.8, 124.6, 121.7 (d, $J_{C-F}$=276.9 Hz), 117.3, 29.3 (d, $J_{C-F}$=2.0 Hz). HRMS (ESI-LTQ) for C$_{14}$H$_{12}$F$_3$N$_2$O [M+H]: calcd, 281.0896; found, 281.0893.

Preparation 3: 5-allyl-4-chloro-2-phenyl-6-(trifluoromethyl)pyrimidine

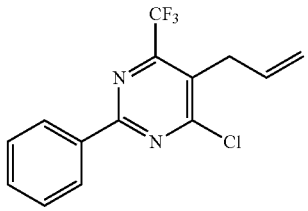 [SMILES: C=CCc1c(Cl)nc(-c2ccccc2)nc1C(F)(F)F]

5-Allyl-2-phenyl-6-(trifluoromethyl)pyrimidin-4-ol (Preparation 2) (2.7 g, 9.6 mmol) was dissolved in neat POCl$_3$ (10 mL), and the resulting solution was stirred for 6 h under reflux. The solvent was evaporated under reduced pressure, and the resulting residue was dissolved in EtOAc (60 mL) and then washed with saturated Na$_2$CO$_3$ (2×25 mL) and brine (25 mL). The organic layer was dried over MgSO$_4$, filtered, and concentrated under reduced pressure to give the crude product. Purification by flash chromatography on silica gel with Hex:EtOAc (10:1) afforded the title compound (2.5 g, 87%) as a yellow oil. $^1$H NMR (250 MHz, CDCl$_3$) δ 8.47 (dd, 2 H, J=1.8, 7.3 Hz), 7.50 (m, 3 H), 5.92 (m, 1 H), 5.22 (d, 1 H, J=11.5 Hz), 5.15 (d, 1 H, J=18.3 Hz), 3.69 (d, 2 H, J=6.0 Hz). $^{13}$C NMR (62.9 MHz, CDCl$_3$) δ 164.9, 162.9, 154.8 (q, J$_{C-F}$=34.5 Hz), 135.0, 132.2, 132.1, 128.8, 128.7, 127.3, 121.1 (d, J$_{C-F}$=277.4 Hz), 118.1, 32.1 (d, J$_{C-F}$=2.1 Hz). HRMS (ESI-LTQ) for C$_{14}$H$_{11}$ClF$_3$N$_2$ [M+H]: calcd, 299.0557; 299.0560.

Preparation 4: ethyl 2-acetylpent-4-enoate

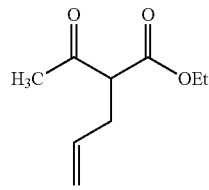

Ethyl 2-acetylpent-4-enoate was prepared by alkylation of ethyl 3-oxobutanoate with a suitable base and solvent by application of existing literature protocols: (a) Zhang, Y.; Raines, A. J.; Flowers, R. A. *Org. Lett.* 2003, 5, 2363-2365. (b) Barbry, D.; Faven, C.; Ajana, A. *Org. Prep. Procedure Int.* 1994, 26, 469 (c) Nakamura, K.; Miyai, T.; Nagar, A.; Oka, S.; Ohno, A. *Bull. Chem. Soc. Jpn.* 1989, 62, 1179-1187.

Preparation 5: ethyl 2-acetylpentanoate

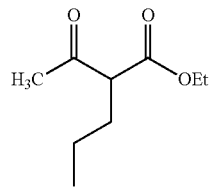

Ethyl 2-acetylpentanoate was prepared by alkylation of ethyl 3-oxobutanoate with a suitable base and solvent by application of existing literature protocol: Nakamura, K.; Miyai, T.; Nagar, A.; Oka, S.; Ohno, A. *Bull. Chem. Soc. Jpn.* 1989, 62, 1179-1187.

Preparation 6: ethyl 2-acetyl-3-methylbutanoate

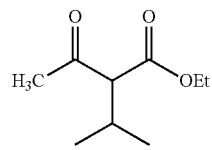

Ethyl 2-acetyl-3-methylbutanoate was prepared by alkylation of ethyl 3-oxobutanoate with a suitable base and solvent by application of existing literature protocol: Beddow, J. E.; Davies, S. G.; Ling, K. B.; Roberts, P. M.; Russel, A. J.; Smith, A. D. *Org. Biomol. Chem.* 2007, 5, 2812-2825.

Preparation 7: ethyl 2-ethyl-3-oxobutanoate

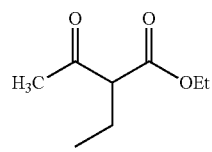

Ethyl 2-ethyl-3-oxobutanoate was prepared by alkylation of ethyl 3-oxobutanoate with a suitable base and solvent by application of existing literature protocols: (a) Beddow, J. E.; Davies, S. G.; Ling, K. B.; Roberts, P. M.; Russel, A. J.; Smith, A. D. *Org. Biomol. Chem.* 2007, 5, 2812-2825. (b) Nakamura, K.; Miyai, T.; Nagar, A.; Oka, S.; Ohno, A. *Bull. Chem. Soc. Jpn.* 1989, 62, 1179-1187.

Preparation 8: 5-allyl-6-methyl-2-phenylpyrimidin-4-ol

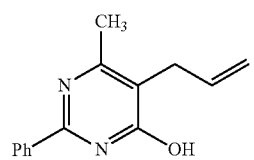 [SMILES: C=CCc1c(C)nc(-c2ccccc2)nc1O]

5-allyl-6-methyl-2-phenylpyrimidin-4-ol was isolated in 78% yield as a white solid according to the procedure described in Preparation 2, starting from the compound of Preparation 4 and benzamidine hydrochloride hydrate. Spectroscopic data were identical to those reported in literature. For experimental details and analytical data, see: Kaim, L. E.; Grimaud, L.; Oble, J. *J. Org. Chem.* 2007, 72, 5835-5838.

Preparation 9:
6-methyl-2-phenyl-5-propylpyrimidin-4-ol

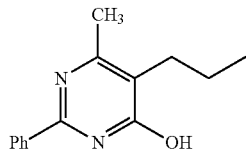 [SMILES: CCCc1c(C)nc(-c2ccccc2)nc1O]

6-methyl-2-phenyl-5-propylpyrimidin-4-ol was isolated in 45% yield as a white solid according to the procedure described in Preparation 2, starting from the compound of Preparation 5 and benzamidine hydrochloride hydrate.

Preparation 10:
5-isopropyl-6-methyl-2-phenylpyrimidin-4-ol

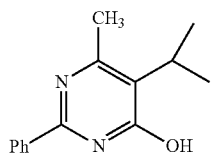 [SMILES: Cc1nc(-c2ccccc2)nc(O)c1C(C)C]

5-isopropyl-6-methyl-2-phenylpyrimidin-4-ol was isolated in 29% yield as a white solid according to the procedure described in Preparation 2, starting from the compound of Preparation 6 and benzamidine hydrochloride hydrate.

Preparation 11:
5-ethyl-6-methyl-2-phenylpyrimidin-4-ol

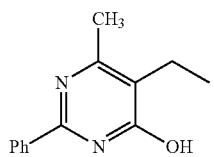 [SMILES: CCc1c(C)nc(-c2ccccc2)nc1O]

5-ethyl-6-methyl-2-phenylpyrimidin-4-ol was isolated in 85% yield as a white solid according to the procedure described in Preparation 2, starting from the compound of Preparation 7 and benzamidine hydrochloride hydrate.

Preparation 12:
5-allyl-2-(4-chlorophenyl)-6-methylpyrimidin-4-ol

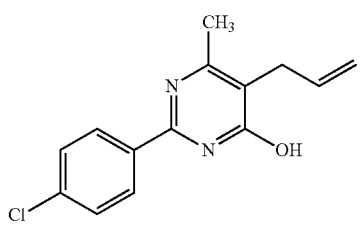 [SMILES: C=CCc1c(C)nc(-c2ccc(Cl)cc2)nc1O]

5-allyl-2-(4-chlorophenyl)-6-methylpyrimidin-4-ol was isolated in 62% yield as a white solid according to the procedure described in Preparation 2, starting from the compound of Preparation 4 and 4-chlorobenzamidine hydroiodide.

Preparation 13:
2-(4-chlorophenyl)-6-methyl-5-propylpyrimidin-4-ol

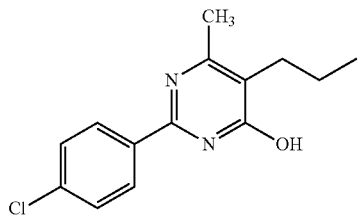 [SMILES: CCCc1c(C)nc(-c2ccc(Cl)cc2)nc1O]

2-(4-chlorophenyl)-6-methyl-5-propylpyrimidin-4-ol was isolated in 59% yield as a white solid according to the procedure described in Preparation 2, starting from the compound of Preparation 5 and 4-chlorobenzamidine hydroiodide.

Preparation 14:
2-(4-chlorophenyl)-5-ethyl-6-methylpyrimidin-4-ol

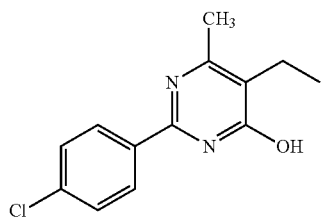 [SMILES: CCc1c(C)nc(-c2ccc(Cl)cc2)nc1O]

2-(4-chlorophenyl)-5-ethyl-6-methylpyrimidin-4-ol was isolated in 33% yield as a white solid according to the procedure described in Preparation 2, starting from the compound of Preparation 7 and 4-chlorobenzamidine hydroiodide.

Preparation 15: 5-allyl-2-(4-chlorophenyl)-6-(trifluoromethyl)pyrimidin-4-ol

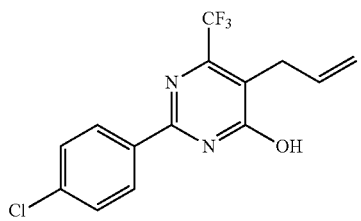 [SMILES: C=CCc1c(O)nc(-c2ccc(Cl)cc2)nc1C(F)(F)F]

5-allyl-2-(4-chlorophenyl)-6-(trifluoromethyl)pyrimidin-4-ol was isolated in 62% yield as a white solid according to the procedure described in Preparation 2, starting from the compound of Preparation 1 and 4-chlorobenzamidine hydroiodide.

Preparation 16: 6-methyl-2-phenylpyrimidin-4-ol

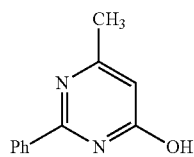

6-methyl-2-phenylpyrimidin-4-ol was prepared from the condensation of ethyl 3-oxobutanoate and benzamidine hydrochloride hydrate according to the procedure described in Preparation 2. It was isolated in 30% yield as a white solid. Spectroscopic data were identical to those reported in literature. For experimental details and analytical data, see: (a) Sun, Q.; Suzenet, F.; Guillaumet, G. *J. Org. Chem.* 2010, 75, 3473-3476. (b) Zanatta, N.; Fantinel, L.; Lourega, R. V.; Bonacorso, H. G.; Martins, M. A. P. *Synthesis* 2008, 358-362.

Preparation 17: 5-allyl-4-chloro-6-methyl-2-phenylpyrimidine

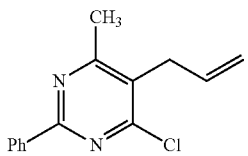

5-allyl-4-chloro-6-methyl-2-phenylpyrimidine was isolated in 59% yield as a beige solid according to the procedure described in Preparation 3, starting from the compound of Preparation 8.

Preparation 18: 4-chloro-6-methyl-2-phenyl-5-propylpyrimidine

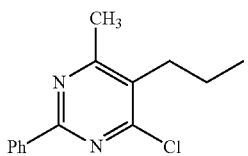 [SMILES: CCCc1c(C)nc(-c2ccccc2)nc1Cl]

4-chloro-6-methyl-2-phenyl-5-propylpyrimidine was isolated in 75% yield as a beige solid according to the procedure described in Preparation 3, starting from the compound of Preparation 9.

Preparation 19: 4-chloro-5-isopropyl-6-methyl-2-phenylpyrimidine

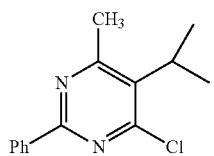 [SMILES: Cc1nc(-c2ccccc2)nc(Cl)c1C(C)C]

4-chloro-5-isopropyl-6-methyl-2-phenylpyrimidine was isolated in 81% yield as a beige solid according to the procedure described in Preparation 3, starting from the compound of Preparation 10.

Preparation 20: 4-chloro-5-ethyl-6-methyl-2-phenylpyrimidine

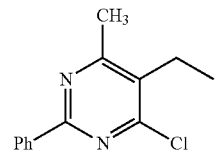 [SMILES: CCc1c(C)nc(-c2ccccc2)nc1Cl]

4-chloro-5-ethyl-6-methyl-2-phenylpyrimidine was isolated in 62% yield as a beige solid according to the procedure described in Preparation 3, starting from the compound of Preparation 11.

Preparation 21: 5-allyl-4-chloro-2-(4-chlorophenyl)-6-methylpyrimidine

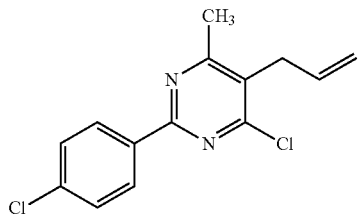 [SMILES: C=CCc1c(C)nc(-c2ccc(Cl)cc2)nc1Cl]

5-allyl-4-chloro-2-(4-chlorophenyl)-6-methylpyrimidine was isolated in 66% yield as a beige solid according to the procedure described in Preparation 3, starting from the compound of Preparation 12.

Preparation 22: 4-chloro-2-(4-chlorophenyl)-6-methyl-5-propylpyrimidine

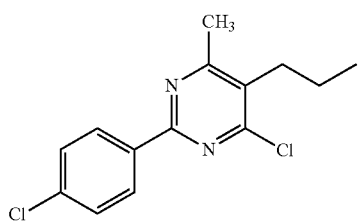 [SMILES: CCCc1c(C)nc(-c2ccc(Cl)cc2)nc1Cl]

4-chloro-2-(4-chlorophenyl)-6-methyl-5-propylpyrimidine was isolated in 72% yield as a beige solid according to the procedure described in Preparation 3, starting from the compound of Preparation 13.

Preparation 23: 4-chloro-2-(4-chlorophenyl)-5-ethyl-6-methylpyrimidine

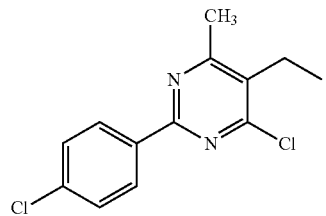 [SMILES: CCc1c(C)nc(-c2ccc(Cl)cc2)nc1Cl]

4-chloro-2-(4-chlorophenyl)-5-ethyl-6-methylpyrimidine was isolated in 70% yield as a beige solid according to the procedure described in Preparation 3, starting from the compound of Preparation 14.

Preparation 24: 5-allyl-4-chloro-2-(4-chlorophenyl)-6-(trifluoromethyl)pyrimidine

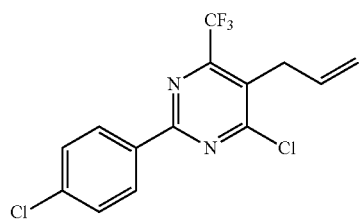

5-allyl-4-chloro-2-(4-chlorophenyl)-6-(trifluoromethyl)pyrimidine was isolated in 76% yield as a beige solid according to the procedure described in Preparation 3, starting from the compound of Preparation 15.

Preparation 25: 4-chloro-6-methyl-2-phenylpyrimidine

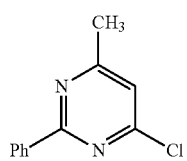

4-chloro-6-methyl-2-phenylpyrimidine was isolated in 59% yield as a beige solid according to the procedure described in Preparation 3, starting from the compound of Preparation 16. For experimental details and analytical data, see: Honma, Y.; Sekine, Y.; Hashiyama, T.; Takeda, M.; Ono, Y.; Tsuzurahara, K. *Chem. Pharm. Bull.* 1982, 30, 4314-4324.

Preparation 26: 4-(5-allyl-6-methyl-2-phenylpyrimidin-4-ylamino)benzoic acid

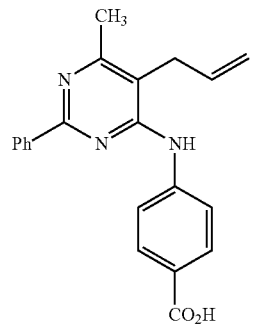 [SMILES: C=CCc1c(C)nc(-c2ccccc2)nc1Nc1ccc(C(=O)O)cc1]

4-(5-allyl-6-methyl-2-phenylpyrimidin-4-ylamino)benzoic acid was isolated in 90% yield as a white solid according to the procedure described in Example 3, starting from the compound of Example 6 or Example 7.

Preparation 27: (S)-tert-butyl 2-(tert-butoxycarbonylamino)-3-(4-hydroxyphenyl)propanoate

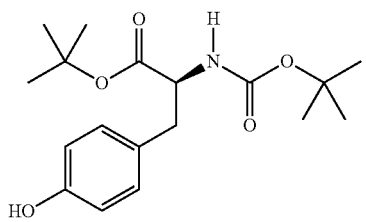 [SMILES: CC(C)(C)OC(=O)N[C@@H](Cc1ccc(O)cc1)C(=O)OC(C)(C)C]

To a solution of commercially available L-tyrosine tert-butyl ester (700 mg, 2.95 mmol) in 50 mL of Dioxane-$H_2O$ (5:1), $NEt_3$(1.23 mL, 8.85 mmol) and $(Boc)_2O$ (966 mg, 4.42 mmol) were added, and the reaction mixture was stirred at room temperature. When TLC indicated the consumption of L-tyrosine tert-butyl ester, the reaction mixture was concentrated under reduced pressure to remove dioxane, and then the resulting solution was diluted with water and extracted with EtOAc (2×50 mL). The combined organic layer was washed with brine, dried over $Na_2SO_4$, filtered, and concentrated under reduced pressure to give the crude product. Purification by flash chromatography on silica gel with MeOH:$CH_2Cl_2$ (1:20) afforded the title compound as a white solid (846 mg, 85%). For more details and analytical data, see: Wang, L.; Qu, W.; Lieberman, B. P.; Plossl, K.; Kung, H. F. *Nucl. Med. Biol.* 2011, 38, 53-62)

Preparation 28: (S)-tert-butyl 2-(tert-butoxycarbonylamino)-3-(4-(3-hydroxypropoxy)phenyl)propanoate

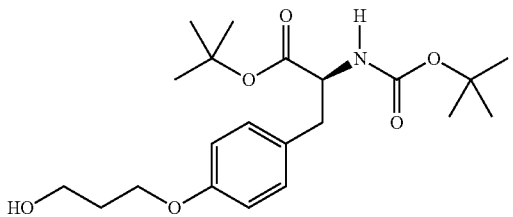 [SMILES: CC(C)(C)OC(=O)N[C@@H](Cc1ccc(OCCCO)cc1)C(=O)OC(C)(C)C]

A solution of (S)-tert-butyl 2-(tert-butoxycarbonylamino)-3-(4-hydroxyphenyl)propanoate (Preparation 27) (200 mg, 0.592 mmol) in DMF (10 mL) was treated with $Cs_2CO_3$ (386 mg, 1.18 mmol) and 3-bromopropanol (80 μL, 0.89 mmol), and the reaction mixture was stirred at room temperature. When TLC indicated the consumption of (S)-tert-butyl 2-(tert-butoxycarbonylamino)-3-(4-hydroxyphenyl)propanoate, the reaction mixture was diluted with water and extracted with EtOAc (2×30 mL). The combined organic layer was washed with brine, dried over $Na_2SO_4$, filtered, and concentrated under reduced pressure to give the crude product. Purification by flash chromatography on silica gel with Hex:EtOAc (1:2) afforded the title compound as a white solid (164 mg, 70%).

Preparation 29: (S)-4-(3-tert-butoxy-2-(tert-butoxycarbonylamino)-3-oxopropyl)phenyl 4-(5-allyl-6-methyl-2-phenylpyrimidin-4-ylamino)benzoate

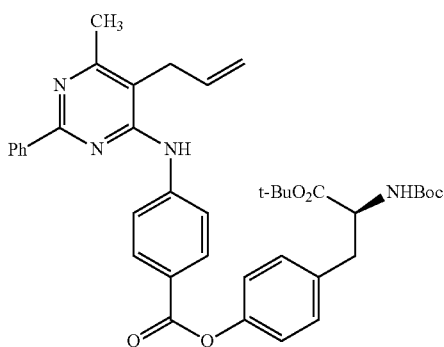

A solution of 4-(5-allyl-6-methyl-2-phenylpyrimidin-4-ylamino)benzoic acid (Preparation 26) (100 mg, 0.29 mmol), $NEt_3$ (81 μL, 0.58 mmol), DMAP (7 mg, 0.058 mmol) and EDCI (68 mg, 0.43 mmol) in 10 mL of $CH_2Cl_2$—$CH_3CN$ (1:1) was treated with (S)-tert-butyl 2-(tert-butoxycarbonylamino)-3-(4-hydroxyphenyl)propanoate (Preparation 27) (147 mg, 0.43 mmol) and the reaction mixture was stirred at room temperature. When TLC indicated the consumption of 4-(5-allyl-6-methyl-2-phenylpyrimidin-4-ylamino)benzoic acid, the reaction mixture was concentrated under reduced pressure to remove the solvent, and then the resulting residue was diluted with water and extracted with EtOAc (2×30 mL). The combined organic layer was washed with brine, dried over $Na_2SO_4$, filtered and concentrated under reduced pressure to give the crude product. Purification by flash chromatography on silica gel with Hex:EtOAc (1:6) afforded the title compound as a white solid (83 mg, 43%).

Preparation 30: (S)-3-(4-(3-tert-butoxy-2-(tert-butoxycarbonylamino)-3-oxopropyl)phenoxy)propyl 4-(5-allyl-6-methyl-2-phenylpyrimidin-4-ylamino)benzoate

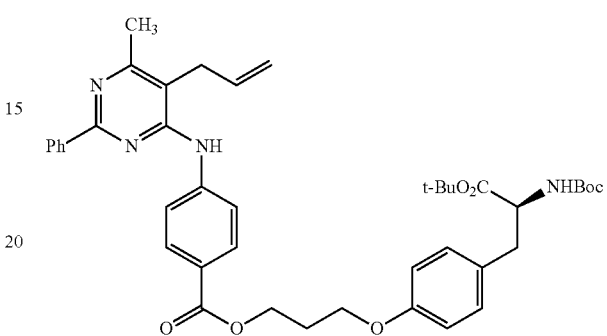

A solution of 4-(5-allyl-6-methyl-2-phenylpyrimidin-4-ylamino)benzoic acid (Preparation 26) (100 mg, 0.29 mmol), $NEt_3$ (81 μL, 0.58 mmol), DMAP (7 mg, 0.058 mmol), and EDCI (68 mg, 0.43 mmol) in 10 mL of $CH_2Cl_2$—$CH_3CN$ (1:1) was treated with (S)-tert-butyl 2-(tert-butoxycarbonylamino)-3-(4-(3-hydroxypropoxy)phenyl)propanoate (Preparation 28) (172 mg, 0.43 mmol) and the reaction mixture was stirred at room temperature. When TLC indicated the consumption of 4-(5-allyl-6-methyl-2-phenylpyrimidin-4-ylamino)benzoic acid, the reaction mixture was concentrated under reduced pressure to remove the solvent, and then the resulting residue was diluted with water and extracted with EtOAc (2×30 mL). The combined organic layer was washed with brine, dried over $Na_2SO_4$, filtered, and concentrated under reduced pressure to give the crude product. Purification by flash chromatography on silica gel with Hex:EtOAc (1:6) afforded the title compound as a white solid (75 mg, 36%).

Example 1: ethyl 4-(5-allyl-2-phenyl-6-(trifluoromethyl)pyrimidin-4-ylamino)benzoate

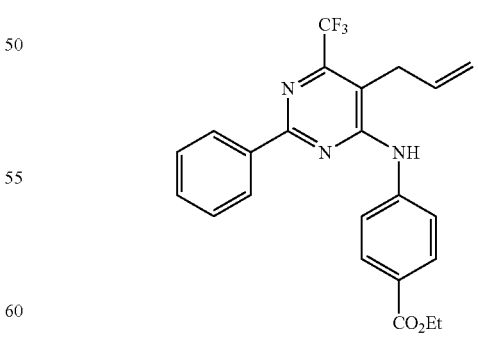

A solution of 5-allyl-4-chloro-2-phenyl-6-(trifluoromethyl)pyrimidine (Preparation 3) (2.5 g, 8.37 mmol), ethyl 4-aminobenzoate (2.5 g, 15.1 mmol), and a catalytic amount of concentrated HCl (2-3 drops) in EtOH (15 mL) was stirred under reflux. The reaction progress was monitored by TLC, and catalytic amounts of concentrated HCl were gradually added to the reaction mixture in order to drive the reaction to completion. When TLC indicated the consumption of 5-allyl-4-chloro-2-phenyl-6-(trifluoromethyl)pyrimidine, the solvent was evaporated under reduced pressure. The resulting residue was treated with water (60 mL) followed by extraction with EtOAc (3×40 mL). The combined organic layer was washed with water (3×25 mL), dried over $MgSO_4$, filtered, and concentrated under reduced pressure to give the crude product. Purification by flash chromatography on silica gel with Hex:EtOAc (10:1 to 6:1) afforded the title compound (1.1 g, 31%) as a yellowish solid. $^1$H NMR (250 MHz, $CDCl_3$) δ 8.44 (m, 2 H), 8.11 (d, 2 H, J=8.8 Hz), 7.74 (d, 2 H, J=8.8 Hz), 7.50 (m, 3 H), 7.23 (s, 1 H), 6.0 (m, 1 H), 5.42 (dd, 1 H, J=0.8, 10.0 Hz), 5.37 (d, 1 H, J=16.8 Hz), 4.40 (q, 2 H, J=7.1 Hz), 3.60 (d, 2 H, J=5.5 Hz), 1.43 (t, 3 H, J=7.1 Hz). $^{13}$C NMR (62.9 MHz, $CDCl_3$) δ 166.3 (C), 162.3 (C), 160.3 (C), 152.8 (C, q, $J_{C-F}$=32.9 Hz), 142.8 (C), 136.8 (C), 133.6 (CH), 131.2 (CH), 130.8 (CH), 128.7 (CH), 128.4 (CH), 125.6 (C), 121.8 (C, d, $J_{C-F}$=276.9 Hz), 119.8 (CH), 118.9 (=$CH_2$), 111.9 (C), 61.0 ($CH_2$), 30.1 ($CH_2$, d, $J_{C-F}$=2.1 Hz), 14.5 ($CH_3$). HRMS (ESI-LTQ) for $C_{23}H_{21}F_3N_3O_2$ [M+H]: calcd, 428.1580; found, 428.1583.

Example 2: ethyl 4-((5-allyl-2-phenyl-6-(trifluoromethyl)pyrimidin-4-yl)(methyl)amino)benzoate

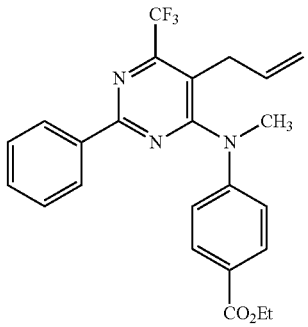

A solution of ethyl 4-(5-allyl-2-phenyl-6-(trifluoromethyl)pyrimidin-4-ylamino)benzoate (Example 1)(1.1 g, 2.58 mmol) in DMF (10 mL) was treated with $Cs_2CO_3$ (1.0 g, 3.07 mmol) and $CH_3I$ (241 μL, 3.87 mmol) and stirred at room temperature overnight. The reaction mixture was then diluted with water (40 mL) and extracted with EtOAc (2×25 mL). The combined organic layer was washed with water (2×20 mL), dried over $MgSO_4$, filtered, and concentrated under reduced pressure to give the crude product. Purification by flash chromatography on silica gel with Hex:EtOAc (10:1 to 6:1) afforded the title compound (1.0 g, 88%) as a yellow solid. $^1$H NMR (250 MHz, $CDCl_3$) δ 8.49 (m, 2 H), 8.02 (d, 2 H J=8.8 Hz), 7.50 (m, 3 H), 7.01 (d, 2 H, J=8.8 Hz), 5.56 (m, 1 H), 4.94 (dd, 1 H, J=1.5, 10.0 Hz), 4.75 (dd, 1 H, J=1.5, 17.0 Hz), 4.38 (q, 2 H, J=7.1 Hz), 3.65 (s, 3 H), 3.05 (d, 2 H, J=6.0 Hz), 1.42 (t, 3 H, J=7.1 Hz). $^{13}$C NMR (62.9 MHz, $CDCl_3$) δ 166.0 (C), 165.5 (C), 162.3 (C), 154.8 (C, q, $J_{C-F}$=32.9 Hz), 150.7 (CH), 136.6 (C), 133.9 (CH), 131.4 (CH), 131.3 (CH), 128.7 (CH), 128.4 (CH), 126.1 (C), 121.8 (C, d, $J_{C-F}$=277.1 Hz), 121.1 (CH), 120.3 (C), 116.6 (=$CH_2$), 61.1 ($CH_2$), 41.1 ($CH_3$), 30.1 ($CH_2$, d, $J_{C-F}$=2.3 Hz), 14.5 ($CH_3$). HRMS (ESI-LTQ) for $C_{24}H_{23}F_3N_3O_2$[M+H]: calcd, 442.1737; found, 442.1740.

Example 3: 4-((5-allyl-2-phenyl-6-(trifluoromethyl)pyrimidin-4-yl)(methyl)amino)benzoic acid

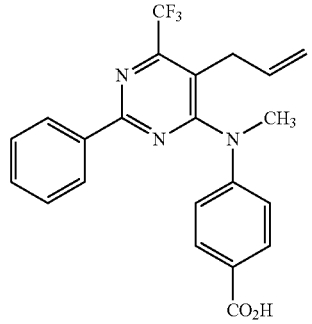

A solution of ethyl 4-((5-allyl-2-phenyl-6-(trifluoromethyl)pyrimidin-4-yl)(methyl)amino)benzoate (Example 2) (1.0 g, 2.27 mmol) in 20 mL of EtOH was treated with 1 N LiOH (5 mL, 5 mmol) and then stirred at room temperature overnight. The solvent was evaporated under reduced pressure, and the resulting residue was treated with 1 N NaOH (50 mL) and then extracted with $Et_2O$ (2×20 mL). The remaining aqueous layer was acidified with 1 N HCl (40 mL) to pH~2-3 and then extracted with EtOAc (3×30 mL). The combined organic layer was washed with 0.1 N HCl (20 mL), dried over $MgSO_4$, filtered, and concentrated under reduced pressure to afford the title compound (800 mg, 85%) as an off-white solid in high purity. The title compound can be further recrystallized in ethanol. $^1$H NMR (250 MHz, $CDCl_3$) δ 8.47 (m, 2 H), 8.05 (d, 2 H, J=8.8 Hz), 7.47 (m, 3 H), 6.98 (d, 2 H, J=8.8 Hz), 5.55 (m, 1 H), 4.93 (dd, 1 H, J=1.0, 10.0 Hz), 4.72 (dd, J=0.9, 17.1 Hz), 3.62 (s, 3 H), 3.08 (d, 2 H, J=5.8 Hz). $^{13}$C NMR (62.9 MHz, $CDCl_3$) δ 171.7 (C), 165.6 (C), 162.6 (C), 155.1 (C, q, $J_{C-F}$=32.9 Hz), 151.5 (C), 136.5 (C), 133.9 (CH), 132.1 (CH), 131.4 (CH), 128.8 (CH), 128.4 (CH), 124.1 (C), 121.8 (C, d, $J_{C-F}$=277.2 Hz), 121.1 (C), 120.2 (CH), 116.7 (=$CH_2$), 40.8 ($CH_3$), 30.6 ($CH_2$, d, $J_{C-F}$=2.1 Hz). HRMS (ESI-LTQ) for $C_{22}H_{19}F_3N_3O_2$[M+H]: calcd, 414.1424; found, 414.1418.

Example 4: 4-(5-allyl-2-phenyl-6-(trifluoromethyl)pyrimidin-4-ylamino)benzoic acid

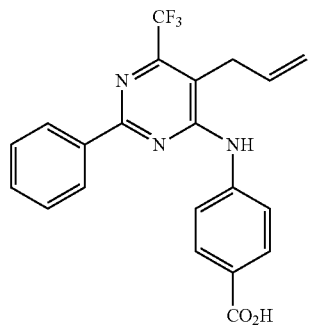 [SMILES: C=CCc1c(Nc2ccc(C(=O)O)cc2)nc(-c2ccccc2)nc1C(F)(F)F]

4-(5-allyl-2-phenyl-6-(trifluoromethyl)pyrimidin-4-ylamino)benzoic acid was isolated in 65% yield as a white solid according to the procedure described in Example 3, starting from the compound of Example 1. It was isolated in a mixture with the isomeric compound of Example 5 (Example 4/Example 5=55/45).

Example 5: (E)-4-(2-phenyl-5-(prop-1-enyl)-6-(trifluoromethyl)pyrimidin-4-ylamino)benzoic acid

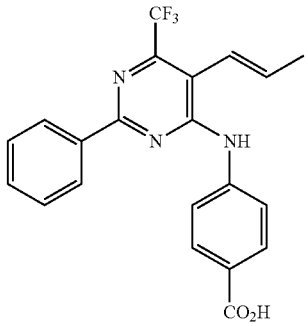 [SMILES: C/C=C/c1c(Nc2ccc(C(=O)O)cc2)nc(-c2ccccc2)nc1C(F)(F)F]

(E)-4-(2-phenyl-5-(prop-1-enyl)-6-(trifluoromethyl)pyrimidin-4-ylamino)benzoic acid was isolated as a white solid according to the procedure described in Example 3, starting from the compound of Example 1. It was isolated in a mixture with the compound of Example 4 (Example 4/Example 5=55/45).

Example 6: ethyl 4-(5-allyl-6-methyl-2-phenylpyrimidin-4-ylamino)benzoate

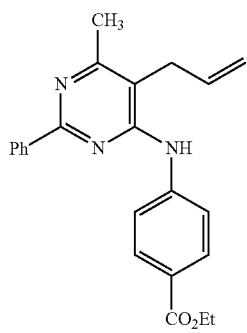 [SMILES: C=CCc1c(C)nc(-c2ccccc2)nc1Nc1ccc(C(=O)OCC)cc1]

Ethyl 4-(5-allyl-6-methyl-2-phenylpyrimidin-4-ylamino)benzoate was isolated in 45% yield as a white solid according to the procedure described in Example 1, starting from the compound of Preparation 17 and ethyl 4-aminobenzoate.

Example 7: methyl 4-(5-allyl-6-methyl-2-phenylpyrimidin-4-ylamino)benzoate

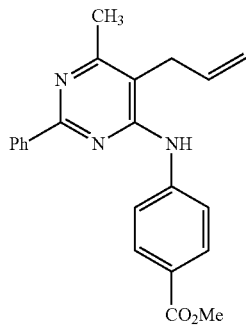 [SMILES: C=CCc1c(C)nc(-c2ccccc2)nc1Nc1ccc(C(=O)OC)cc1]

Methyl 4-(5-allyl-6-methyl-2-phenylpyrimidin-4-ylamino)benzoate was isolated in 45% yield as a white solid according to the procedure described in Example 1, starting from the compound of Preparation 17 and methyl 4-aminobenzoate.

Example 8: ethyl 4-((5-allyl-6-methyl-2-phenylpyrimidin-4-yl)(methyl)amino)benzoate

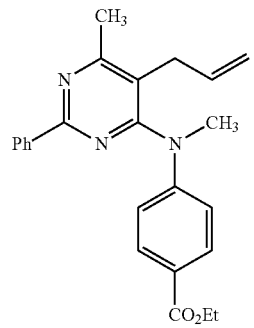 [SMILES: C=CCc1c(C)nc(-c2ccccc2)nc1N(C)c1ccc(C(=O)OCC)cc1]

Ethyl 4-((5-allyl-6-methyl-2-phenylpyrimidin-4-yl)(methyl)amino)benzoate was isolated in 56% yield as a white solid according to the procedure described in Example 2, starting from the compound of Example 6 and iodomethane.

Example 9: methyl 4-((5-allyl-6-methyl-2-phenylpyrimidin-4-yl)(methyl)amino)benzoate

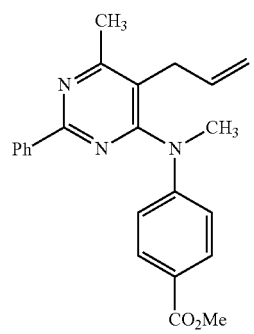 [SMILES: C=CCc1c(C)nc(-c2ccccc2)nc1N(C)c1ccc(C(=O)OC)cc1]

Methyl 4-((5-allyl-6-methyl-2-phenylpyrimidin-4-yl)(methyl)amino)benzoate was isolated in 58% yield as a white solid according to the procedure described in Example 2, starting from the compound of Example 7 and iodomethane.

Example 10: 4-((5-allyl-6-methyl-2-phenylpyrimidin-4-yl)(methyl)amino)benzoic acid

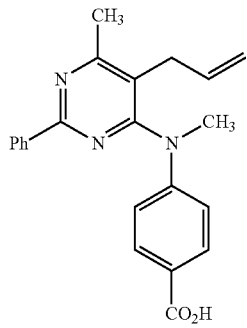

4-((5-allyl-6-methyl-2-phenylpyrimidin-4-yl)(methyl)amino)benzoic acid was isolated in 63% yield as a white solid according to the procedure described in Example 3, starting from the compound of Example 8 or Example 9.

Example 11: 4-(6-methyl-2-phenyl-5-propylpyrimidin-4-ylamino)benzoic acid

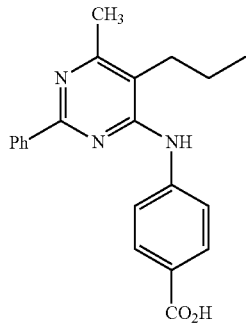

4-(6-methyl-2-phenyl-5-propylpyrimidin-4-ylamino)benzoic acid was prepared according to the procedures described in Examples 1 and 3, employing the coupling of compound of Preparation 18 and ethyl 4-aminobenzoate followed by ester hydrolysis of the resulting ethyl 4-(6-methyl-2-phenyl-5-propylpyrimidin-4-ylamino)benzoate to give the title compound as a beige solid (36% yield for two steps).

Example 12: 4-(5-isopropyl-6-methyl-2-phenylpyrimidin-4-ylamino)benzoic acid

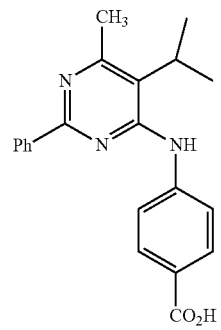 [SMILES: Cc1nc(-c2ccccc2)nc(Nc2ccc(C(=O)O)cc2)c1C(C)C]

4-(5-isopropyl-6-methyl-2-phenylpyrimidin-4-ylamino)benzoic acid was prepared according to the procedures described in Examples 1 and 3, employing the coupling of compound of Preparation 19 and ethyl 4-aminobenzoate followed by ester hydrolysis of the resulting ethyl 4-(5-isopropyl-6-methyl-2-phenylpyrimidin-4-ylamino)benzoate to give the title compound as a beige solid (41% yield for two steps).

Example 13: 4-(5-ethyl-6-methyl-2-phenylpyrimidin-4-ylamino)benzoic acid

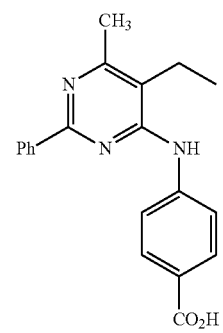 [SMILES: CCc1c(C)nc(-c2ccccc2)nc1Nc1ccc(C(=O)O)cc1]

4-(5-ethyl-6-methyl-2-phenylpyrimidin-4-ylamino)benzoic acid was prepared according to the procedures described in Examples 1 and 3, employing the coupling of compound of Preparation 20 and ethyl 4-aminobenzoate followed by ester hydrolysis of the resulting ethyl 4-(5-ethyl-6-methyl-2-phenylpyrimidin-4-ylamino)benzoate to give the title compound as a beige solid (33% yield for two steps).

Example 14: 4-(5-allyl-2-(4-chlorophenyl)-6-methylpyrimidin-4-ylamino)benzoic acid

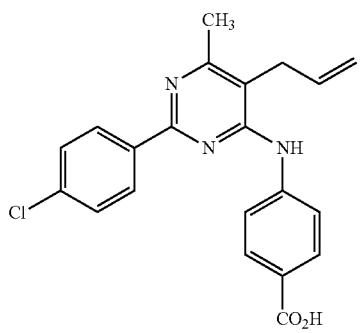 [SMILES: C=CCc1c(C)nc(-c2ccc(Cl)cc2)nc1Nc1ccc(C(=O)O)cc1]

4-(5-allyl-2-(4-chlorophenyl)-6-methylpyrimidin-4-ylamino)benzoic acid was prepared according to the procedures described in Examples 1 and 3, employing the coupling of compound of Preparation 21 and ethyl 4-aminobenzoate followed by ester hydrolysis of the resulting ethyl 4-(5-allyl-2-(4-chlorophenyl)-6-methylpyrimidin-4-ylamino)benzoate to give the title compound as a beige solid (44% yield for two steps).

Example 15: 4-(2-(4-chlorophenyl)-6-methyl-5-propylpyrimidin-4-ylamino)benzoic acid

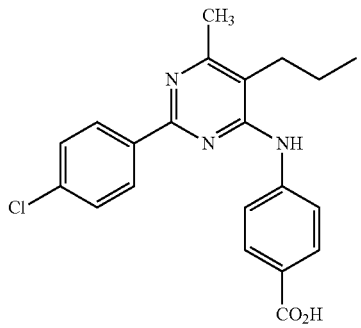 [SMILES: CCCc1c(C)nc(-c2ccc(Cl)cc2)nc1Nc1ccc(C(=O)O)cc1]

4-(2-(4-chlorophenyl)-6-methyl-5-propylpyrimidin-4-ylamino)benzoic acid was prepared according to the procedures described in Examples 1 and 3, employing the coupling of compound of Preparation 22 and ethyl 4-aminobenzoate followed by ester hydrolysis of the resulting ethyl 4-(2-(4-chlorophenyl)-6-methyl-5-propylpyrimidin-4-ylamino)benzoate to give the title compound as a white solid (45% yield for two steps).

Example 16: 4-(2-(4-chlorophenyl)-5-ethyl-6-methylpyrimidin-4-ylamino)benzoic acid

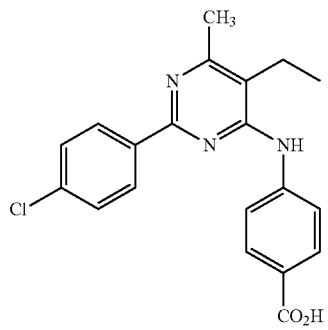

4-(2-(4-chlorophenyl)-5-ethyl-6-methylpyrimidin-4-ylamino)benzoic acid was prepared according to the procedures described in Examples 1 and 3, employing the coupling of compound of Preparation 23 and ethyl 4-aminobenzoate followed by ester hydrolysis of the resulting ethyl 4-(2-(4-chlorophenyl)-5-ethyl-6-methylpyrimidin-4-ylamino)benzoate to give the title compound as a white solid (50% yield for two steps).

Example 17: 4-(5-allyl-6-methyl-2-phenylpyrimidin-4-ylamino)-2-fluorobenzoic acid

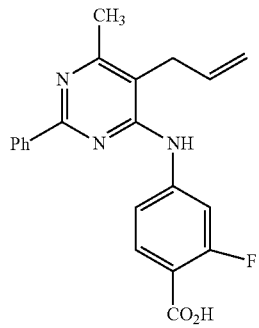 [SMILES: C=CCc1c(C)nc(-c2ccccc2)nc1Nc1ccc(C(=O)O)c(F)c1]

4-(5-allyl-6-methyl-2-phenylpyrimidin-4-ylamino)-2-fluorobenzoic acid was prepared according to the procedures described in Examples 1 and 3, employing the coupling of compound of Preparation 17 and methyl 4-amino-2-fluorobenzoate followed by ester hydrolysis of the resulting ethyl 4-(5-allyl-6-methyl-2-phenylpyrimidin-4-ylamino)-2-fluorobenzoate to give the title compound as a white solid (46% yield for two steps).

Example 18: 4-(5-allyl-6-methyl-2-phenylpyrimidin-4-ylamino)-3-methylbenzoic acid

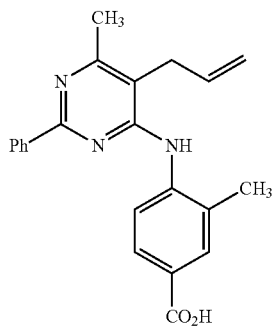 [SMILES: C=CCc1c(C)nc(-c2ccccc2)nc1Nc1ccc(C(=O)O)cc1C]

4-(5-allyl-6-methyl-2-phenylpyrimidin-4-ylamino)-3-methylbenzoic acid was prepared according to the procedures described in Examples 1 and 3, employing the coupling of compound of Preparation 17 and methyl 4-amino-3-methylbenzoate followed by ester hydrolysis of the resulting methyl 4-(5-allyl-6-methyl-2-phenylpyrimidin-4-ylamino)-3-methylbenzoate to give the title compound as a beige solid (35% yield for two steps).

Example 19: 4-(5-allyl-2-(4-chlorophenyl)-6-(trifluoromethyl)pyrimidin-4-ylamino)benzoic acid

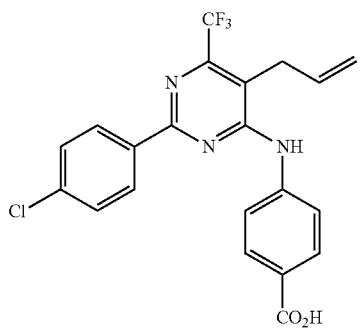

4-(5-allyl-2-(4-chlorophenyl)-6-(trifluoromethyl)pyrimidin-4-ylamino)benzoic acid was prepared according to the procedures described in Examples 1 and 3, employing the coupling of compound of Preparation 24 and ethyl 4-aminobenzoate followed by ester hydrolysis of the resulting ethyl 4-(5-allyl-2-(4-chlorophenyl)-6-(trifluoromethyl)pyrimidin-4-ylamino)benzoate to give the title compound as a white solid (25% yield for two steps). It was isolated in a mixture with the isomeric compound of Example 20 (Example 19/Example 20=60/40).

Example 20: (E)-4-(2-(4-chlorophenyl)-5-(prop-1-enyl)-6-(trifluoromethyl)pyrimidin-4-ylamino)benzoic acid

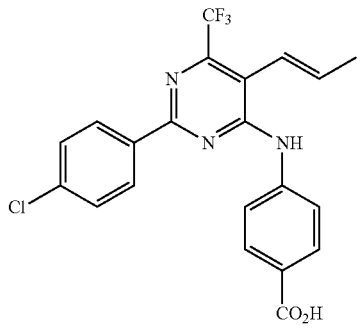 [SMILES: C/C=C/c1c(Nc2ccc(C(=O)O)cc2)nc(-c2ccc(Cl)cc2)nc1C(F)(F)F]

(E)-4-(2-(4-chlorophenyl)-5-(prop-1-enyl)-6-(trifluoromethyl)pyrimidin-4-ylamino)benzoic acid was prepared according to the procedures described in Examples 1 and 3, employing the coupling of compound of Preparation 24 and ethyl 4-aminobenzoate followed by ester hydrolysis of the resulting ethyl 4-(5-allyl-2-(4-chlorophenyl)-6-(trifluoromethyl)pyrimidin-4-ylamino)benzoate to give the title compound as a white solid (25% yield for two steps). It was isolated in a mixture with the compound of Example 19 (Example 19/Example 20=60/40).

Example 21: 3-(5-allyl-6-methyl-2-phenylpyrimidin-4-ylamino)benzoic acid

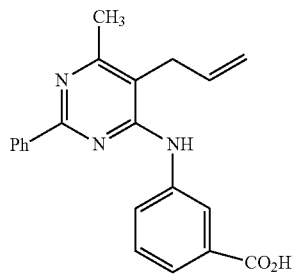 [SMILES: C=CCc1c(C)nc(-c2ccccc2)nc1Nc1cccc(C(=O)O)c1]

3-(5-allyl-6-methyl-2-phenylpyrimidin-4-ylamino)benzoic acid was prepared according to the procedures described in Examples 1 and 3, employing the coupling of compound of Preparation 17 and ethyl 3-aminobenzoate followed by ester hydrolysis of the resulting ethyl 3-(5-allyl-6-methyl-2-phenylpyrimidin-4-ylamino)benzoate to give the title compound as a beige solid (28% yield for two steps).

Example 22: 3-((5-allyl-6-methyl-2-phenylpyrimidin-4-yl)(methyl)amino)benzoic acid

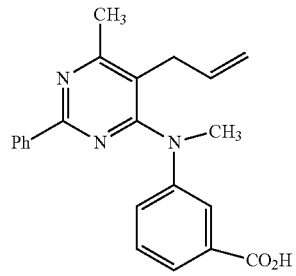 [SMILES: C=CCc1c(C)nc(-c2ccccc2)nc1N(C)c1cccc(C(=O)O)c1]

3-((5-allyl-6-methyl-2-phenylpyrimidin-4-yl)(methyl) amino)benzoic acid was prepared according to the procedures described in Examples 1, 2, and 3, employing the coupling of compound of Preparation 17 and ethyl 3-aminobenzoate to give ethyl 3-(5-allyl-6-methyl-2-phenylpyrimidin-4-ylamino)benzoate. Subsequent N-methylation resulted in ethyl 3-((5-allyl-6-methyl-2-phenylpyrimidin-4-yl)(methyl)amino)benzoate which underwent an ester hydrolysis to give the title compound as a white solid (28% yield for three steps).

Example 23: 4-((5-allyl-6-methyl-2-phenylpyrimidin-4-yl)(methyl)amino)-2-fluorobenzoic acid

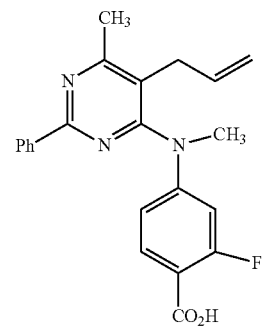 [SMILES: C=CCc1c(C)nc(-c2ccccc2)nc1N(C)c1ccc(C(=O)O)c(F)c1]

4-((5-allyl-6-methyl-2-phenylpyrimidin-4-yl)(methyl) amino)-2-fluorobenzoic acid was prepared according to the procedures described in Examples 1, 2, and 3, employing the coupling of compound of Preparation 17 and methyl 4-amino-2-fluorobenzoate to give methyl 4-(5-allyl-6-methyl-2-phenylpyrimidin-4-ylamino)-2-fluorobenzoate. Subsequent N-methylation resulted in methyl 4-((5-allyl-6-methyl-2-phenylpyrimidin-4-yl)(methyl)amino)-2-fluorobenzoate which underwent an ester hydrolysis to give the title compound as a beige solid (35% yield for three steps).

Example 24: 4-((5-allyl-6-methyl-2-phenylpyrimidin-4-yl)(methyl)amino)-3-methylbenzoic acid

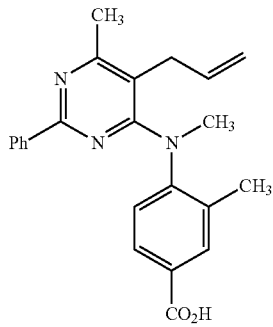 [SMILES: C=CCc1c(C)nc(-c2ccccc2)nc1N(C)c1ccc(C(=O)O)cc1C]

4-((5-allyl-6-methyl-2-phenylpyrimidin-4-yl)(methyl)amino)-3-methylbenzoic acid was prepared according to the procedures described in Examples 1, 2, and 3, employing the coupling of compound of Preparation 17 and methyl 4-amino-3-methylbenzoate to give methyl 4-(5-allyl-6-methyl-2-phenylpyrimidin-4-ylamino)-3-methylbenzoate. Subsequent N-methylation resulted in methyl 4-((5-allyl-6-methyl-2-phenylpyrimidin-4-yl)(methyl)amino)-3-methylbenzoate which underwent an ester hydrolysis to give the title compound as a white solid (30% yield for three steps).

Example 25: 4-((5-allyl-2-(4-chlorophenyl)-6-methylpyrimidin-4-yl)(methyl)amino)benzoic acid

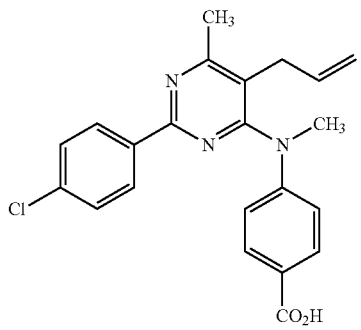 [SMILES: C=CCc1c(C)nc(-c2ccc(Cl)cc2)nc1N(C)c1ccc(C(=O)O)cc1]

4-((5-allyl-2-(4-chlorophenyl)-6-methylpyrimidin-4-yl)(methyl)amino)benzoic acid was prepared according to the procedures described in Examples 1, 2, and 3, employing the coupling of compound of Preparation 21 and ethyl 4-aminobenzoate to give ethyl 4-(5-allyl-2-(4-chlorophenyl)-6-methylpyrimidin-4-ylamino)benzoate. Subsequent N-methylation resulted in ethyl 4-((5-allyl-2-(4-chlorophenyl)-6-methylpyrimidin-4-yl)(methyl)amino)benzoate which underwent an ester hydrolysis to give the title compound as a white solid (35% yield for three steps).

Example 26: 4-((2-(4-chlorophenyl)-5-ethyl-6-methylpyrimidin-4-yl)(methyl)amino)benzoic acid

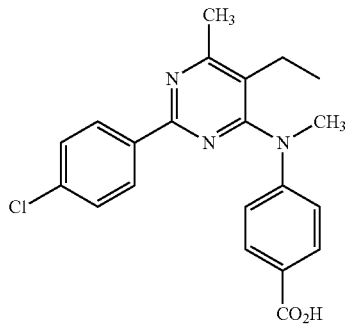 [SMILES: CCc1c(C)nc(-c2ccc(Cl)cc2)nc1N(C)c1ccc(C(=O)O)cc1]

4-((2-(4-chlorophenyl)-5-ethyl-6-methylpyrimidin-4-yl)(methyl)amino)benzoic acid was prepared according to the procedures described in Examples 1, 2, and 3, employing the coupling of compound of Preparation 23 and ethyl 4-aminobenzoate to give ethyl 4-(2-(4-chlorophenyl)-5-ethyl-6-methylpyrimidin-4-ylamino)benzoate. Subsequent N-methylation resulted in ethyl 4-((2-(4-chlorophenyl)-5-ethyl-6-methylpyrimidin-4-yl)(methyl)amino)benzoate which underwent an ester hydrolysis to give the title compound as a white solid (32% yield for three steps).

Example 27: 4-(6-methyl-2-phenylpyrimidin-4-ylamino)benzoic acid

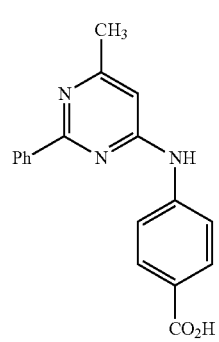 [SMILES: Cc1cc(Nc2ccc(C(=O)O)cc2)nc(-c2ccccc2)n1]

4-(6-methyl-2-phenylpyrimidin-4-ylamino)benzoic acid was prepared according to the procedures described in Examples 1 and 3, employing the coupling of compound of Preparation 25 and ethyl 4-aminobenzoate followed by ester hydrolysis of the resulting ethyl 4-(6-methyl-2-phenylpyrimidin-4-ylamino)benzoate to give the title compound as a white solid (48% yield for two steps).

Example 28: 4-(allyl(6-methyl-2-phenylpyrimidin-4-yl)amino)benzoic acid

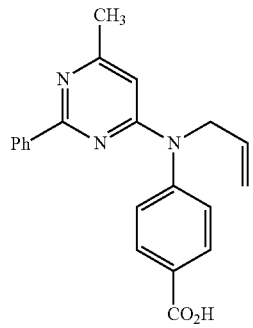 [SMILES: C=CCN(c1ccc(C(=O)O)cc1)c1cc(C)nc(-c2ccccc2)n1]

4-(allyl(6-methyl-2-phenylpyrimidin-4-yl)amino)benzoic acid was prepared according to the procedures described in Examples 1, 2, and 3, employing the coupling of compound of Preparation 25 and ethyl 4-aminobenzoate to give ethyl 4-(6-methyl-2-phenylpyrimidin-4-ylamino)benzoate. Subsequent N-alkylation with allyl bromide resulted in ethyl 4-(allyl(6-methyl-2-phenylpyrimidin-4-yl)amino)benzoate which underwent an ester hydrolysis to give the title compound as a white solid (29% yield for three steps).

Example 29: 4-((6-methyl-2-phenylpyrimidin-4-yl)(propyl)amino)benzoic acid

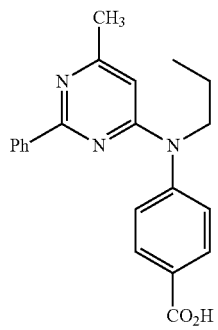 [SMILES: CCCN(c1ccc(C(=O)O)cc1)c1cc(C)nc(-c2ccccc2)n1]

4-((6-methyl-2-phenylpyrimidin-4-yl)(propyl)amino) benzoic acid was prepared according to the procedures described in Examples 1, 2, and 3, employing the coupling of compound of Preparation 25 and ethyl 4-aminobenzoate to give ethyl 4-(6-methyl-2-phenylpyrimidin-4-ylamino) benzoate. Subsequent N-alkylation with 1-propylbromide resulted in ethyl 4-((6-methyl-2-phenylpyrimidin-4-yl)(propyl)amino)benzoate which underwent an ester hydrolysis to give the title compound as a white solid (32% yield for three steps).

Example 30: pivaloyloxymethyl 4-(5-allyl-6-methyl-2-phenylpyrimidin-4-ylamino)benzoate

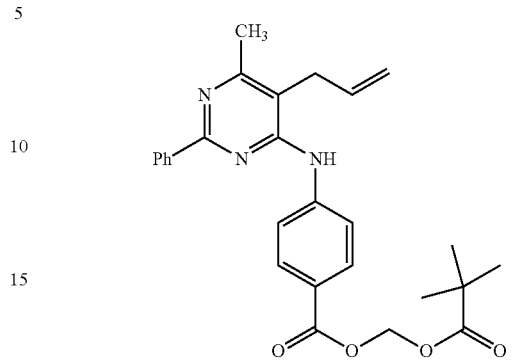

A solution of 4-(5-allyl-6-methyl-2-phenylpyrimidin-4-ylamino)benzoic acid (Preparation 26) (100 mg, 0.29 mmol) in DMF (5 mL) was treated with $Cs_2CO_3$ (189 mg, 0.58 mmol) and chloromethyl pivalate (50 μL, 0.35 mmol). The reaction mixture was stirred at room temperature until TLC indicated the consumption of 4-(5-allyl-6-methyl-2-phenylpyrimidin-4-ylamino)benzoic acid. It was then diluted with water and extracted with EtOAc (2×25 mL). The combined organic layer was washed with brine, dried over $MgSO_4$, filtered, and concentrated under reduced pressure to give the crude product. Purification by flash chromatography on silica gel with Hex:EtOAc (10:1) afforded the title compound as a white solid (107 mg, 80%).

Example 31: (S)-2-(4-(4-(5-allyl-6-methyl-2-phenylpyrimidin-4-ylamino)benzoyloxy)phenyl)-1-carboxyethanaminium chloride

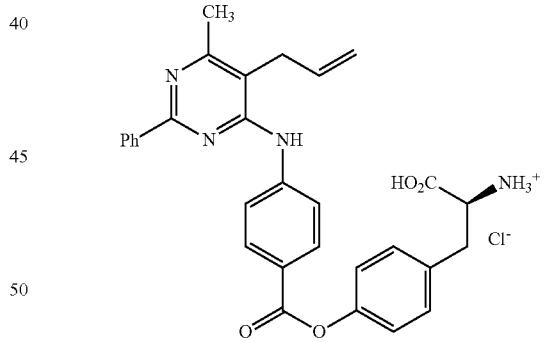

A solution of (S)-4-(3-tert-butoxy-2-(tert-butoxycarbonylamino)-3-oxopropyl)phenyl 4-(5-allyl-6-methyl-2-phenylpyrimidin-4-ylamino)benzoate (Preparation 29) (50 mg, 0.075 mmol) in dioxane was treated with 4 M HCl in dioxane (187 μL, 0.75 mmol), and the reaction mixture was stirred at room temperature. When TLC indicated the consumption of (S)-4-(3-tert-butoxy-2-(tert-butoxycarbonylamino)-3-oxopropyl)phenyl 4-(5-allyl-6-methyl-2-phenylpyrimidin-4-ylamino)benzoate, the reaction mixture was concentrated under reduced pressure to give the crude product. Purification by reverse phase preparative HPLC with a $CH_3CN$—$H_2O$ (0.1% TFA) solution (90:10) as the eluent, afforded the title compound as a white solid (11 mg, 28%).

Example 32: (S)-2-(4-(3-(4-(5-allyl-6-methyl-2-phenylpyrimidin-4-ylamino)benzoyloxy)propoxy)phenyl)-1-carboxyethanaminium chloride

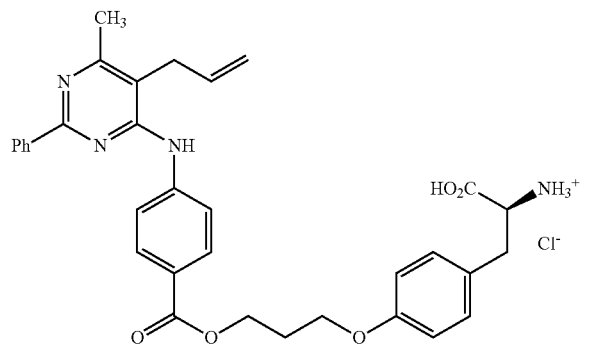 [SMILES: C=CCc1c(C)nc(-c2ccccc2)nc1Nc1ccc(C(=O)OCCCOc2ccc(C[C@H]([NH3+])C(=O)O)cc2)cc1 ; [Cl-]]

A solution of (S)-3-(4-(3-tert-butoxy-2-(tert-butoxycarbonylamino)-3-oxopropyl)phenoxy)propyl 4-(5-allyl-6-methyl-2-phenylpyrimidin-4-ylamino)benzoate (Preparation 30) (50 mg, 0.069 mmol) in dioxane was treated with 4 M HCl in dioxane (173 μL, 0.69 mmol), and the reaction mixture was stirred at room temperature. When TLC indicated the consumption of (S)-3-(4-(3-tert-butoxy-2-(tert-butoxycarbonylamino)-3-oxopropyl)phenoxy)propyl 4-(5-allyl-6-methyl-2-phenylpyrimidin-4-ylamino)benzoate, the reaction mixture was concentrated under reduced pressure to give the crude product. Purification by reverse phase preparative HPLC with a $CH_3CN$—$H_2O$ (0.1% TFA) solution (90:10) as the eluent, afforded the title compound as a white solid (15 mg, 36%).

Example 33: ethyl 4-(5-allyl-2-(4-chlorophenyl)-6-(trifluoromethyl)pyrimidin-4-yloxy)benzoate

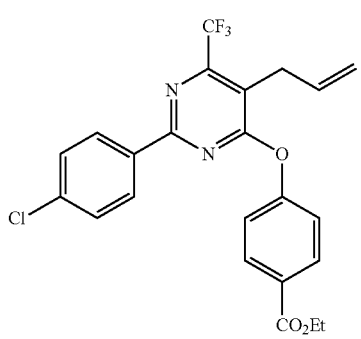

A solution of 5-allyl-4-chloro-2-(4-chlorophenyl)-6-(trifluoromethyl)pyrimidine (Preparation 24) (100 mg, 0.30 mmol) in DMF (10 mL) was treated with $Cs_2CO_3$ (196 mg, 0.60 mmol) and ethyl 4-hydroxybenzoate (75 mg, 0.45 mmol), and the reaction mixture was stirred at room temperature. When TLC indicated the consumption of 5-allyl-4-chloro-2-(4-chlorophenyl)-6-(trifluoromethyl)pyrimidine, the reaction mixture was diluted with water and extracted with EtOAc (2×25 mL). The combined organic layer was washed with aq. $NaHCO_3$, brine, dried over $Na_2SO_4$, filtered, and concentrated under reduced pressure to give the crude product. Purification by flash chromatography on silica gel with Hex:EtOAc (1:6) afforded the title compound in a mixture with the isomeric compound of Example 34 (Example 33/Example 34=½). Further purification by reverse phase preparative HPLC with a $CH_3CN$—$H_2O$ (0.1% TFA) solution (90:10) as the eluent, enabled the isolation of the title compound as a white solid (19 mg, 14%).

Example 34: (E)-ethyl 4-(2-(4-chlorophenyl)-5-(prop-1-enyl)-6-(trifluoromethyl)pyrimidin-4-yloxy)benzoate

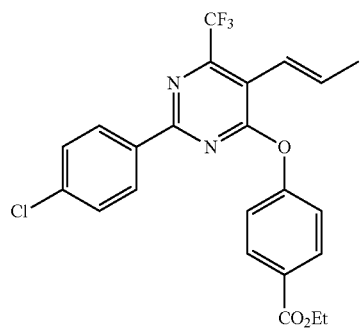

A solution of 5-allyl-4-chloro-2-(4-chlorophenyl)-6-(trifluoromethyl)pyrimidine (Preparation 24) (100 mg, 0.30 mmol) in DMF (10 mL) was treated with $Cs_2CO_3$ (196 mg, 0.60 mmol) and ethyl 4-hydroxybenzoate (75 mg, 0.45 mmol), and the reaction mixture was stirred at room temperature. When TLC indicated the consumption of 5-allyl-4-chloro-2-(4-chlorophenyl)-6-(trifluoromethyl)pyrimidine, the reaction mixture was diluted with water and extracted with EtOAc (2×25 mL). The combined organic layer was washed with aq. $NaHCO_3$, brine, dried over $Na_2SO_4$, filtered and concentrated under reduced pressure to give the crude product. Purification by flash chromatography on silica gel with Hex:EtOAc (1:6) afforded the title compound in a mixture with the isomeric compound of Example 33 (Example 33/Example 34=½). Further purification by reverse phase preparative HPLC with a $CH_3CN$—$H_2O$ (0.1% TFA) solution (90:10) as the eluent, enabled the isolation of compound of the title compound as a white solid (40 mg, 29%).

Example 35: 4-(5-allyl-6-methyl-2-phenylpyrimidin-4-yloxy)benzoic acid

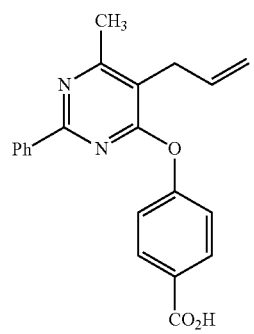 [SMILES: C=CCc1c(C)nc(-c2ccccc2)nc1Oc1ccc(C(=O)O)cc1]

4-(5-allyl-6-methyl-2-phenylpyrimidin-4-yloxy)benzoic acid was prepared according to the procedures described in Examples 33 and 3, employing the coupling of compound of Preparation 17 and ethyl 4-hydroxybenzoate followed by ester hydrolysis of the resulting ethyl 4-(5-allyl-6-methyl-2-phenylpyrimidin-4-yloxy)benzoate to give the title compound as a white solid (45% yield for two steps). It was isolated in a mixture with the isomeric compound of Example 36 (Example 35/Example 36=¼).

Example 36: (E)-4-(6-methyl-2-phenyl-5-(prop-1-enyl)pyrimidin-4-yloxy)benzoic acid

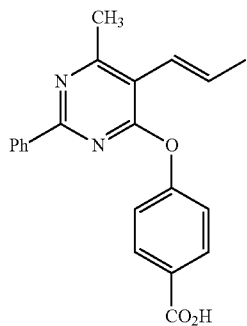

(E)-4-(6-methyl-2-phenyl-5-(prop-1-enyl)pyrimidin-4-yloxy)benzoic acid was prepared according to the procedures described in Examples 33 and 3, employing the coupling of compound of Preparation 17 and ethyl 4-hydroxybenzoate followed by ester hydrolysis of the resulting ethyl 4-(5-allyl-6-methyl-2-phenylpyrimidin-4-yloxy)benzoate to give the title compound as a white solid (45% yield for two steps). It was isolated in a mixture with the isomeric compound of Example 35 (Example 35/Example 36=¼).

Example 37: 4-(5-allyl-2-(4-chlorophenyl)-6-methylpyrimidin-4-yloxy)benzoic acid

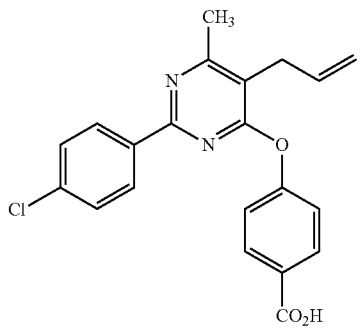

4-(5-allyl-2-(4-chlorophenyl)-6-methylpyrimidin-4-yloxy)benzoic acid was prepared according to the procedures described in Examples 33 and 3, employing the coupling of compound of Preparation 21 and ethyl 4-hydroxybenzoate followed by ester hydrolysis of the resulting ethyl 4-(5-allyl-2-(4-chlorophenyl)-6-methylpyrimidin-4-yloxy)benzoate to give the title compound as a white solid (47% yield for two steps). It was isolated in a mixture with the isomeric compound of Example 38 (Example 37/Example 38=¼).

Example 38: (E)-4-(2-(4-chlorophenyl)-6-methyl-5-(prop-1-enyl)pyrimidin-4-yloxy)benzoic acid

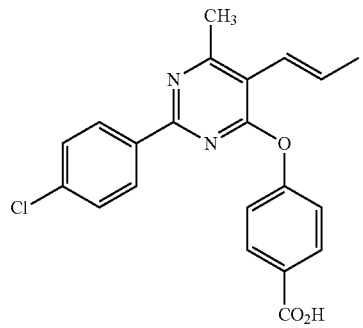

(E)-4-(2-(4-chlorophenyl)-6-methyl-5-(prop-1-enyl)pyrimidin-4-yloxy)benzoic acid was prepared according to the procedures described in Examples 33 and 3, employing the coupling of compound of Preparation 21 and ethyl 4-hydroxybenzoate followed by ester hydrolysis of the resulting ethyl 4-(5-allyl-2-(4-chlorophenyl)-6-methylpyrimidin-4-yloxy)benzoate to give the title compound as a white solid (47% yield for two steps). It was isolated in a mixture with the isomeric compound of Example 37. (Example 37/Example 38=¼).

Example 39: 4-(5-allyl-6-methyl-2-phenylpyrimidin-4-yloxy)-2-fluorobenzoic acid

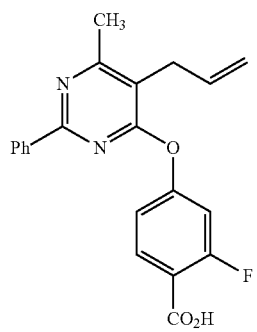 [SMILES: C=CCc1c(C)nc(-c2ccccc2)nc1Oc1ccc(C(=O)O)c(F)c1]

4-(5-allyl-6-methyl-2-phenylpyrimidin-4-yloxy)-2-fluorobenzoic acid was prepared according to the procedures described in Examples 33 and 3, employing the coupling of compound of Preparation 17 and ethyl 2-fluoro-4-hydroxybenzoate followed by ester hydrolysis of the resulting ethyl 4-(5-allyl-6-methyl-2-phenylpyrimidin-4-yloxy)-2-fluorobenzoate to give the title compound as a mixture with the isomeric compound of Example 40 (Example 39/Example 40=½). Further purification by reverse phase preparative HPLC with a $CH_3CN$—$H_2O$ (0.1% TFA) solution (90:10) as the eluent, enabled the isolation of the title compound as a beige solid (17%).

Example 40: (E)-2-fluoro-4-(6-methyl-2-phenyl-5-(prop-1-enyl)pyrimidin-4-yloxy)benzoic acid

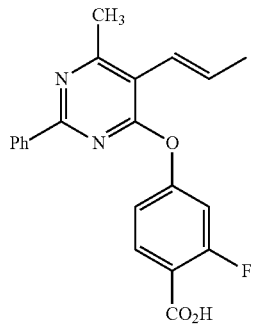 [SMILES: C/C=C/c1c(C)nc(-c2ccccc2)nc1Oc1ccc(C(=O)O)c(F)c1]

(E)-2-fluoro-4-(6-methyl-2-phenyl-5-(prop-1-enyl)pyrimidin-4-yloxy)benzoic acid was prepared according to the procedures described in Examples 33 and 3, employing the coupling of compound of Preparation 17 and ethyl 2-fluoro-4-hydroxybenzoate followed by ester hydrolysis of the resulting ethyl 4-(5-allyl-6-methyl-2-phenylpyrimidin-4-yloxy)-2-fluorobenzoate to give the title compound in a mixture with the isomeric compound of Example 39 (Example 39/Example 40=½). Further purification by reverse phase preparative HPLC with a $CH_3CN$—$H_2O$ (0.1% TFA) solution (90:10) as the eluent, enabled the isolation of the title compound as a white solid (34%).

Example 41: 4-(6-methyl-2-phenyl-5-propylpyrimidin-4-yloxy)benzoic acid

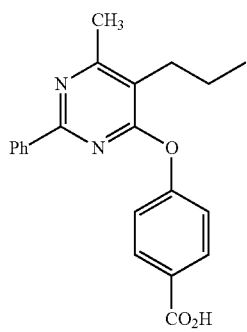 [SMILES: CCCc1c(C)nc(-c2ccccc2)nc1Oc1ccc(C(=O)O)cc1]

4-(6-methyl-2-phenyl-5-propylpyrimidin-4-yloxy)benzoic acid was prepared according to the procedures described in Examples 33 and 3, employing the coupling of compound of Preparation 18 and ethyl 4-hydroxybenzoate followed by ester hydrolysis of the resulting ethyl 4-(6-methyl-2-phenyl-5-propylpyrimidin-4-yloxy)benzoate to give the title compound as a white solid (44% yield for two steps).

Example 42: 4-(5-isopropyl-6-methyl-2-phenylpyrimidin-4-yloxy)benzoic acid

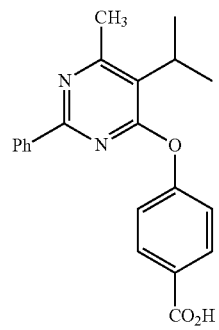 [SMILES: Cc1nc(-c2ccccc2)nc(Oc2ccc(C(=O)O)cc2)c1C(C)C]

4-(5-isopropyl-6-methyl-2-phenylpyrimidin-4-yloxy)benzoic acid was prepared according to the procedures described in Examples 33 and 3, employing the coupling of compound of Preparation 19 and ethyl 4-hydroxybenzoate followed by ester hydrolysis of the resulting ethyl 4-(5-isopropyl-6-methyl-2-phenylpyrimidin-4-yloxy)benzoate to give the title compound as a beige solid (42% yield for two steps).

Example 43: 4-(5-ethyl-6-methyl-2-phenylpyrimidin-4-yloxy)benzoic acid

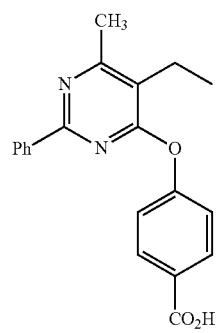 [SMILES: CCc1c(C)nc(-c2ccccc2)nc1Oc1ccc(C(=O)O)cc1]

4-(5-ethyl-6-methyl-2-phenylpyrimidin-4-yloxy)benzoic acid was prepared according to the procedures described in Examples 33 and 3, employing the coupling of compound of Preparation 20 and ethyl 4-hydroxybenzoate followed by ester hydrolysis of the resulting ethyl 4-(5-ethyl-6-methyl-2-phenylpyrimidin-4-yloxy)benzoate to give the title compound as a white solid (44% yield for two steps).

Example 44: 4-(2-(4-chlorophenyl)-5-ethyl-6-methylpyrimidin-4-yloxy)benzoic acid

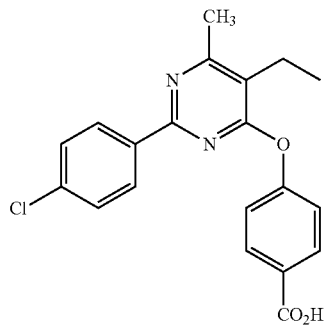 [SMILES: CCc1c(C)nc(-c2ccc(Cl)cc2)nc1Oc1ccc(C(=O)O)cc1]

4-(2-(4-chlorophenyl)-5-ethyl-6-methylpyrimidin-4-yloxy)benzoic acid was prepared according to the procedures described in Examples 31 and 3, employing the coupling of compound of Preparation 23 and ethyl 4-hydroxybenzoate followed by ester hydrolysis of the resulting ethyl 4-(2-(4-chlorophenyl)-5-ethyl-6-methylpyrimidin-4-yloxy)benzoate to give the title compound as a white solid (42% yield for two steps).

Example 45: 4-(4,6-dimethyl-2-phenyl-7H-pyrrolo[2,3-d]pyrimidin-7-yl)benzoic acid

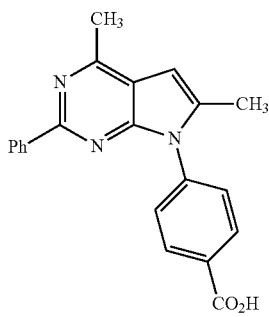

A solution of 4-(5-allyl-6-methyl-2-phenylpyrimidin-4-ylamino)benzoic acid (Preparation 26) (20 mg, 0.058 mmol) in glacial acetic acid (5 mL) was treated with bromine (12 µL, 0.232 mmol) as a solution in acetic acid (0.2 mL). The reaction mixture was stirred at room temperature for 1 h and then concentrated under reduced pressure. The resulting residue was dissolved in EtOH (4 mL), treated with a solution of 5% KOH in EtOH (1 mL) and then refluxed for 5 h. After cooling at room temperature, the solvent was evaporated under reduced pressure, and the resulting residue was treated with 1 N NaOH (5 mL) and then extracted with Et$_2$O (2×20 mL). The remaining aqueous layer was acidified with 1 N HCl to pH~2-3 and then extracted with EtOAc (3×30 mL). The combined organic layer was dried over MgSO$_4$, filtered, and concentrated under reduced pressure to afford the crude product. Purification by reverse phase preparative HPLC with a CH$_3$CN—H$_2$O (0.1% TFA) solution (90:10) as the eluent, enabled the isolation of the title compound as a beige solid (4 mg, 20%).

Example 46: 3-bromo-4-(4,6-dimethyl-2-phenyl-7H-pyrrolo[2,3-d]pyrimidin-7-yl)benzoic acid

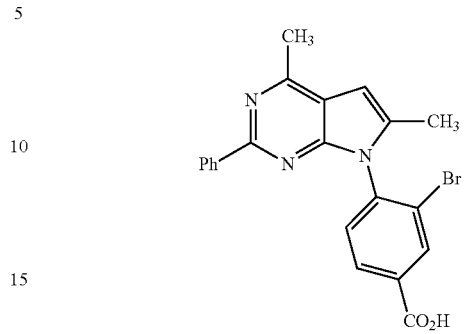

A solution of 4-(5-allyl-6-methyl-2-phenylpyrimidin-4-ylamino)benzoic acid (Preparation 26) (20 mg, 0.058 mmol) in glacial acetic acid (5 mL) was treated with bromine (12 µL, 0.232 mmol) as a solution in acetic acid (200 µL). The reaction mixture was stirred at room temperature overnight and then concentrated under reduced pressure. The resulting residue was dissolved in EtOH (4 mL), treated with a solution of 5% KOH in EtOH (1 mL) and then refluxed for 5 h. After cooling at room temperature, the solvent was evaporated under reduced pressure, and the resulting residue was treated with 1 N NaOH (5 mL) and then extracted with Et$_2$O (2×20 mL). The remaining aqueous layer was acidified with 1 N HCl to pH~2-3 and then extracted with EtOAc (3×30 mL). The combined organic layer was dried over MgSO$_4$, filtered, and concentrated under reduced pressure to afford the crude product. Purification by reverse phase preparative HPLC with a CH$_3$CN—H$_2$O (0.1% TFA) solution (90:10) as the eluent, enabled the isolation of the title compound as a beige solid (7 mg, 27%).

Example 47: 4-(6-methyl-2-phenyl-4-(trifluoromethyl)-7H-pyrrolo[2,3-d]pyrimidin-7-yl)benzoic acid

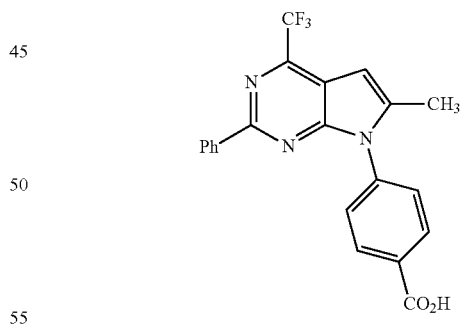

A solution of ethyl 4-(5-allyl-2-phenyl-6-(trifluoromethyl)pyrimidin-4-ylamino)benzoate (Example 1) (20 mg, 0.047 mmol) in glacial acetic acid (5 mL) was treated with bromine (10 µL, 0.188 mmol) as a solution in acetic acid (200 µL). The reaction mixture was stirred at room temperature for 5 h and then concentrated under reduced pressure. The resulting residue was dissolved in EtOH (4 mL), treated with a solution of 5% KOH in EtOH (1 mL), and then refluxed for 5 h. After cooling at room temperature, the resulting solution was treated with 1 N LiOH (100 µL, 0.1 mmol) and then stirred at room temperature overnight. The solvent was evaporated under reduced pressure and the resulting residue was treated with 1 N NaOH (5 mL) and then extracted with Et$_2$O (2×20 mL). The remaining aqueous layer was acidified with 1 N HCl to pH~2-3 and then extracted with EtOAc (3×30 mL). The combined organic layer was dried over MgSO$_4$, filtered, and concentrated under reduced pressure to afford the crude product. Purification by reverse phase preparative HPLC with a CH$_3$CN—H$_2$O (0.1% TFA) solution (90:10) as the eluent, enabled the isolation of the title compound as a beige solid (6 mg, 32%).

II. Nurr1:RXRα-Dependent Transcription-Activating Capabilities of Synthesized Compounds of the Invention Synthesized compounds of the invention and their analogs, shown in Table 1, below, were evaluated for activity in cellular assays. The in vitro transactivation assay determined the capacity of the compounds of the invention to activate the Nurr1:RXR heterodimers. Naive SHSY-5Y cells were transiently co-transfected, using Lipofectamine 2000 (Invitrogen), with a plasmid expressing the human receptor Nurr1, a plasmid expressing the RXR human receptor (RXRα or RXRγ receptor) and a reporter plasmid DR5-TK-Luc. After 24 hours, the culture medium was changed. The test compounds were added (final concentration between 0.5, 2.5 and 12.5 μM) in the culture medium. After incubation overnight, the expression of luciferase was measured (FIG. 1A). Positive control cells were treated with XCT0135908 (1 μM; WO 2005/047268) which induces activation of the Nurr1:RXR heterodimer and results in maximal expression of luciferase. The transcription-activating activities of various compounds of the invention are shown in FIG. 1B, as well as in Table 1, below. In the transactivation assay, compound 3 exhibited an EC$_{50}$ value of (0.9 μM) (FIG. 1C). Furthermore, compound 3 is selective for the Nurr1:RXRα heterodimer over the Nurr1:RXRγ heterodimer (FIG. 1D).

TABLE 1

Transcription-activating properties of select compounds of the invention as assessed in a Nurr1:RXRα-dependent luciferase reporter assay

| Example | Compound | EC$_{50}$ (μM) |
|---|---|---|
| 1 | [structure: 2-phenyl-4-(4-ethoxycarbonylphenylamino)-5-allyl-6-trifluoromethylpyrimidine] | >50 |
| 2 | [structure: 2-phenyl-4-(N-methyl-4-ethoxycarbonylphenylamino)-5-allyl-6-trifluoromethylpyrimidine] | Not tested |
| 3 | [structure: 2-phenyl-4-(N-methyl-4-carboxyphenylamino)-5-allyl-6-trifluoromethylpyrimidine] | 0.9 |

TABLE 1-continued
Transcription-activating properties of select compounds of the invention as assessed in a Nurr1:RXRα-dependent luciferase reporter assay
| Example | Compound | EC$_{50}$ (μM) |
|---------|----------|----------------|
| 4 | 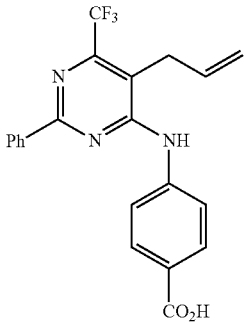 [SMILES: C=CCc1c(Nc2ccc(C(=O)O)cc2)nc(-c2ccccc2)nc1C(F)(F)F] | 0.2 (sample contained 45% of the styryl isomer of Example 5) |
| 5 | 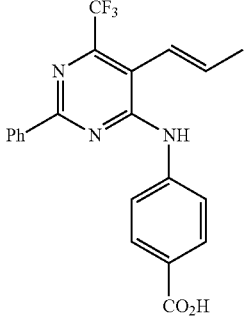 [SMILES: C/C=C/c1c(Nc2ccc(C(=O)O)cc2)nc(-c2ccccc2)nc1C(F)(F)F] | 0.3 |
| 6 | 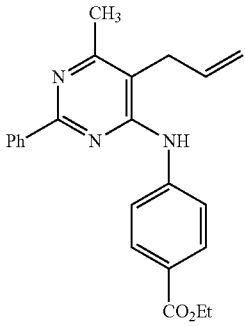 | >100 |
| 7 | 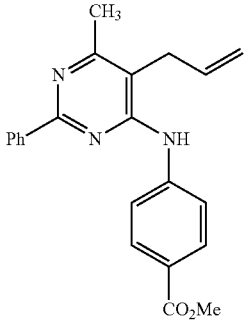 | Not tested |

TABLE 1-continued

Transcription-activating properties of select compounds of the invention as assessed in a Nurr1:RXRα-dependent luciferase reporter assay

| Example | Compound | EC$_{50}$ (μM) |
|---|---|---|
| 8 | 2-Ph, 4-[N(CH$_3$)(4-CO$_2$Et-C$_6$H$_4$)], 5-allyl, 6-CH$_3$ pyrimidine | Not tested |
| 9 | 2-Ph, 4-[N(CH$_3$)(4-CO$_2$Me-C$_6$H$_4$)], 5-allyl, 6-CH$_3$ pyrimidine | >100 |
| 10 | 2-Ph, 4-[N(CH$_3$)(4-CO$_2$H-C$_6$H$_4$)], 5-allyl, 6-CH$_3$ pyrimidine | >20 |
| 11 | 2-Ph, 4-[NH(4-CO$_2$H-C$_6$H$_4$)], 5-propyl, 6-CH$_3$ pyrimidine | 1 |

TABLE 1-continued

Transcription-activating properties of select compounds of the invention as assessed in a Nurr1:RXRα-dependent luciferase reporter assay

| Example | Compound | EC$_{50}$ (μM) |
|---|---|---|
| 12 | 2-phenyl-4-methyl-5-isopropyl-6-(4-carboxyphenylamino)pyrimidine | 1 |
| 13 | 2-phenyl-4-methyl-5-ethyl-6-(4-carboxyphenylamino)pyrimidine | 5 |
| 14 | 2-(4-chlorophenyl)-4-methyl-5-allyl-6-(4-carboxyphenylamino)pyrimidine | 2 |
| 15 | 2-(4-chlorophenyl)-4-methyl-5-propyl-6-(4-carboxyphenylamino)pyrimidine | >10 |

TABLE 1-continued

Transcription-activating properties of select compounds of the invention as assessed in a Nurr1:RXRα-dependent luciferase reporter assay

| Example | Compound | EC$_{50}$ (µM) |
|---|---|---|
| 16 | [structure: pyrimidine with CH$_3$, ethyl, 4-chlorophenyl, and NH-phenyl-CO$_2$H substituents] | 2 |
| 17 | [structure: pyrimidine with CH$_3$, allyl, Ph, and NH-(3-fluoro-4-carboxyphenyl) substituents] | Not tested |
| 18 | [structure: pyrimidine with CH$_3$, allyl, Ph, and NH-(2-methyl-4-carboxyphenyl) substituents] | Not tested |
| 19 | [structure: pyrimidine with CF$_3$, allyl, 4-chlorophenyl, and NH-phenyl-CO$_2$H substituents] | 10 (sample contained 40% of the styryl isomer of Example 20) |

TABLE 1-continued
Transcription-activating properties of select compounds of the invention as assessed in a Nurr1:RXRα-dependent luciferase reporter assay
| Example | Compound | EC$_{50}$ (μM) |
|---------|----------|----------------|
| 20 | 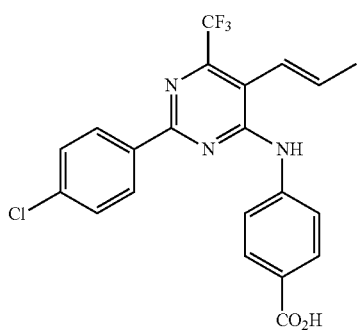 [SMILES: C/C=C/c1c(Nc2ccc(C(=O)O)cc2)nc(-c2ccc(Cl)cc2)nc1C(F)(F)F] | >10 |
| 21 | 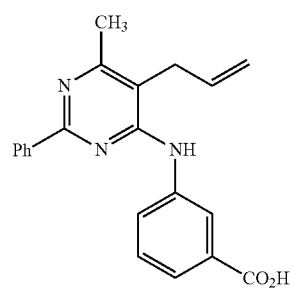 [SMILES: C=CCc1c(C)nc(-c2ccccc2)nc1Nc1cccc(C(=O)O)c1] | Not tested |
| 22 | 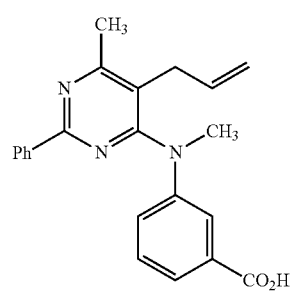 [SMILES: C=CCc1c(C)nc(-c2ccccc2)nc1N(C)c1cccc(C(=O)O)c1] | Not tested |
| 23 | 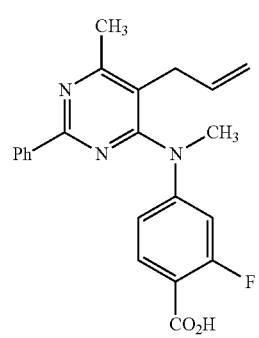 | 7 |

TABLE 1-continued

Transcription-activating properties of select compounds of the invention as assessed in a Nurr1:RXRα-dependent luciferase reporter assay

| Example | Compound | EC$_{50}$ (μM) |
| --- | --- | --- |
| 24 | 2-phenyl-4-methyl-5-allyl-6-[N-methyl-N-(2-methyl-4-carboxyphenyl)amino]pyrimidine | >100 |
| 25 | 2-(4-chlorophenyl)-4-methyl-5-allyl-6-[N-methyl-N-(4-carboxyphenyl)amino]pyrimidine | 7 |
| 26 | 2-(4-chlorophenyl)-4-methyl-5-ethyl-6-[N-methyl-N-(4-carboxyphenyl)amino]pyrimidine | 4 |
| 27 | 2-phenyl-4-methyl-6-[(4-carboxyphenyl)amino]pyrimidine | Not tested |

TABLE 1-continued

Transcription-activating properties of select compounds of the invention as assessed in a Nurr1:RXRα-dependent luciferase reporter assay

| Example | Compound | EC$_{50}$ (μM) |
|---|---|---|
| 28 | (structure: 6-methyl-2-phenylpyrimidin-4-yl with N-allyl and 4-carboxyphenyl substituents) | Not tested |
| 29 | (structure: 6-methyl-2-phenylpyrimidin-4-yl with N-propyl and 4-carboxyphenyl substituents) | 10 |
| 30 | (structure: 5-allyl-6-methyl-2-phenylpyrimidin-4-yl-NH-phenyl-C(O)O-CH$_2$-O-C(O)-tBu) | 2 |
| 31 | (structure: 5-allyl-6-methyl-2-phenylpyrimidin-4-yl-NH-phenyl-C(O)O-phenyl-CH$_2$-CH(NH$_3^+$)-CO$_2$H) | 10 |

TABLE 1-continued

Transcription-activating properties of select compounds of the invention as assessed in a Nurr1:RXRα-dependent luciferase reporter assay

| Example | Compound | EC$_{50}$ (μM) |
|---|---|---|
| 32 | | 5 |
| 33 | | Not tested |
| 34 | | Not tested |
| 35 | | >100 (sample contained 80% of the styryl isomer of Example 36) |

TABLE 1-continued

Transcription-activating properties of select compounds of the invention as assessed in a Nurr1:RXRα-dependent luciferase reporter assay

| Example | Compound | $EC_{50}$ (μM) |
|---|---|---|
| 36 | (structure) | >10 |
| 37 | (structure) | >100 (sample contained 80% of the styryl isomer of Example 38) |
| 38 | (structure) | Not tested |
| 39 | (structure) | >10 |

TABLE 1-continued
Transcription-activating properties of select compounds of the invention as assessed in a Nurr1:RXRα-dependent luciferase reporter assay
| Example | Compound | $EC_{50}$ (μM) |
|---------|----------|----------------|
| 40 | 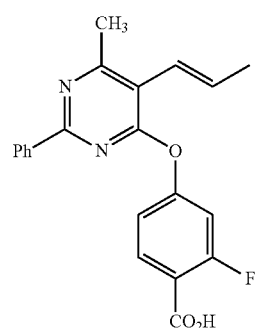 | Not tested |
| 41 | 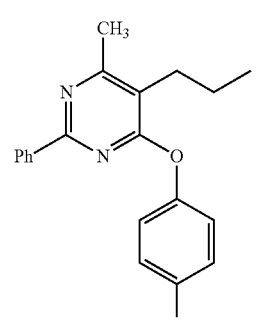 | >100 |
| 42 | 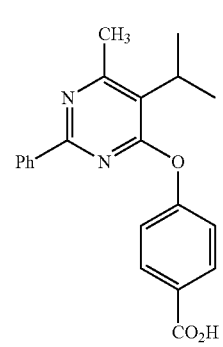 [SMILES: Cc1nc(-c2ccccc2)nc(Oc2ccc(C(=O)O)cc2)c1C(C)C] | 1 |
| 43 | 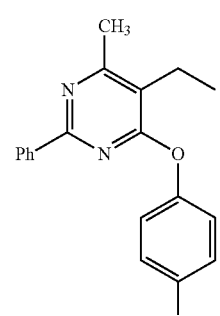 | >100 |

TABLE 1-continued

Transcription-activating properties of select compounds of the invention as assessed in a Nurr1:RXRα-dependent luciferase reporter assay

| Example | Compound | EC$_{50}$ (μM) |
|---|---|---|
| 44 | [structure: 4-methyl-5-ethyl-2-(4-chlorophenyl)-6-(4-carboxyphenoxy)pyrimidine] | >10 |
| 45 | [structure: 4-methyl-2-phenyl-6-methyl-7-(4-carboxyphenyl)-7H-pyrrolo[2,3-d]pyrimidine] | 2.5 |
| 46 | [structure: 4-methyl-2-phenyl-6-methyl-7-(2-bromo-4-carboxyphenyl)-7H-pyrrolo[2,3-d]pyrimidine] | 0.7 |
| 47 | [structure: 4-trifluoromethyl-2-phenyl-6-methyl-7-(4-carboxyphenyl)-7H-pyrrolo[2,3-d]pyrimidine] | Not tested |

Compound 3 specifically activates Nurr1:RXRα heterodimers over other RXR-containing transcription co-activator complexes. Specificity assays fusing DNA sequences of the gal4 DNA binding domain to the nuclear receptor Ligand-Binding-Domain (LDB) and to vp16 were performed as follows: Human SHSY-5Y cells were cotransfected with 20 ng of MH100-tk -luciferase, 10 ng of CMX-bgal, 20 ng of CMX-GAL4-RXRα-LBD and 20 ng of CMX-VP16-NR-LBD, where NR stands for either Nurr1, VDR, PPARγ. CMX-VP16-VDR-LBD and CMX-VP16-PPARγ-LBD were kindly provided by Dr Makishima (Nikon University School of Medicine). CMX-VP16-Nurr1-LBD was produced by cloning the Nurr1 LBD in the CMX-VP16 vector using KpnI. More specifically, Nurr1-LBD was isolated by PCR from a vector containing the Nurr1 cDNA using a set of primers flanking the Nurr1 LBD sequence and carrying at both sides the KpnI restriction sites, namely Nurr1 Forward TGCGGTACCAGGAGCCCTCTCCCCCTTC (SEQ ID NO: 1) and Nurr1 Reverse TGCGGTACCT-TAGAAAGGTAAAGTGTCCA (SEQ ID NO: 2). To exclude the possibility that compound 3 might transactivate RXRγ:Nurr1 heterodimers, CMX-GAL4-RXRγ-LBD was constructed by cloning the RXRγ LBD that was isolated by PCR from a vector containing the RXRγ cDNA (RIKEN, Tokyo, Japan) using the following Forward and Reverse primers carrying KpnI and NheI restriction sites, respectively, namely RXRγ Forward TGCGGTACCGAGCGAGCTGAGAGTGAG (SEQ ID NO: 3) and RXRγ LBD Reverse TGCGCTAGCTCAGGTGATCTGCAGC (SEQ ID NO: 4). 17 hours after transfection the compound was added to the medium at the corresponding concentrations and left for another 12 hours. Then the cells were assayed for luciferase activity normalized to galactosidase activity.

III. Neuroprotective Effect of Compounds of the Invention in Mice

To assess the neuroprotective effect of compound 3, this compound was dosed to wt mice intraperitoneally (IP) at 10 mg/kg injections of compound 3 in Ethanol:PG:Saline 10:30:60. After 2 h and 4 h animals (n=3 per time point) were sacrificed, and their brains obtained. After extraction c-jun and tyrosine hydroxylase (TH) levels in brain extract were determined by qPCR (FIG. 1E, 1F).

IV. Neuroprotective Effect of Compounds of the Invention In Vitro

MPP+, eradicates approximately 75% of the cells in 24 hours. Addition of compound 3 approximately doubles the number of surviving cells (FIG. 1 C, D, E). Naive Neuro2A cells (FIG. 2A) or SH-SY5Y neuroblastoma cells FIG. 2B,C) were cultured in RPMI 1640, 10% fetal bovine serum at 37° C. Cells were pretreated with compound 3 for 12-24 h. Subsequent change of culture medium with addition of 0, 1, 2 and 4 mM MPP+ induced cell death. MTT assays determined the relative number of surviving cells FIG. 2D).

V. SHSY5Y Cells are Protected from $H_2O_2$-Induced Death by Compound 3

Figure 2:
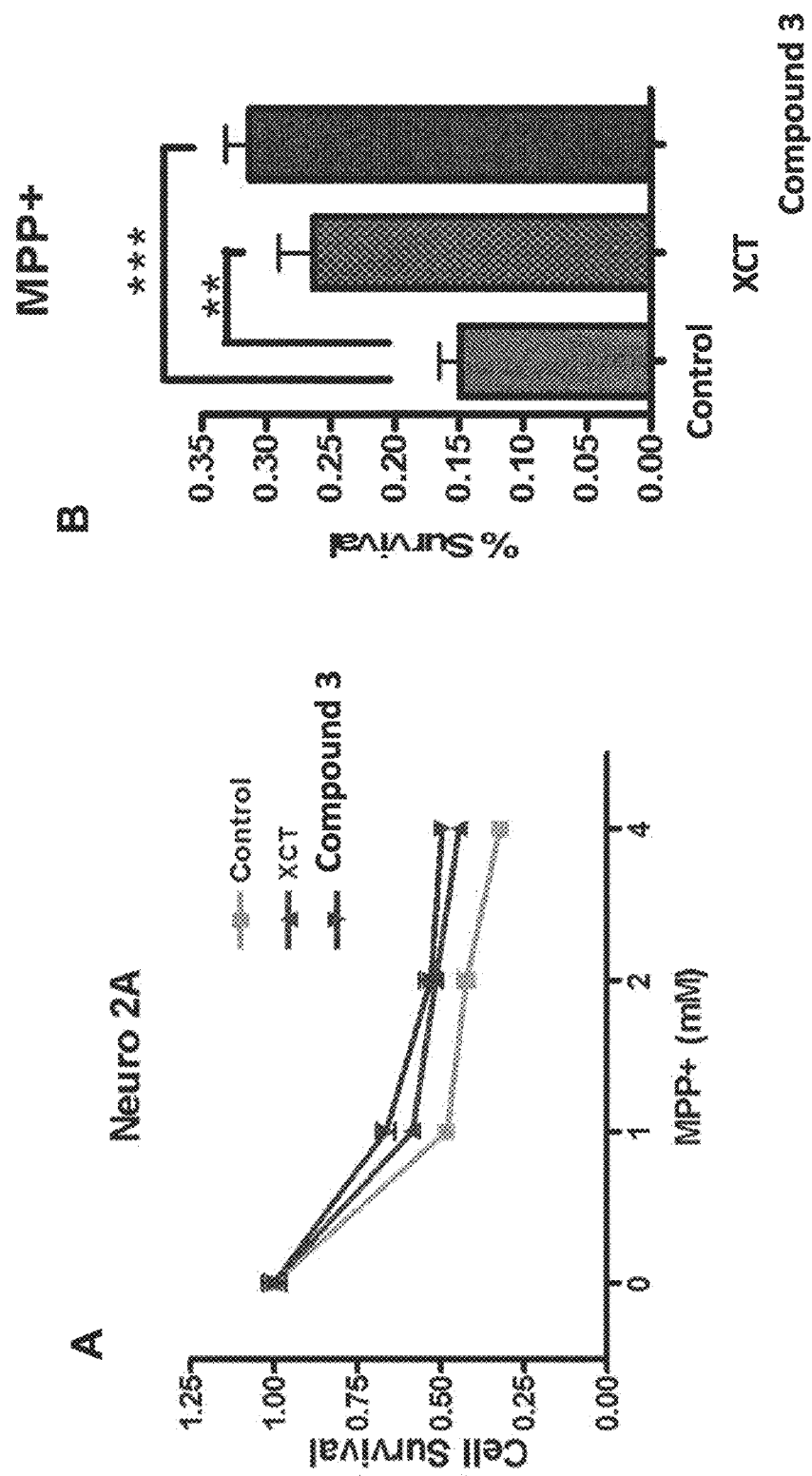
FIGS. 2A-2G show the biochemical activity of compounds evaluated in neuroprotection assays.
Figure 2:
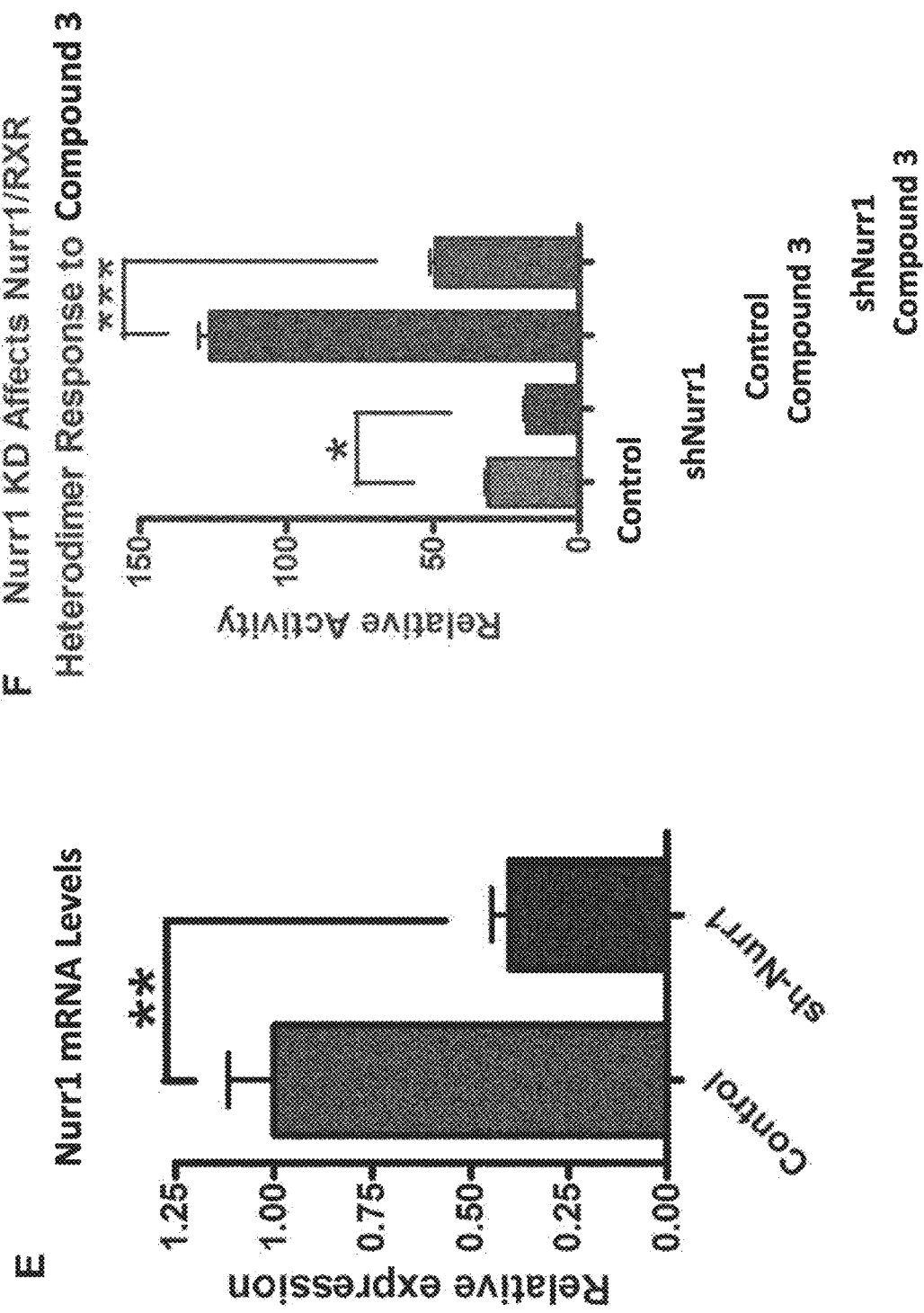
Figure 2:
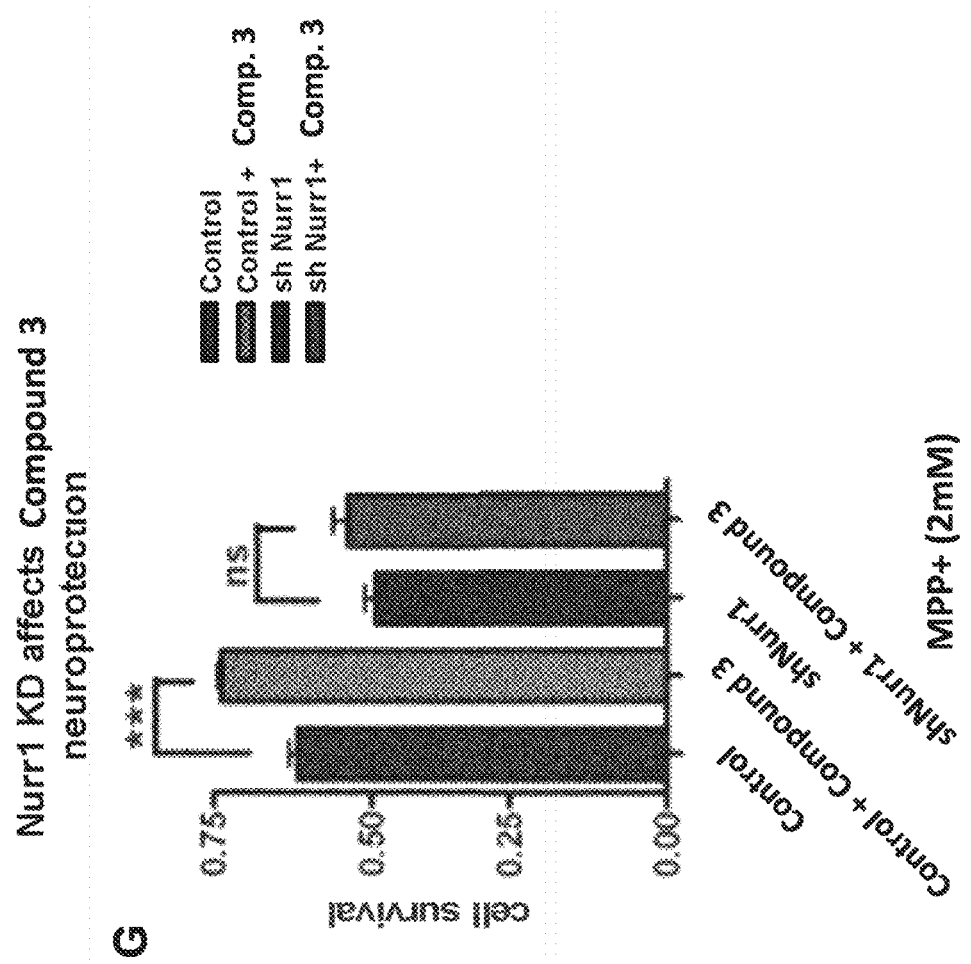

The neuroprotective effect in SHSY5Y cells is Nurr1 dependent. Decreasing Nurr1 mRNA levels by 60% using a retrovirus caring shNurr1 sequences (FIG. 2E), which decrease its transcriptional activity as assessed by luciferase assays (FIG. 2F), also decreases the neuroprotective effect of compound 3 treatment against MPP+ and increases the sensitivity of the cells to this toxin (FIG. 2G).

VI. Single IP Administration of Compound 3 (20 mg/kg) Increased Striatal DA Levels and Dopamine Metabolite Levels in Wild Type C57/BL6 Mice Single IP administration of the compound of the invention compound 3 (20 mg/kg) increased striatal DA levels and dopamine metabolite (DOPAC and HVA) levels in wild type C57/BL6 mice by 33% (FIG. 3B). 4 hours after dosing, animals were killed by cervical dislocation, brains were removed, and the striata were dissected on ice. The samples were immediately frozen and stored at −80° C. until use. The tissues were processed for the analysis by high performance liquid chromatography (HPLC) with an electrochemical detector (ECD) (Emmanouil et al., 2006). The dissected tissues were weighed, homogenized, and deproteinized in 0.2N perchloric acid solution containing 7.9 mM $Na_2S_2O_5$ and 1.3 mM $Na_2EDTA$. The homogenate was centrifuged at 37,000×g for 30 minutes, and the supernatant was stored at −80° C. until assayed. A reverse-phase ion-pair chromatography was used in all analyses, and the mobile phase consisted of an acetonitrile-50 mM phosphate buffer at pH 3.0, containing 5-octylsulfate sodium salt (300 mg/L) as the ion-pair reagent and (20 mg/L) $Na_2EDTA$. Reference standards were prepared in 0.2 N perchloric acid solution containing 7.9 mM $Na_2S_2O_5$ and 1.3 mM $Na_2EDTA$. Samples were quantified by comparison of the areas under the peaks with those of reference standards using HPLC software (Chromatography Station for Windows™, Watrex International Inc., San Francisco, Calif.).

Figure 3:
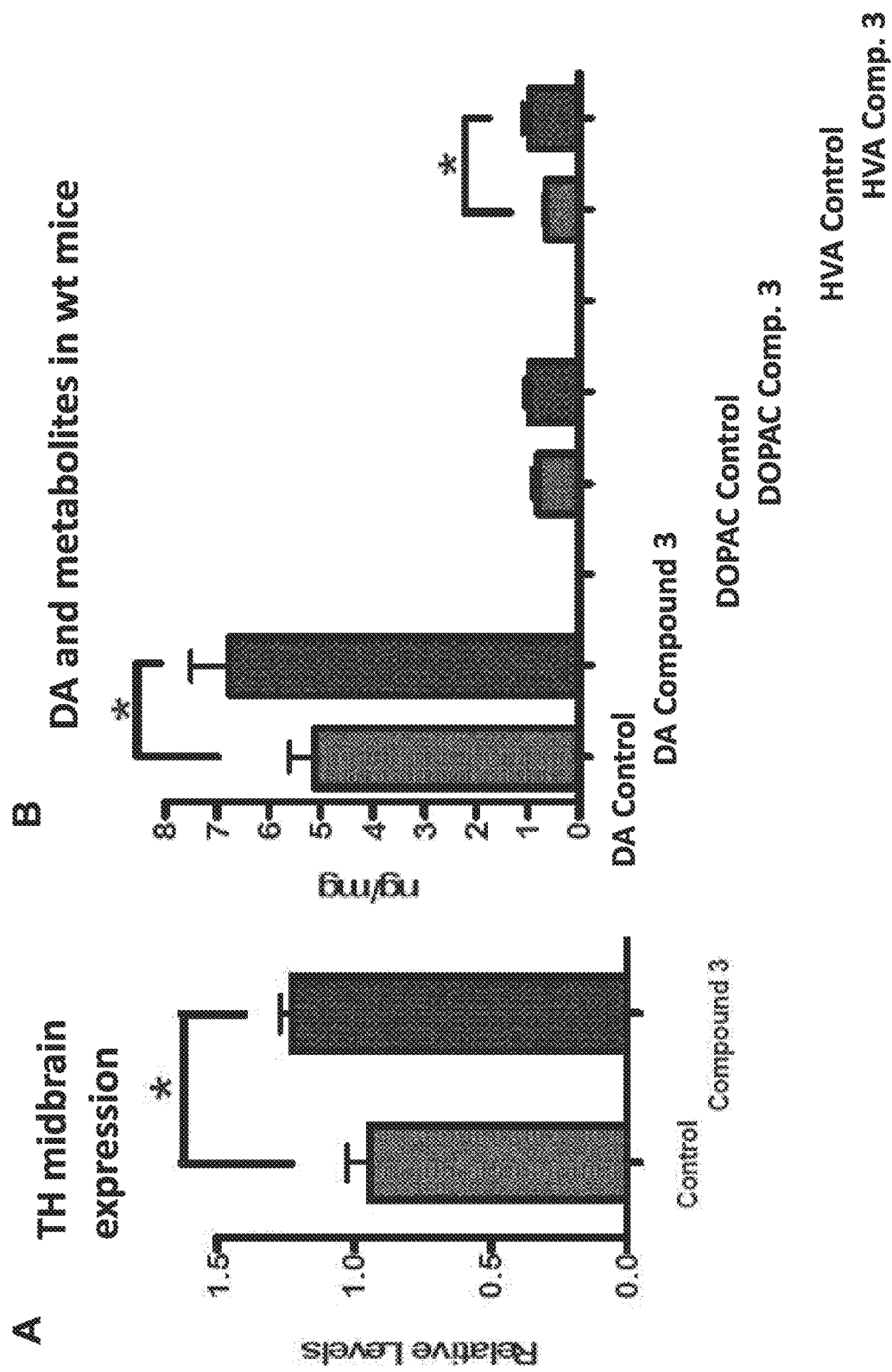
FIGS. 3A-3D show that C57/BL6 or TH promoter driven ASYN 120 transgenic mice injected intraperitoneally (IP) with 20 mg/kg compound 3 exhibit an increase in dopamine (DA) and 5HT (serotonin) levels 4 h post injection. Vehicle IP injections were used as control.
Figure 3:
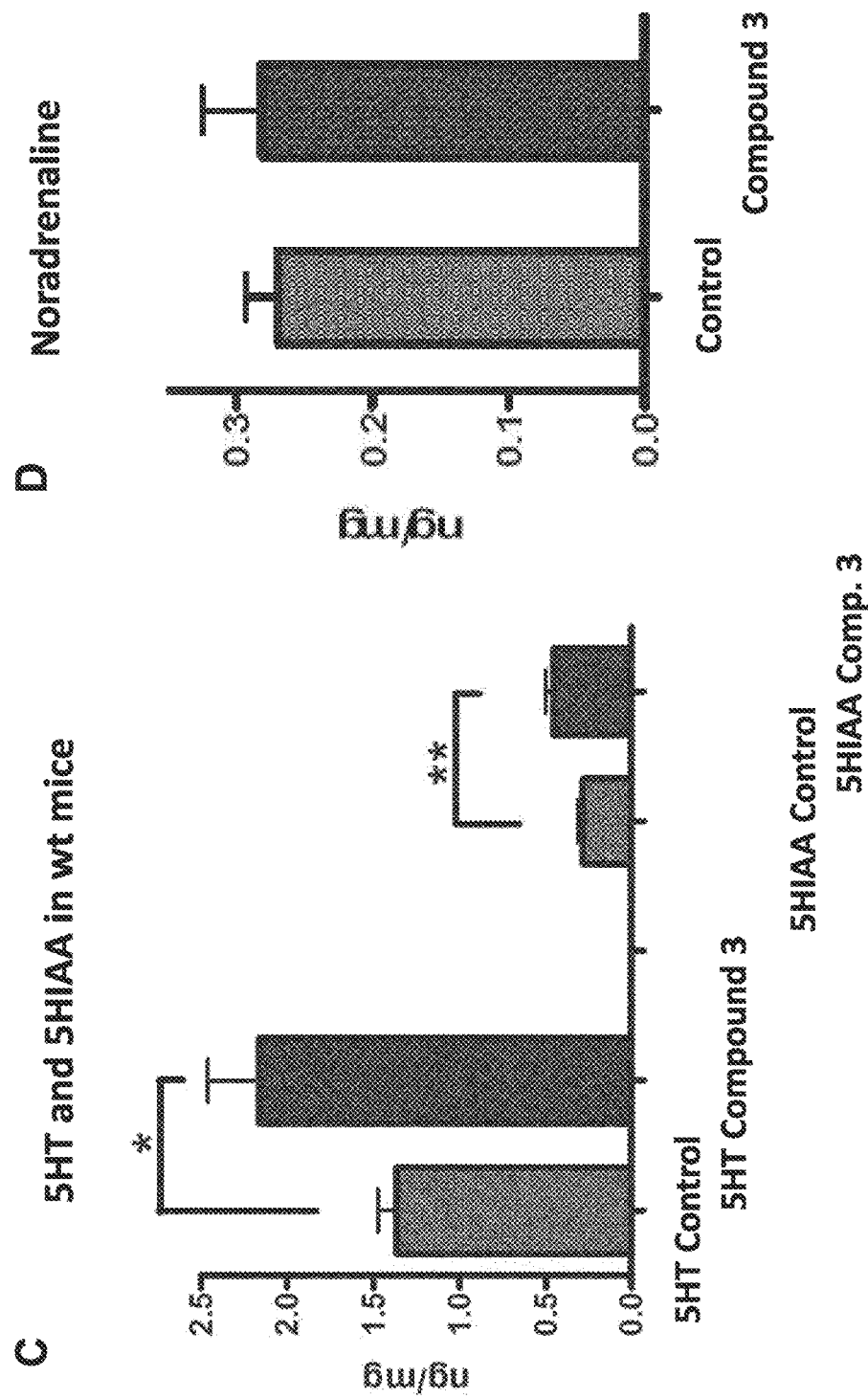

VII. Single IP Administration of Compound 3 (20 mg/kg) Increased TH Levels in Wild Type C57/BL6 Mice We measured striatal 5-HT levels, and we detected 5-HT and 5-HIAA in wild type C57/BL6 mice. 4 hours after dosing animals were killed by cervical dislocation, brains were removed, and the striata were dissected on ice. The samples were immediately frozen and stored at −80° C. until use. The tissues were processed for the analysis by high performance liquid chromatography (HPLC) with an electrochemical detector (ECD) (Emmanouil et al., 2006). The dissected tissues were weighed, homogenized, and deproteinized in 0.2 N perchloric acid solution containing 7.9 mM $Na_2S_2O_5$ and 1.3 mM $Na_2EDTA$. The homogenate was centrifuged at 37,000×g for 30 minutes, and the supernatant was stored at −80° C. until assayed. A reverse-phase ion-pair chromatography was used in all analyses, and the mobile phase consisted of an acetonitrile-50 mM phosphate buffer at pH 3.0, containing 5-octylsulfate sodium salt (300 mg/L) as the ion-pair reagent and (20 mg/L) $Na_2EDTA$. Reference standards were prepared in 0.2 N perchloric acid solution containing 7.9 mM $Na_2S_2O_5$ and 1.3 mM $Na_2EDTA$. Samples were quantified by comparison of the areas under the peaks with those of reference standards using HPLC software (Chromatography Station for Windows™, Watrex International Inc., San Francisco, Calif.) (FIG. 3C).

VIII. Single IP Administration of Compound 3 (20 mg/kg) Did not Increase Noradrenaline Levels in Wild Type C57/BL6 Mice Single IP administration of the compound of the invention compound 3 (20 mg/kg) did not increase noradrenaline levels in wild type C57/BL6 mice. 4 hours after dosing animals were killed by cervical dislocation, brains were removed, and the striata were dissected on ice. The samples were immediately frozen and stored at −80° C. until use. The tissues were processed for the analysis by high performance liquid chromatography (HPLC) with an electrochemical detector (ECD) (Emmanouil et al., 2006). The dissected tissues were weighed, homogenized, and deproteinized in 0.2 N perchloric acid solution containing 7.9 mM $Na_2S_2O_5$ and 1.3 mM $Na_2EDTA$. The homogenate was centrifuged at 37,000×g for 30 minutes, and the supernatant was stored at −80° C. until assayed. A reverse-phase ion-pair chromatography was used in all analyses, and the mobile phase consisted of an acetonitrile-50 mM phosphate buffer at pH 3.0, containing 5-octylsulfate sodium salt (300 mg/L) as the ion-pair reagent and (20 mg/L) $Na_2EDTA$. Reference standards were prepared in 0.2 N perchloric acid solution containing 7.9 mM $Na_2S_2O_5$ and 1.3 mM $Na_2EDTA$. Samples were quantified by comparison of the areas under the peaks with those of reference standards using HPLC software (Chromatography Station for Windows™, Watrex International Inc., San Francisco, Calif.) (FIG. 3D).

Figure 4:
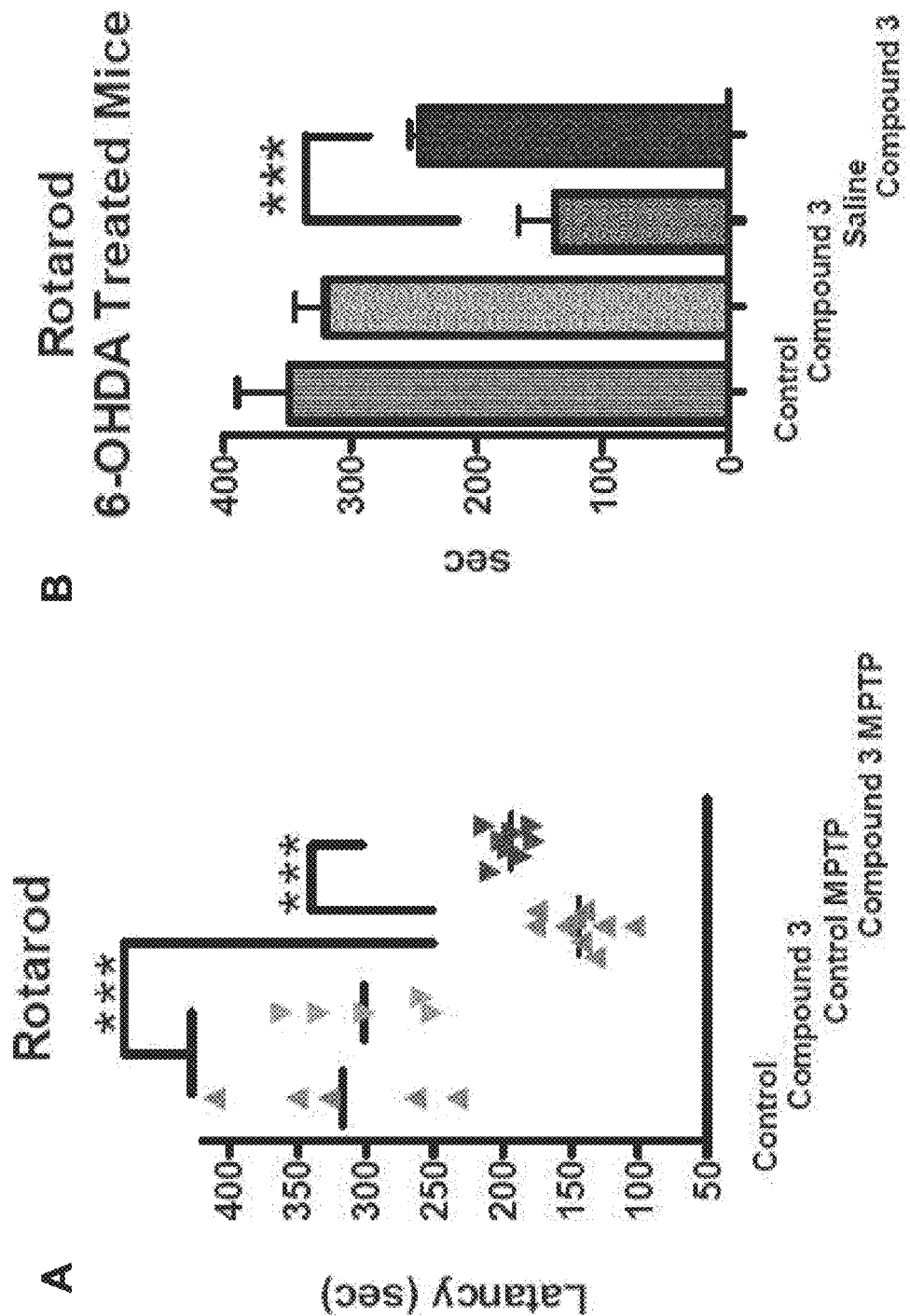
FIGS. 4A-4E show the effect of tested compounds on mouse behavior.
Figure 4:
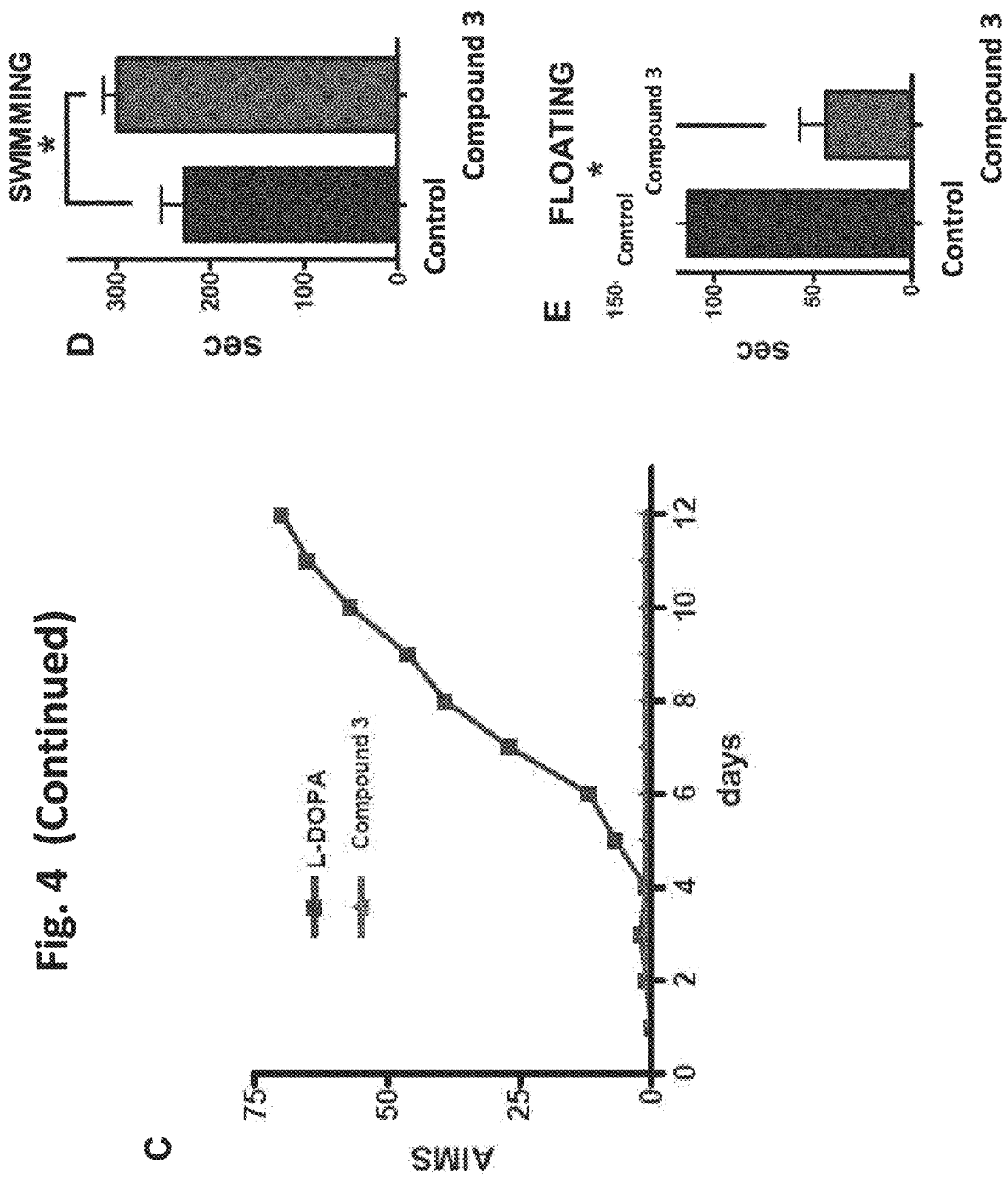

IX. Single IP Administration of Compound 3 (20 mg/kg) Increased Movement Coordination in Wild Type C57/BL6 PD Mice without Inducing Dyskinesia Single IP administration of the compound of the invention compound 3 (20 mg/kg) increased movement coordination in wild type C57/BL6 PD mice treated with MPTP. 20 mg/kg MPTP injections were administered 4 times at the zero day of treatment spaced 2 hours apart. 7 days after the MPTP injections there was approximately an 80% reduction in striatal projections and 40%-50% dopaminergic neuron death in the SN. Motor coordination and balance were tested using a Rota-Rod treadmill (Ugo Basile, Comerio, Italy), set with accelerating revolution (4-40 revolutions per min) over a 5 min period. Each mouse was placed on a rotating drum, and the latency (in seconds) of each subject to fall from the rod was measured. Mice were given one training trial and 2 experimental trials for 2 days (FIG. 4A).

Single IP administration of compound 3 (20 mg/kg) also increased movement coordination in wild type C57/BL6 PD mice treated with 6-OHDA. 6-OHDA-HCl dissolved in PBS containing 0.02% ascorbic acid at a concentration of 3.7 mg/ml was injected intracerebrally and unilaterally at the level of MFB in anaesthetized mice. This regimen leads to 70%-80% dopaminergic cell death within 2 weeks after surgery. Motor coordination and balance were tested using a Rota-Rod treadmill (Ugo Basile, Comerio, Italy), set with accelerating revolution (4-40 revolutions per min) over a 5 min period. Each mouse was placed on a rotating drum, and the latency (in seconds) of each subject to fall from the rod was measured. Mice were given one training trial and 2 experimental trials for 2 days (FIG. 4B).

IP administration of compound 3 (20 mg/kg) repeated for 14 days did not induce dyskinesias with abnormal involuntary movements (AIMs) in wild type C57/BL6 PD mice treated with 6-OHDA. 6-OHDA-HCl dissolved in PBS containing 0.02% ascorbic acid at a concentration of 3.7 mg/ml was injected intracerebrally and unilaterally at the level of MFB in anaesthetized mice. This regimen leads to 70%-80% dopaminergic cell death within 2 weeks after surgery. 6-OHDA mice were left to recover after the surgery for 3 weeks. At that time, the degree of dopaminergic degeneration was assessed for each mouse by the number of the apomorphine-induced turns it makes contralateral to the lesion. This test was used to create a relatively homogeneous group of mice with approximately equal degrees of neurodegeneration. This group was subsequently separated in 3 groups that were treated daily with an IP injection of either saline, L-DOPA, or compound 3 (20 mg/kg) for 14 days. At that time, abnormal involuntary movements were evaluated for each of the 3 groups. Briefly, each mouse was observed individually for 1 minute every 20 minutes for 3 hours, starting 20 minutes after LDOPA/compound 3/saline administration. The AIMs were classified into three different subtypes based on their topographic distribution: (i) axial AIMs, i.e., twisting of the neck and upper body towards the side contralateral to the lesion; (ii) orolingual AIMs, i.e., jaw movements and contralateral tongue protrusion; (iii) forelimb AIMs, i.e., purposeless movements of the contralateral forelimb. The mice were evaluated using this test a total of 3 times during the chronic L-DOPA treatment period. It was concluded that IP administration of the compound of the invention compound 3 20 mg/kg) repeated for 12-17 days did not induce dyskinesias with abnormal involuntary movements (AIMs). In contrast, treatment of mice with L-DOPA, used as reference, induced dyskinesias with abnormal involuntary movements (AIMs) within 7 days (FIG. 4C).

X. Single IP Administration of Compound 3 (20 mg/kg) Increased Forced Swim Test Performance in Wild Type C57/BL6 PD Mice The chronic mild stress (CMS) procedure was applied semi randomly to each mouse and consisted of a variety of unpredictable mild environmental, social and physical stressors, including confinement in a small tube (1 hours), an empty cage without sawdust (15 hours), water and food deprivation (15 hours), food restriction (approximately 50 mg of food pellets, 3 hours), cage tilted at 45° (1-3 hours), damp sawdust (approximately 200 ml of water per 100 g of sawdust, 3 hours), paired housing in damp sawdust (18 hours), reversal of the light/dark cycle, 2-hour light/dark succession every 30 minutes, as well as light (15-17 hours) and dark (4-6 hours). Compound 3 (2×10 mg/kg spaced 2 hours apart) or vehicle control (Ethanol:PG:Saline, 10:30:60), was administered IP to mice. 4 hours after the last injection, mice were evaluated in the Porsolt forced swim test. Mice aged 7-10 weeks were placed individually in a Plexiglas cylinder (diameter, 15 cm) containing water (14-16 cm, 22-24.5° C.) The mice were videotaped for 5 min. Recorded behaviors for "floating" (the mouse is completely still in the water, except for isolated movements to right itself) and "swimming" (movement of all four legs with body aligned horizontally in the water) were measured (in seconds) for each mouse. Administration of compound 3 increased the swimming time by 31.7% and decreased the floating time by 61.48% (FIG. 4D, 4E).

XI. IP Administration of Compound 3 (10 mg/kg) Protected Wild Type C57/BL6 PD Mice from Midbrain Dopaminergic Neuronal Loss IP administration of the compound of the invention compound 3 (10 mg/kg) repeated for 15 days every 12 hours protected wild type C57/BL6 PD mice treated with 6-OHDA from midbrain dopaminergic neuronal loss. 6-OHDA-HCl dissolved in PBS containing 0.02% ascorbic acid at a concentration of 3.7 mg/ml was injected intracerebrally and unilaterally at the level of MFB in anaesthetized mice. This regimen leads to 70%-80% dopaminergic cell death within 2 weeks after surgery. 6-OHDA-treated mice were left to recover after the surgery for 3 weeks. At that time, the degree of dopaminergic degeneration was assessed for each mouse by the number of the apomorphine-induced turns it makes contralateral to the lesion. This test was used to create a relatively homogeneous group of mice with approximately equal degrees of neurodegeneration. Mice were anaesthetized deeply with $CO_2$ and perfused intracardially with ice-cold phosphate buffer (PBS; pH 7.2) and subsequently with 4% paraformaldehyde in 0.1M PBS (PFA). Brains were quickly removed, post-fixed in PFA overnight at 4° C., cryoprotected in 15% sucrose in 0.1M PBS for 24 hours and in 30% sucrose in 0.1M PBS for 24 hours at 4° C., frozen, and stored at −80° C. until sectioning. Free-floating cryostat-cut sections (30 µm) were collected using a Bright cryostat at −20° C. at the levels of striatum (AP, 0.2 mm from bregma) and the entire midbrain (AP, −5.6 mm from bregma) (Franklin and Paxinos, 2001). As previously described (Jackson-Lewis et al., 2000), sections first were quenched for 10 minutes in 3% $H_2O_{2/10}$% methanol. Then sections were pre-incubated with 10% goat serum for 1 hour and incubated with a polyclonal anti-TH antibody (1:2,000; Calbiochem, San Diego, Calif.) for 48 h in 4° C., followed by incubation with biotinylated anti-rabbit antibody (1:1500; Vector Laboratories, Burlingame, Calif.) in 1% goat serum for 1 hour and avidin-biotin peroxidase complex for 1 hour in RT (ABC Elite; Vector Laboratories). Staining was visualized using DAB (Sigma; St. Louis, Mo.) as a chromogen (Vila et al., 2000). The specificity was tested in adjacent sections with the primary or the secondary antibody omitted. The sections were stained with cresyl violet (Nissl staining) as described previously (Franklin and Paxinos, 2001), and then dehydrated in graded ethanols and cover slipped. Total numbers of TH- and Nissl-positive cells were counted in both hemi-brainstems by using stereological methods (see, e.g., Jackson-Lewis et al., 2000). The total number of TH-positive and Nissl-stained SNpc were counted by using the optical fractionator, an unbiased method of cell counting that is not affected by either the volume of reference or the size of the counted neurons. The SNpc was delineated by using a computer-assisted image analysis system (Jackson-Lewis et al., 2000). TH- and NissI-stained neurons were counted in every fourth section throughout the entire extent of the SNpc. The standard mouse atlas was used as an anatomical reference (Franklin and Paxinos, 2001). Compound 3 treatment increased the number of surviving neuronal bodies by 256.55% (FIGS. 5A and 5B).

Figure 5:
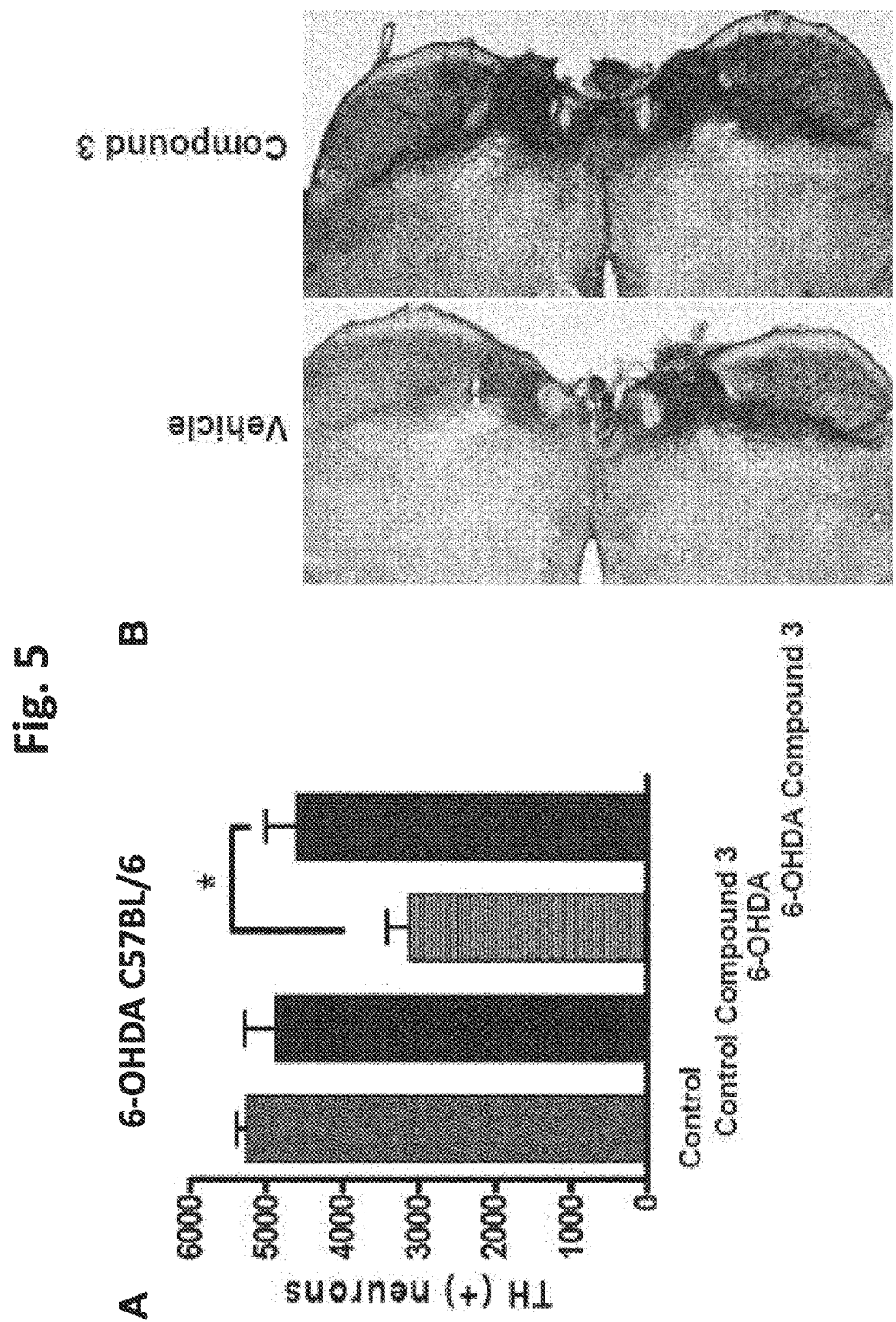
FIGS. 5A-5E show the biochemical activity of compounds evaluated in neuroprotection experiments.
Figure 5:
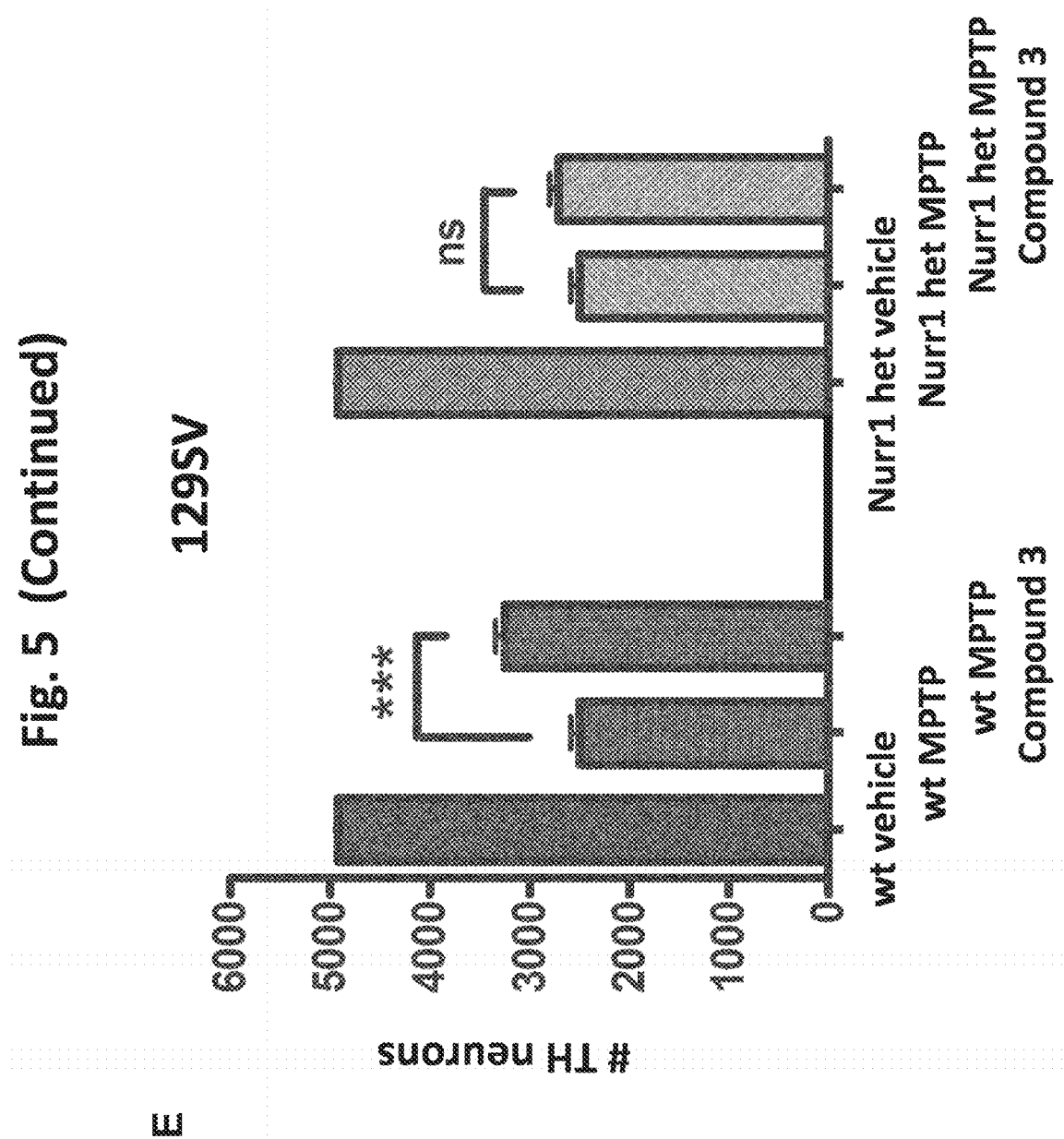
Figure 6:
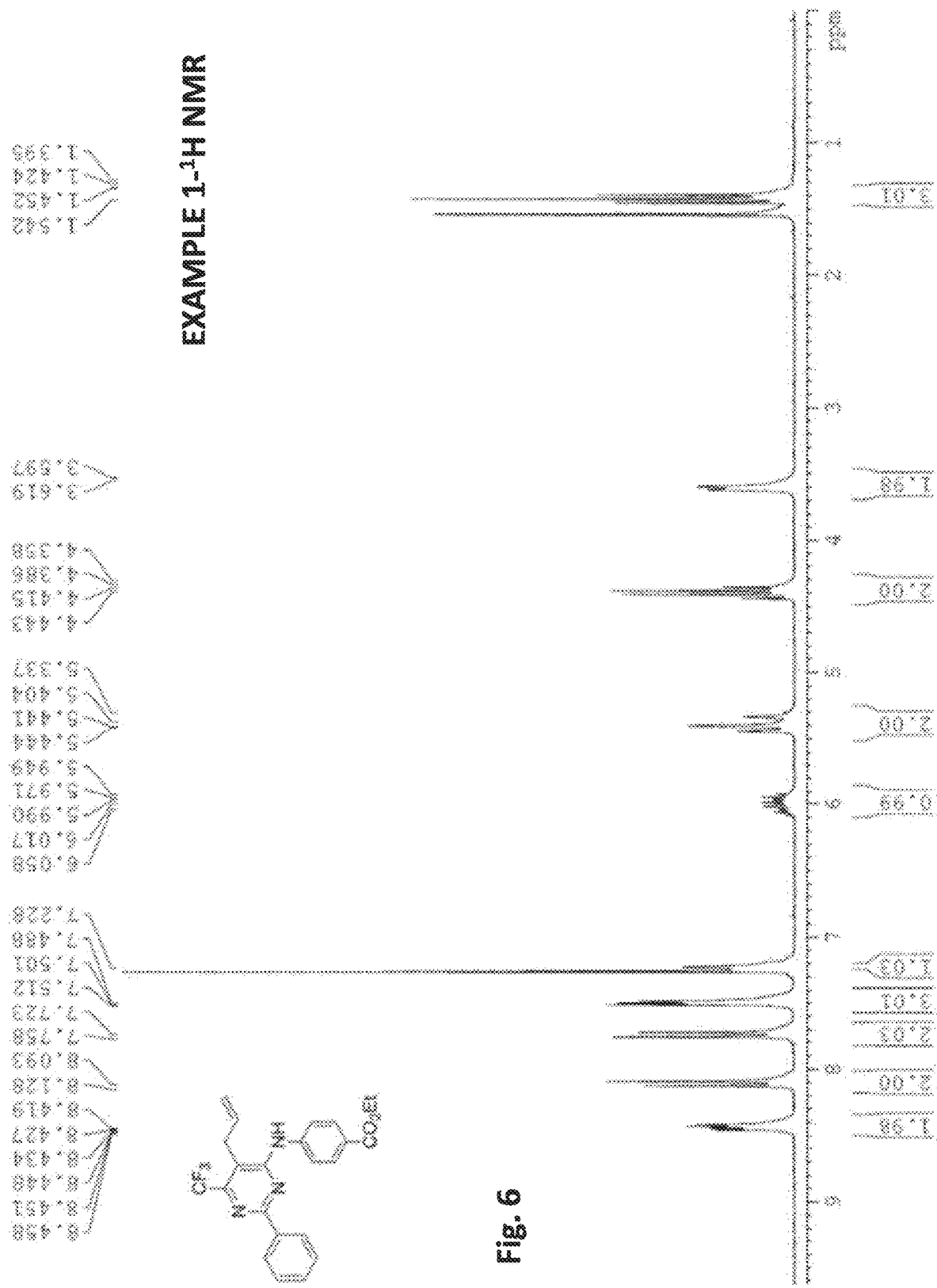
FIGS. 6-66 show $^1$H and $^{13}$C NMR spectra for example compounds 1-46. Example numbers listed in these figures refer to the number assigned to each compound in Table 1.
Figure 7:
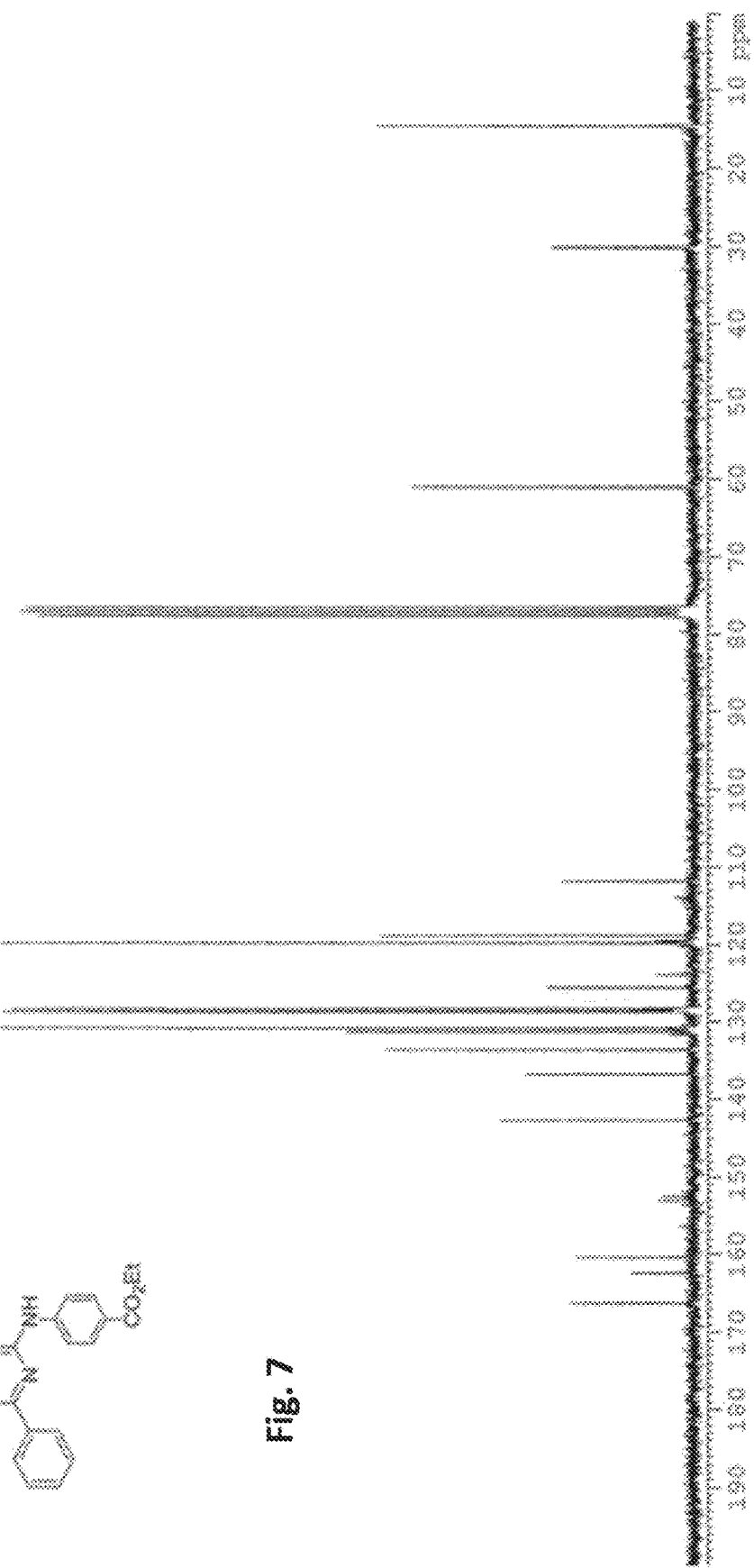
Figure 8:
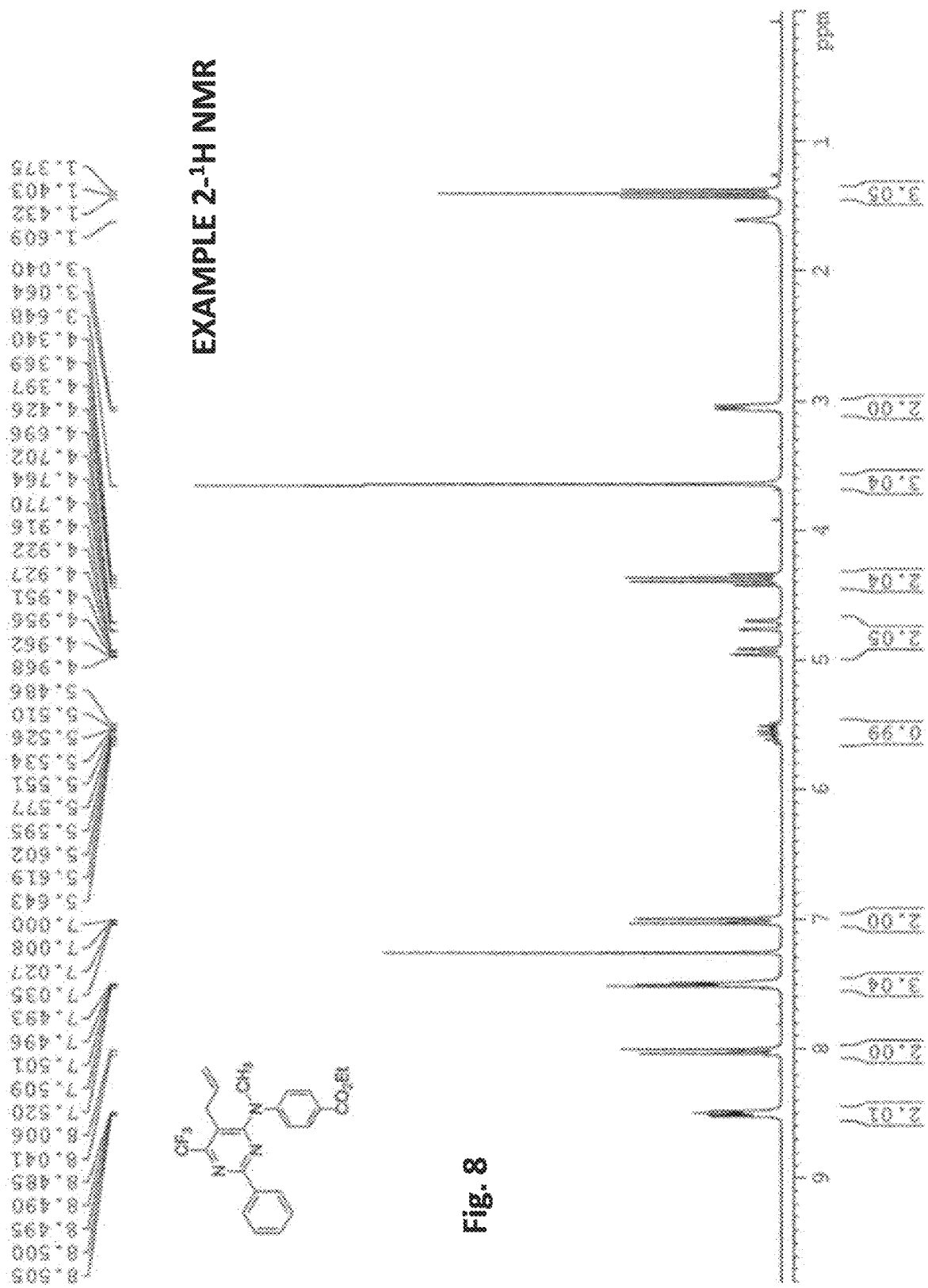
Figure 10:
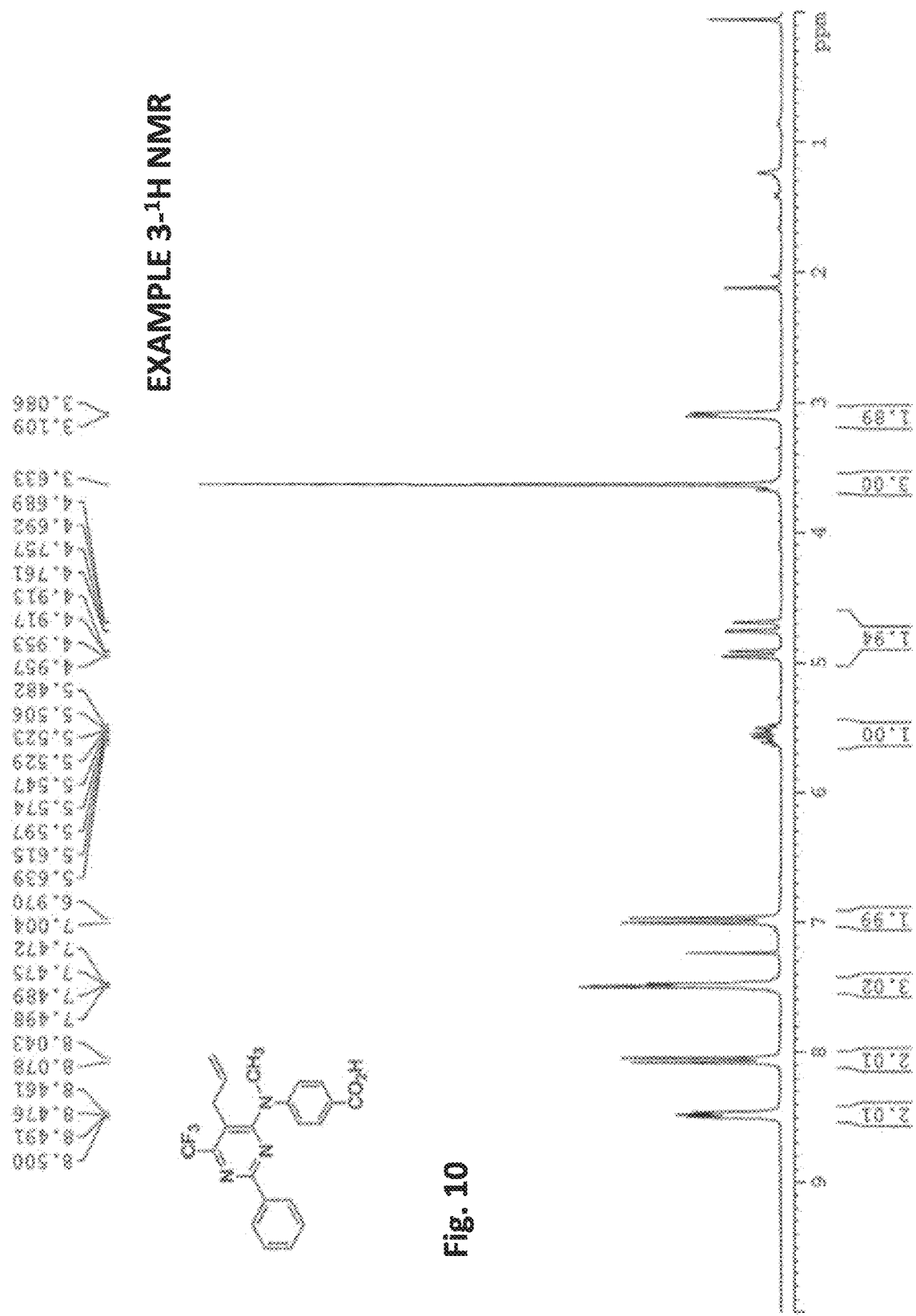
Figure 11:
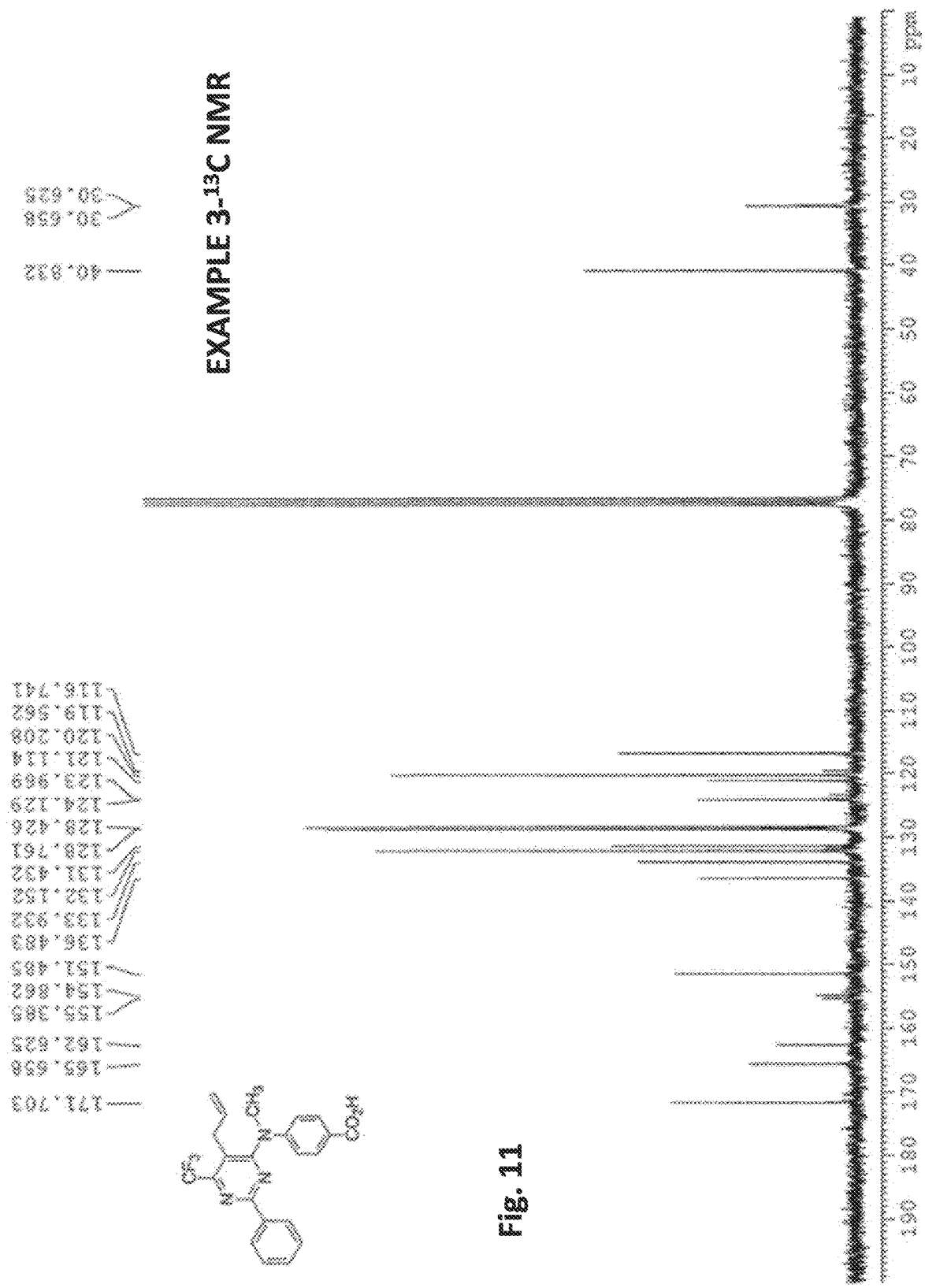
Figure 12:
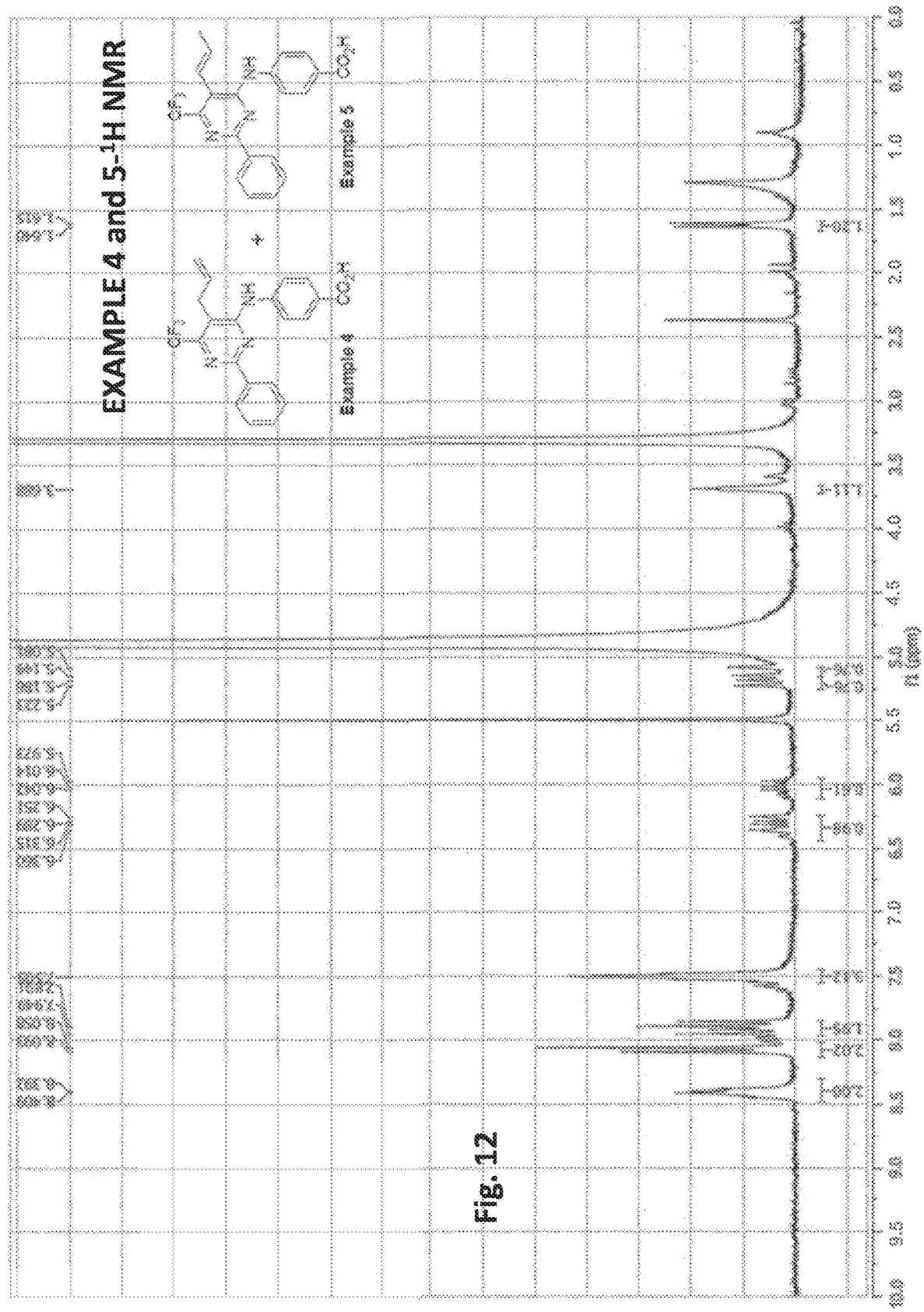
Figure 13:
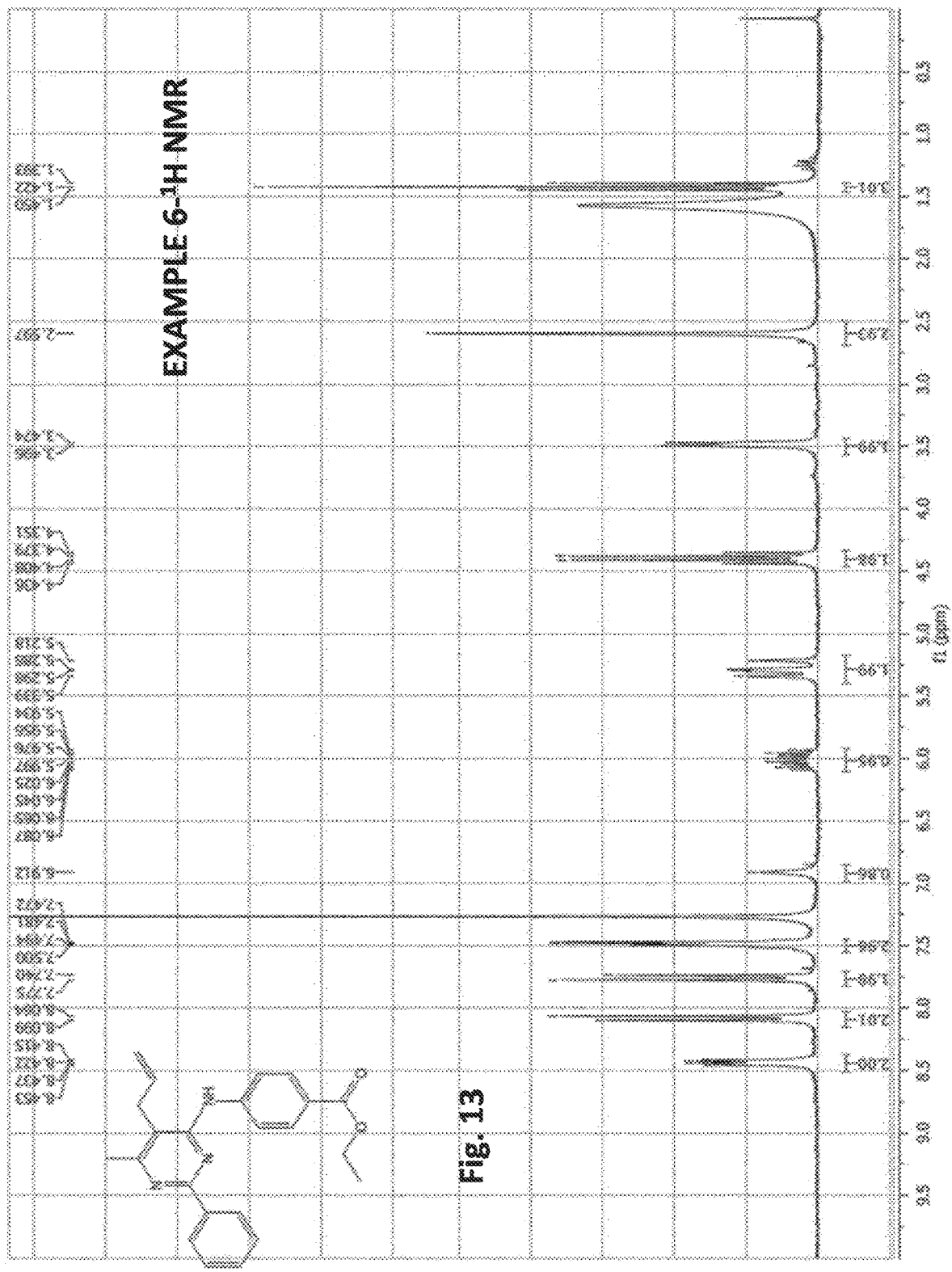
Figure 14:
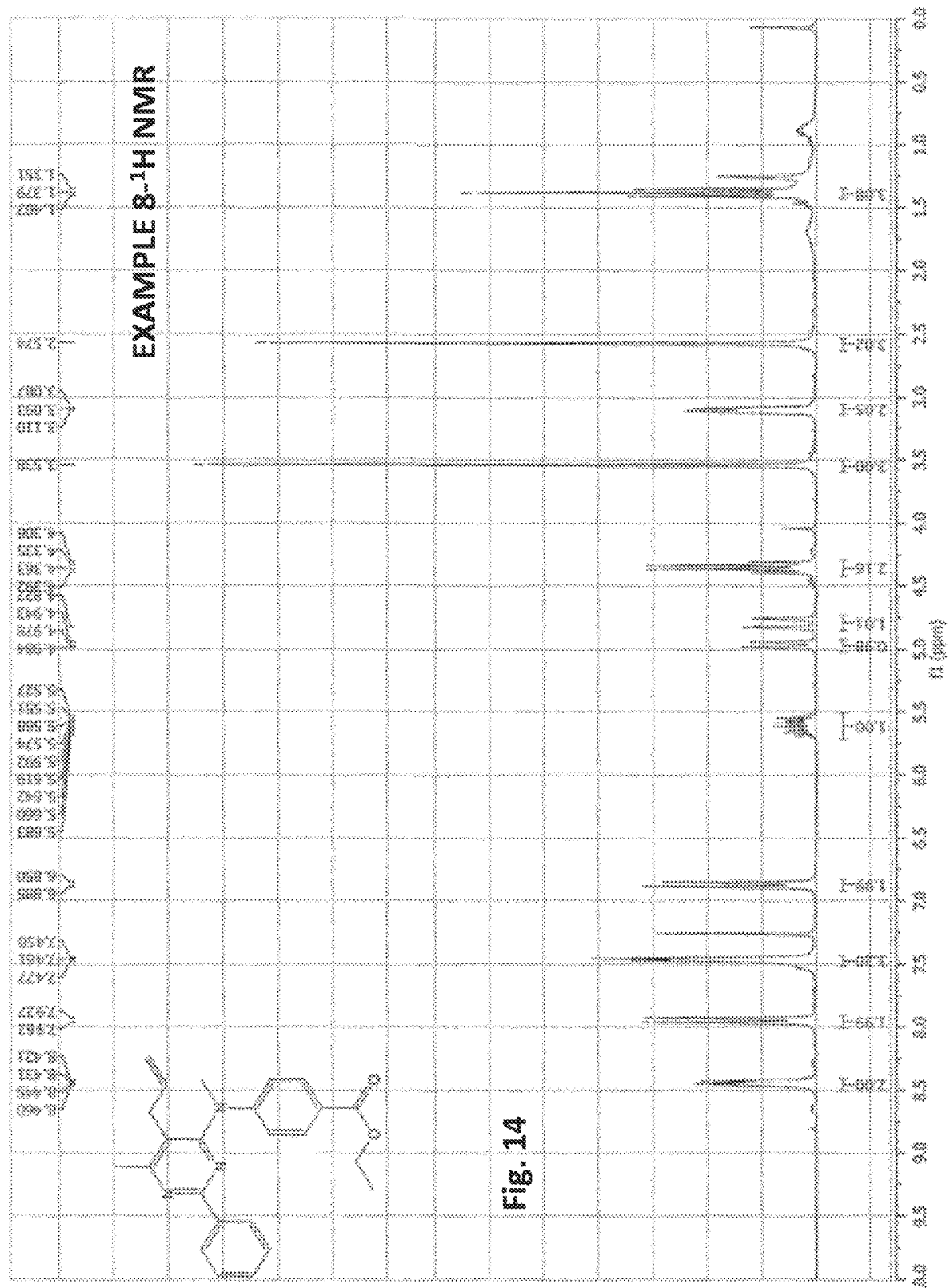
Figure 15:
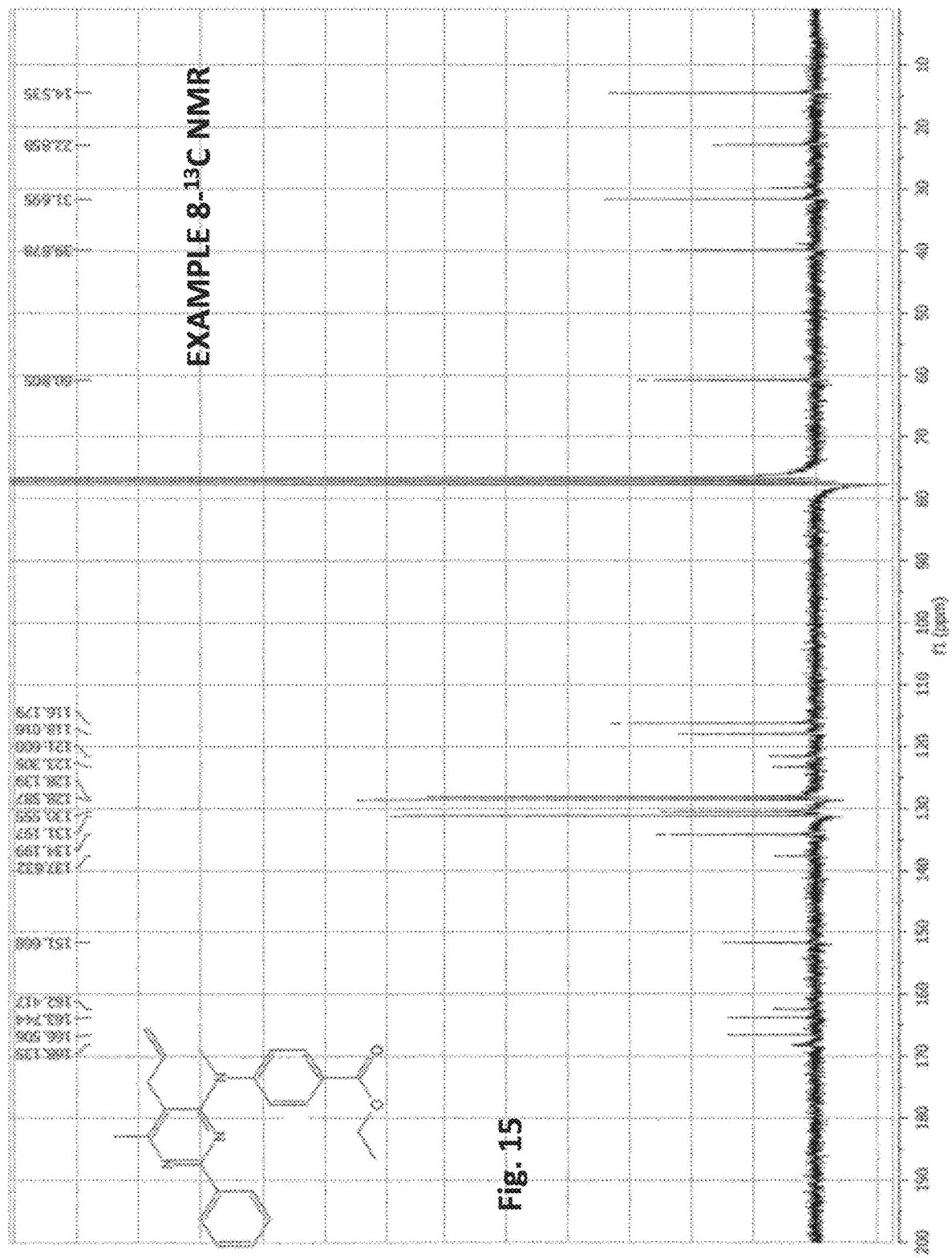
Figure 16:
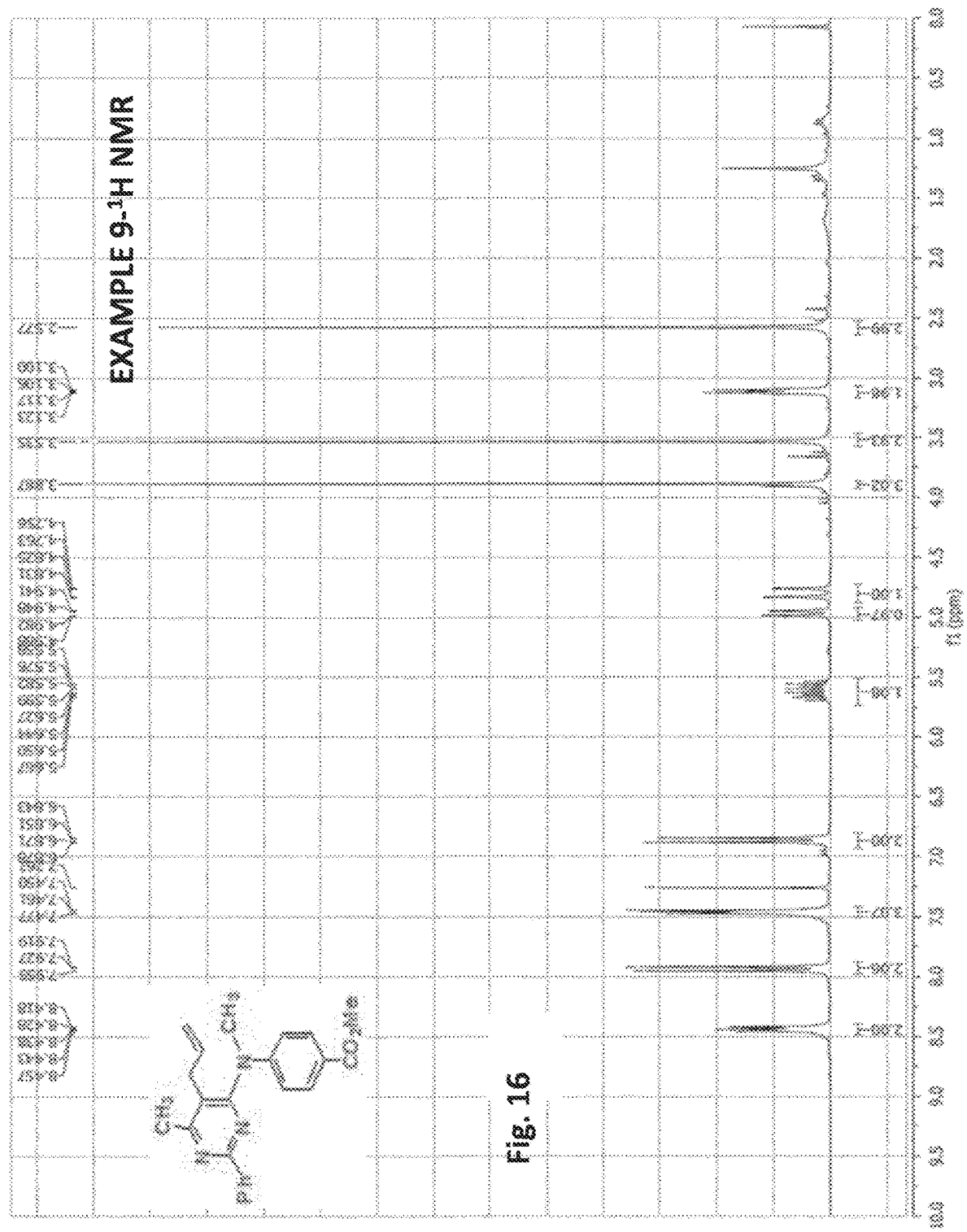
Figure 17:
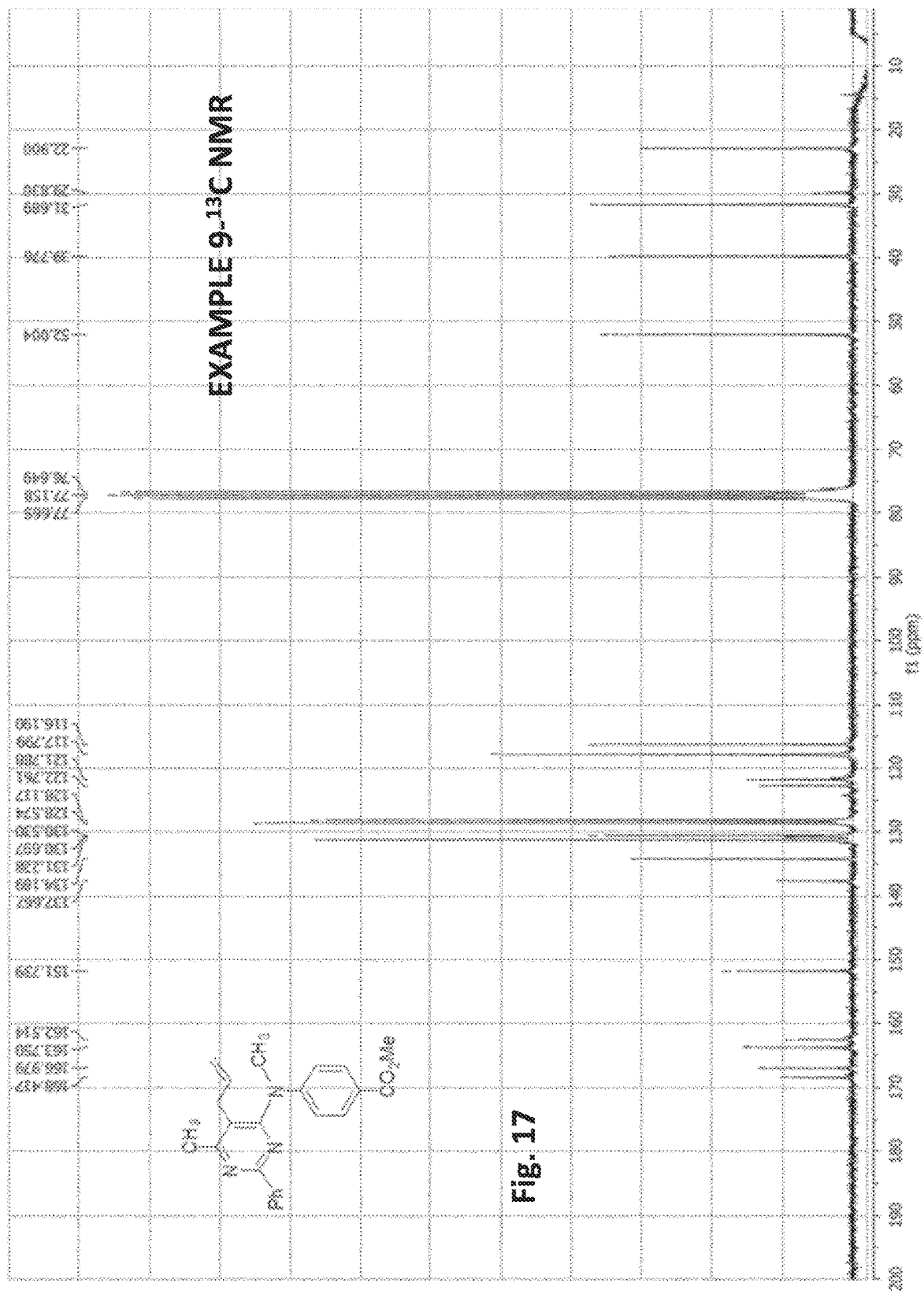
Figure 18:
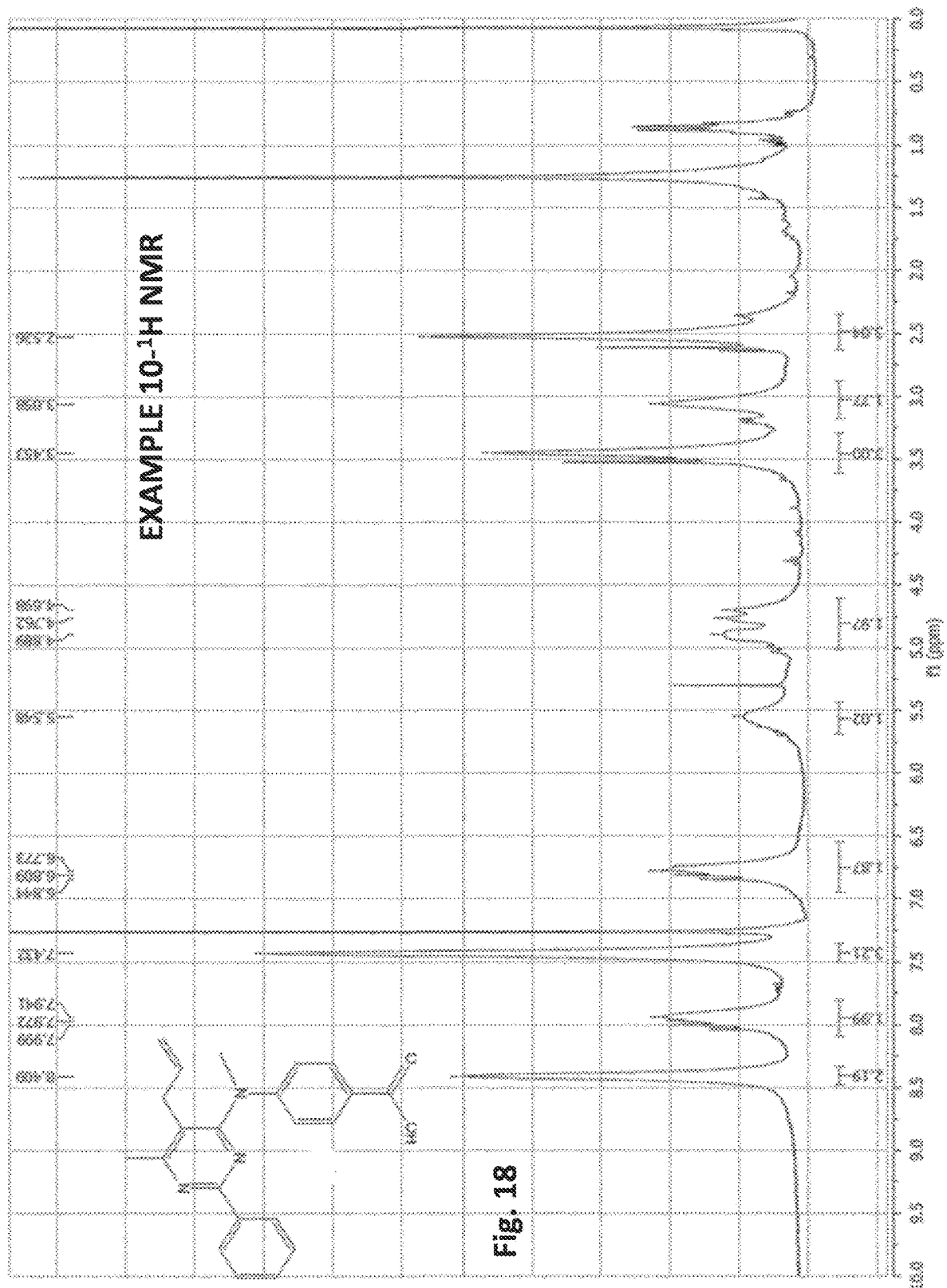
Figure 19:
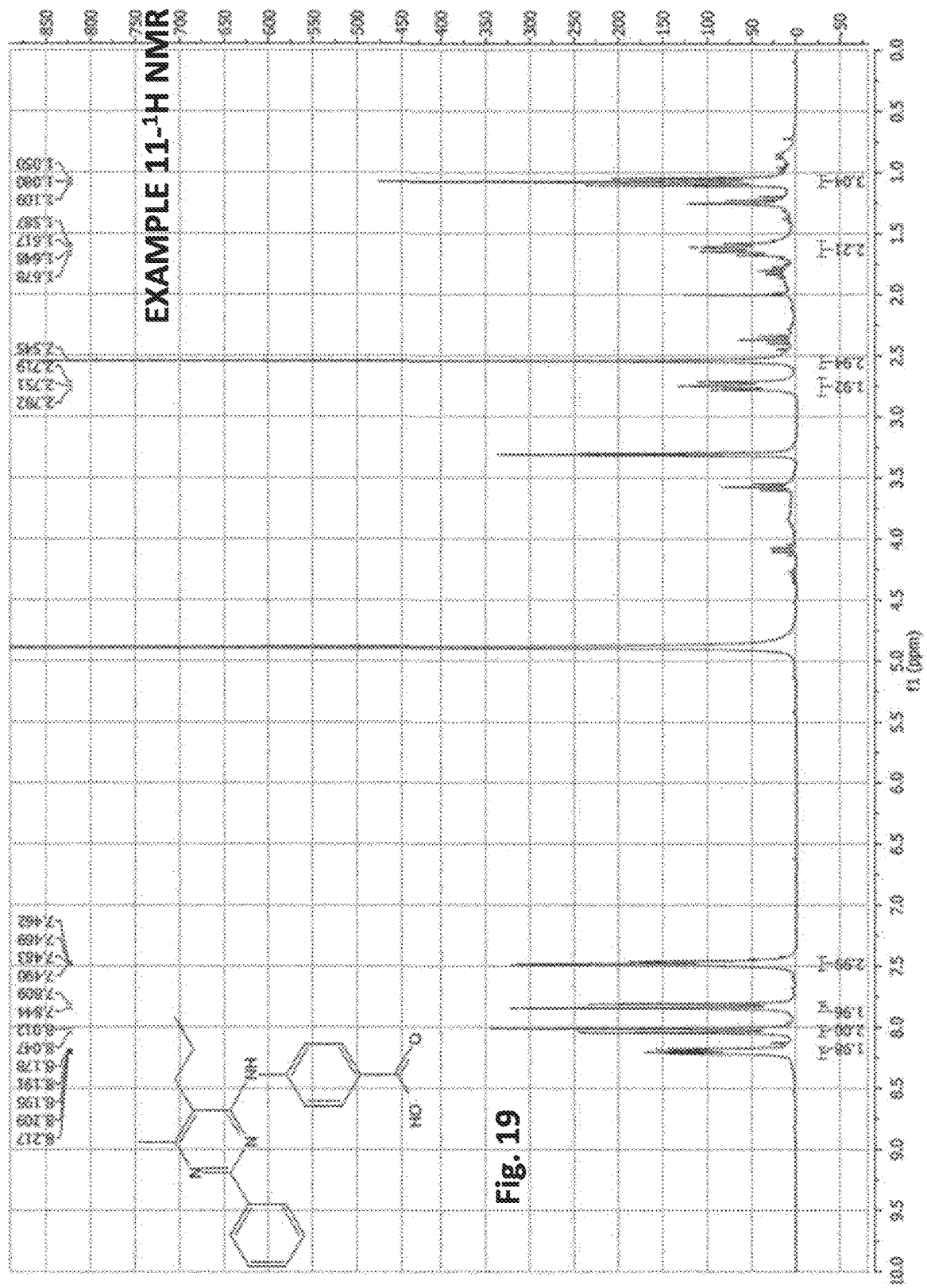
Figure 20:
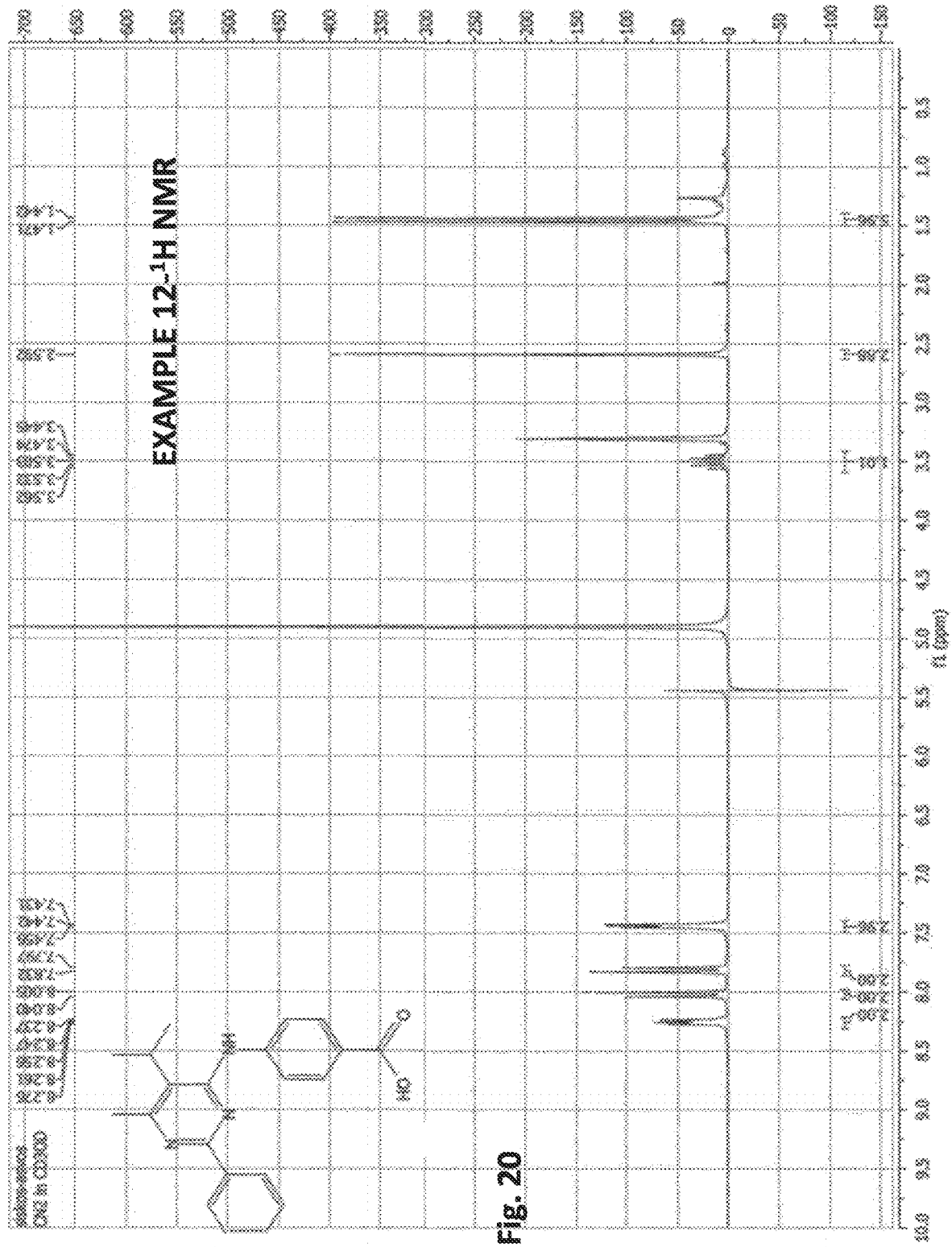
Figure 21:
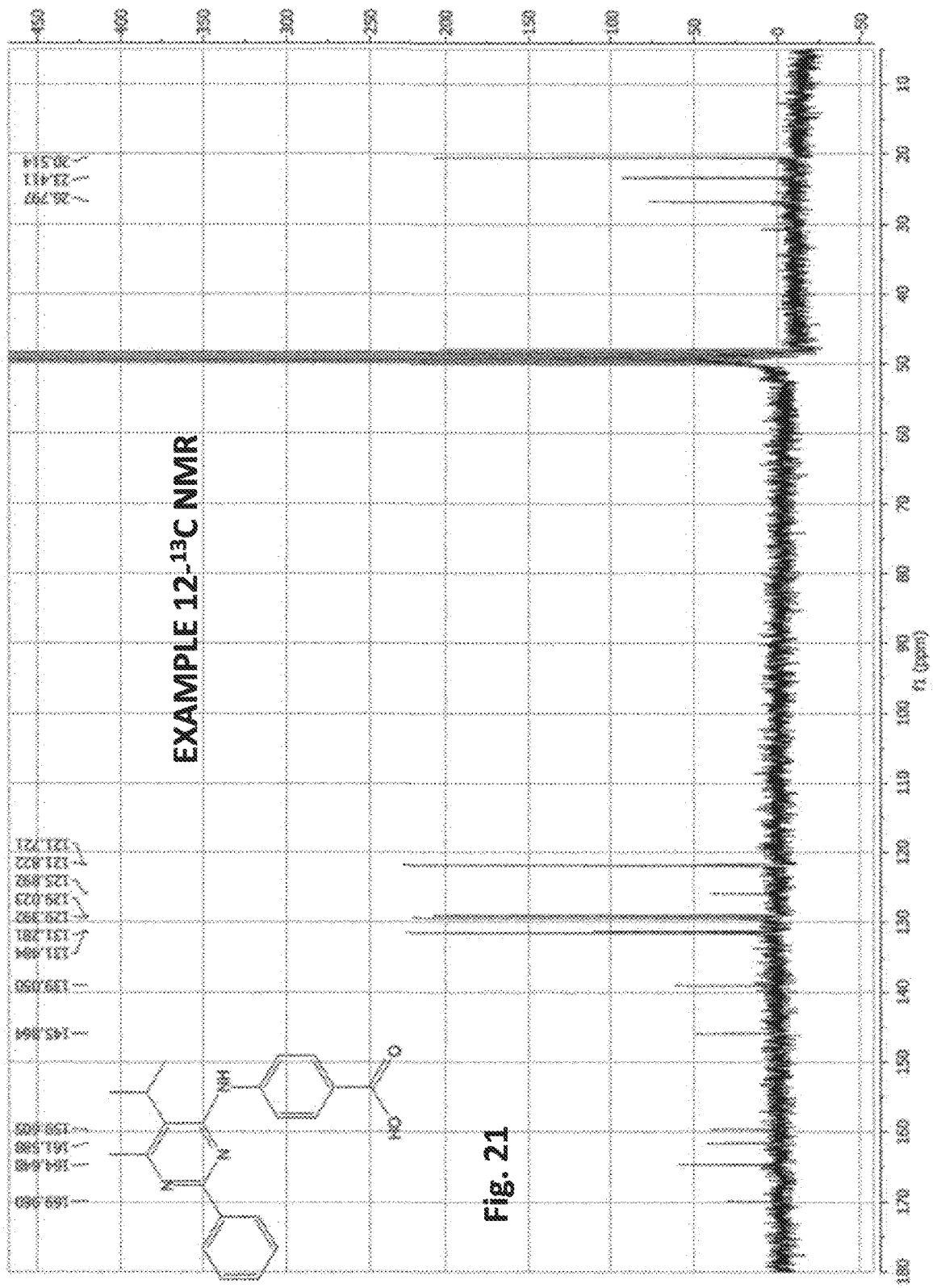
Figure 22:
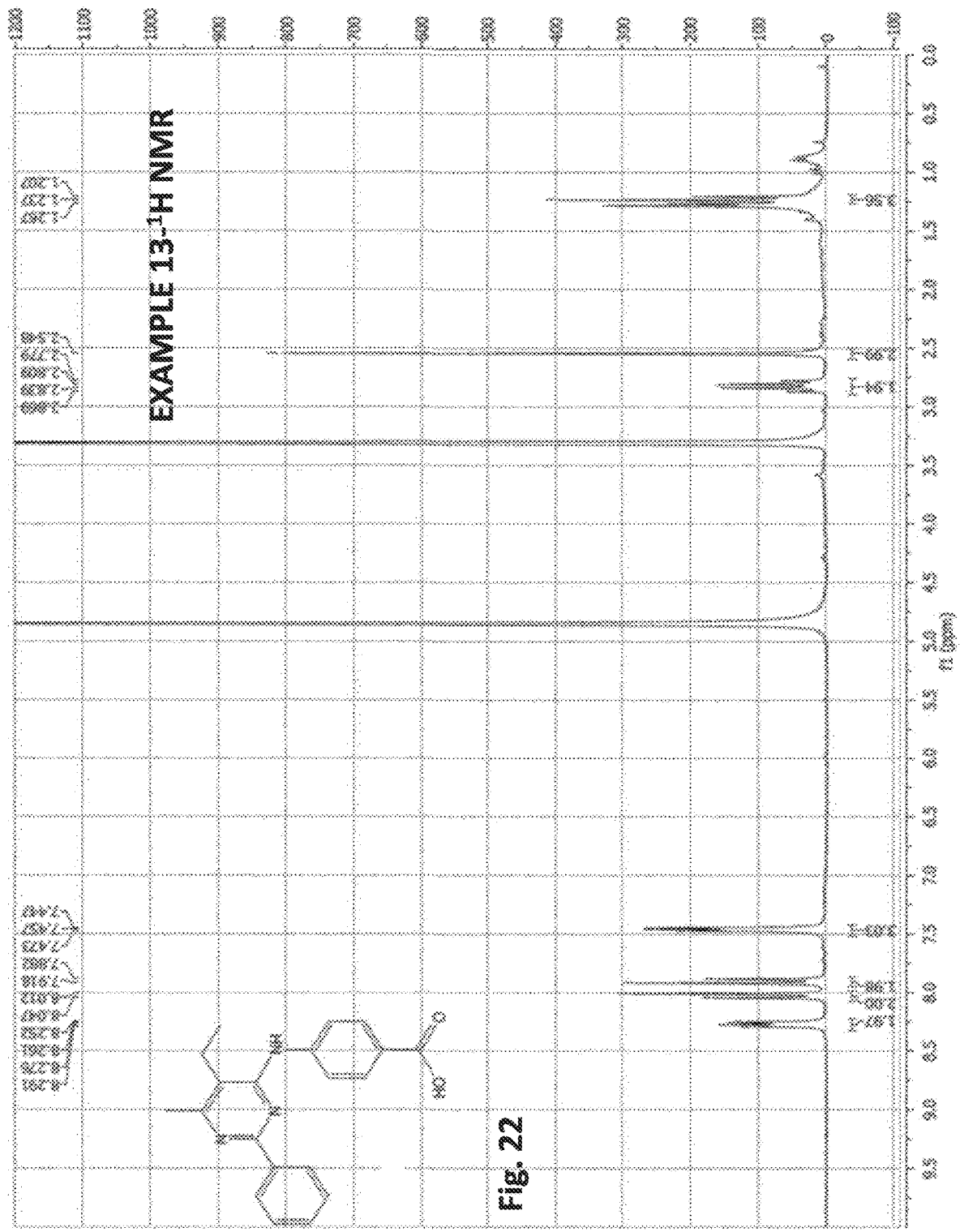
Figure 23:
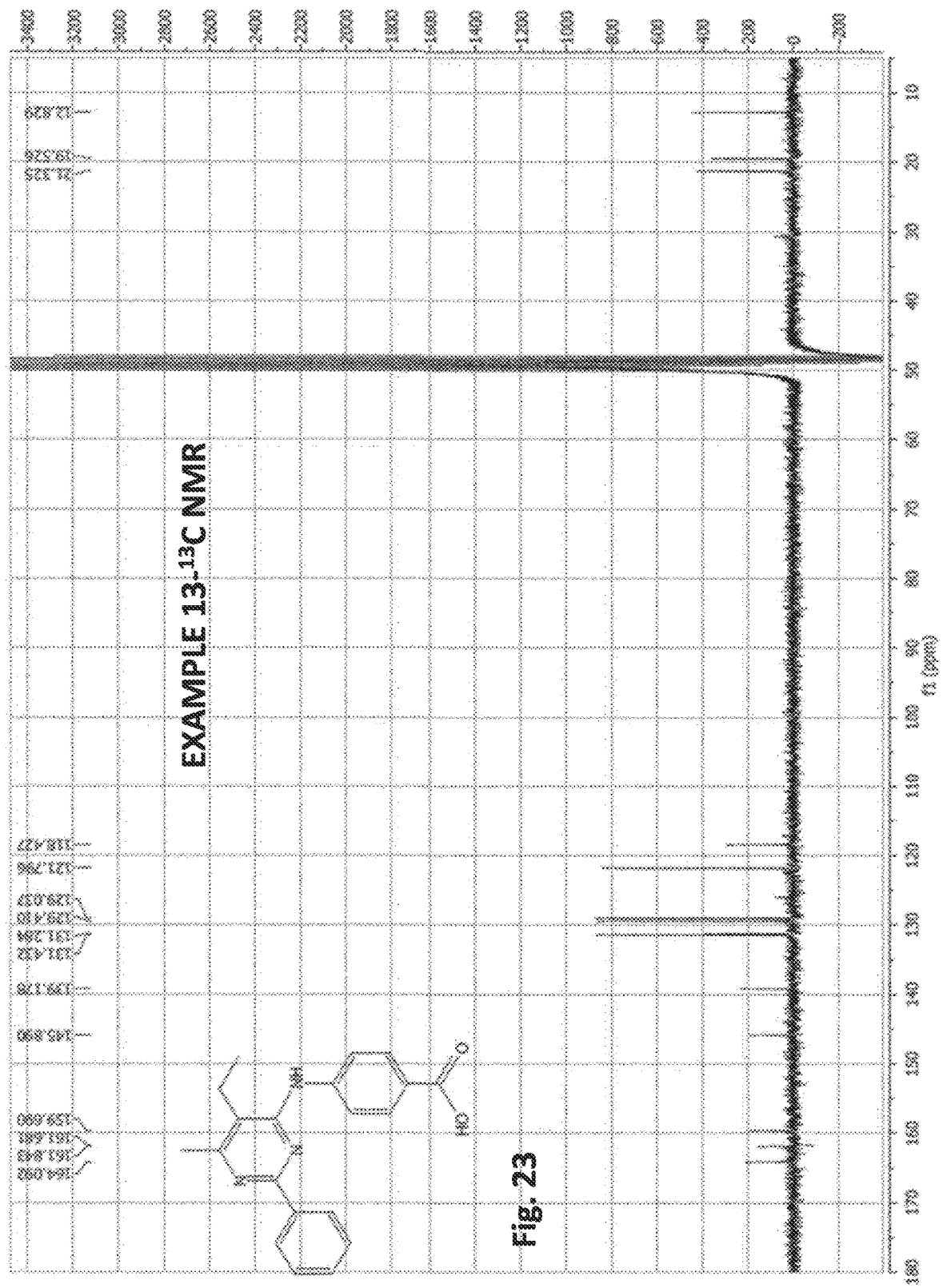
Figure 24:
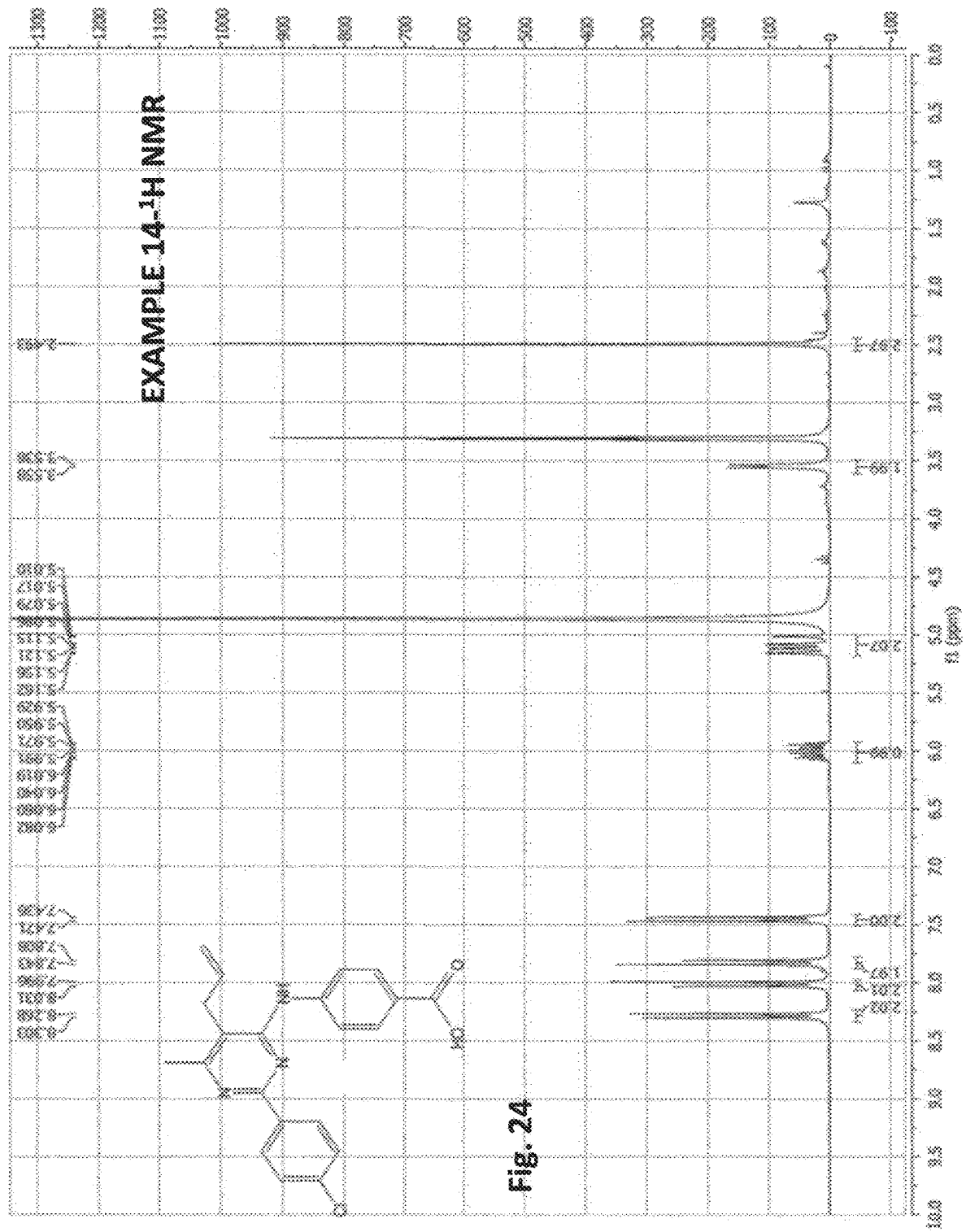
Figure 25:
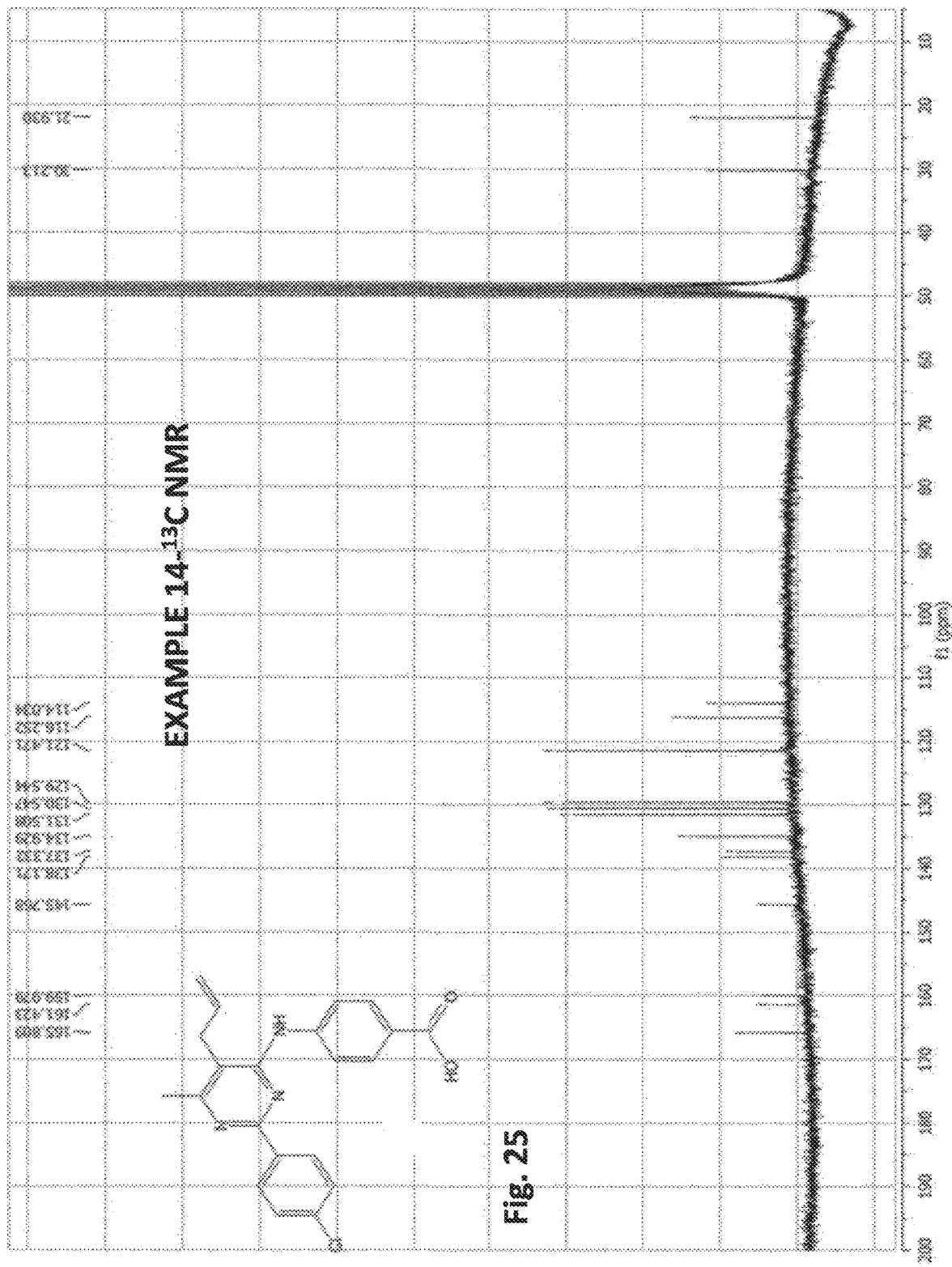
Figure 26:
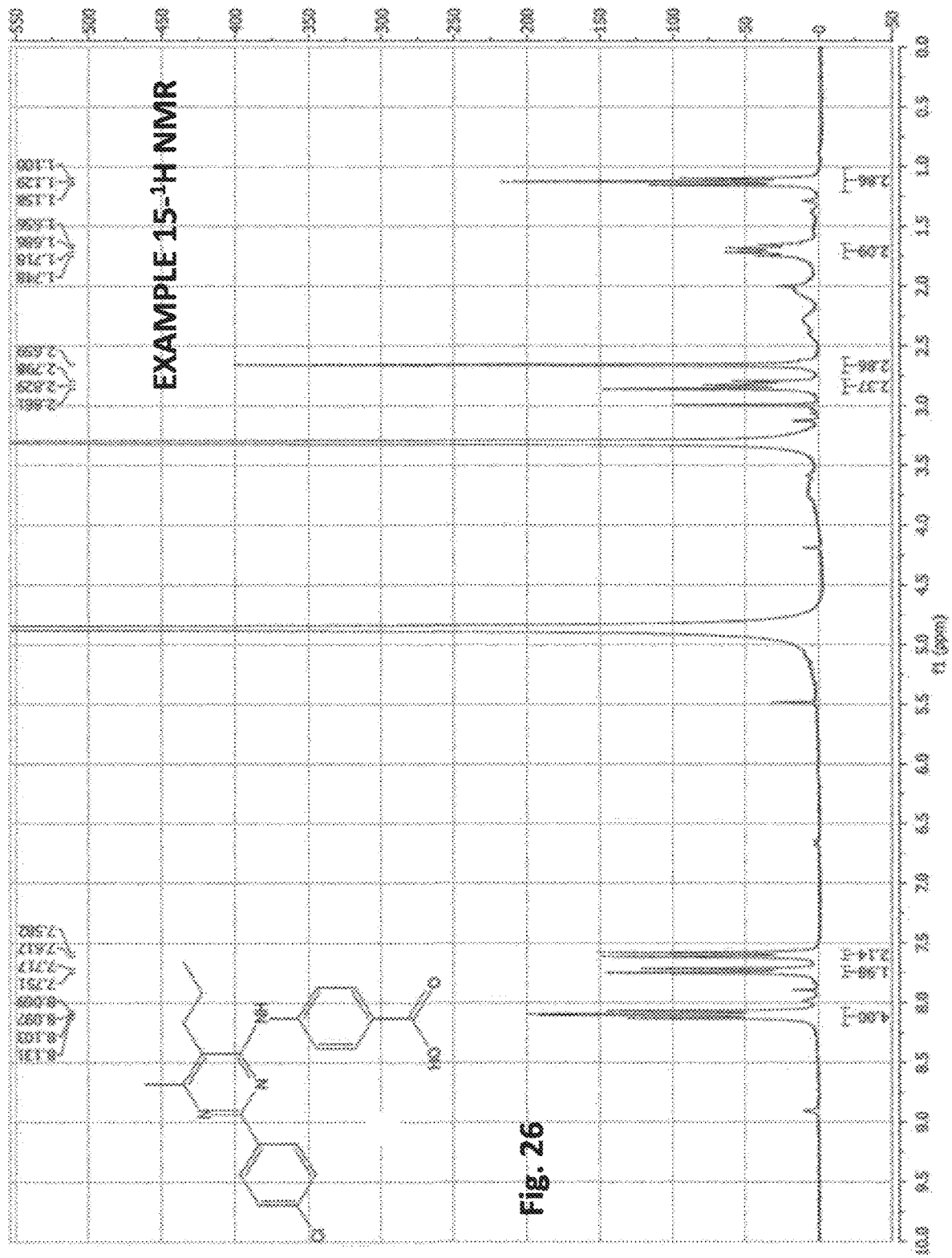
Figure 27:
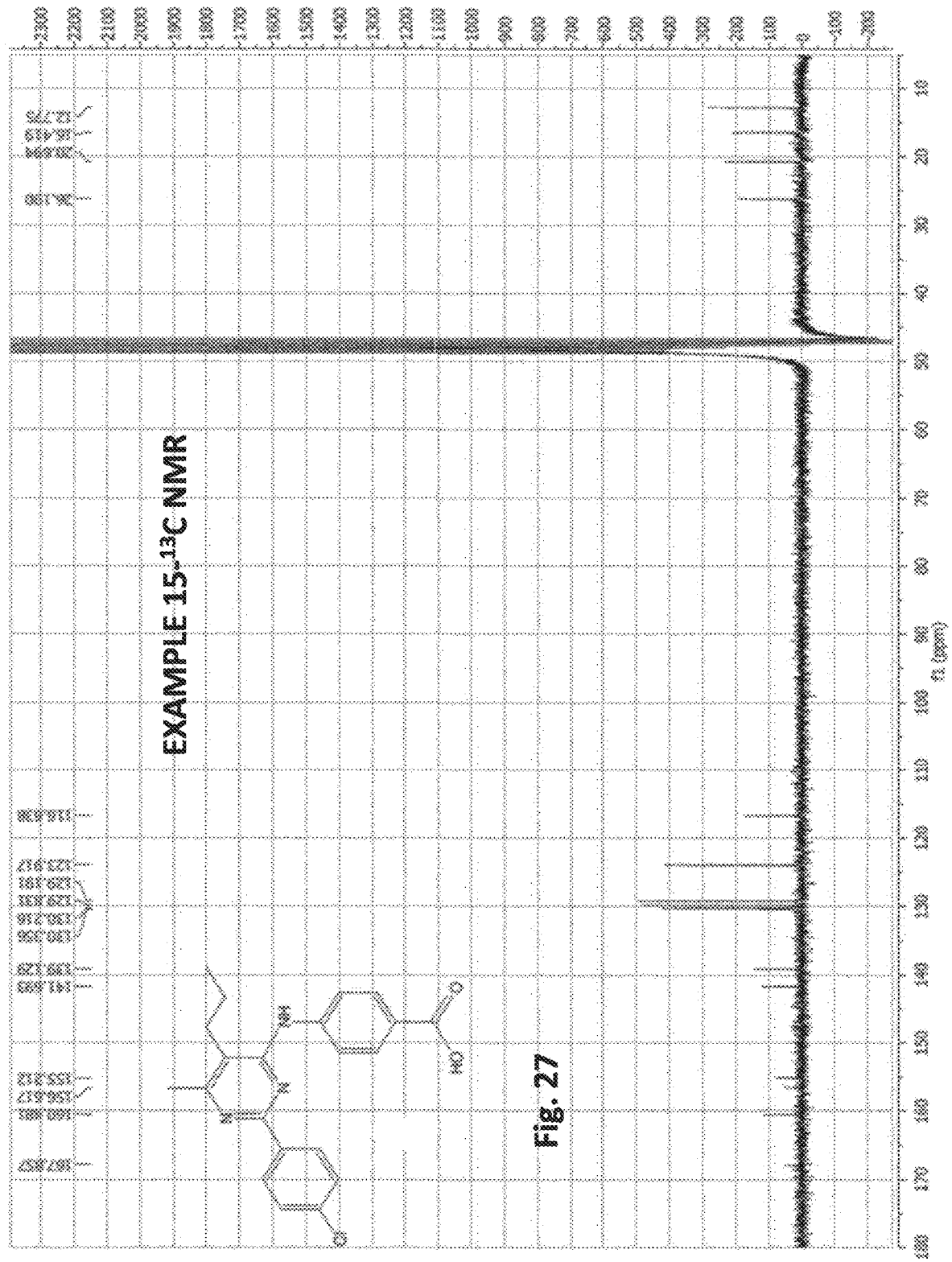
Figure 28:
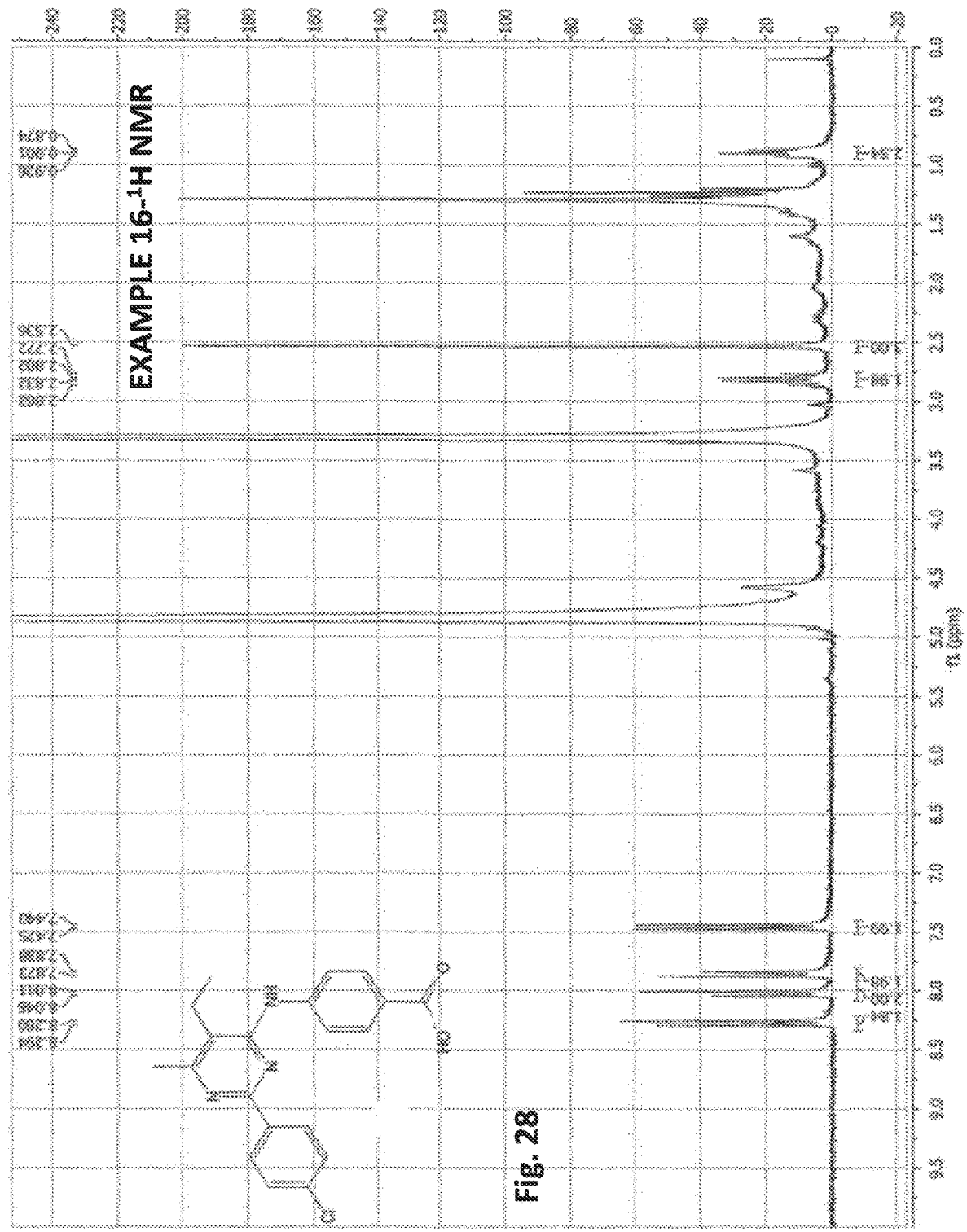
Figure 29:
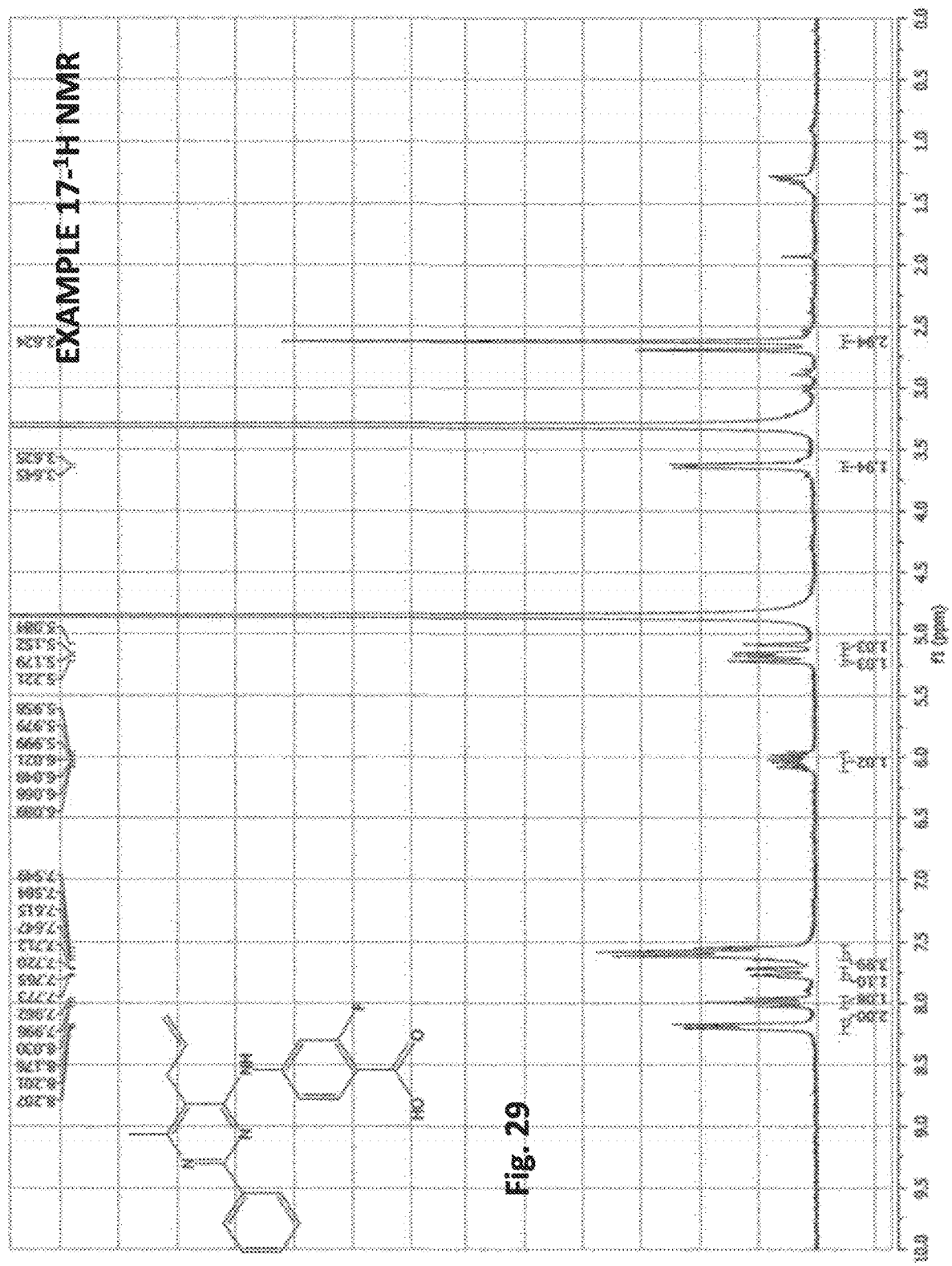
Figure 30:
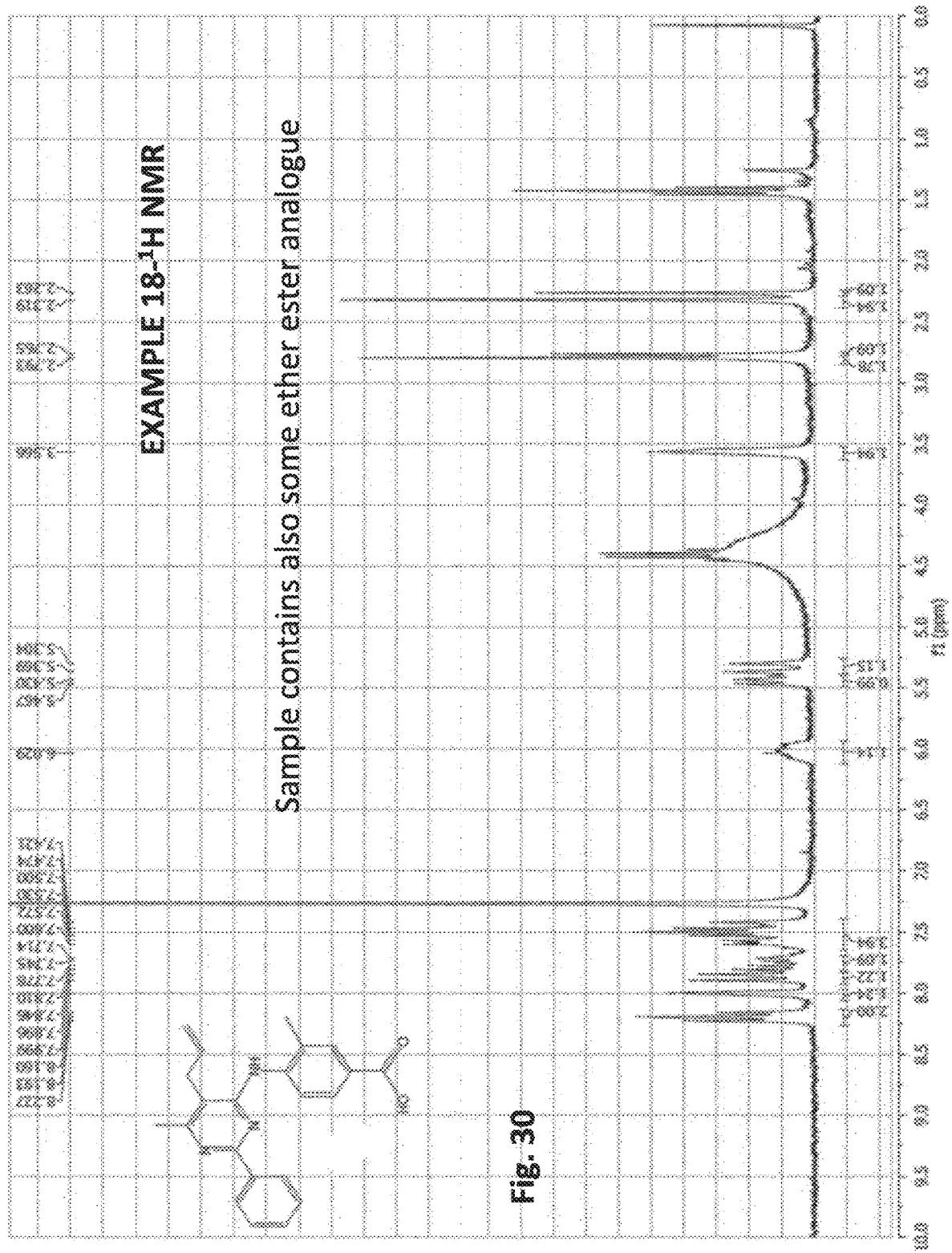
Figure 31:
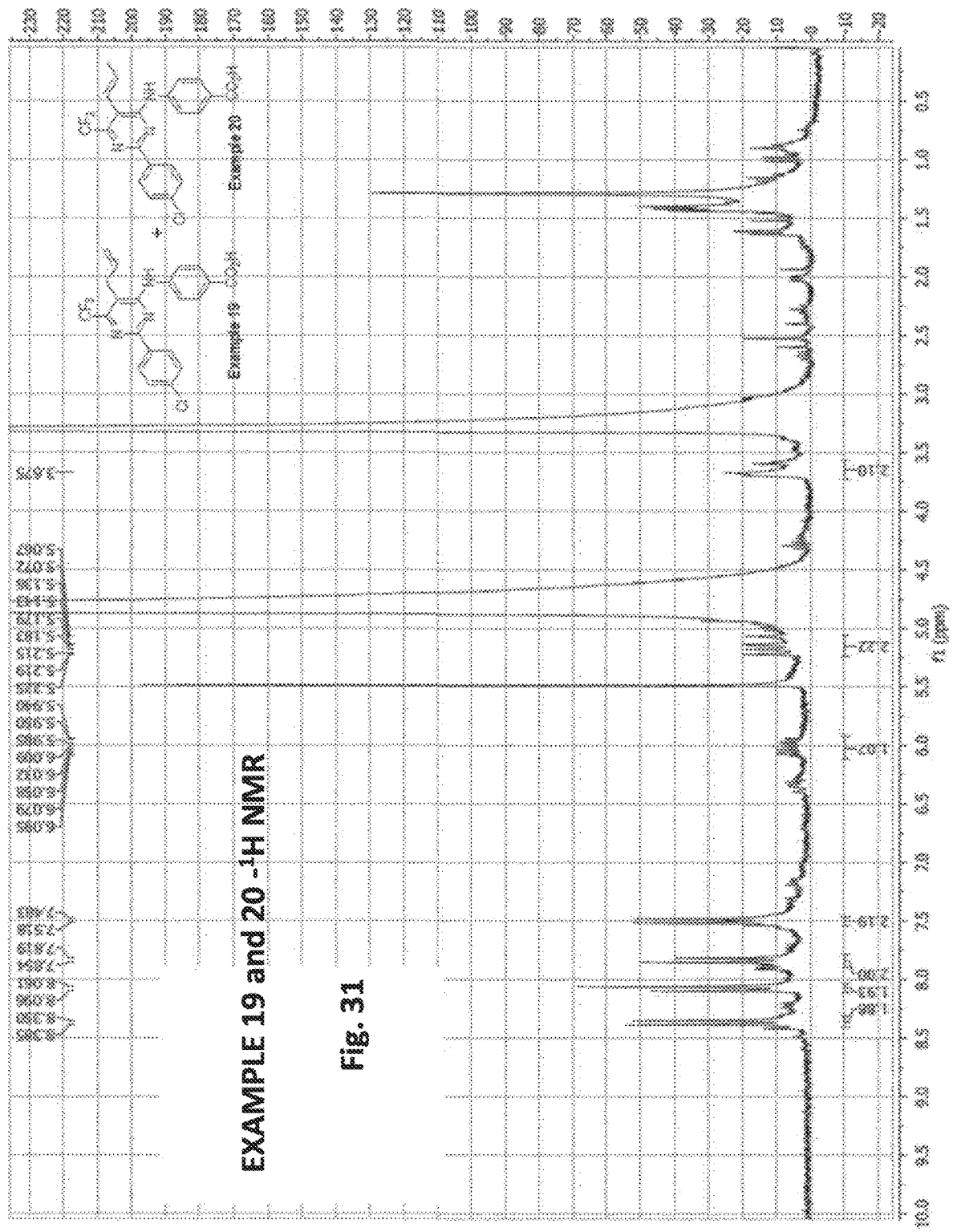
Figure 32:
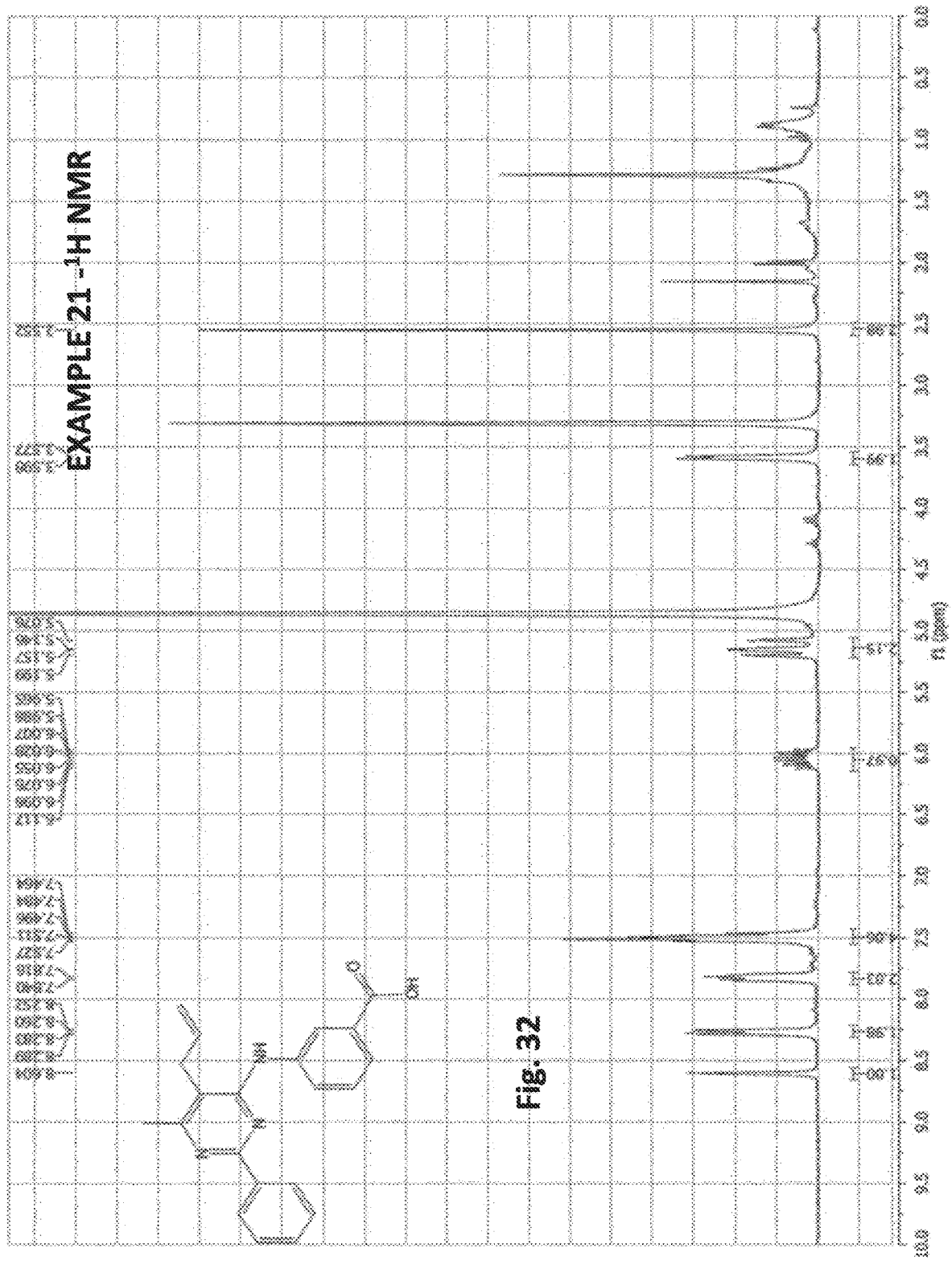
Figure 33:
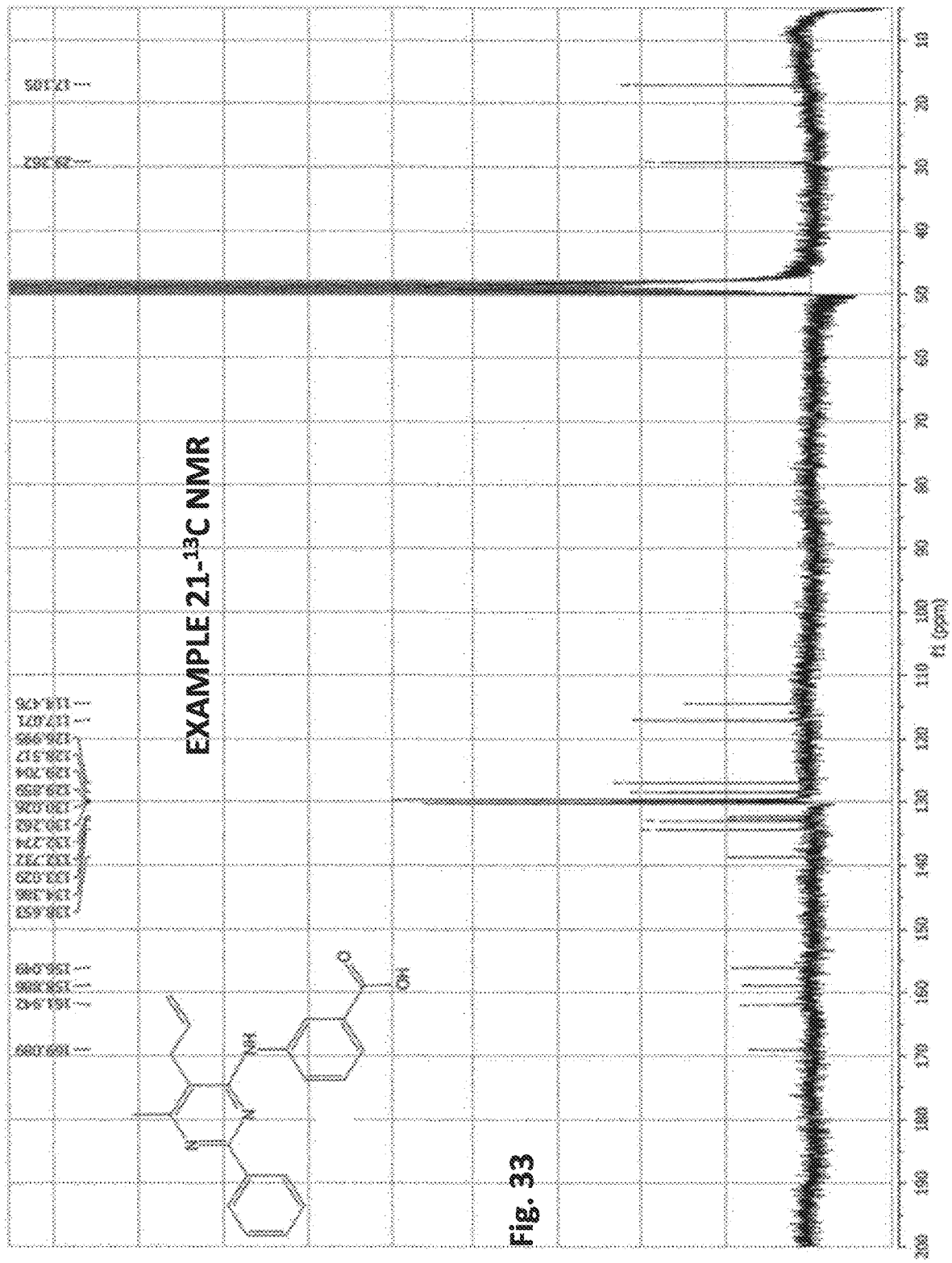
Figure 34:
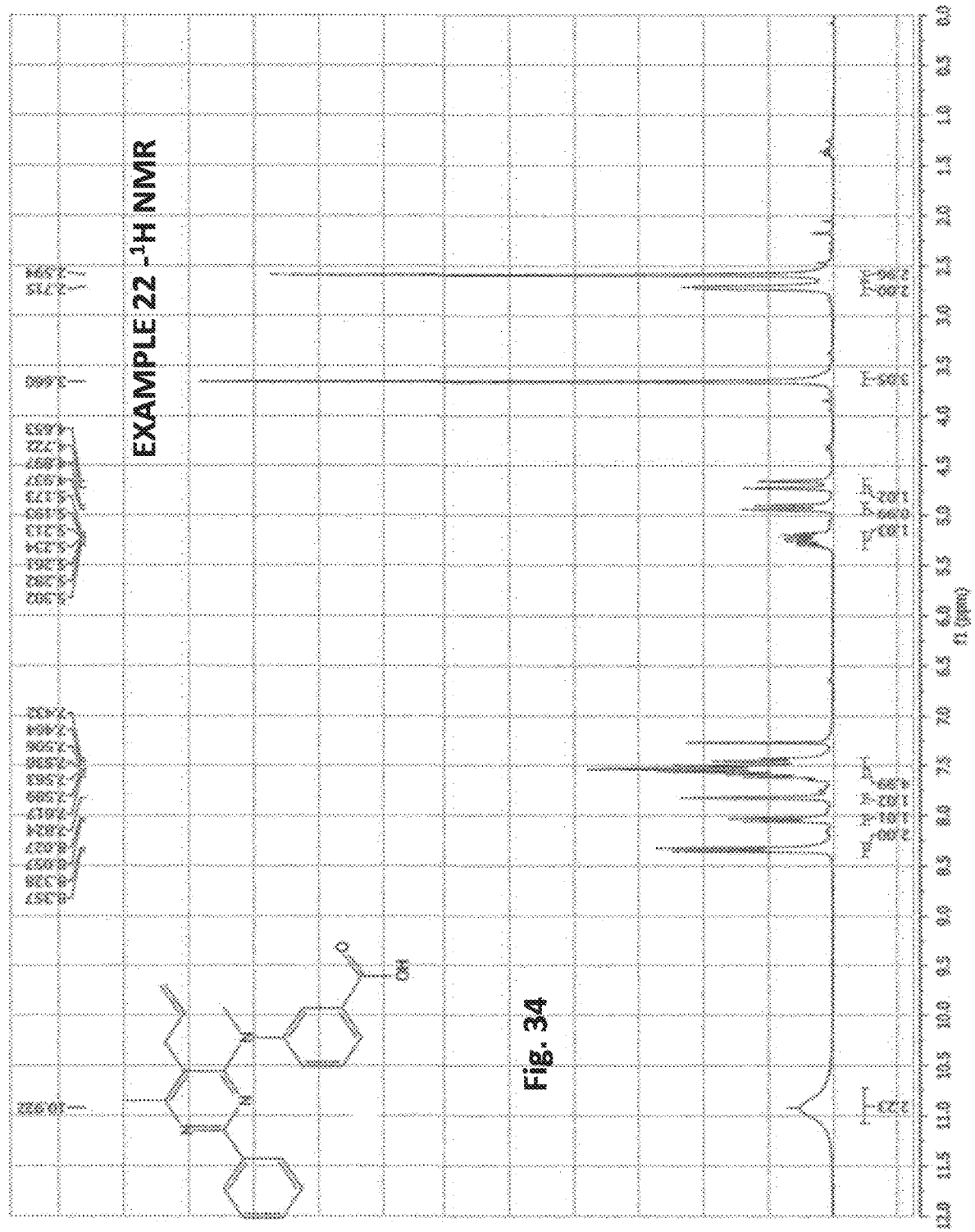
Figure 35:
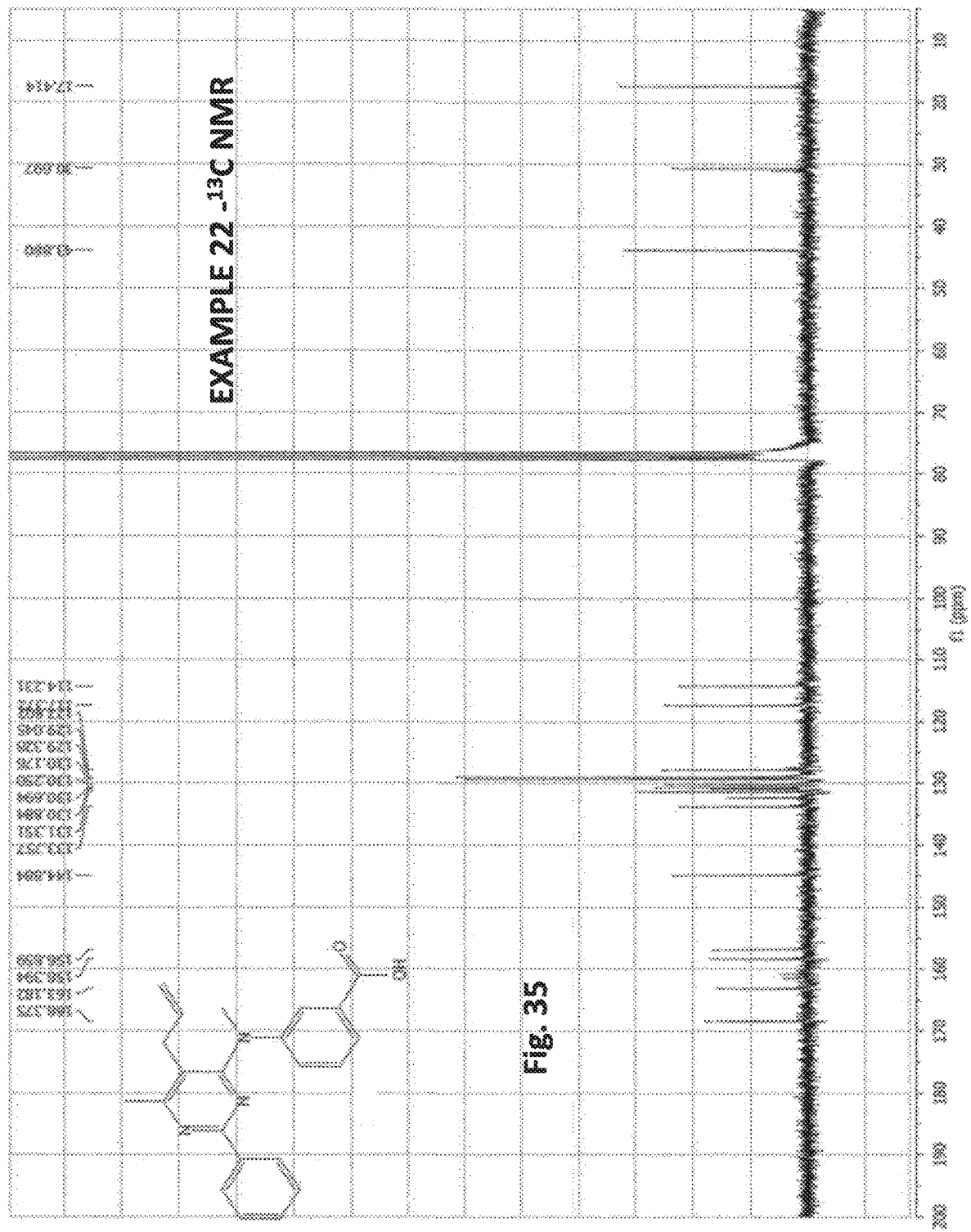
Figure 36:
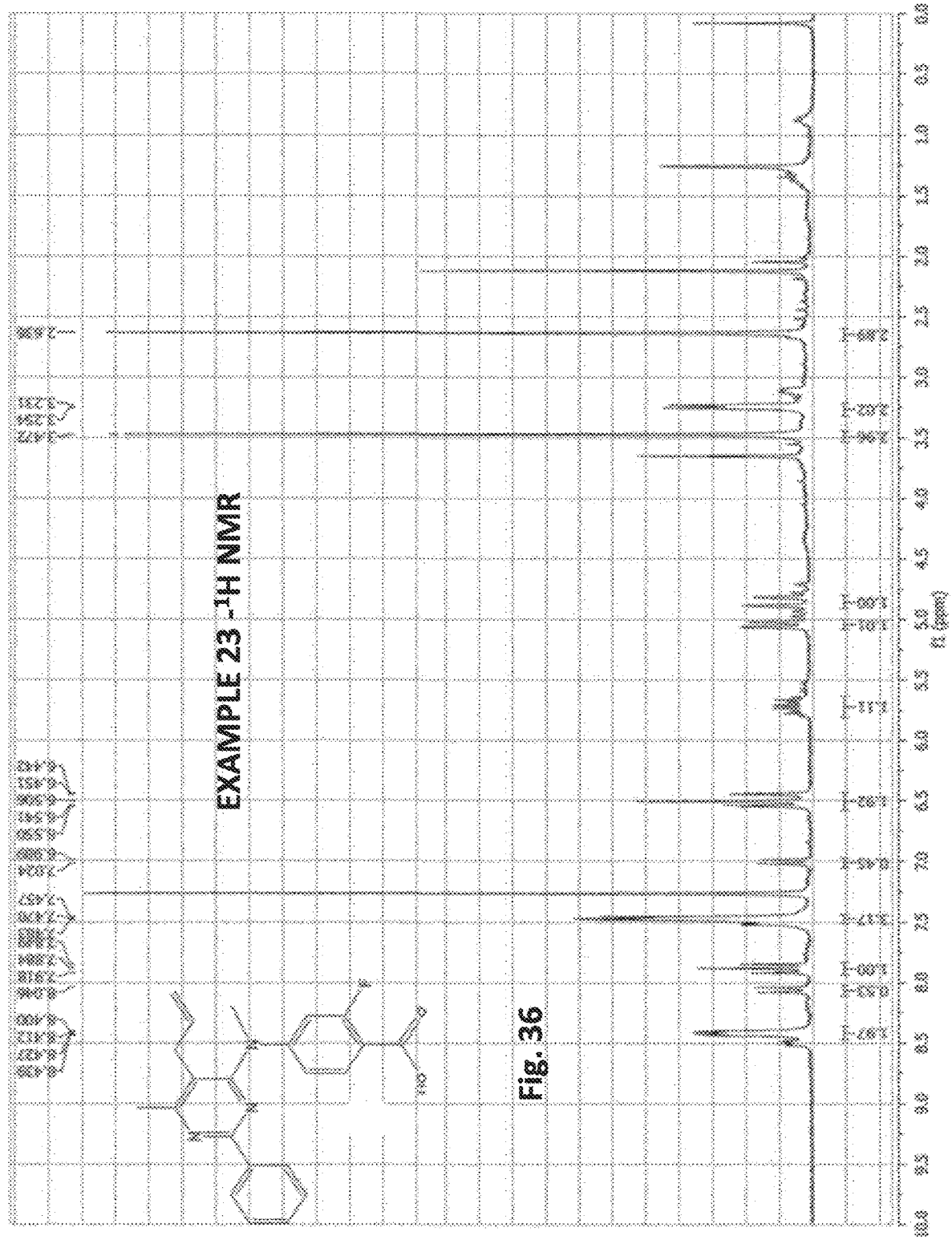
Figure 37:
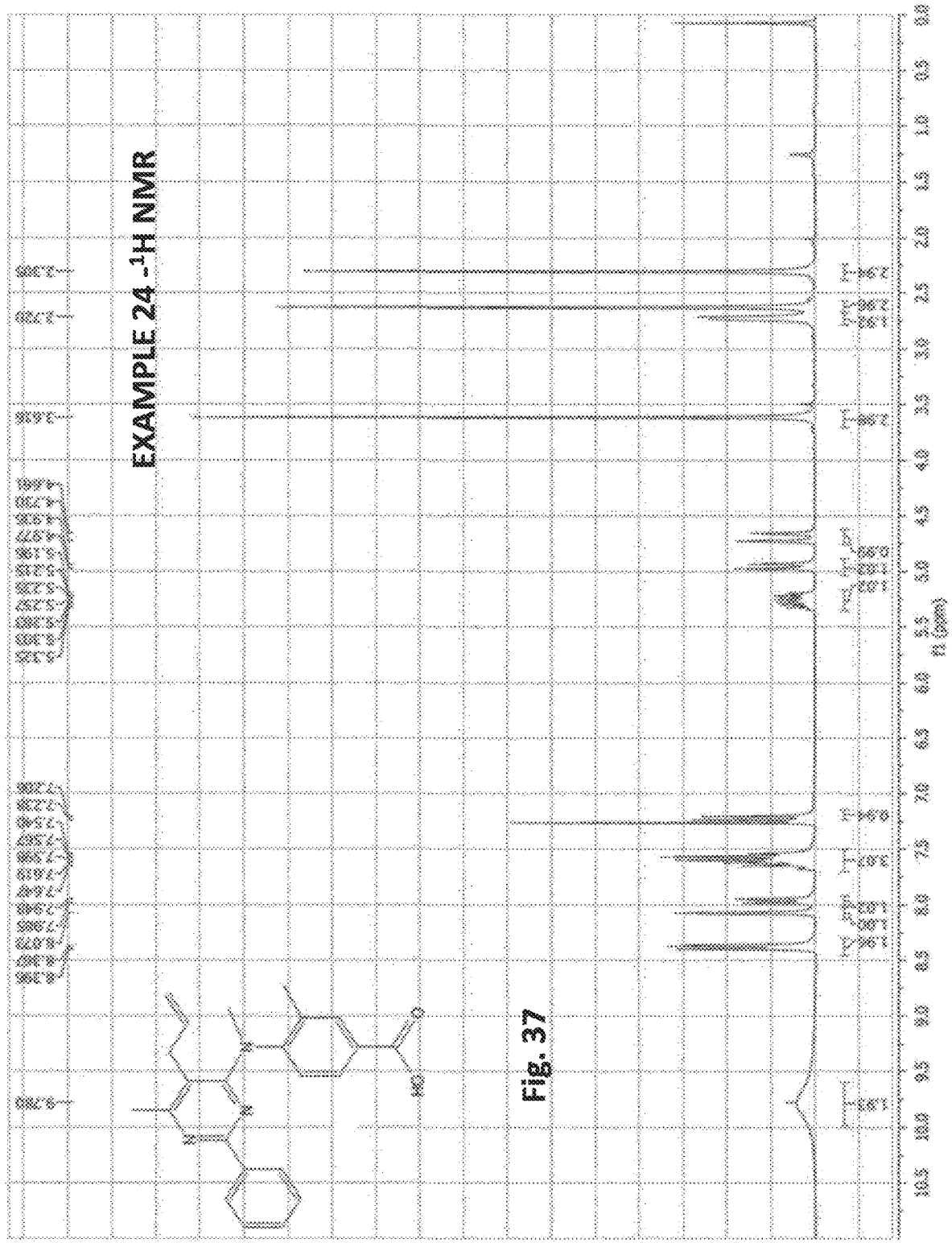
Figure 38:
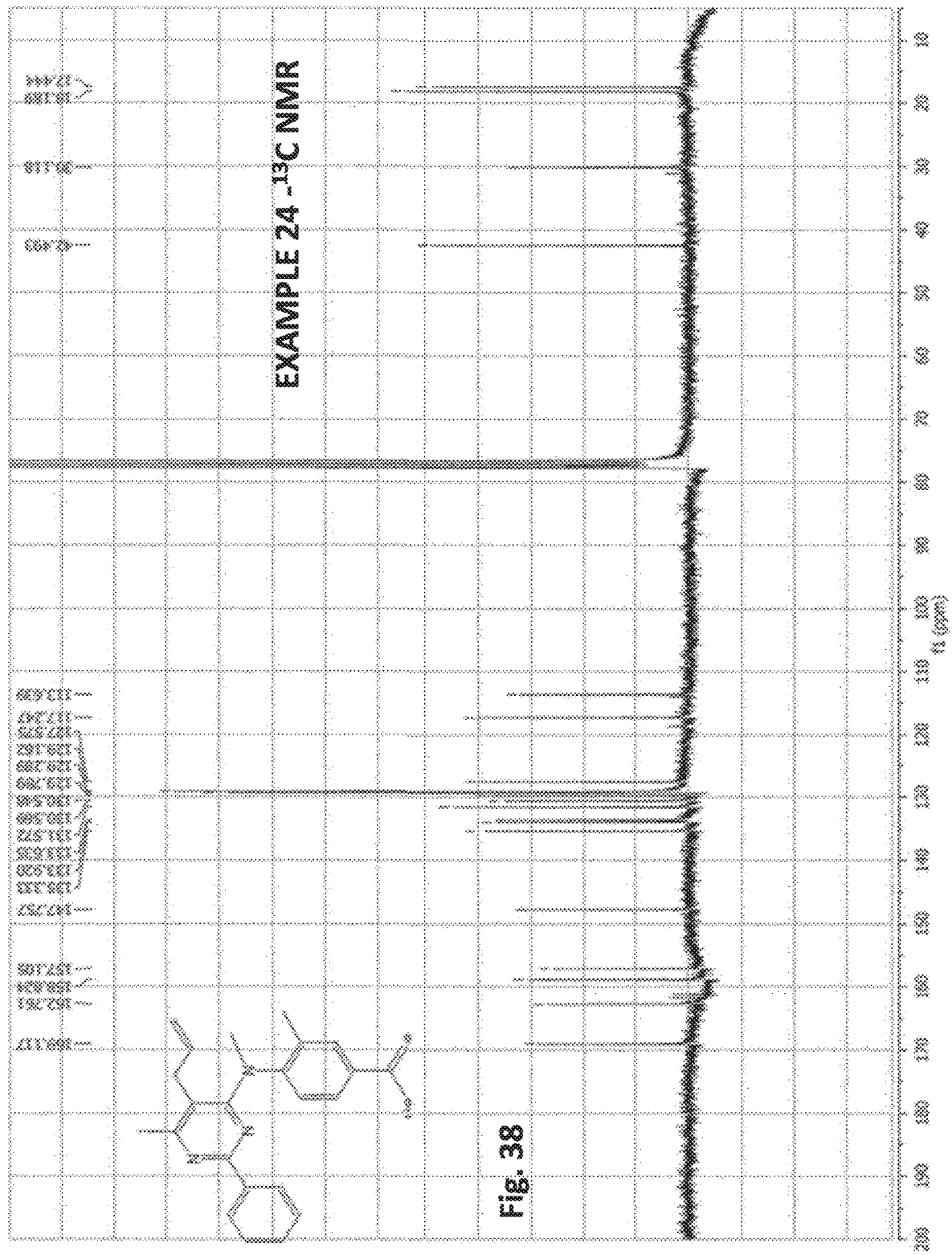
Figure 39:
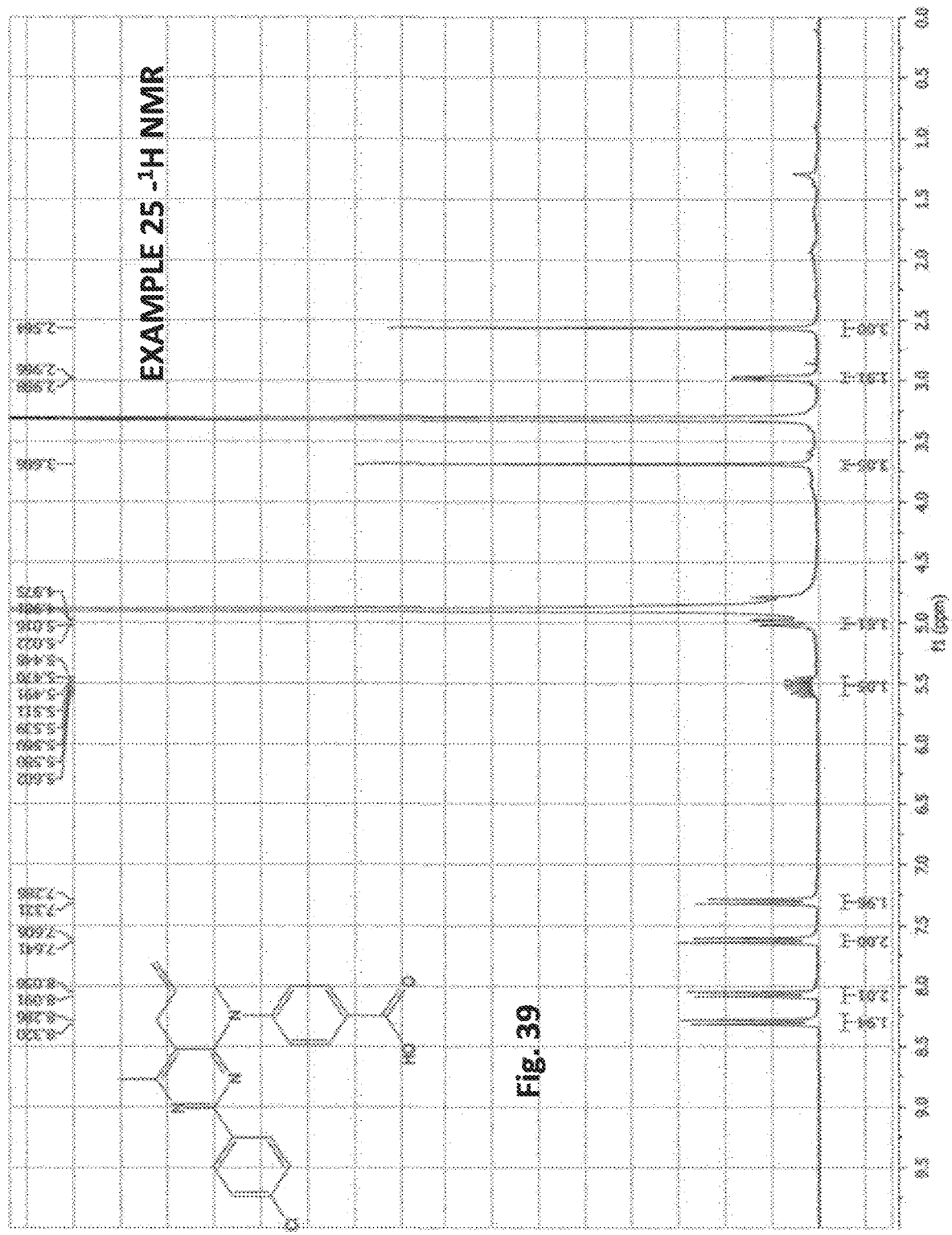
Figure 40:
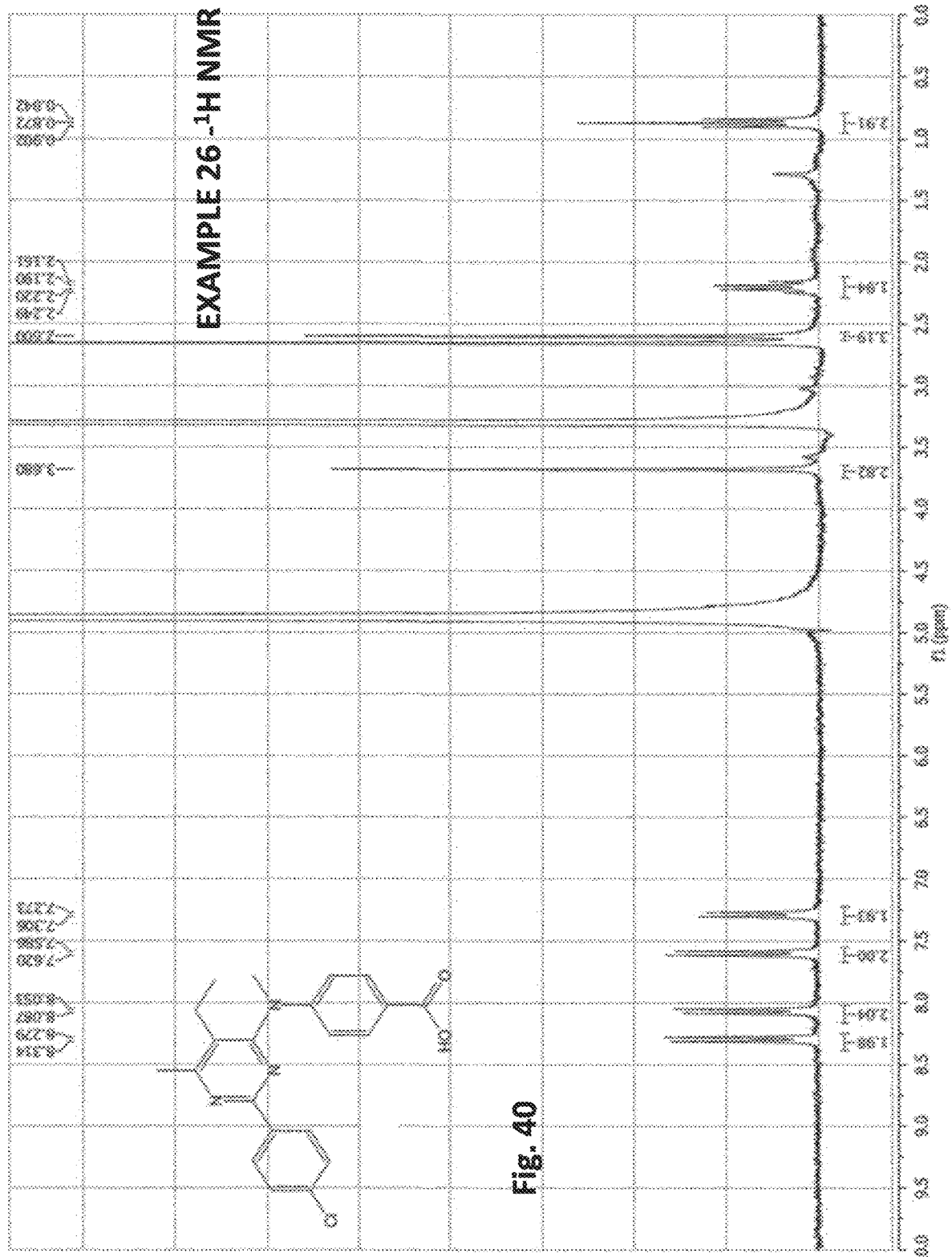
Figure 41:
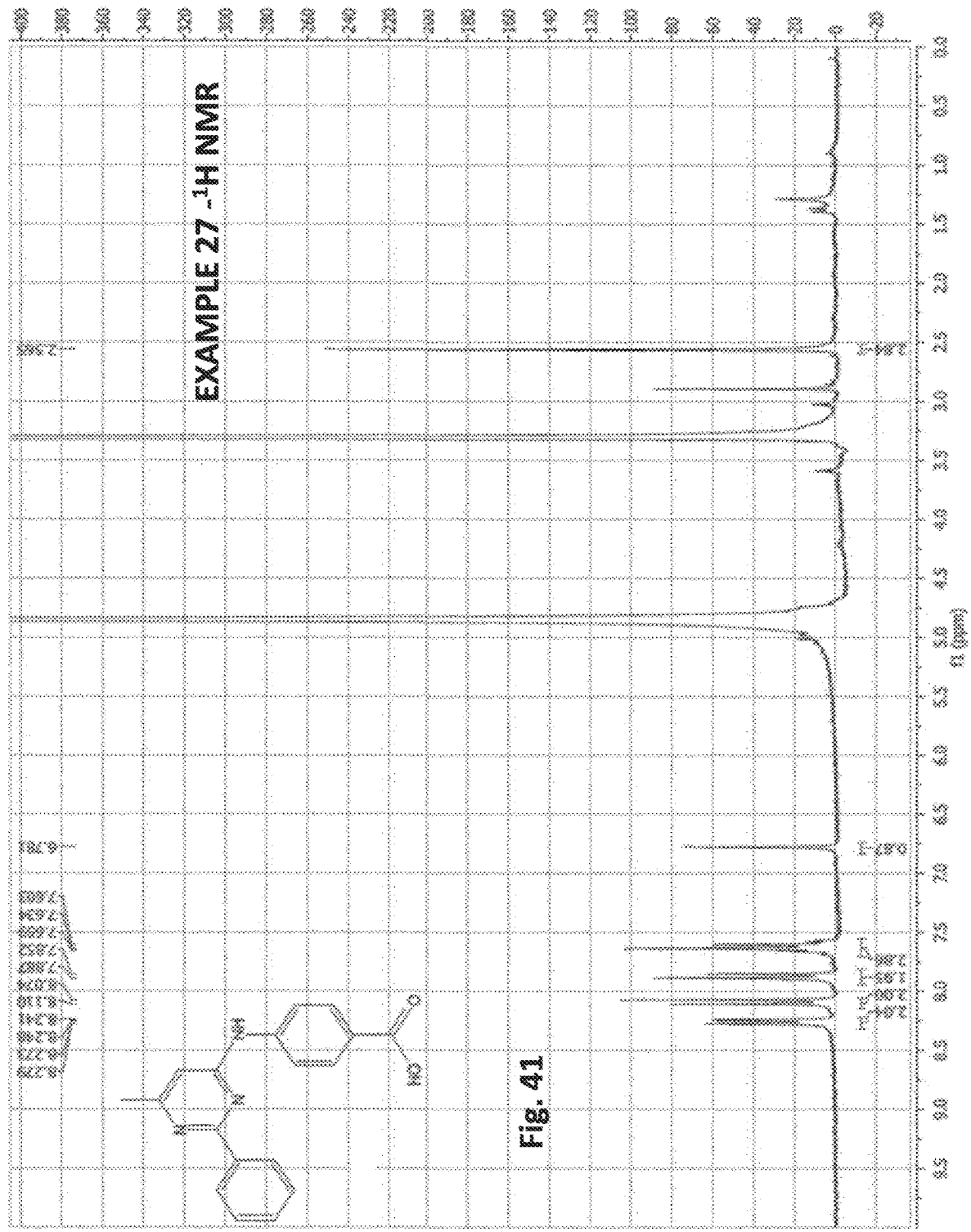
Figure 42:
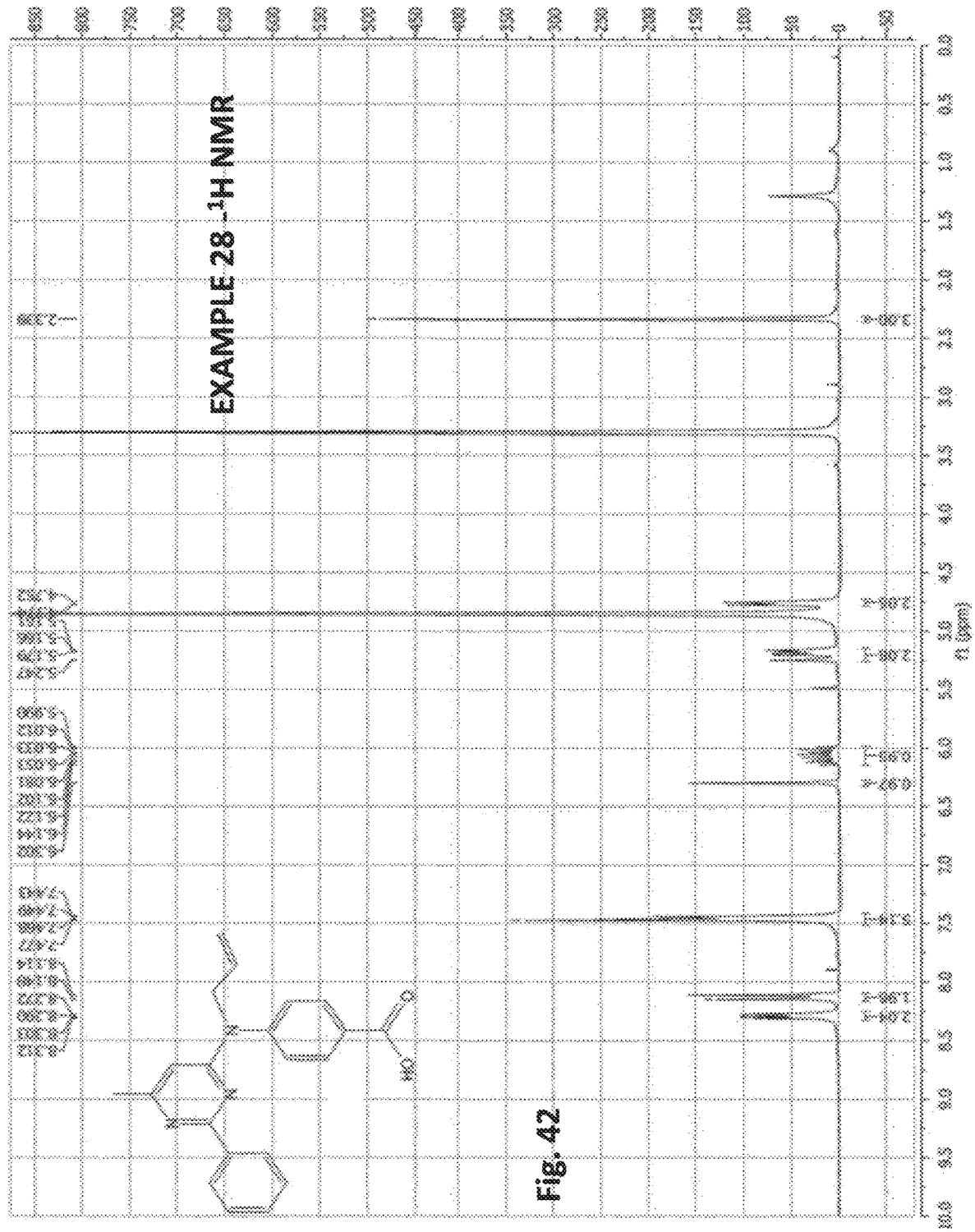
Figure 43:
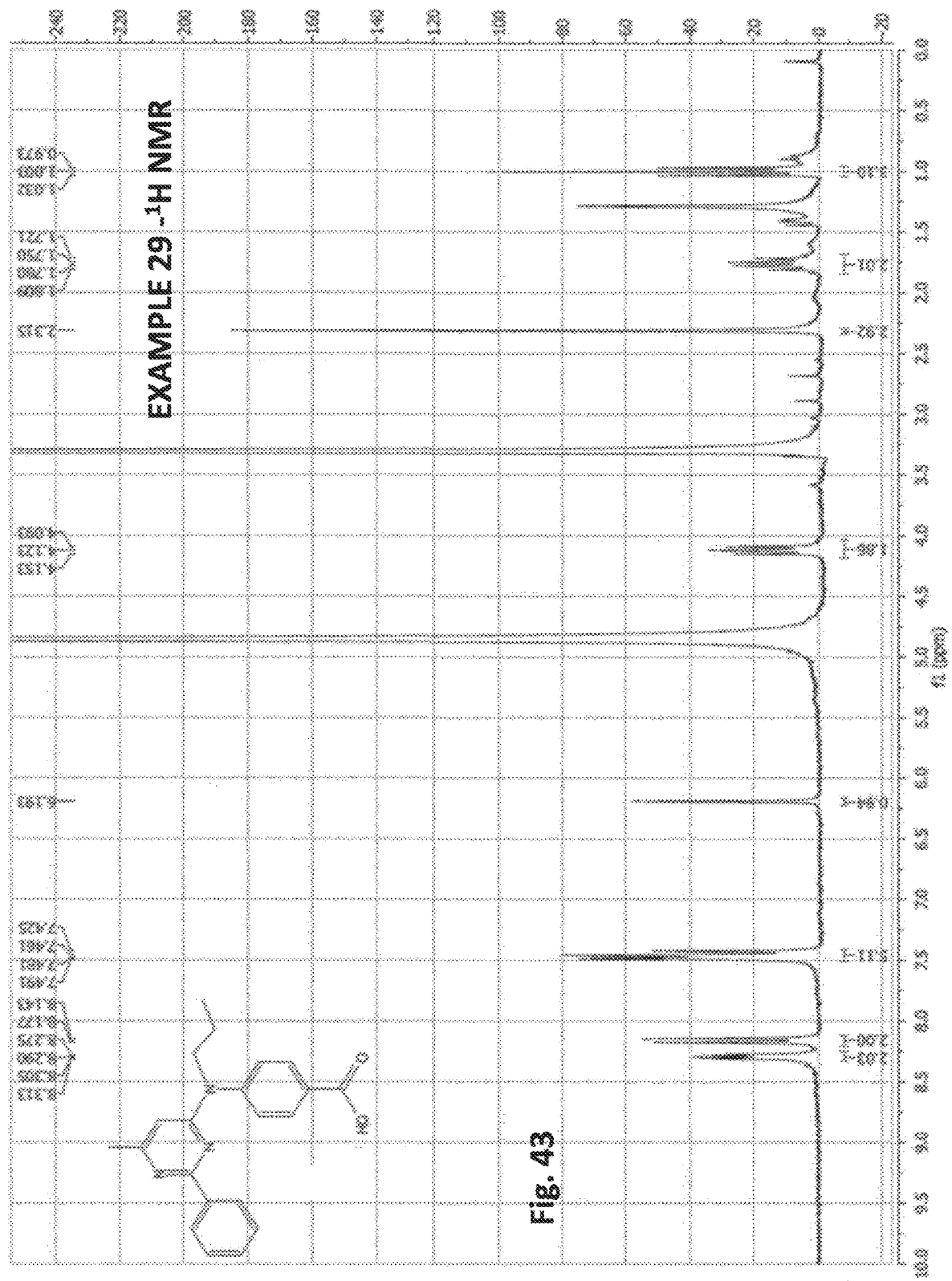
Figure 44:
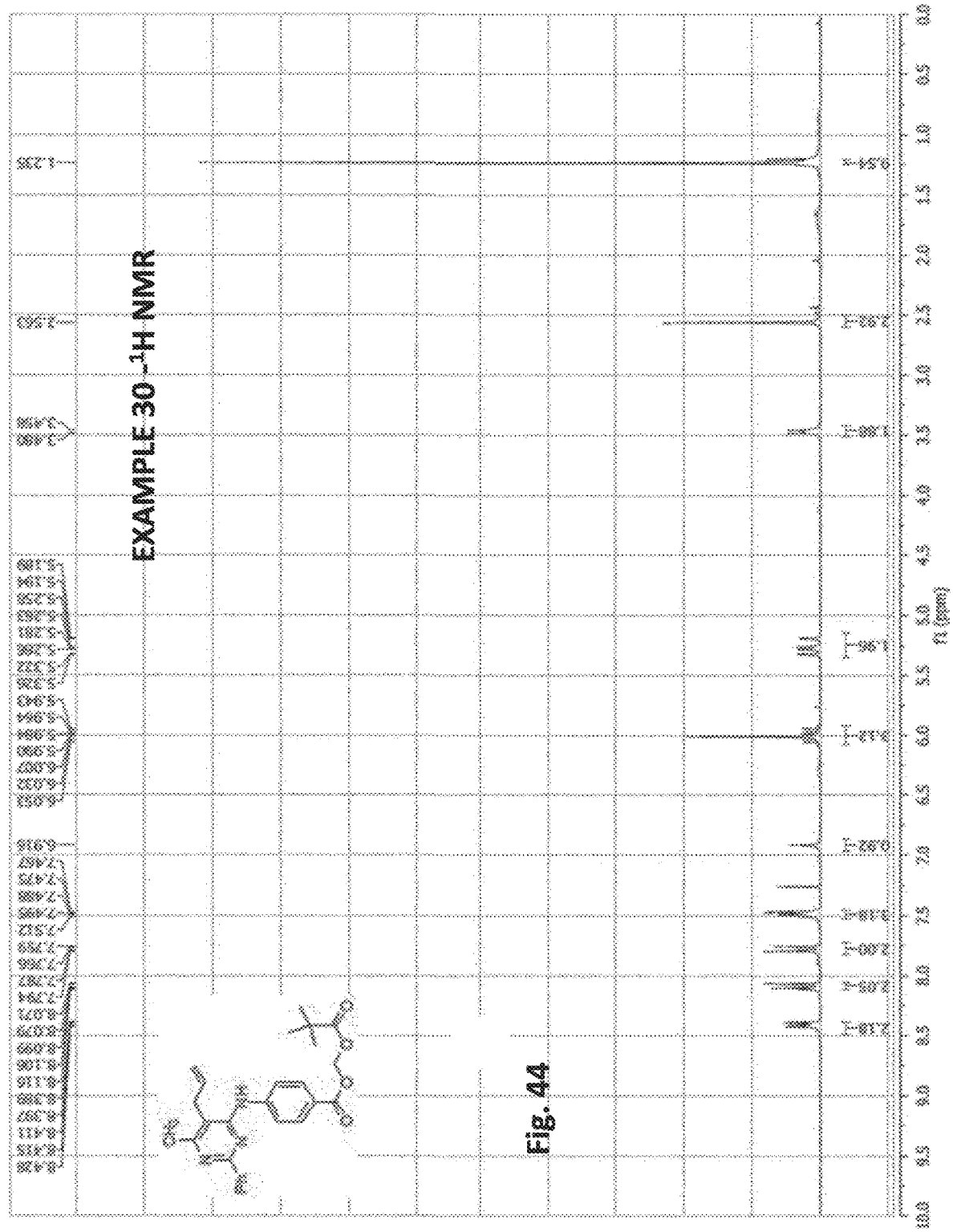
Figure 45:
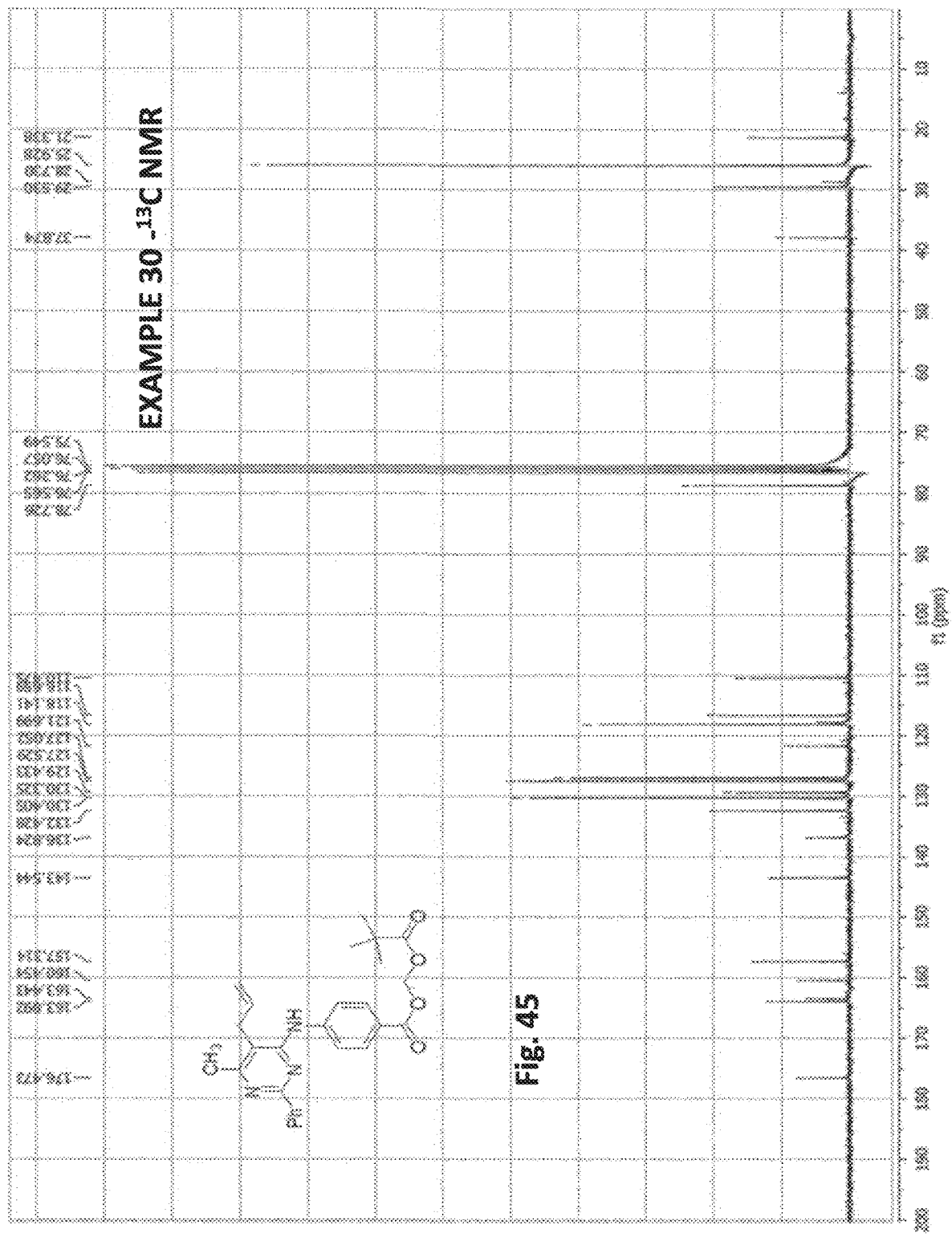
Figure 46:
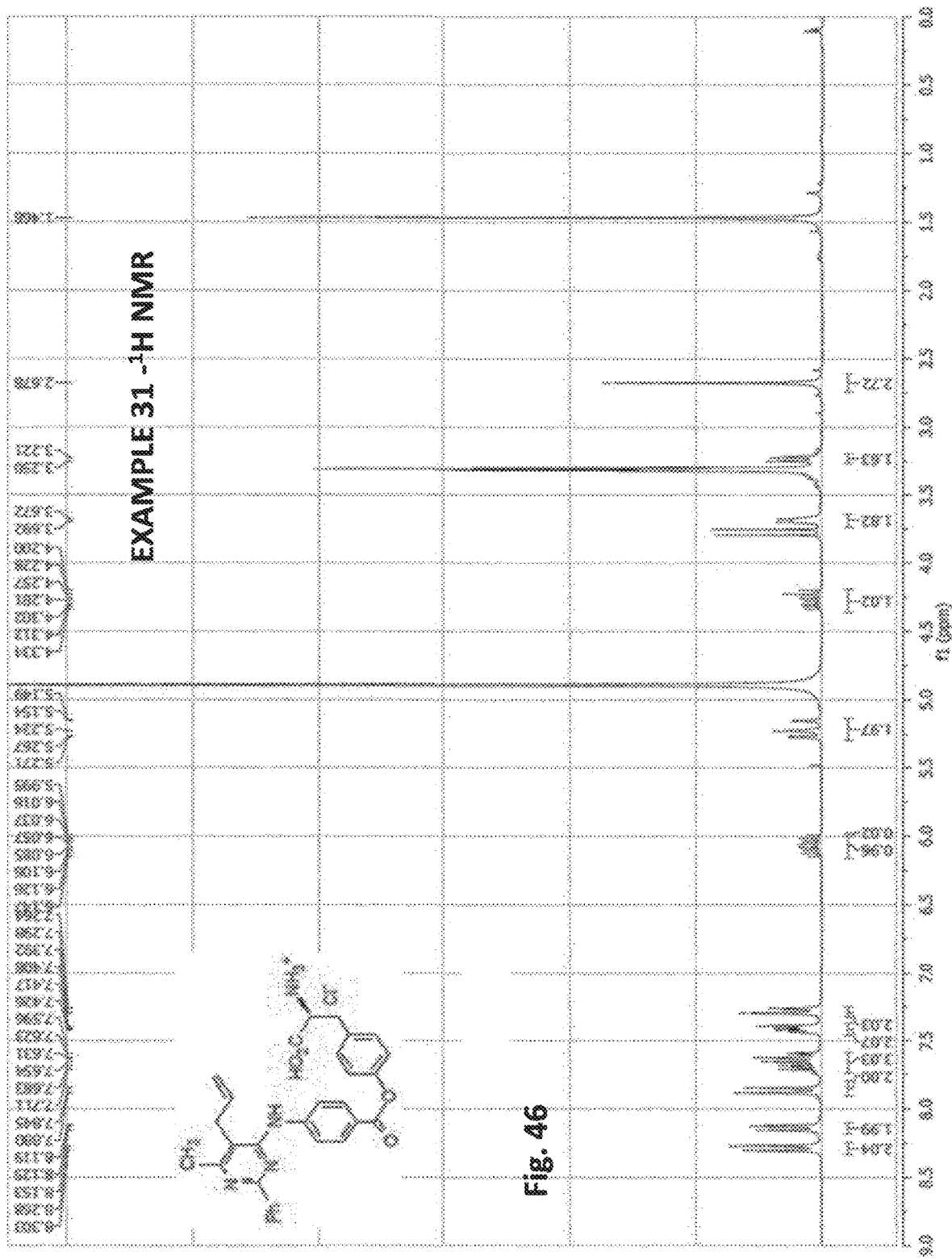
Figure 47:
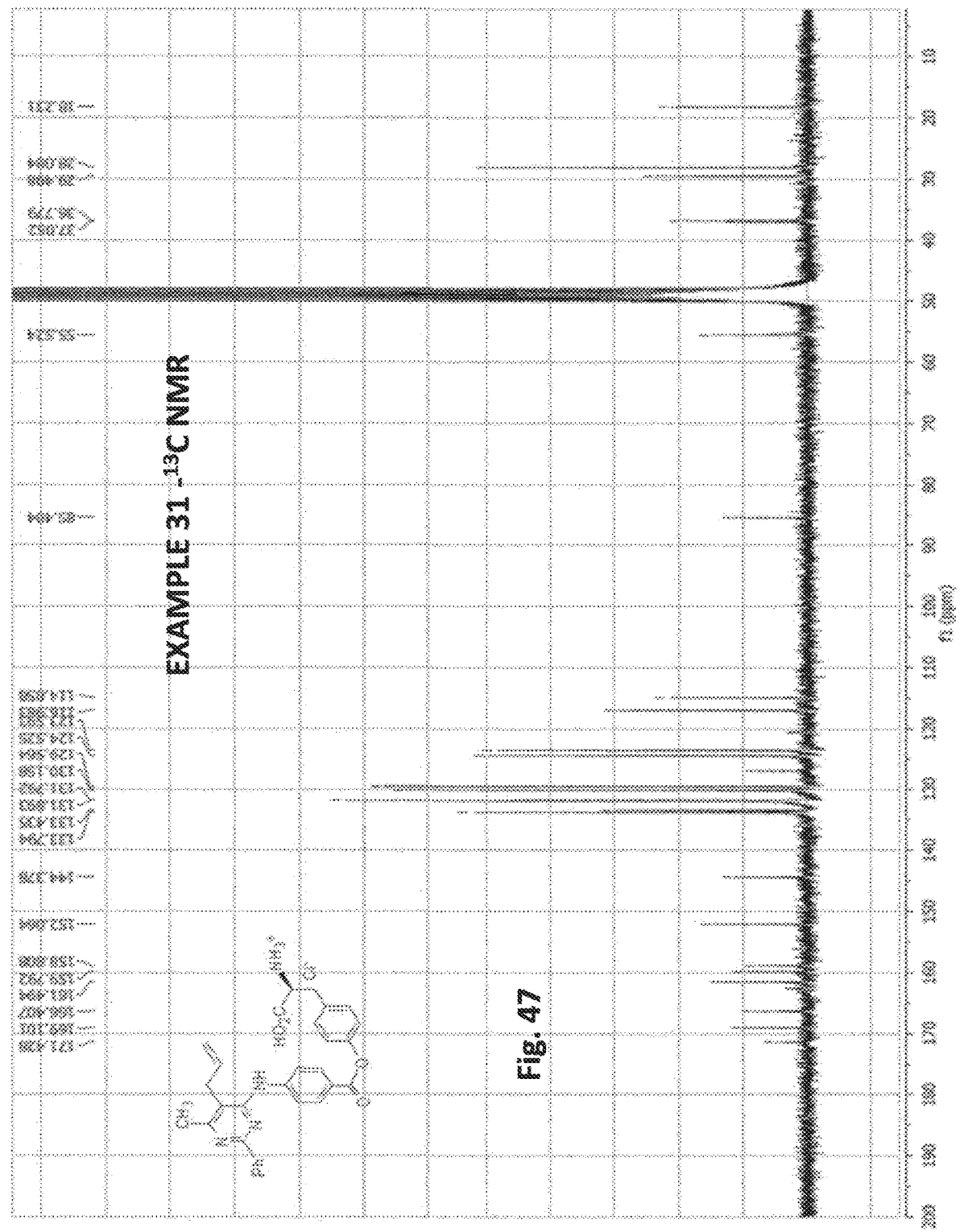
Figure 48:
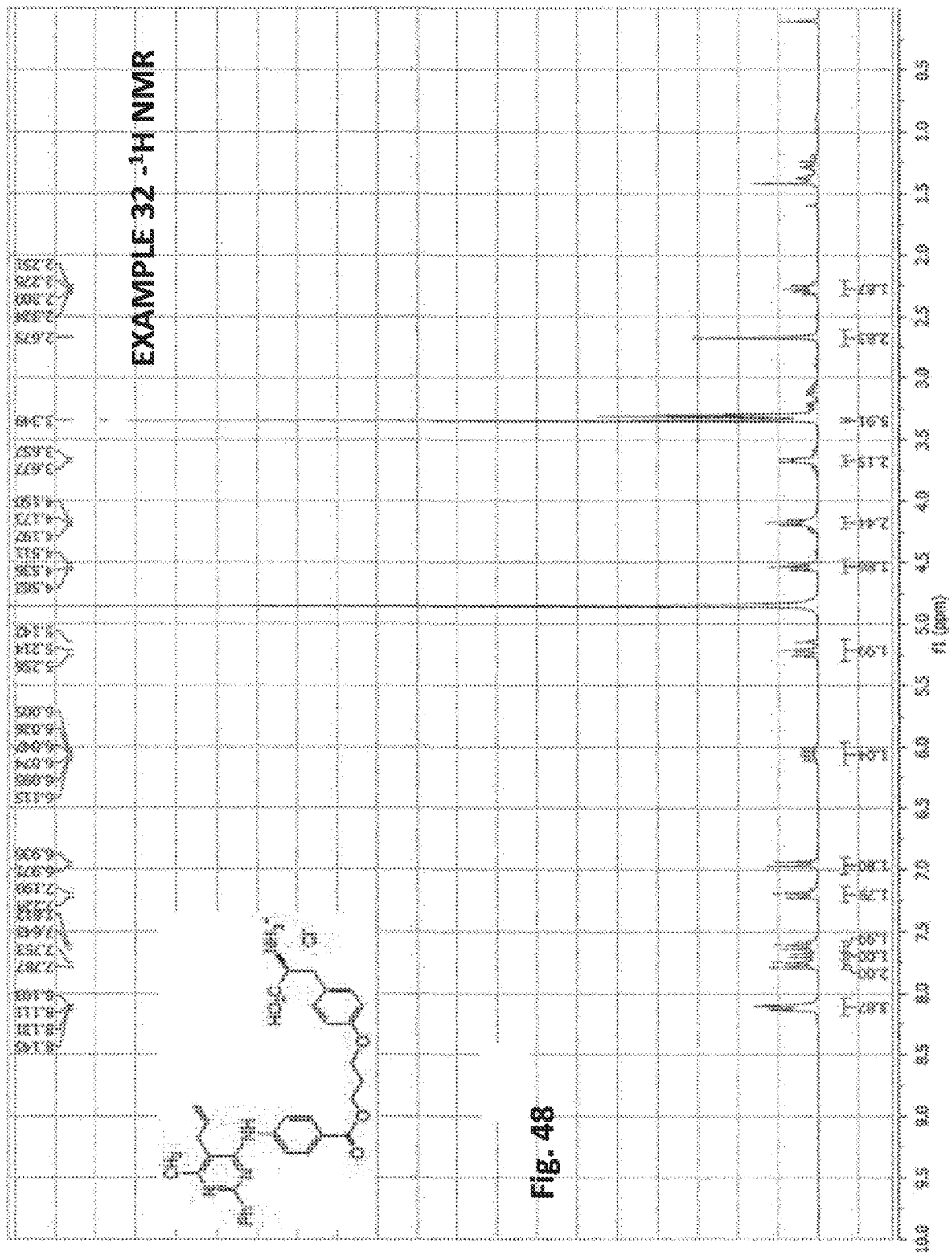
Figure 49:
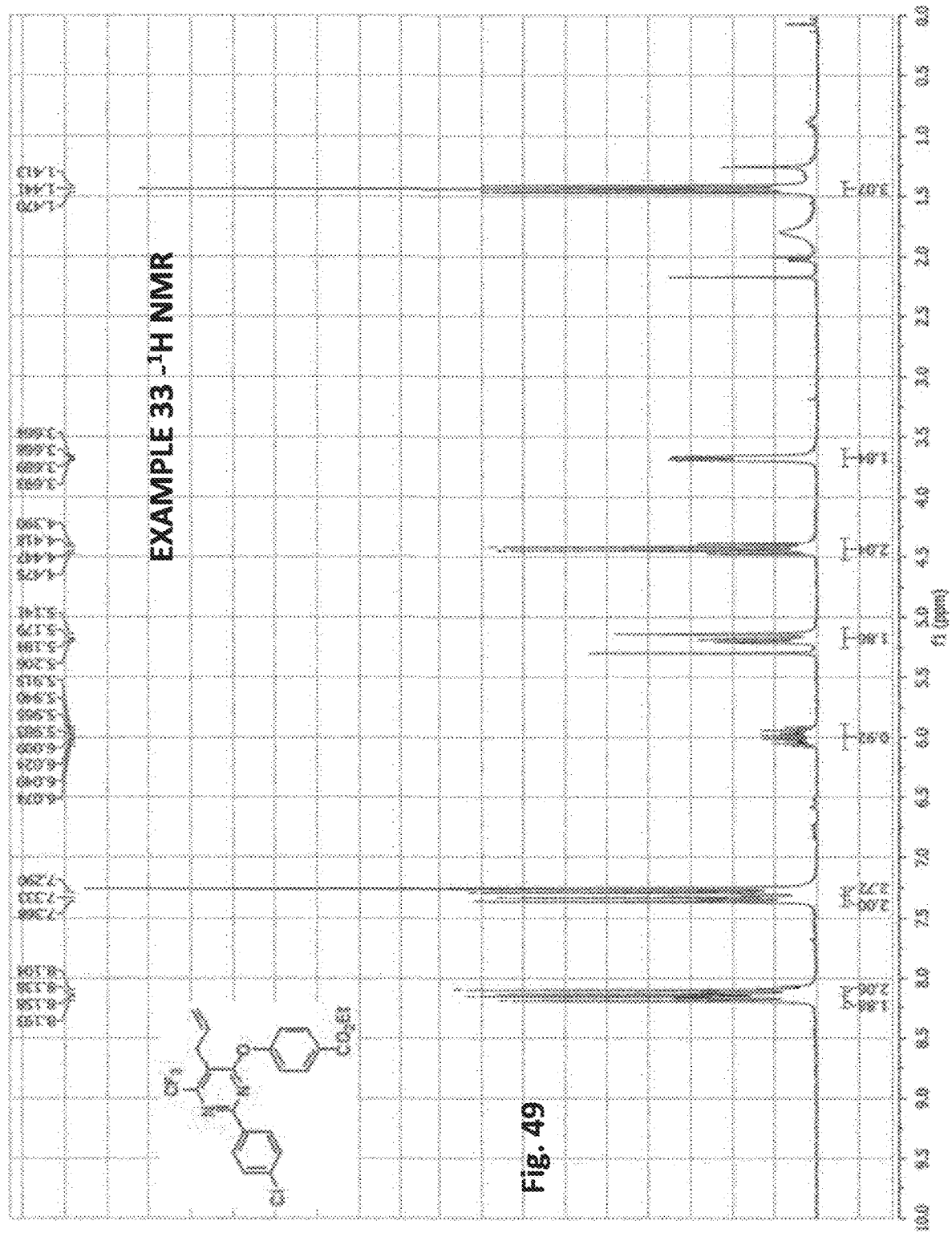
Figure 50:
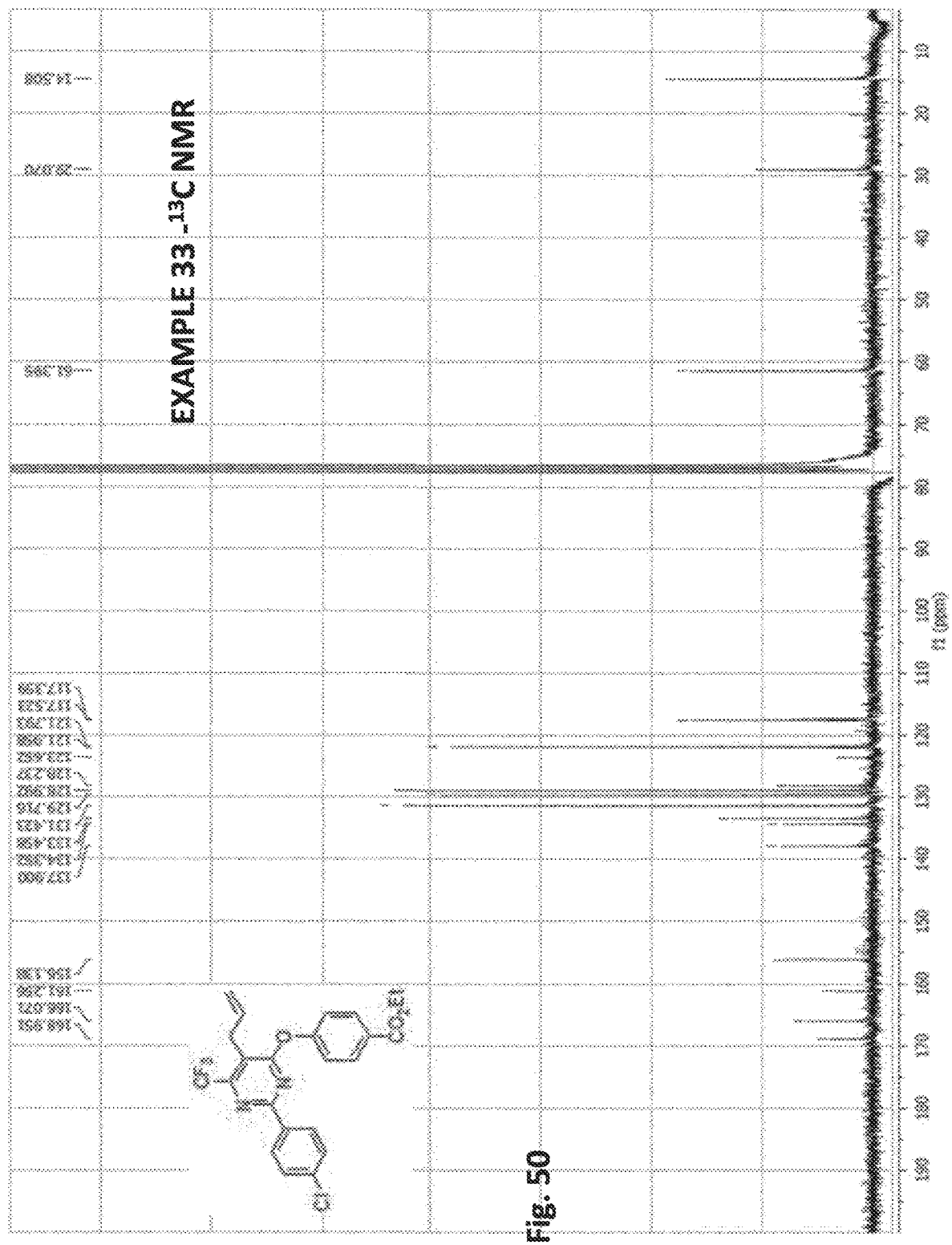
Figure 51:
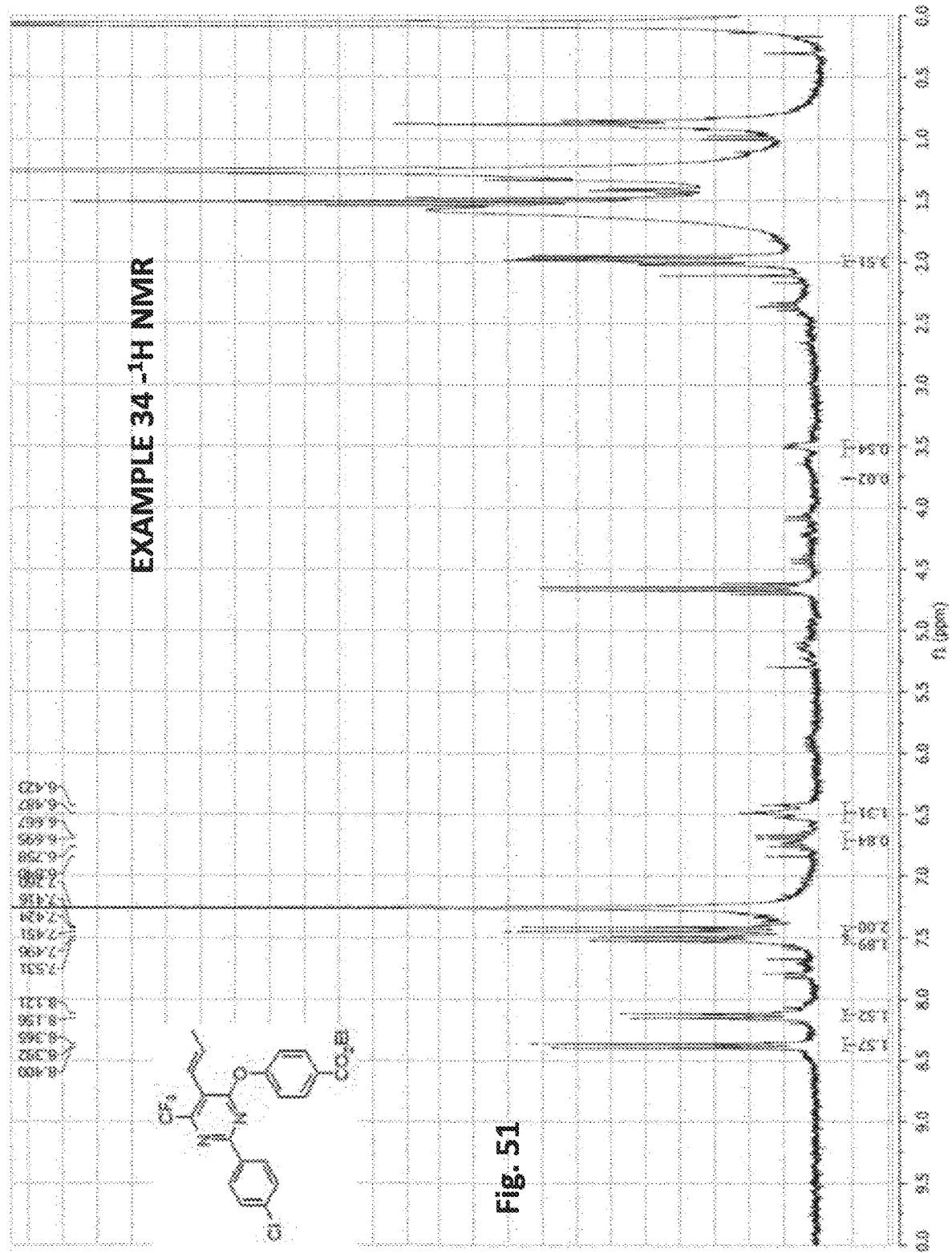
Figure 52:
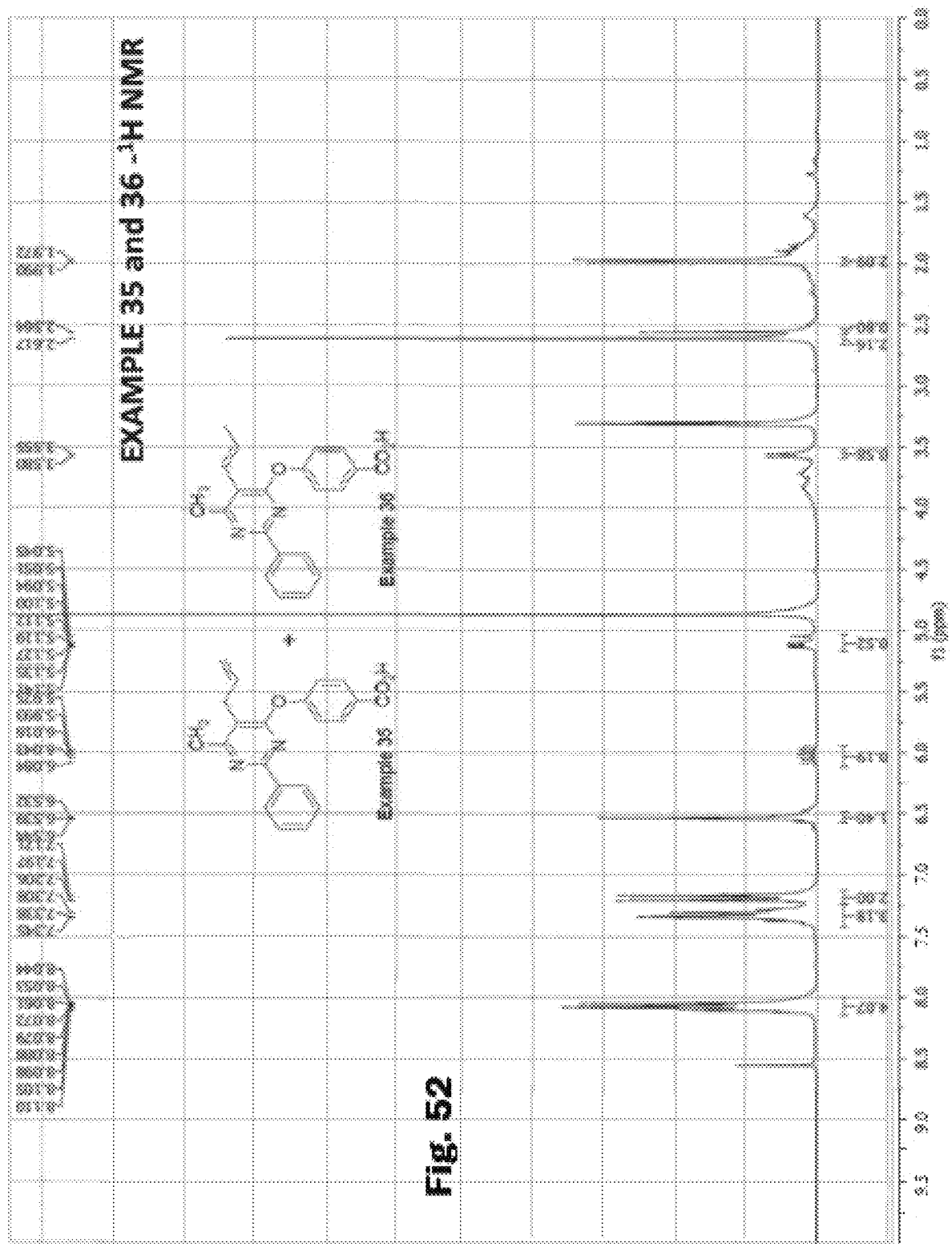
Figure 53:
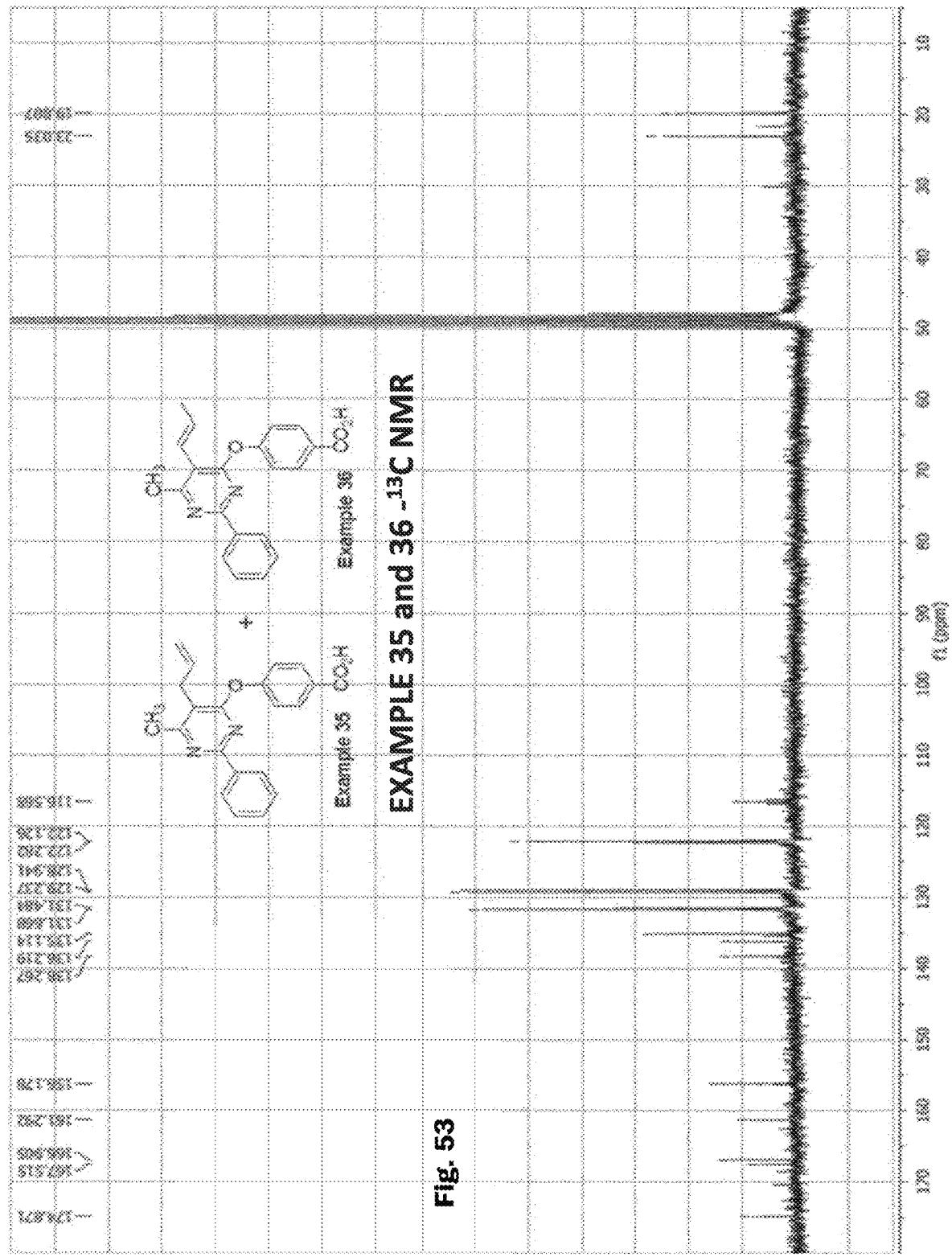
Figure 54:
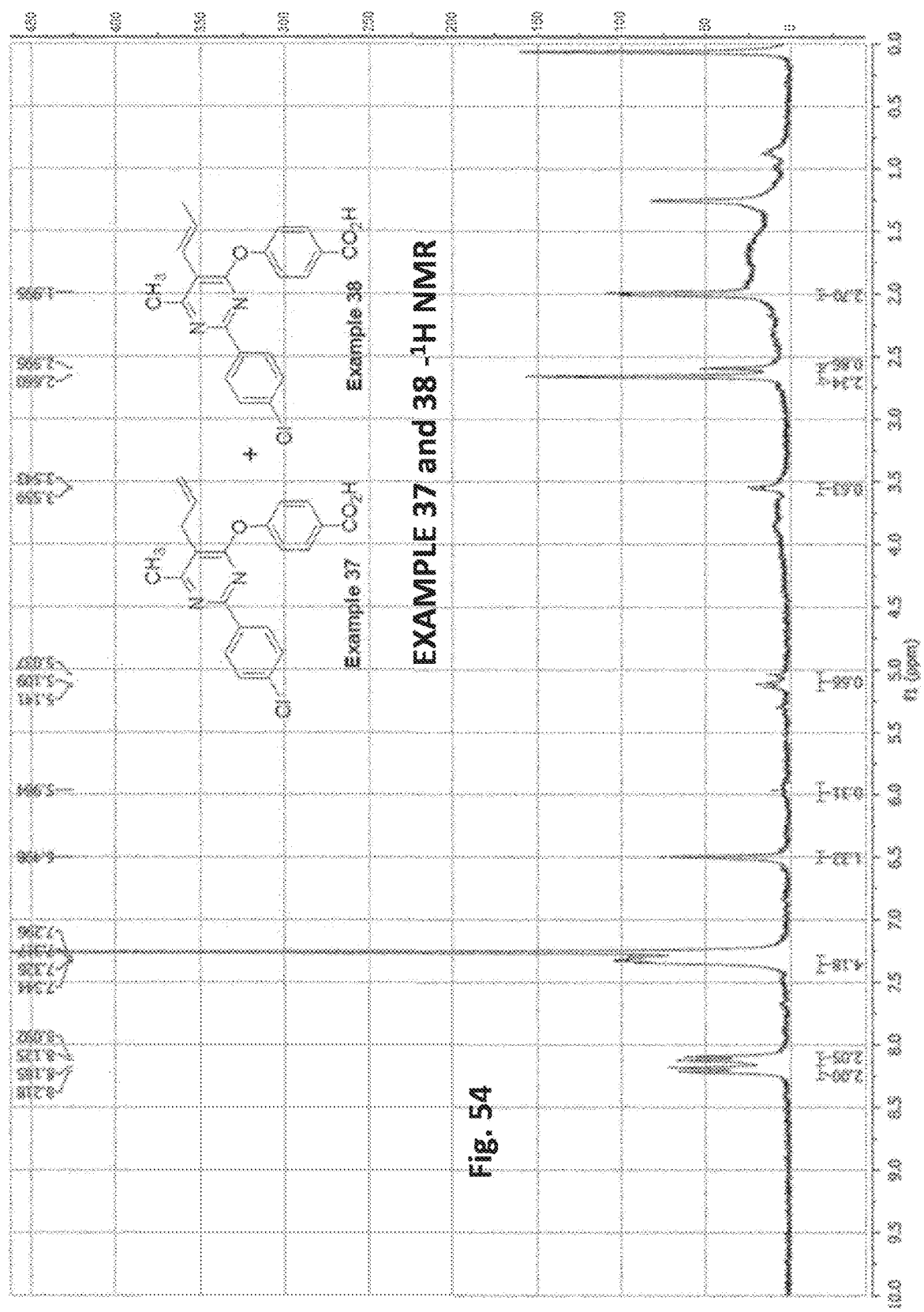
Figure 55:
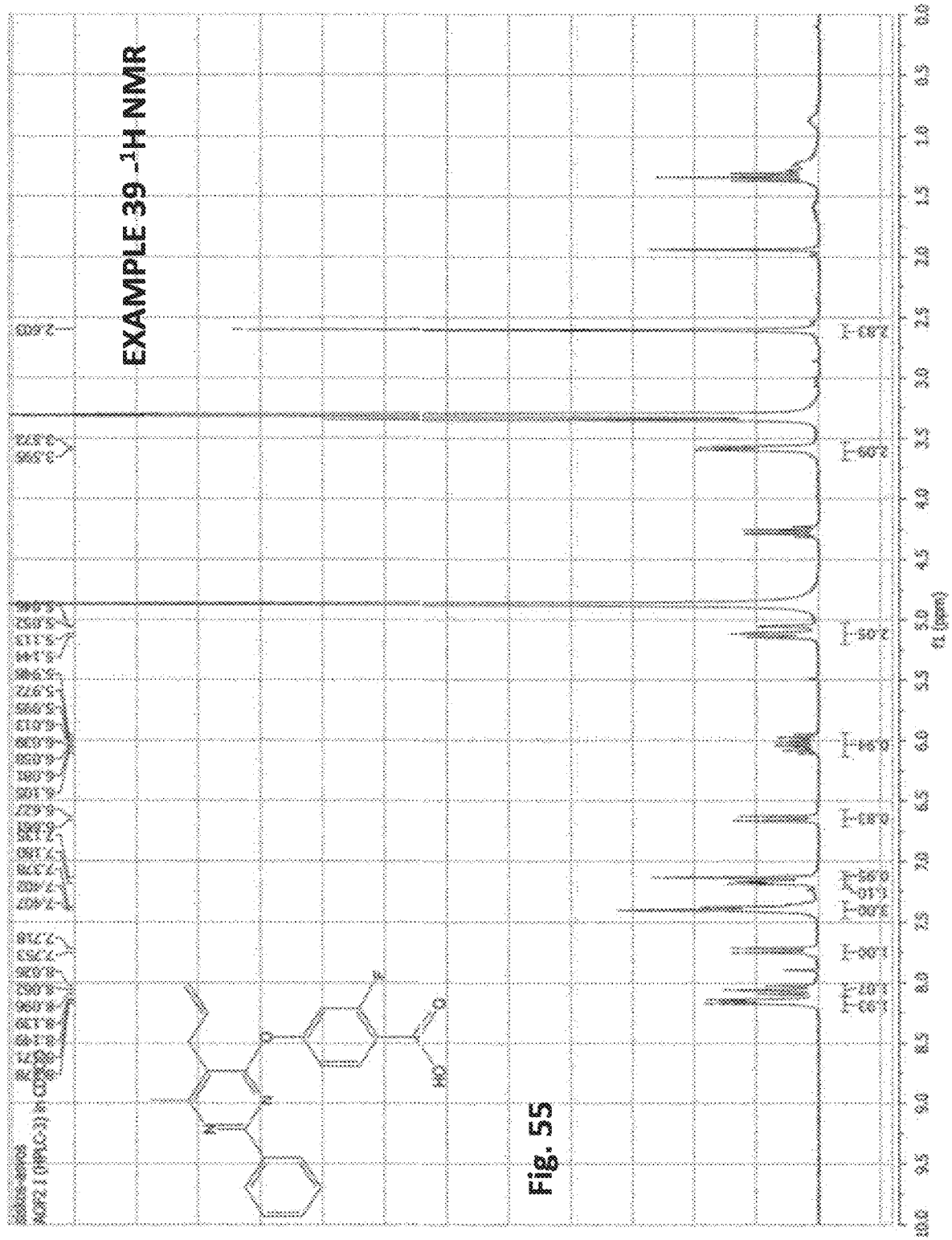
Figure 56:
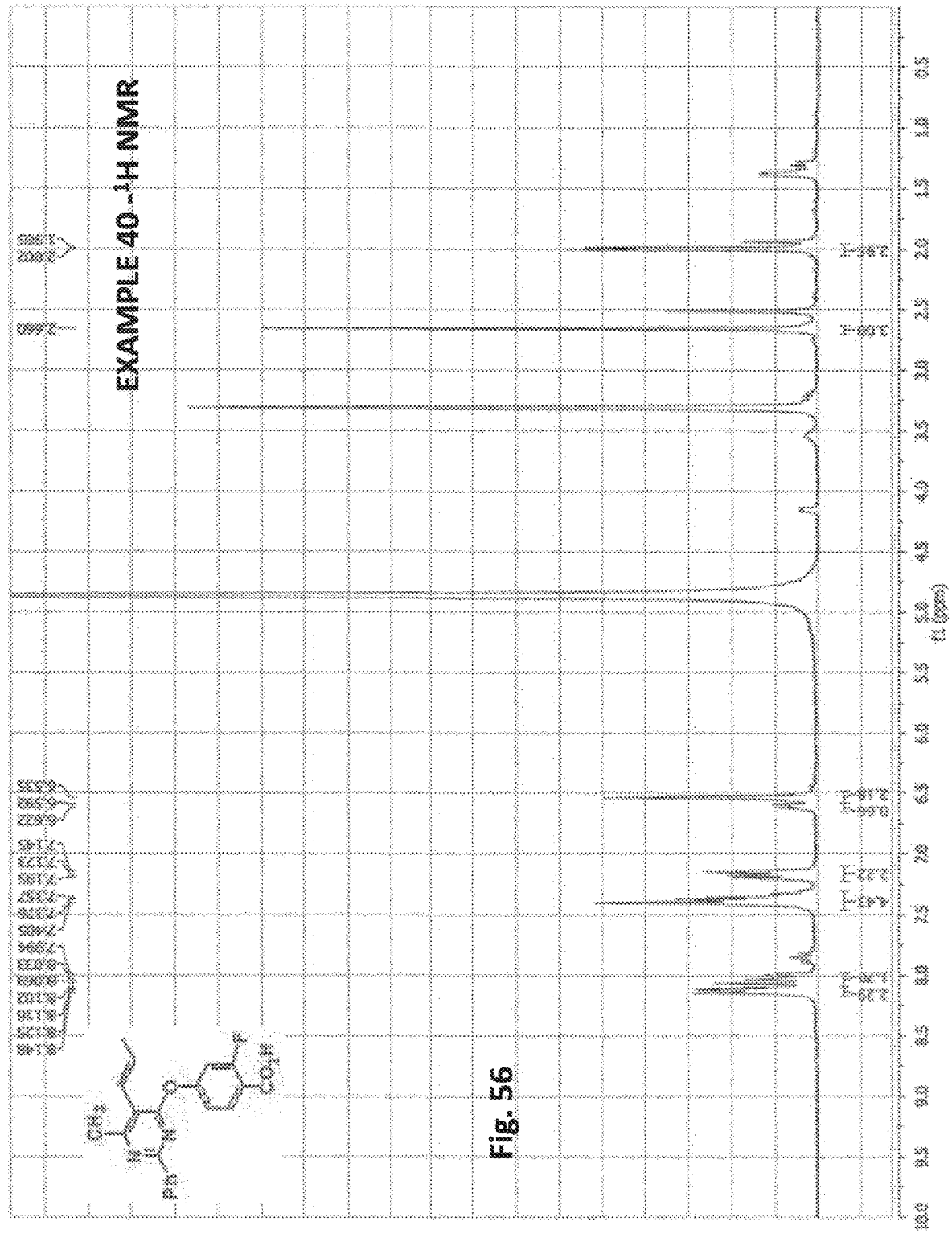
Figure 57:
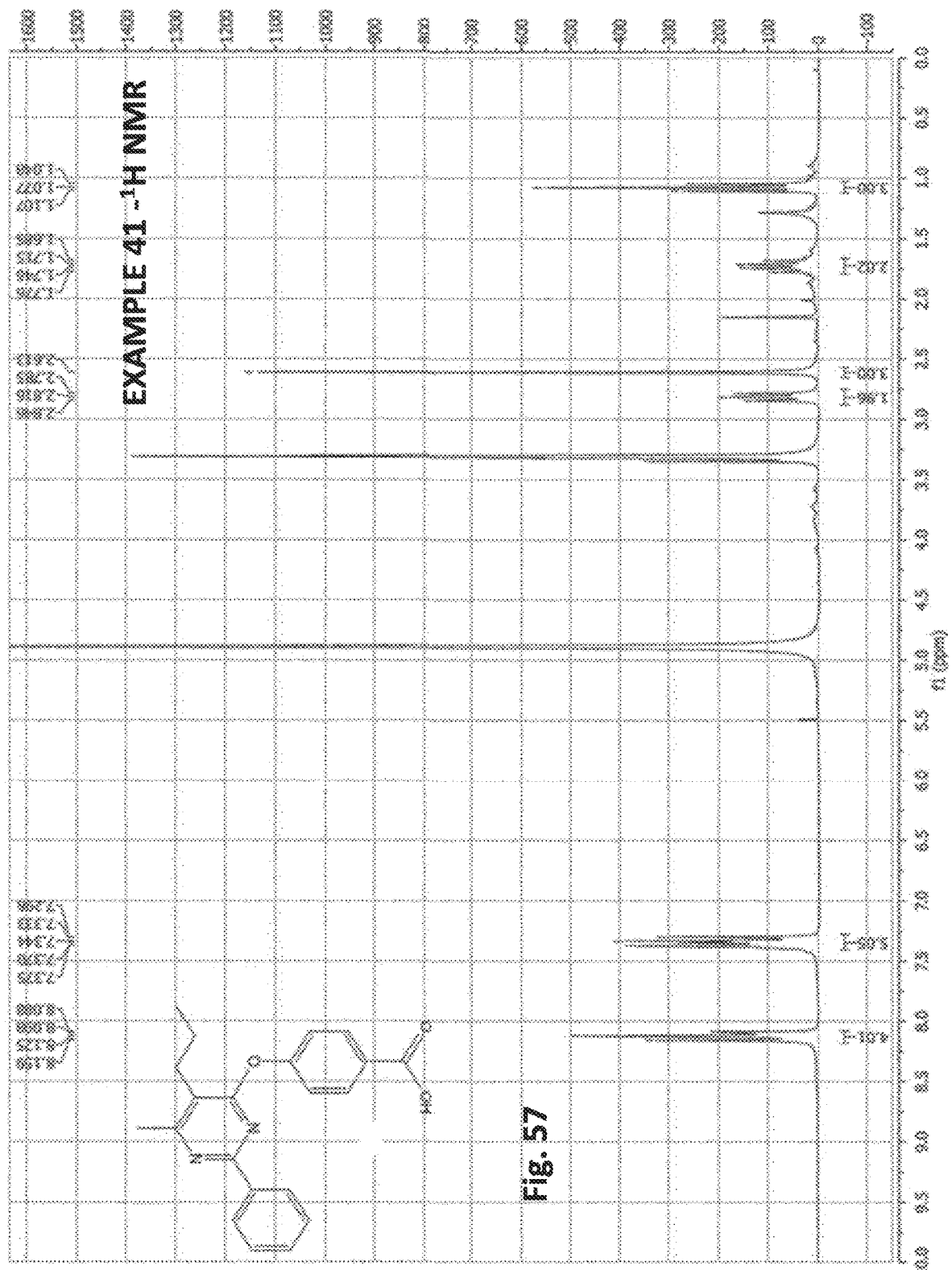
Figure 58:
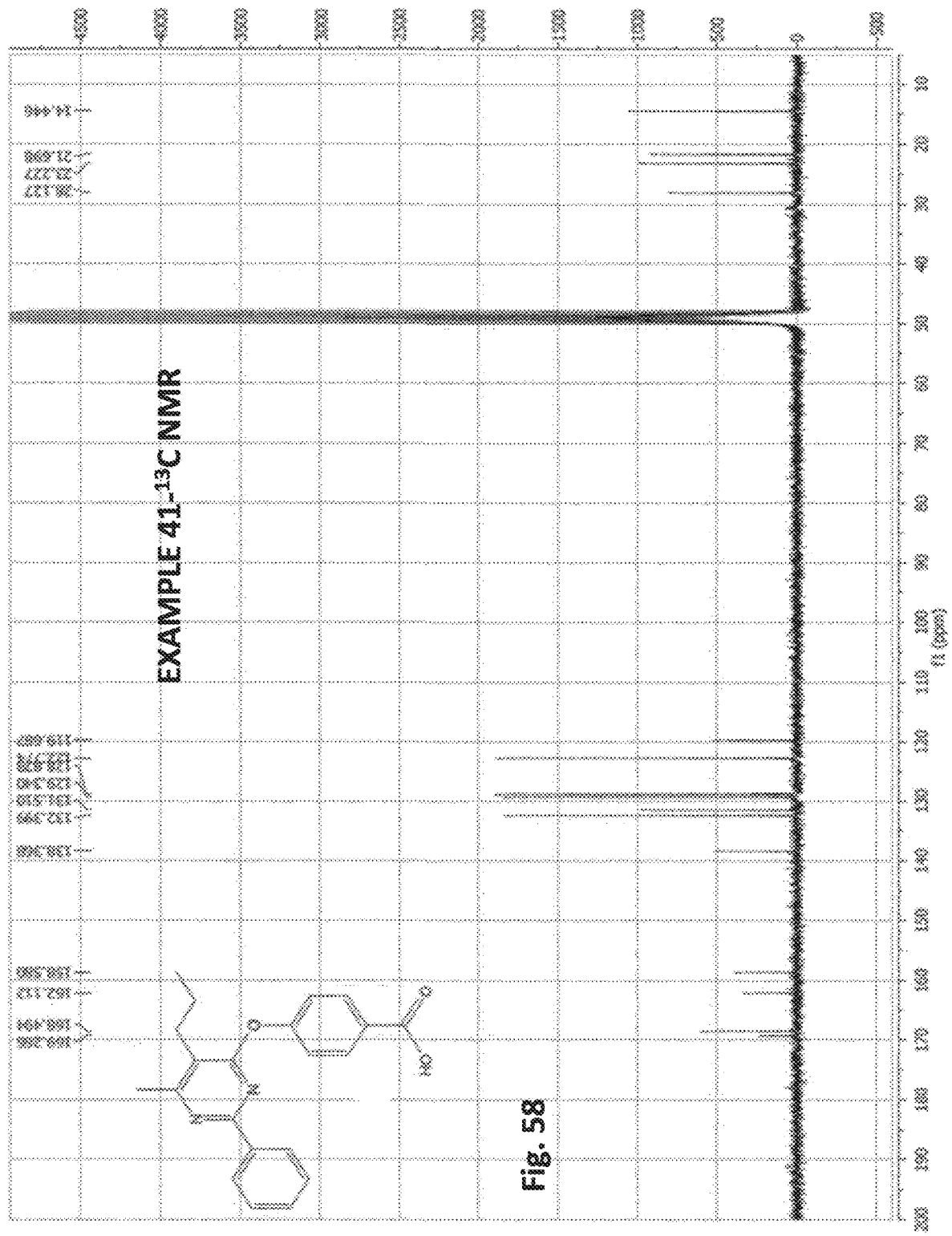
Figure 59:
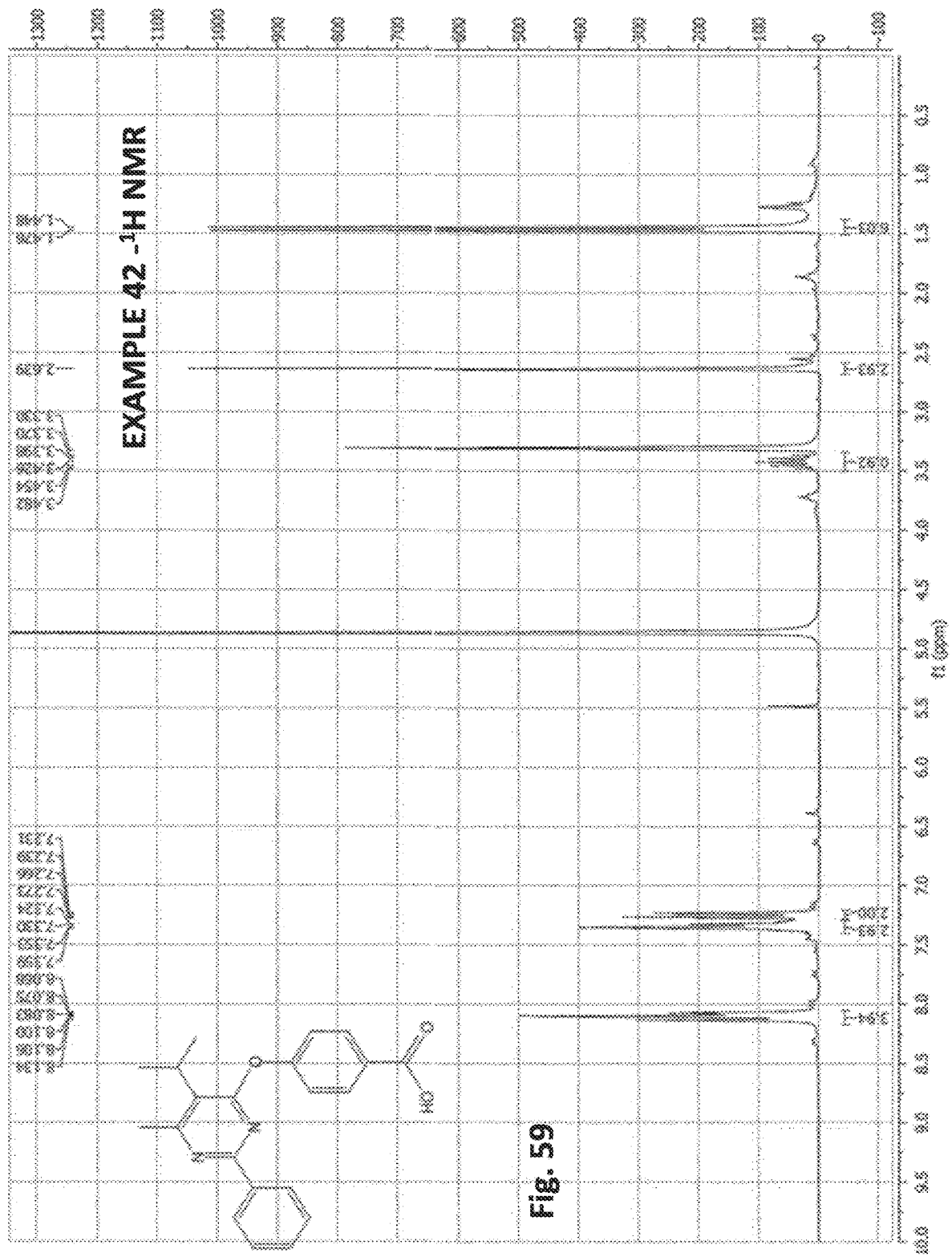
Figure 60:
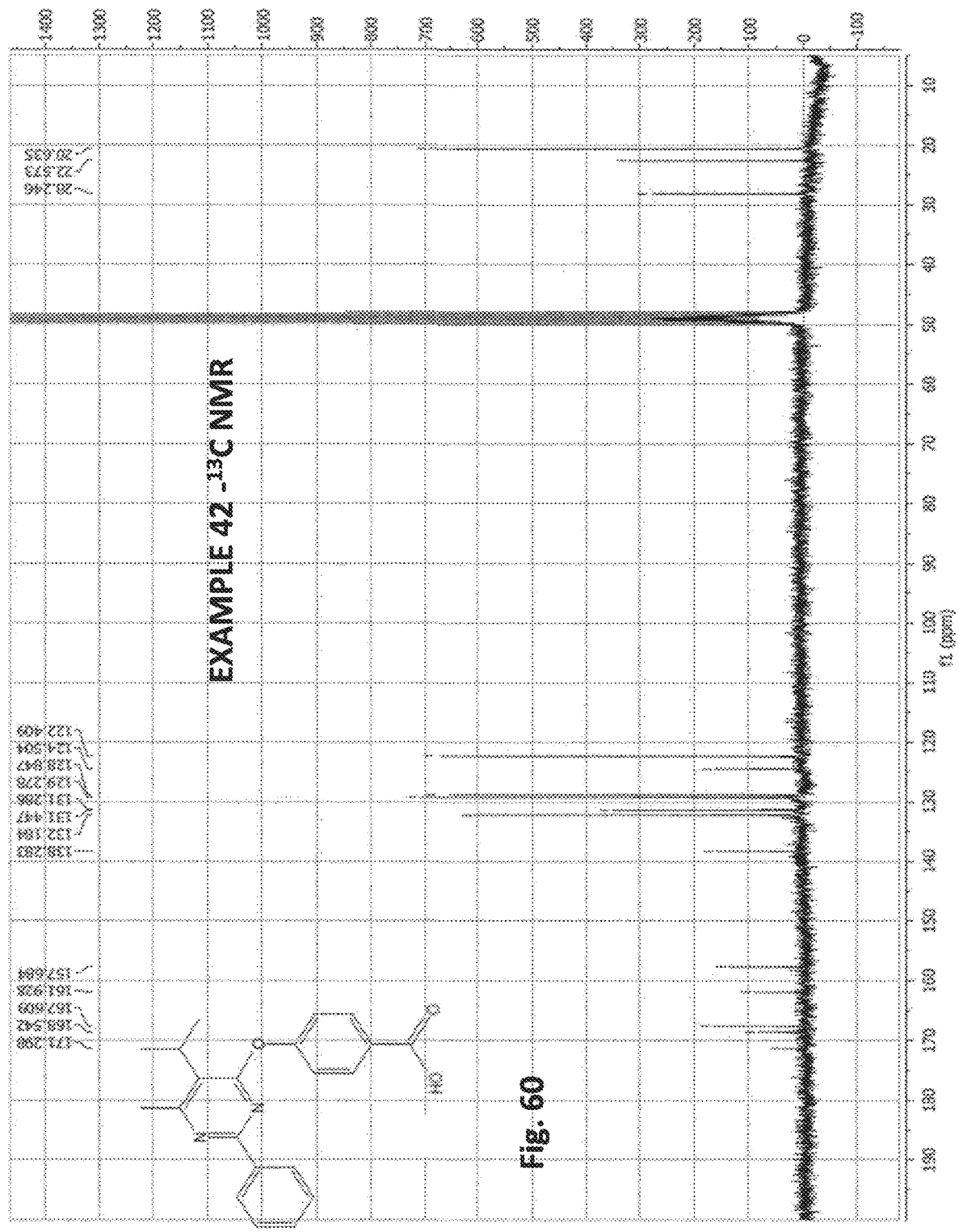
Figure 61:
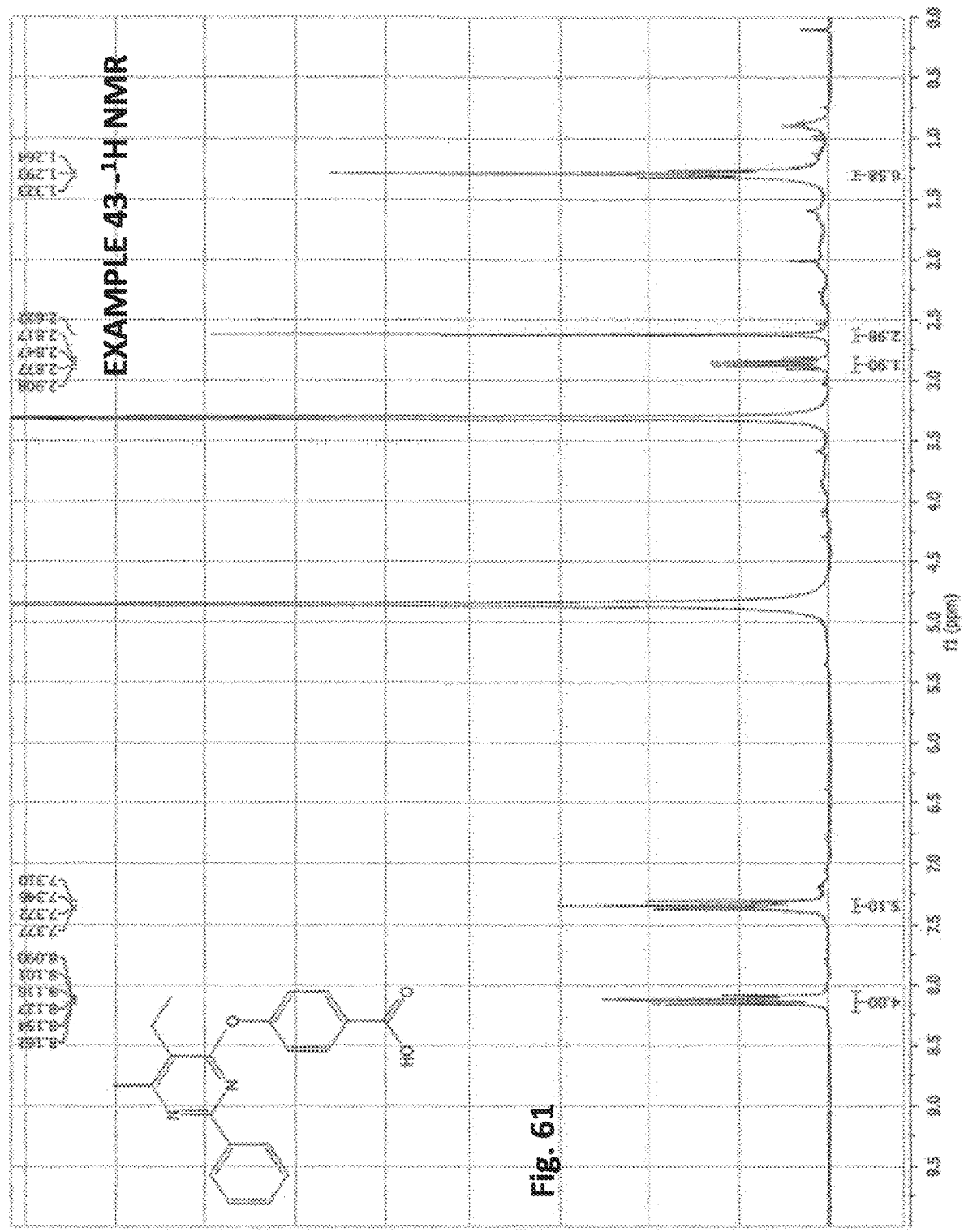
Figure 62:
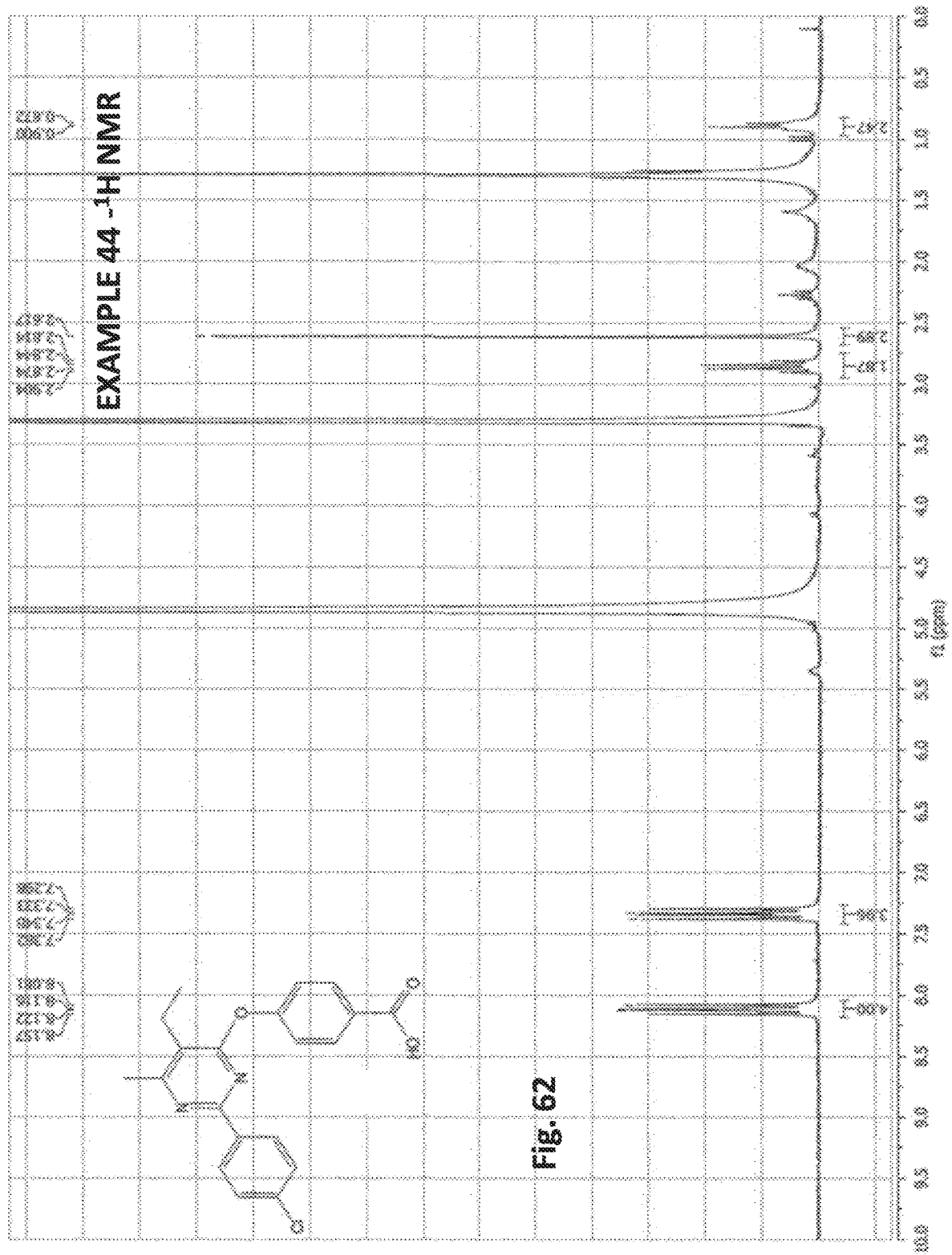
Figure 63:
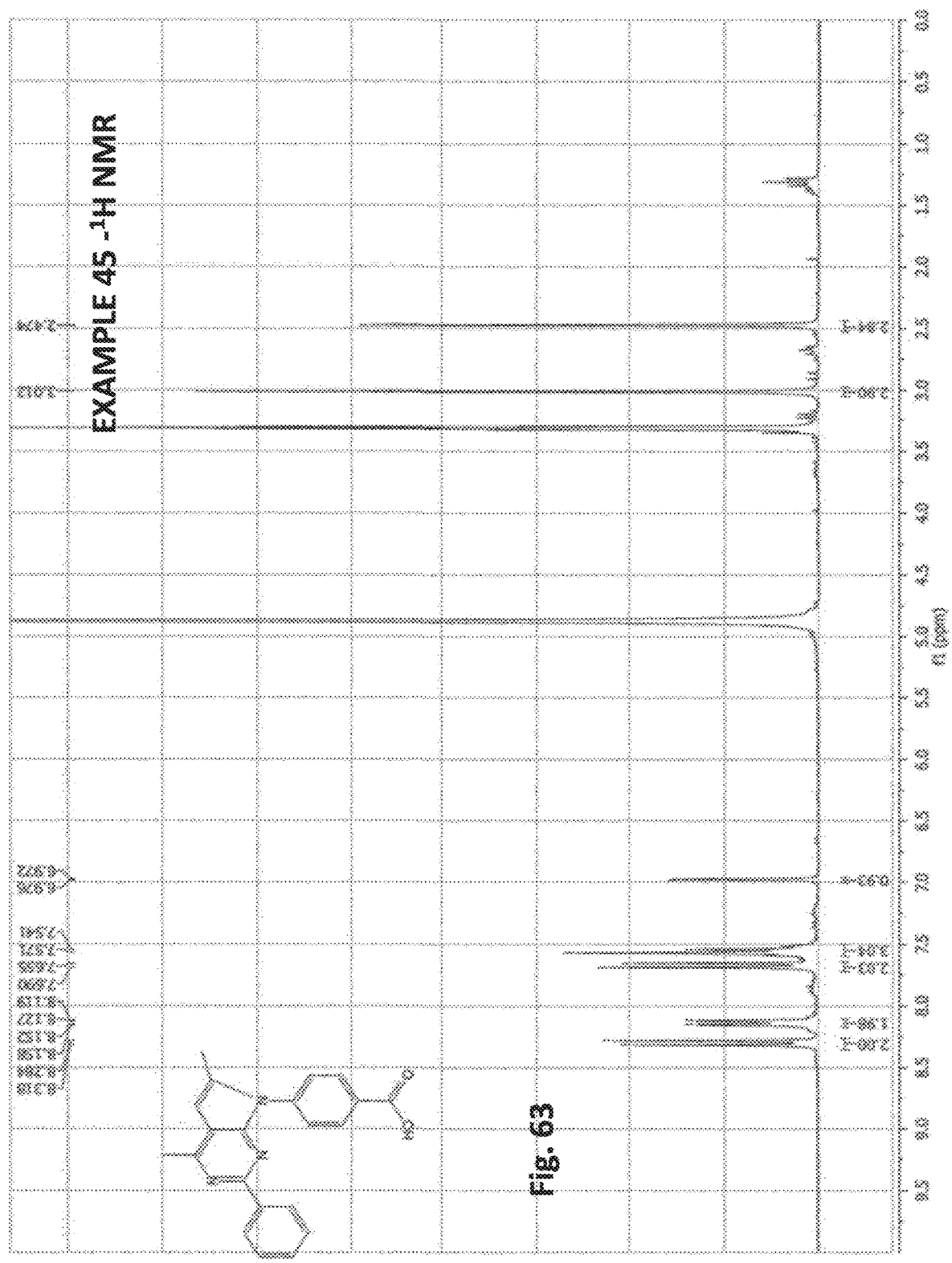
Figure 64:
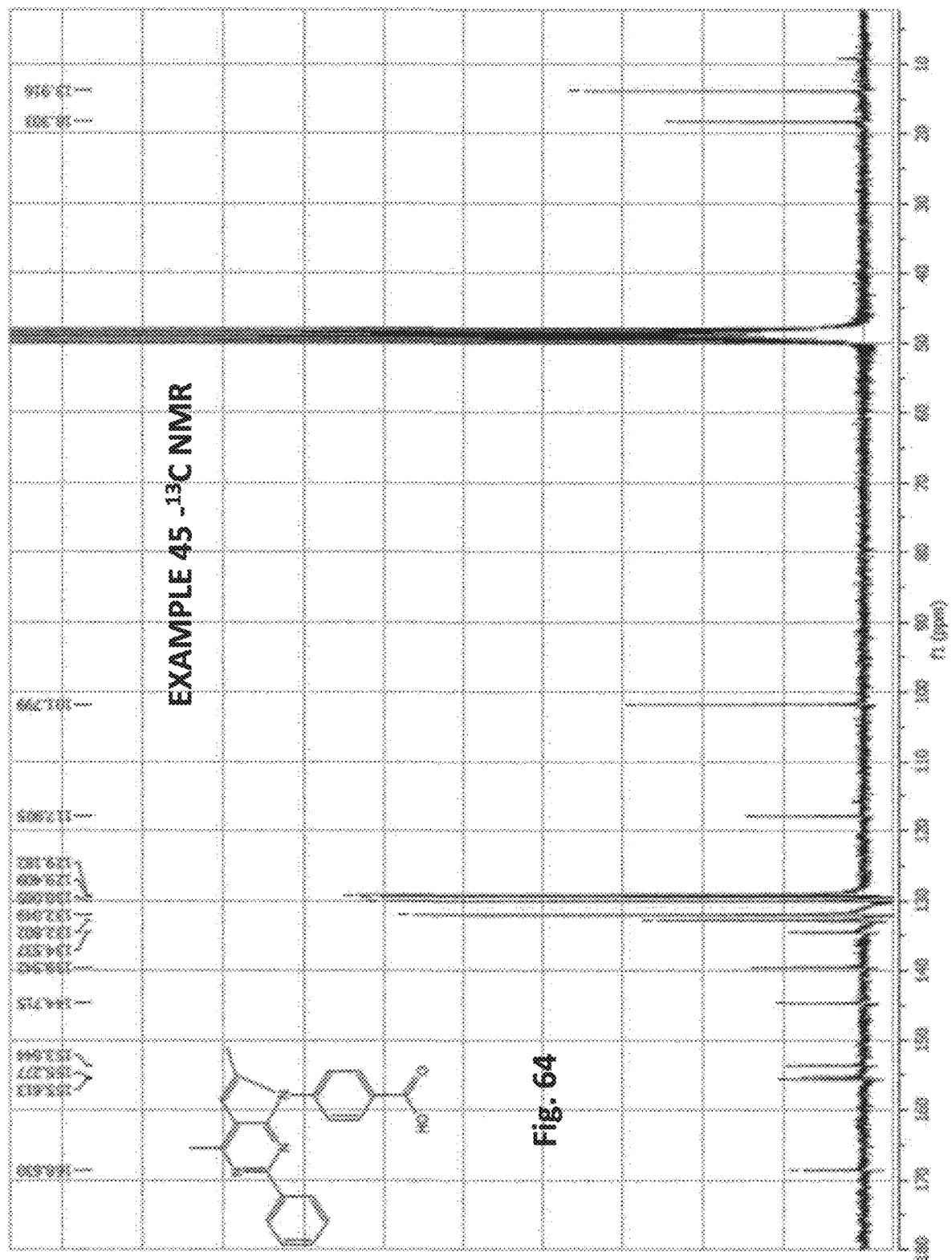
Figure 65:
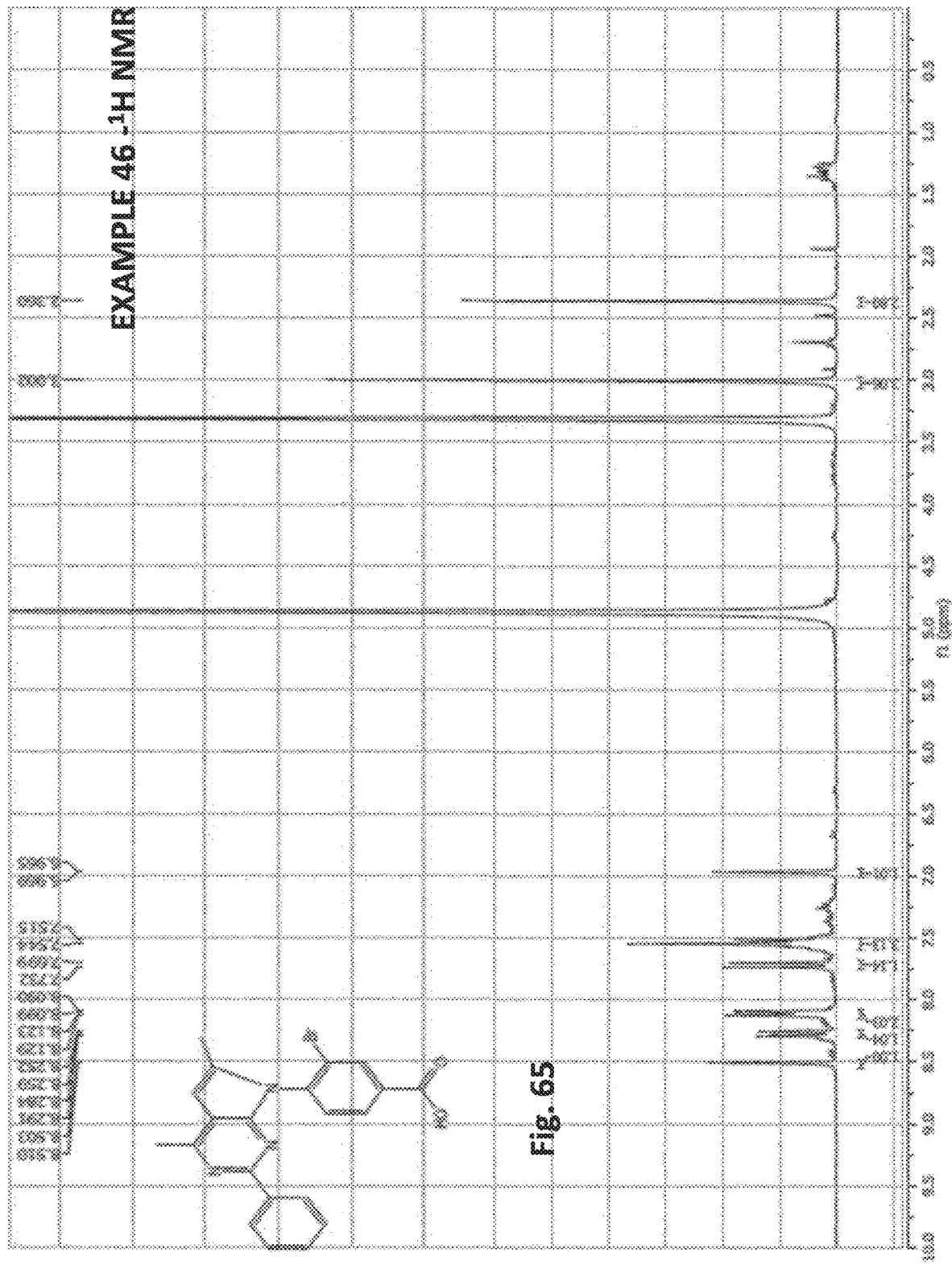
Figure 66:
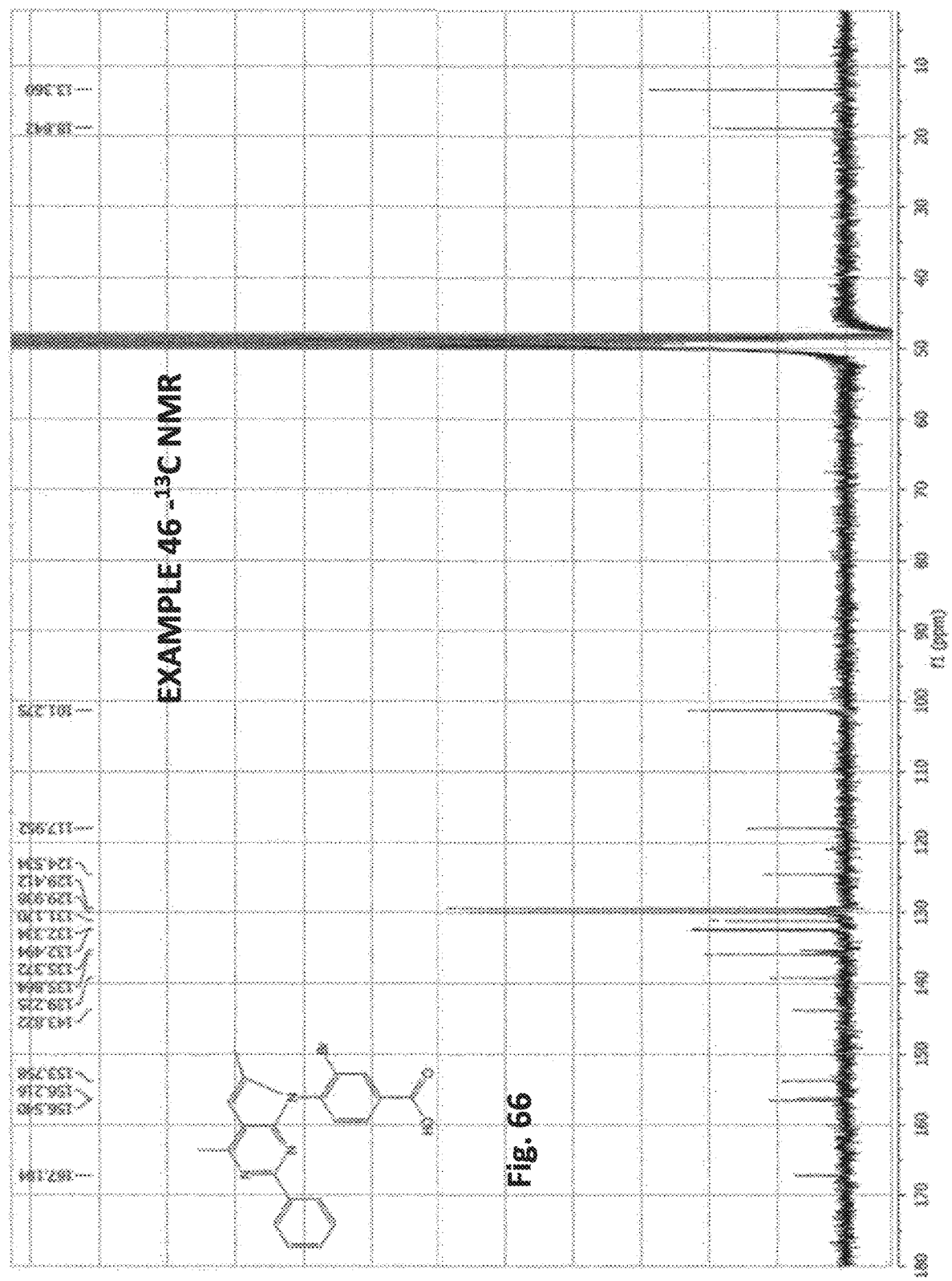

IP administration of compound 3 (10 mg/kg) repeated for 8 days every 12 hours protected wild type C57/BL6 PD mice treated MPTP from midbrain dopaminergic neuronal loss. 20 mg/kg MPTP injections were administered 4 times at the zero day of treatment spaced 2 hours apart. 7 days after the MPTP injections there was approximately an 80% reduction in striatal projections and 40%-50% dopaminergic neuron death in the SN. Mice were anaesthetized deeply with $CO_2$ and perfused intracardially with ice-cold phosphate buffer (PBS; pH 7.2) and subsequently with 4% paraformaldehyde in 0.1 M PBS (PFA). Brains were quickly removed, post-fixed in PFA overnight at 4° C., cryoprotected in 15% sucrose in 0.1 M PBS for 24 hours and in 30% sucrose in 0.1 M PBS for 24 hours at 4° C., frozen, and stored at −80° C. until sectioning. Free-floating cryostat-cut sections (30 µm) were collected using a Bright cryostat at −20° C. at the levels of striatum (AP, 0.2 mm from bregma) and the entire midbrain (AP, −5.6 mm from bregma) (Franklin and Paxinos, 2001). As previously described (Jackson-Lewis et al., 2000), sections first were quenched for 10 minutes in 3% $H_2O_2$/10% methanol. Then sections were pre-incubated with 10% goat serum for 1 hour and incubated with a polyclonal anti-TH antibody (1:2,000; Calbiochem, San Diego, Calif.) for 48 hours at 4° C., followed by incubation with biotinylated anti-rabbit antibody (1:1500; Vector Laboratories, Burlingame, Calif.) in 1% goat serum for 1 hour and avidin-biotin peroxidase complex for 1 hour at room temperature (ABC Elite; Vector Laboratories). Staining was visualized using DAB (Sigma; St. Louis, Mo.) as a chromogen (Vila et al., 2000). The specificity was tested in adjacent sections with the primary or the secondary antibody omitted. The sections were stained with cresyl violet (NissI staining) as described previously (Franklin and Paxinos, 2001), and then dehydrated in graded ethanols and cover slipped. Total numbers of TH- and NissI-positive cells were counted in both hemi-brainstems by using stereological methods (see, e.g., Jackson-Lewis et al., 2000). The total number of TH-positive and NissI-stained SNpc were counted by using the optical fractionator, an unbiased method of cell counting that is not affected by either the volume of reference or the size of the counted neurons. The SNpc was delineated by using a computer-assisted image analysis system (Jackson-Lewis et al., 2000). TH- and NissI-stained neurons were counted in every fourth section throughout the entire extent of the SNpc. T standard mouse atlas was used as an anatomical reference (Franklin and Paxinos, 2001). Compound 3 treatment increased the number of surviving neuronal bodies by 33.5% (FIGS. 5 C and 5D).

IP administration of the compound of the invention compound 3 (10 mg/kg) every 12 hours for 8 days protected wild type 128/SV PD mice treated with MPTP from midbrain dopaminergic neuronal loss but not Nurr1 heterozygote 129/SV mice treated with the same toxin. 20 mg/kg MPTP injections were administered 4 times at the zero day of treatment, spaced 2 hours apart. 7 days after the MPTP injections there was approximately an 80% reduction in striatal projections and 40%-50% dopaminergic neuron death in the SN. Mice were anaesthetized deeply with $CO_2$ and perfused intracardially with ice-cold phosphate buffer (PBS; pH 7.2) and subsequently with 4% paraformaldehyde in 0.1M PBS (PFA). Brains were quickly removed, post-fixed in PFA overnight at 4° C., cryoprotected in 15% sucrose in 0.1M PBS for 24 h and in 30% sucrose in 0.1M PBS for 24 h at 4° C., frozen, and stored at −80° C. until sectioning. Free-floating cryostat-cut sections (30 µ) were collected using a Bright cryostat at −20° C. at the levels of striatum (AP, 0.2 mm from bregma) and the entire midbrain (AP, −5.6 mm from bregma) (Franklin and Paxinos, 2001). As previously described (Jackson-Lewis et al., 2000), sections first were quenched for 10 min in 3% $H_2O_2$/10% methanol. Then sections were preincubated with 10% goat serum for 1 h and incubated with a polyclonal anti-TH antibody (1:2,000; Calbiochem, San Diego, Calif.) for 48 h in 4° C., followed by incubation with biotinylated anti-rabbit antibody (1:1500; Vector Laboratories, Burlingame, Calif.) in 1% goat serum for 1 h and avidin-biotin peroxidase complex for 1 h in RT (ABC Elite; Vector Laboratories). Staining was visualized using DAB (Sigma; St. Louis, Mo.) as a chromogen (Vila et al., 2000). The specificity was tested in adjacent sections with the primary or the secondary antibody omitted. The sections were stained with cresyl violet (NissI staining) as described previously (Franklin and Paxinos, 2001), and then dehydrated in graded ethanols and cover slipped. Total numbers of TH- and NissI-positive cells were counted in both hemi-brainstems by using stereological methods (see below (Jackson-Lewis et al., 2000). The total number of TH-positive and NissI-stained SNpc were counted by using the optical fractionator, an unbiased method of cell counting that is not affected by either the volume of reference or the size of the counted neurons. The SNpc was delineated by using a computer-assisted image analysis system (Jackson-Lewis et al., 2000). TH- and NissI-stained neurons were counted in every fourth section throughout the entire extent of the Snpc. As an anatomical reference the standard mouse atlas was used (Franklin and Paxinos, 2001). Compound 3 treatment increased the number of surviving neuronal bodies by 33.5% in wild type 129/SV mice but did not lead to a statistically significant increase in surviving neuronal bodies in Nurr1 heterozygote 129/SV mice (FIG. 5E).

XII. Bioavailability and Neuroprotective Effects of Compound 46

Compound 46 was found to be highly bioavailable and capable of crossing the blood brain barrier. Administration by IP injection to mice revealed significant c-jun transcriptional activation in the midbrain as determined by qPCR 2 hours after administration (FIG. 70A).

Additionally, experiments were conducted to assess whether compound 46 possesses neuroprotective properties. Such assays were performed, for instance, by adding compound 46 (12.5 µM) to human origin SHSY-5Y dopaminergic cells in which death was induced by the mitochondria complex I inhibitor MPP+ (1-methyl-4-phenylpyridinium), the active metabolite of MPTP (1-methyl-4-phenyl-1,2,3,6-tetrahydropyridine). Pretreatment of the cells with compound 46 for 12 to 24 hours prior to incubation with MPP+ significantly increased the survival of cells against varying concentrations of the toxic stimulus. Most of the MPP+-treated cells receiving vehicle died, while the few surviving cells remained attached to the plate but were rounded and had lost all projections. These morphological changes indicated impaired neuronal function. On the contrary, cells treated with compound 46 appeared healthy, flattened, well-attached, and their projections remained intact. The relative survival of SHSY-5Y dopaminergic cells treated with and without compound 46 is shown in FIG. 70B.

XIII. Summary of Biological Activity of Compound 3

Parkinson's disease (PD) is a progressive neurodegenerative disorder characterized by the loss of dopaminergic neurons in the substantia nigra and the gradual depletion of dopamine. Current treatments aim to replenish the dopamine deficit and to improve symptoms, but, over time, they induce dyskinesias while neuroprotective therapies are nonexistent. Here, we report that Nurr1:RXRα activation has a double therapeutic potential for PD, offering both neuroprotective and symptomatic improvement. We designed compound 3, a unique in vivo active Nurr1:RXRα-selective lead small molecule, which prevented dopaminergic neuron demise against PD-causing toxins and PD-related genetic mutations, in a Nurr1-dependent manner, in both patient iPSc-derived dopaminergic neurons and in preclinical mouse PD models. Compound 3 in vivo maintained striatal dopaminergic innervation and alleviated motor symptoms. Remarkably, besides neuroprotection, compound 3 upregulated TH, AADC and GCH1 transcription, increased striatal dopamine in vivo and had symptomatic efficacy in two post-neurodegeneration PD models, without inducing dyskinesias upon chronic daily treatment. The combined neuroprotective and symptomatic effects of compound 3 designates Nurr1:RXRα activation as a potential monotherapy approach in PD.

XCT0135908 In Vivo: Low Stability and Low Brain Penetration

XCT0135908 was administered to mice to test its bioactivity. Intraperitoneal (IP) or intracerebroventricular XCT0135908 (1 and 10 mg/kg) injections did not result in any expression alterations of midbrain genes such c-jun or TH at different time points after administration. LC-MS/MS analysis of blood plasma or brain homogenates and targeted search of the parent compound 1 and 2 hours after IP XCT0135908 (1 μg/kg) administration indicated low compound stability and minimal brain penetration (brain/blood<0.03) (FIGS. 68A-B).

Nurr1:RXRα Activator Compound 3

Figure 71:
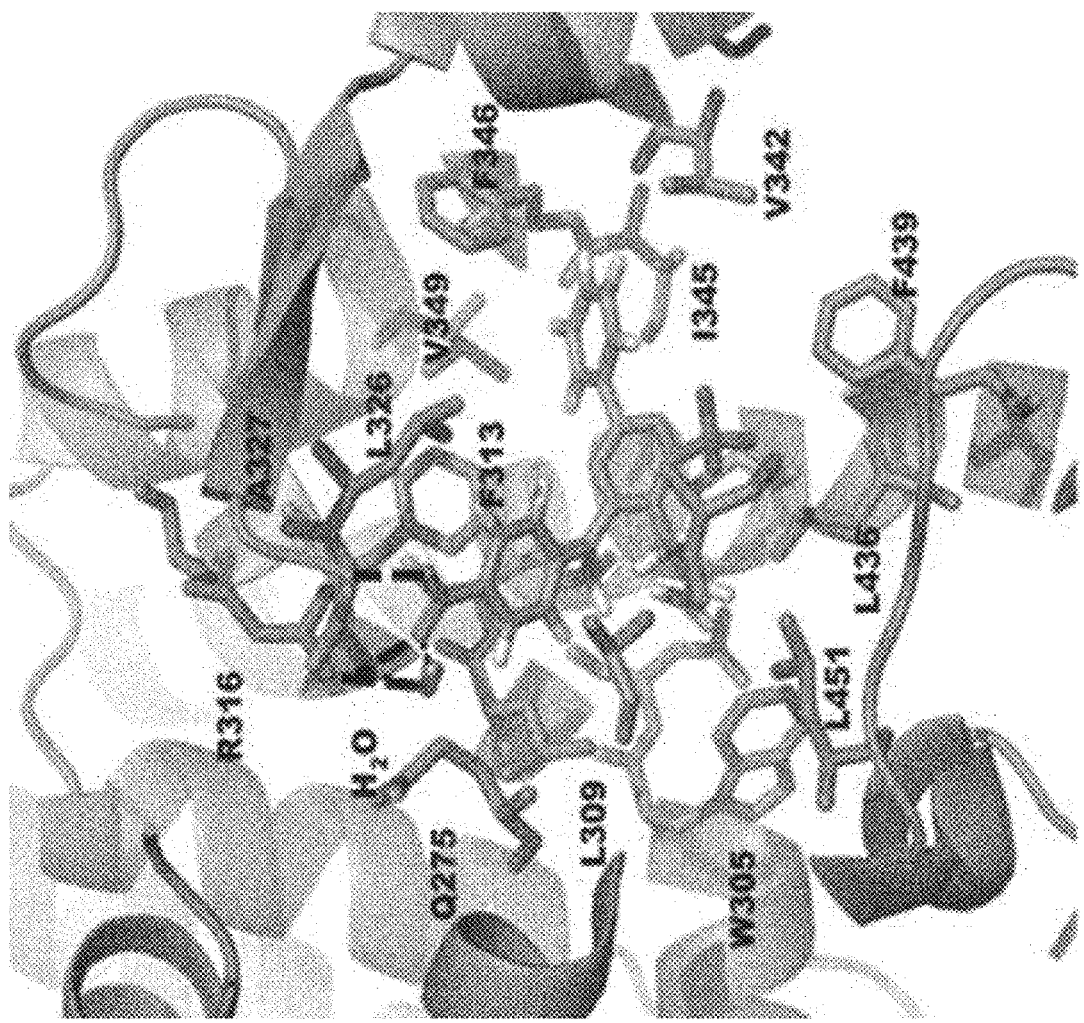
FIG. 71 shows a schematic representation of the intermolecular interactions between compound 3 within the RXRα binding pocket (PDB ID: 1MV9). Relevant hydrogen bonds and amino acids are indicated.

In silico docking simulations show compound 3 to complement the hydrophobic L-shaped binding pocket of RXRα (pdb1MV9). The carboxylic group of compound 3, with the participation of a water molecule, forms a hydrogen bond with the backbone amide of A327 and a salt bridge with the side chain of R316. The phenyl ring of compound 3 participates in π-π interactions with F346 and stabilizes the molecule in the RXRα binding pocket contributing to target affinity (calculated ΔG −16.7 kcal/mol) (FIG. 71). These simulations were validated by methyl or ethyl ester carboxylic group modification, which abolished activation, increasing EC50 by 50 to 100 fold. In addition, halogenation of the compound 3 phenyl ring disturbs the π-π interactions with F346 and also increases the EC50 by approximately 7-fold.

Specificity of Compound 3 for Nurr1:RXRα Heterodimers and Brain Penetration

Compound 3 activated Nurr1:RXRα heterodimers (FIG. 1C) but did not activate Nurr1:RXRγ heterodimers (FIG. 1D), indicating specificity for RXRα and that it does not bind to Nurr1. In naïve SHSY-5Y cells, compound 3 activated endogenous Nurr1:RXRα heterodimers, as verified by loss of activity after knocking-down Nurr1 by approximately 60% using a retrovirus carrying shNurr1 sequences (FIG. 2E) indicating that Nurr1 is required for compound 3 activity (FIG. 2F).

To test off-target effects of compound 3 on complexes aside from Nurr1:RXRα heterodimers, we fused the ligand binding domains of Nurr1, RXRα and a variety of related nuclear receptors to GAL4 DNA-binding domain to create chimeric proteins, while the ligand-binding domain of RXRα was also fused with VP16. These molecular chimeras were co-transfected in pairs with the RXRα:VP16 along with a GAL4-responsive luciferase reporter in SHSY-5Y, which were stimulated with compound 3. Compound 3 strongly activated Nurr1GAL4:RXRαVP16 heterodimer chimeras but failed to activate other RXRαVP16 heterodimer chimeras with VDRGAL4, RXRγGAL4, PPARγGAL4 as well as RXRαGAL4 homodimer chimeras (FIG. 1E). Nur77GAL4:RXRαVP16 heterodimers were partially activated but, Nur77, unlike Nurr1, is not associated with PD and Nur77 knock-down enhances cell survival (Wei et al. Mol Neurobiol. doi:10.1007/s12035-015-9477-7, 2015). The above experiments indicate the high degree of selectivity of compound 3 and point to its neuroprotective potential.

IP administration of compound 3 (1 mg/kg) in mice resulted in compound 3 reaching the brain. This compound exhibited an approximate half-life of about 2 hours in both blood and brain as assessed by LC-MS/MS (brain/blood concentration AUC ratio 1.7, FIGS. 69A-B) and was bioactive, as it increased midbrain c-jun expression (FIG. 69C).

Compound 3 Induces Transcription of DA Biosynthesis Genes and Protects DAergic Cell Lines and Human iPSC Derived DAergic Neurons Against PD Associated Damage Nurr1 regulates the transcription of DA biosynthesis genes (Kim et al. *J. Neurochem.* 85:622-634, 2003 and Gil et al. *J Neurochem* 101:142-150, 2007); however, whether this process is mediated by Nurr1:RXRα heterodimers is unknown. In the human DAergic cell line SHSY-5Y, compound 3, but not vehicle, increased the expression of the three genes required for DA biosynthesis, TH by about 90% (n=6, t-test p=0.0374), aromatic L-amino acid decarboxylase (AADC) by about 70% (n=6, t-test p<0.0001), and GCH1 by about 42% (n=6, t-test p<0.0001), (FIG. 72A), indicating that this up-regulation depends upon Nurr1:RXRα heterodimer activation.

Figure 72:
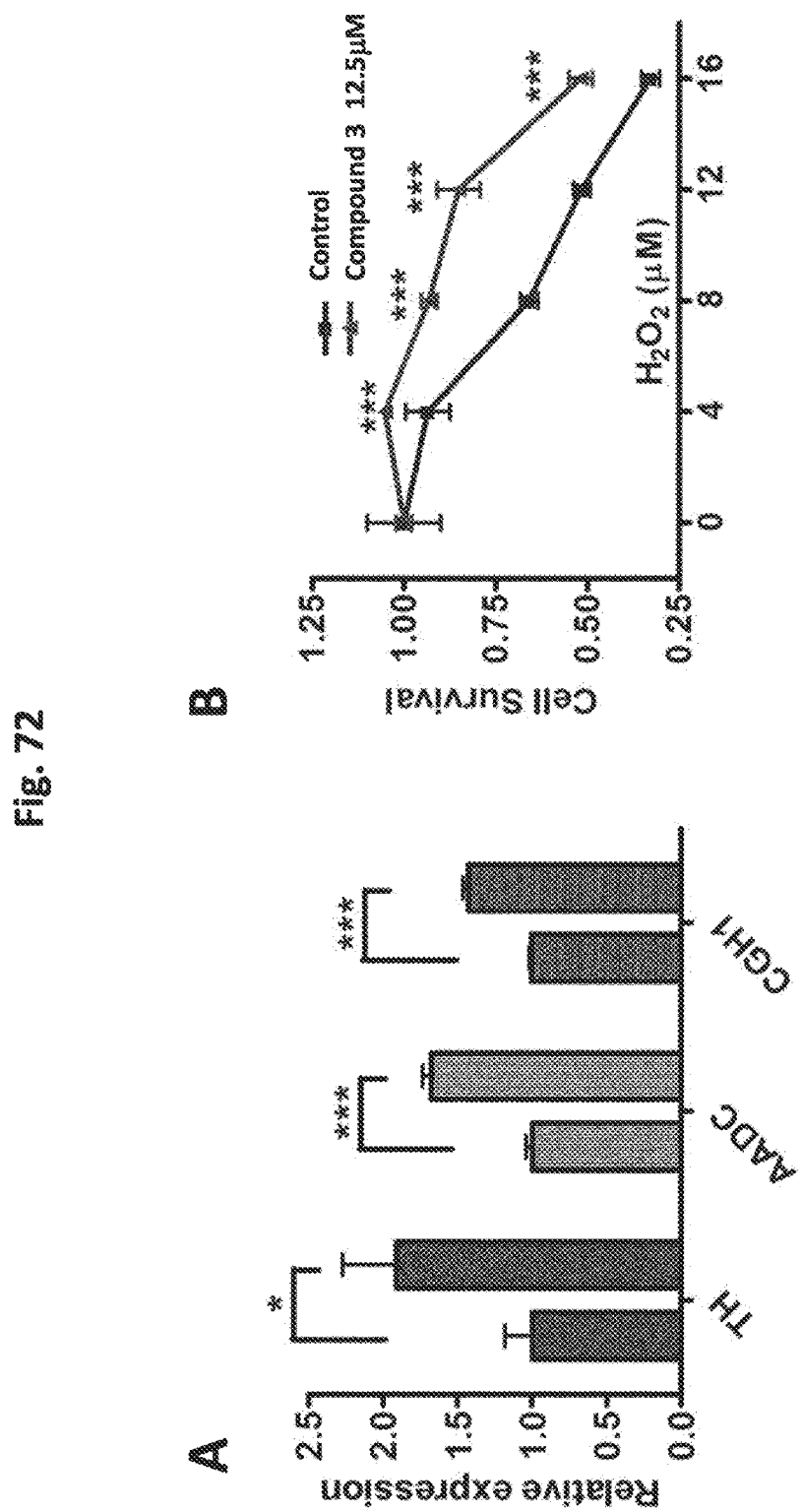
Figure 72:
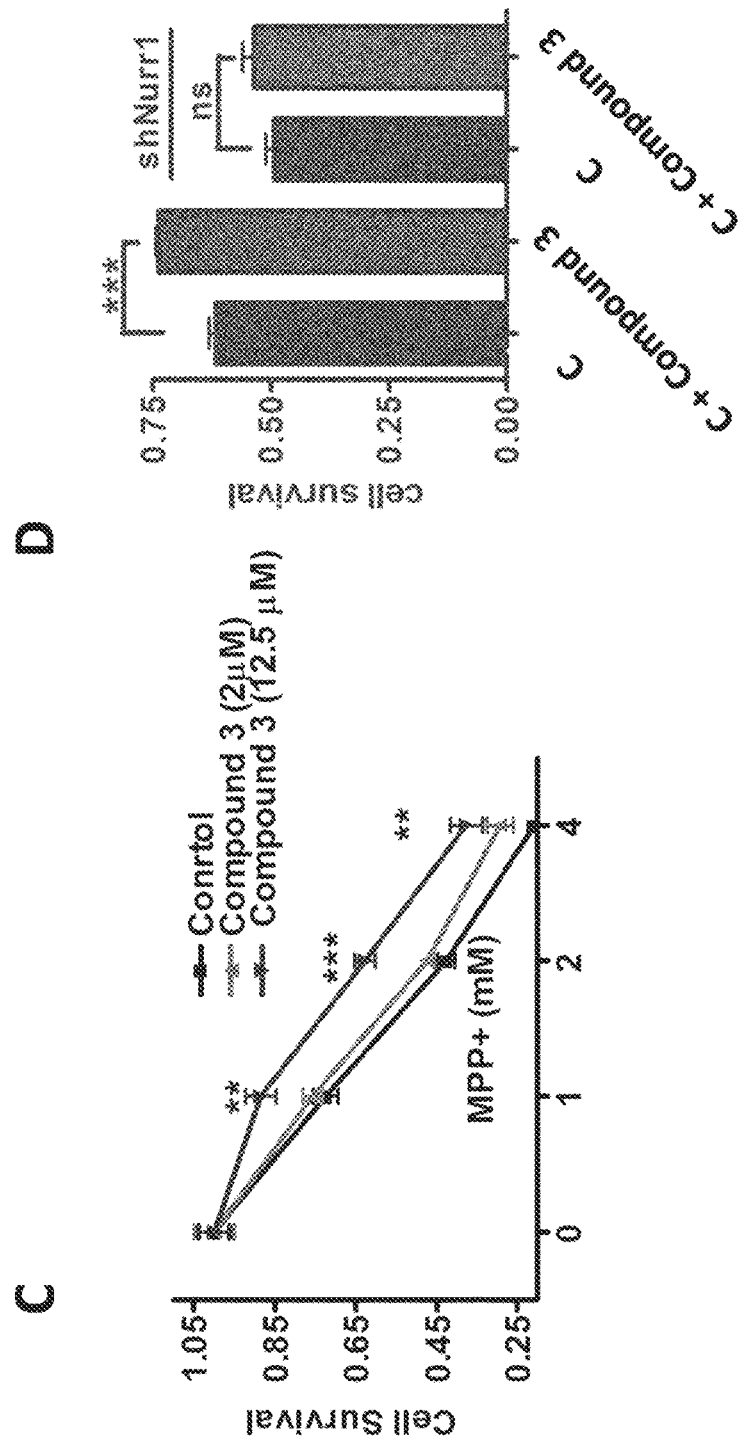
Figure 72:
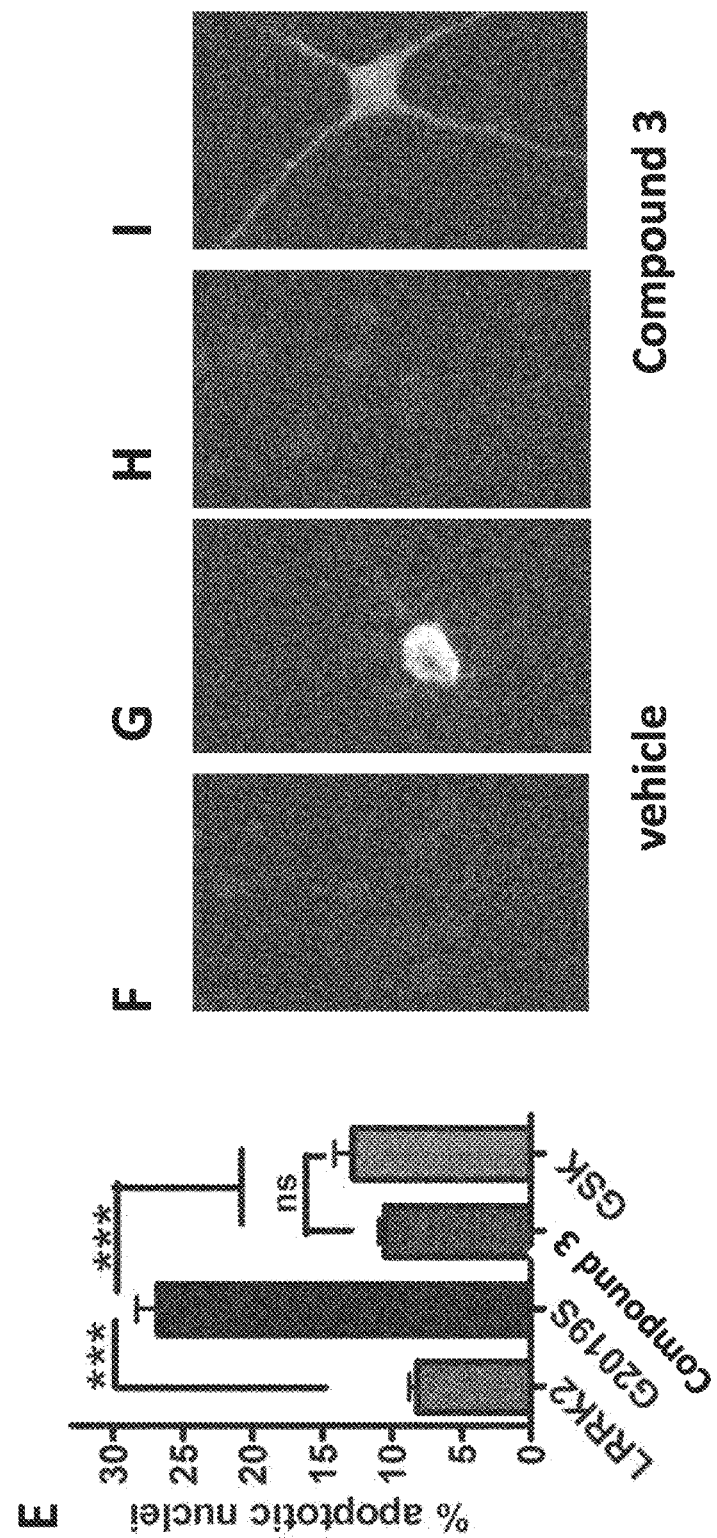
Figure 72:
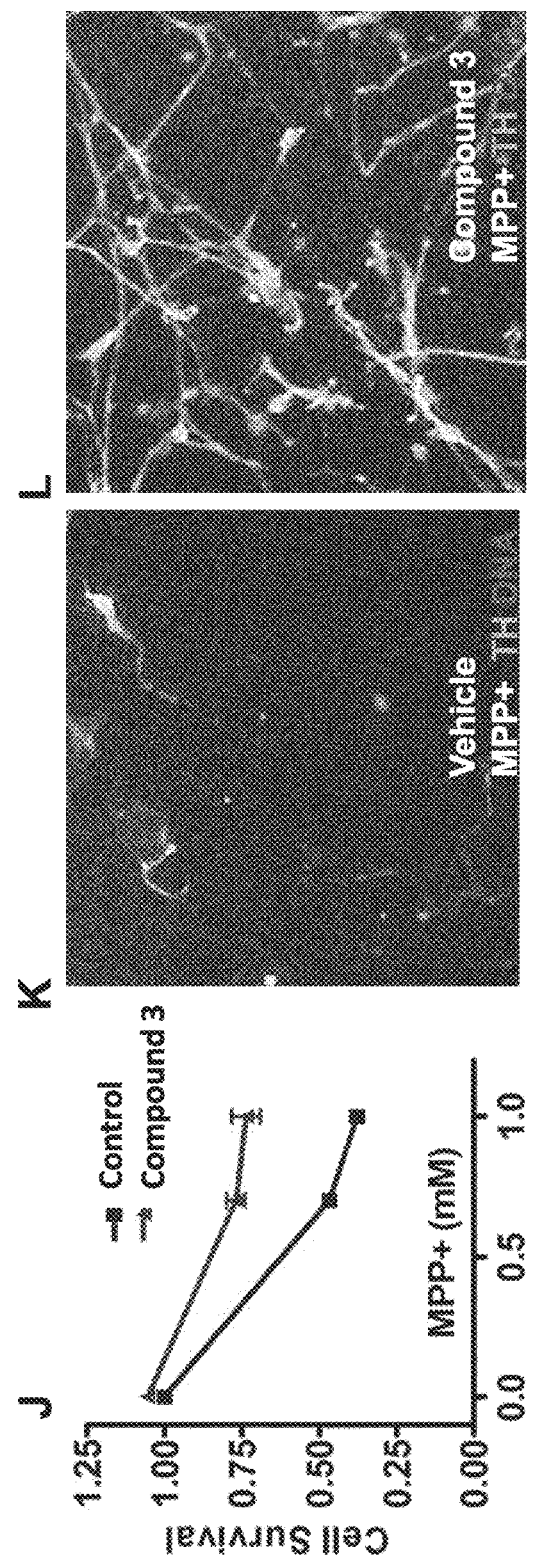
Figure 72:
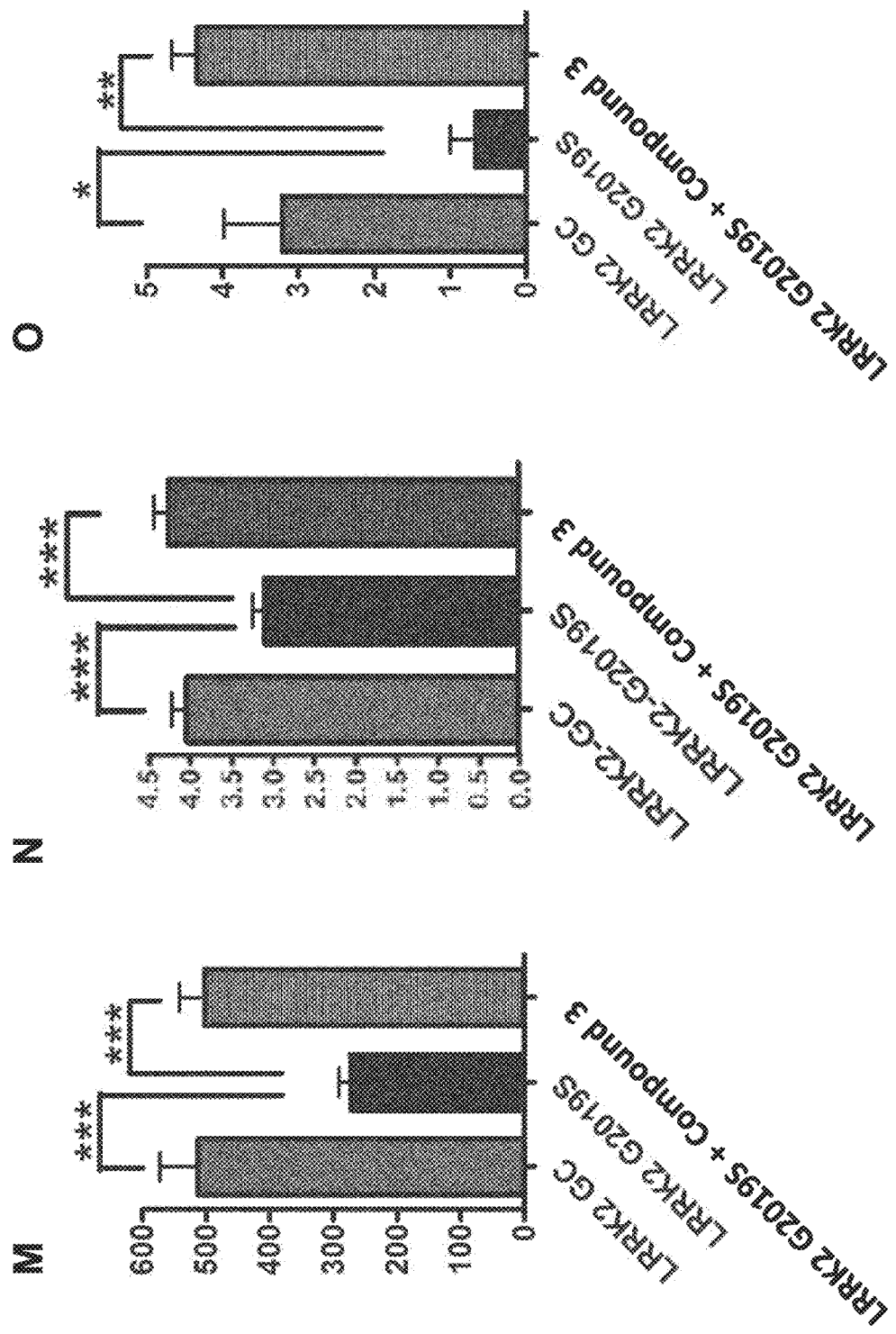
Figure 72:
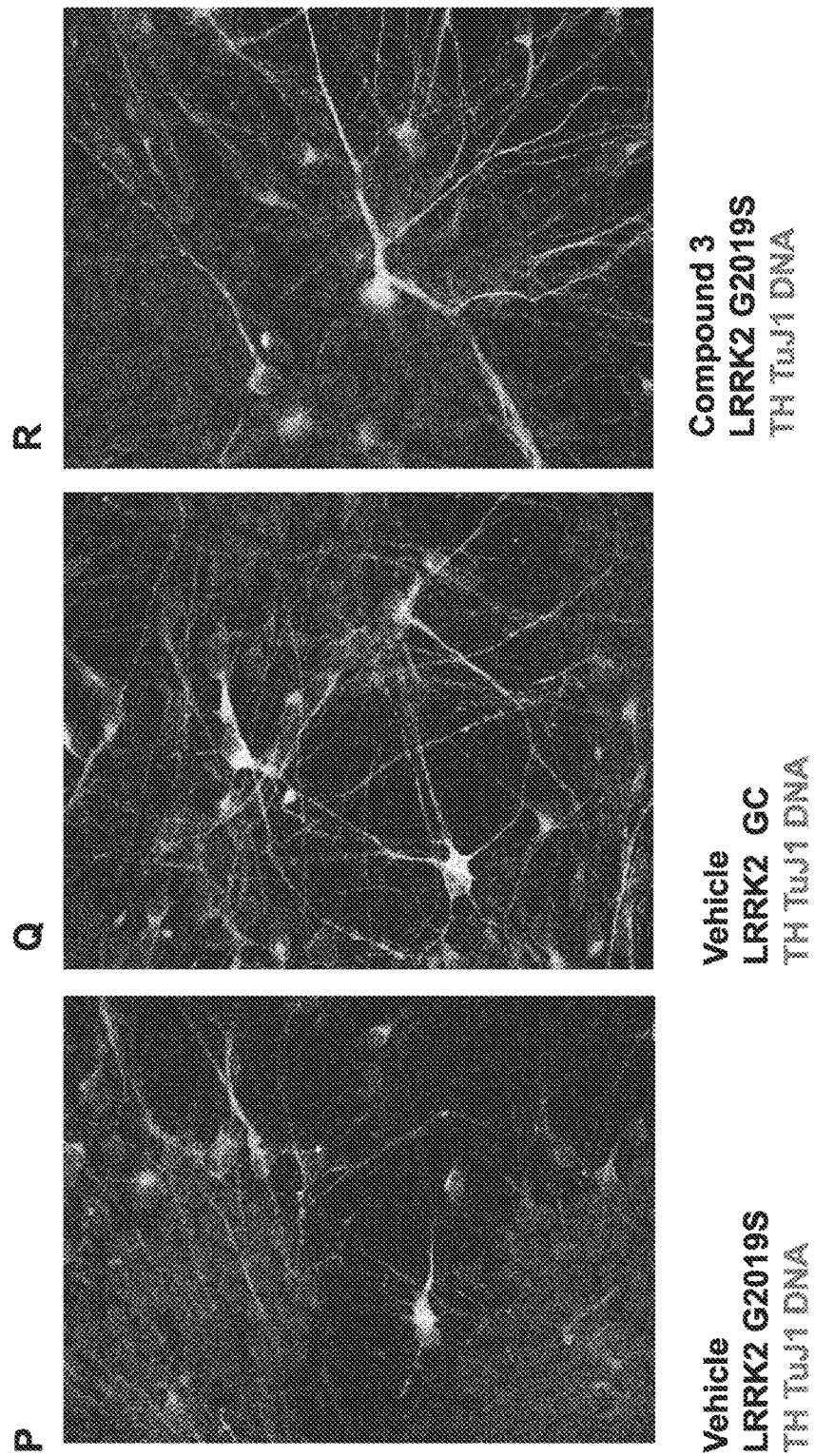

We examined the neuroprotective capability of Nurr1:RXRα heterodimer activation in SHSY-5Y cells where death was induced by either the oxidative stress related $H_2O_2$ or the mitochondria complex I inhibitor MPP+ (1-methyl-4-phenylpyridinium) (FIG. 72B). Compound 3 (12.5 μM) significantly increased cell survival against varying concentrations of the toxic stimuli (2-way ANOVA P<0.0001) in a compound 3 dose-dependent manner (FIG. 72C). The protection conferred by compound 3 was Nurr1-dependent, since it was abrogated by knocking-down endogenous Nurr1 mRNA (FIGS. 1E and 72D). The neuroprotective effects of compound 3 extend to damage induced by the PD-associated mutation G2019S in the Leucine-Rich Repeat Kinase 2 (LRRK2) gene, the most common genetic defect associated with clinical PD (Tofaris et al. *J. Neurosci.* 26:3942-3950, 2006). Rat cortical neurons, co-transfected with CMV-GFP for identification, and CMVLRRK2-G2019S cDNAs show increased apoptosis as assessed by DAPI staining, compared to control neurons co-transfected with a LRRK2 wt cDNA. Compound 3 treatment reduced apoptosis to control levels, comparable to those the LRRK2 inhibitor GSK2578215A (1-way ANOVA P<0.0001) (FIGS. 72E-72I).

To ascertain the translational therapeutic potential of compound 3, we tested whether human midbrain-specific iPSc-derived DAergic neurons, as indicated by positive staining and qPCR for the neuronal markers MAP2, TH, FoxA2, Lmx1 and En1, can be protected from MPP+ toxicity. Compound 3 was able to double the number of surviving neurons after MPP+ exposure within 24 hours, compared to vehicle (FIGS. 72J-72L). The surviving control neurons had fewer and retreating projections, indicating compromised function (FIG. 72K) while the neurons that had received compound 3 had retained a complex network of projections and contacts (FIG. 72L). In addition, we tested compound 3 in iPSc-derived DAergic neurons from a PD patient carrying the LRRK2-G2019S mutation. These neurons showed contracted neurites with reduced branching, phenomena that can be reversed upon correction (LRRK2GC) of the LRRK2-G2019S mutation (Tofaris et al. J. Neurosci. 26:3942-3950, 2006). Treatment of the LRRK2-G2019S mutated DAergic neurons with compound 3 (12.5 µM) for 14 days (FIGS. 72M-72Q) also increased neurite length, number and branching by 83% (1-way ANOVA $p<0.0007$; Kruskal-Wallis $p<0.01$), 38% (1-way ANOVA $p<0.0001$; Kruskal-Wallis $p<0.001$) and 650% respectively (1-way ANOVA $p<0.01$; Kruskal-Wallis $p<0.05$) (FIGS. 72M-72O).

These experiments demonstrate the in vitro potential of Nurr1:RXRα activation to shield human DAergic neurons from diverse PD related neuronal death stimuli such as toxins and the LRRK2-G2019S mutation.

Neuroprotection of Compound 3 In Vivo in Preclinical Mouse PD Models

Figure 73:
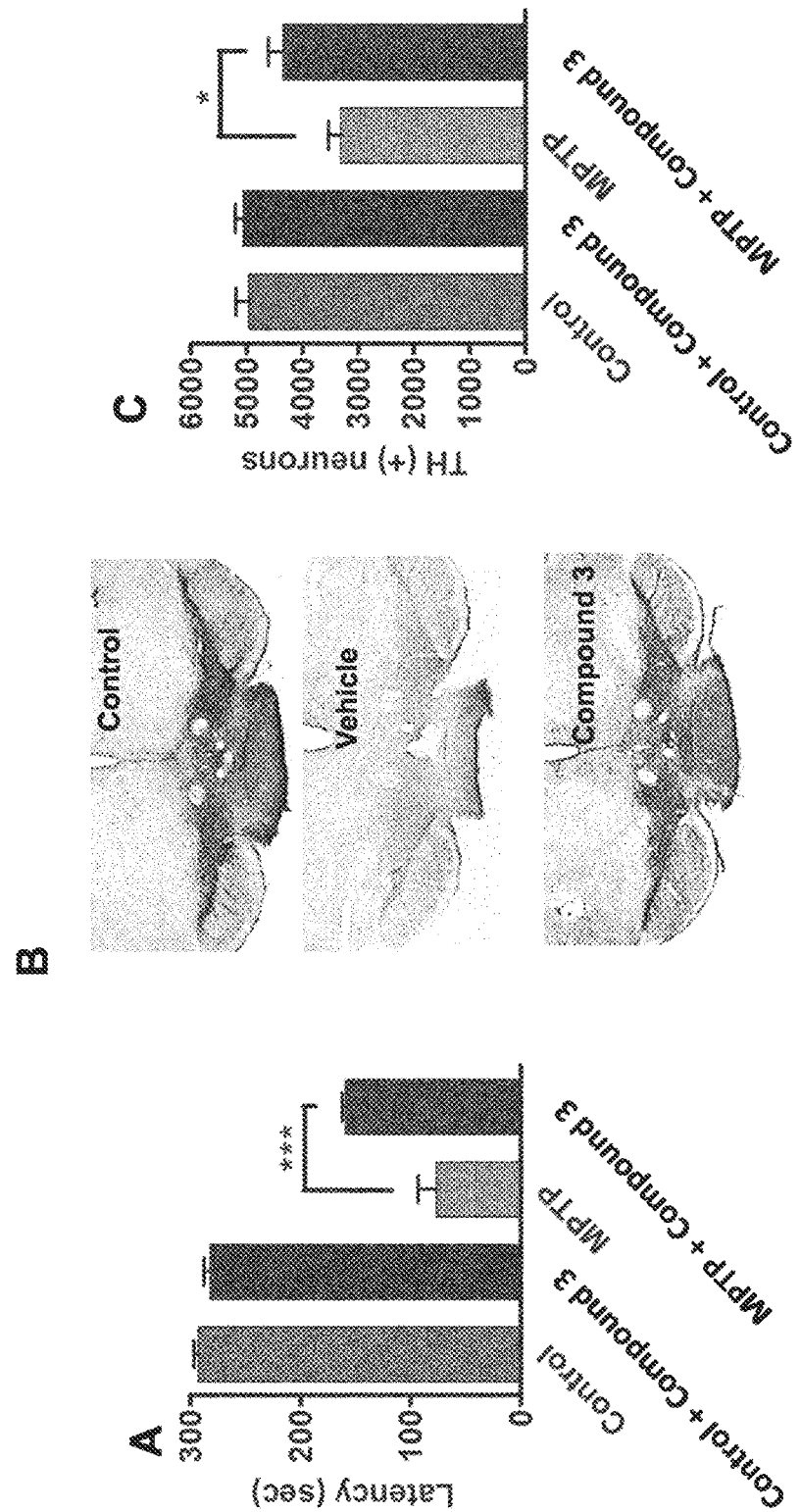
FIG. 73 shows images of TH ICH in the substantia nigra of control C57BL/6 mice or mice exposed to MPTP and receiving either vehicle or compound 3 treatment.
Figure 73:
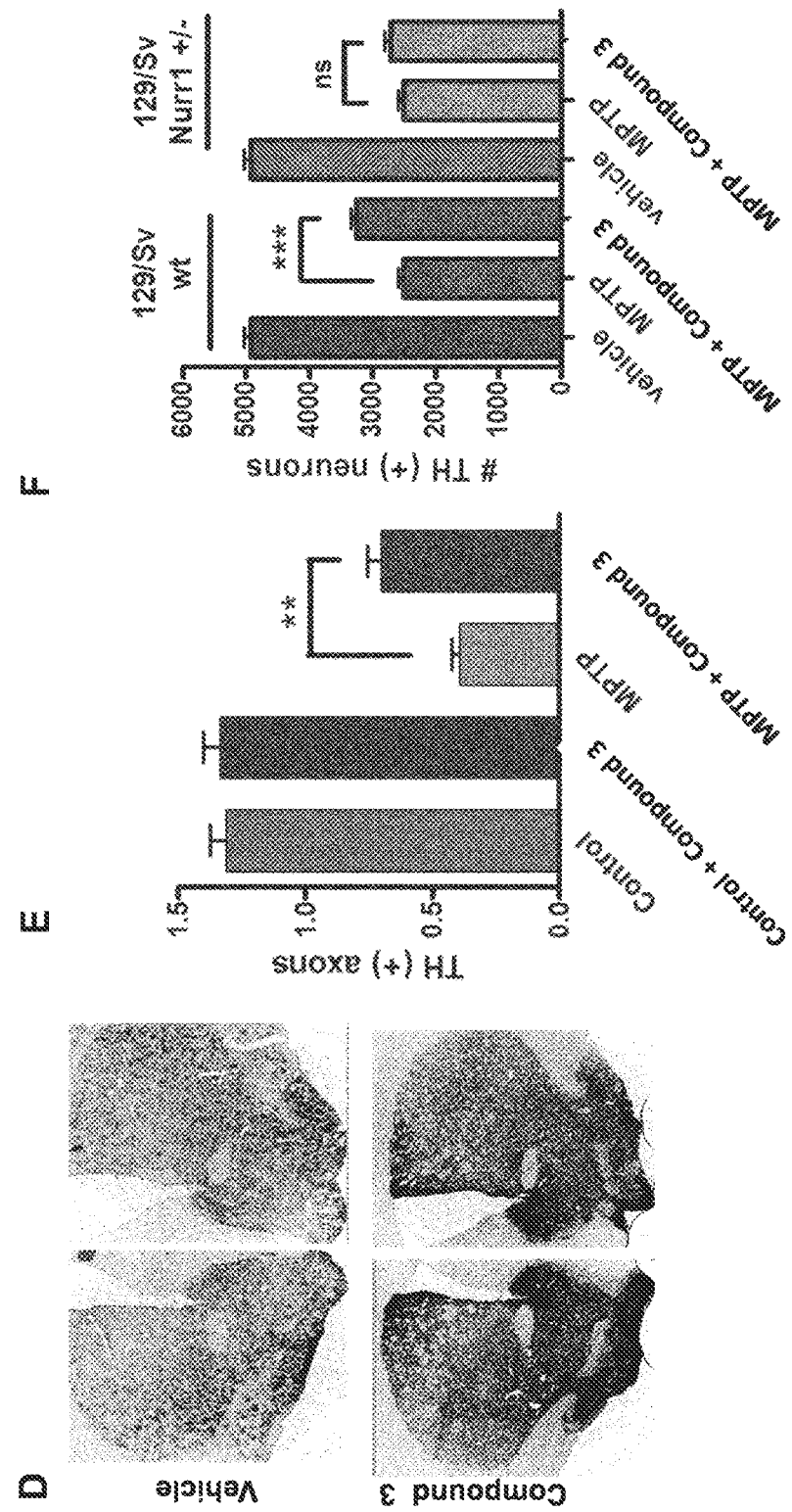

We assessed the neuroprotective effects of Nurr1:RXRα heterodimer activation in vivo in two established preclinical C57BL/6 mouse PD models: the acute MPTP and the unilateral 6-OHDA injection in the SN. Compound 3 IP injections (10 mg/kg) every 12 hours, starting 12 hours before toxin administration, were continued for 6 days (MPTP) and 14 days (6-OHDA). To distinguish phenotypic effects, lasting 4-8 hours, from neuroprotection, compound 3 administration was discontinued 24-36 hours before behavioral and histological examination of the mice. In the MPTP model, mice receiving compound 3 had considerably improved motor coordination (>100%) (1 way ANOVA, $P<0.0001$) than vehicle-injected mice, as assessed by the accelerating rotarod (FIG. 73A). SN unbiased stereological neuronal counting showed that TH(+) midbrain neuron survival was increased by 31% (1 way ANOVA, $p=0.0003$) in compound 3-treated animals, to a value not significantly different from control mice (FIGS. 73B-C). Additionally, compound 3 protected SN axonal projections to the striatum, doubling the number of remaining terminals (1 way ANOVA, $P<0.0001$) (FIGS. 73D-E). The neuroprotection was compound 3 dependent because a once-a-day injection regimen (20 mg/kg) was ineffective. Compound 3 neuroprotection against MPTP toxicity was equally effective in 129sv wt mice (1 way ANOVA, $P<0.001$), but it was abolished in Nurr1+/− 129sv animals, validating that the in vivo neuroprotective effects of compound 3 require Nurr1:RXRα heterodimers (FIG. 73F).

Figure 74:
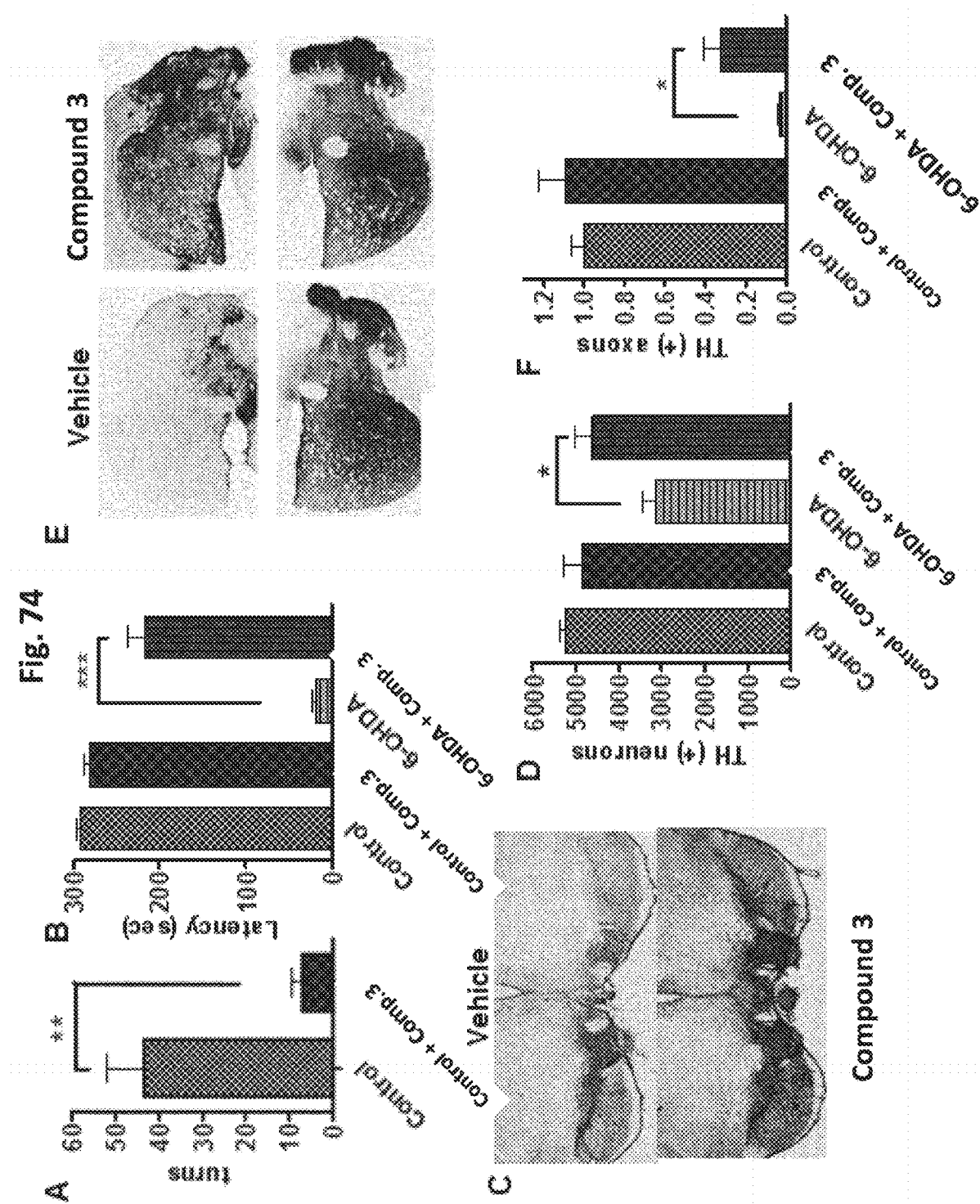
FIGS. 74A-74L show the neuroprotective effects of compound 3 against 6-OHDA and AAV-ASYN toxicity in mice.
Figure 74:
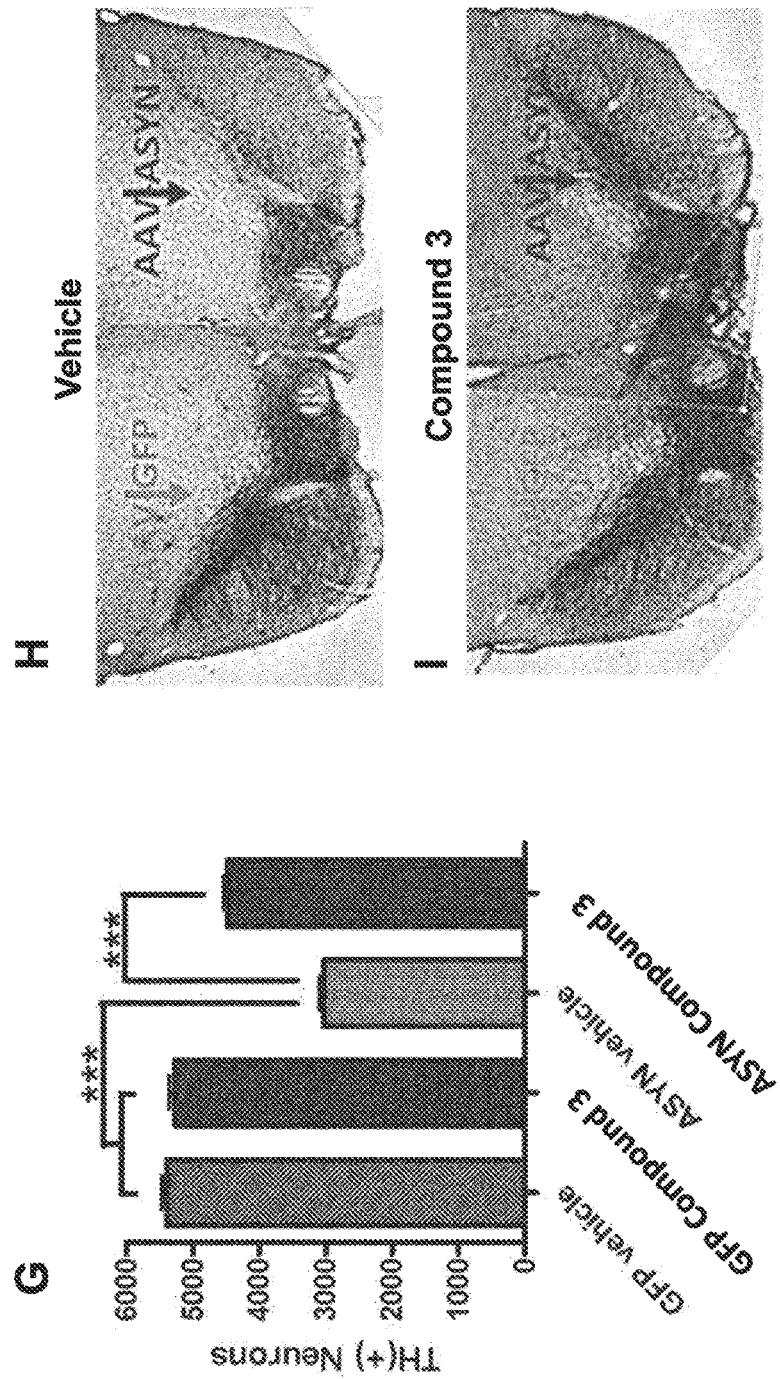
Figure 74:
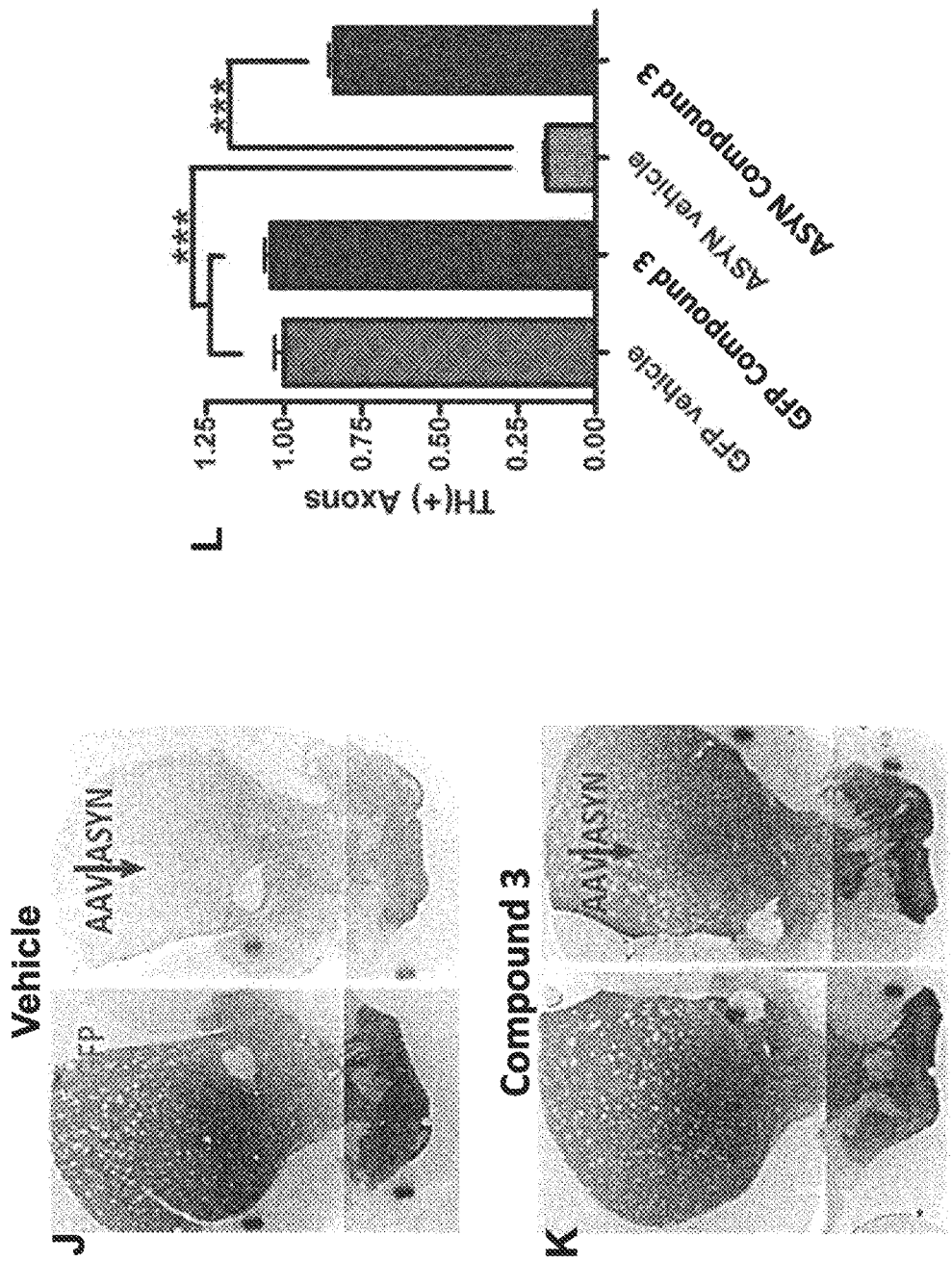

Nurr1:RXRα activation showed even more striking effects in the 6-OHDA model. Compound 3 produced a dramatic reduction of apomorphine induced contralateral turns by approximately 8-fold (Mann Whitney, $p=0.0159$) (FIG. 74A), while motor coordination was almost entirely restored to control levels, as evaluated by the rotarod test (1 way ANOVA, $P<0.0001$, Mann Whitney $p=0.0079$) (FIG. 74B). The number of surviving TH(+) neurons in the SN of compound 3-treated mice was increased by 47%, (1 way ANOVA, $P<0.05$, Mann Whitney, $p=0.0317$) to the level of complete restoration, as indicated by unbiased stereological neuronal counting (FIGS. 74C-D). Total neuronal determination by NueN staining showed similar results. Striatal innervation, which was practically obliterated in the vehicle-treated control mice, also showed a 10-fold higher preservation of TH(+) DAergic projections (1 way ANOVA $p<0.0001$, Mann Whitney $p=0.0159$) (FIGS. 74E-F).

Because the predictive validity of toxin-based mouse PD models for neuroprotection in humans is questionable, we proceeded to test the effect of compound 3 in a mouse model, where AAV viruses overexpressing wt alpha-synuclein (AAV-ASYN) under the chicken beta-actin promoter were unilaterally injected, combined with contralateral injections of (AAV-GFP). The same compound 3 (10 mg/kg every 12 h for 2 weeks) or vehicle treatment regimen was followed as in the toxin models. Unbiased stereology showed that the vehicle-treated AAV ASYN injected animals suffered a 44% decrease of TH(+) and NeuN(+) midbrain neurons in comparison to the AAV-GFP injected side (FIGS. 74G-I). On the contrary, in compound 3-treated AAV-ASYN-injected animals, unbiased stereology showed that the number of NeuN(+) midbrain neurons increased (Wilcoxon $p<0.05$; Mann-Whitney $p=0.00214$) and the quantity of TH(+) midbrain neurons was increased by about 47% (Wilcoxon $p<0.05$; Mann-Whitney $p=0.00214$) in comparison to AAV-ASYN injected animals treated with vehicle (FIG. 74G). Striatal innervation of unilaterally AAV-ASYN injected brains resulted in a dramatic depletion of TH(+) axons by almost 85% in animals treated with vehicle, wheareas in compound 3-treated animals striatal TH(+) axons were increased over 5 fold (1 way ANOVA, $P<0.001$, Wilcoxon $p<0.0156$)(FIGS. 74J-L).

These experiments demonstrate DAergic neuroprotective effects of Nurr1:RXRα activation in both toxin-based and genetic preclinical animal models of PD.

Figure 75:
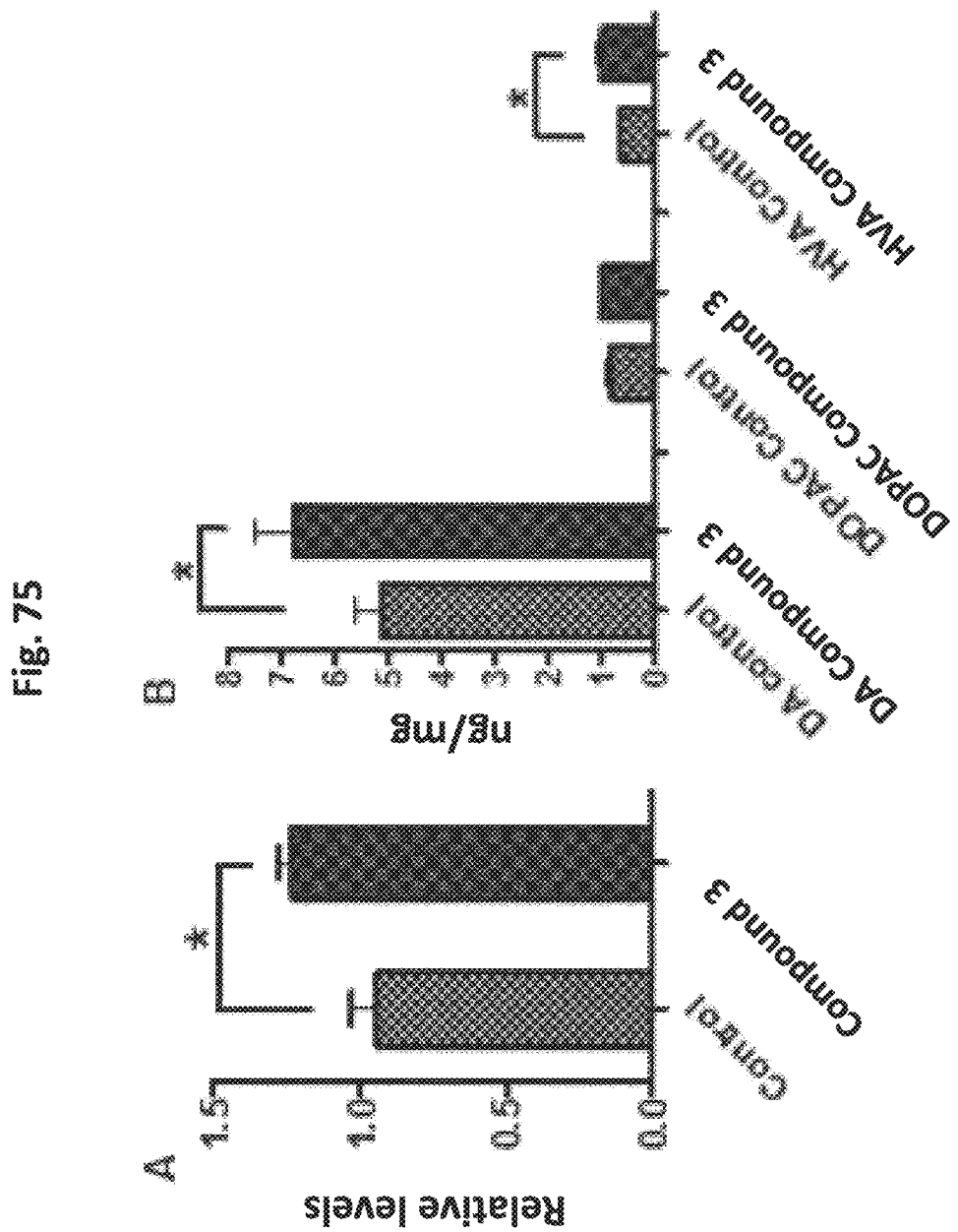
FIGS. 75A-75J show that compound 3 induces dopamine biosynthesis and symptomatic relief without dyskinesias in vivo in PD mouse models.
Figure 75:
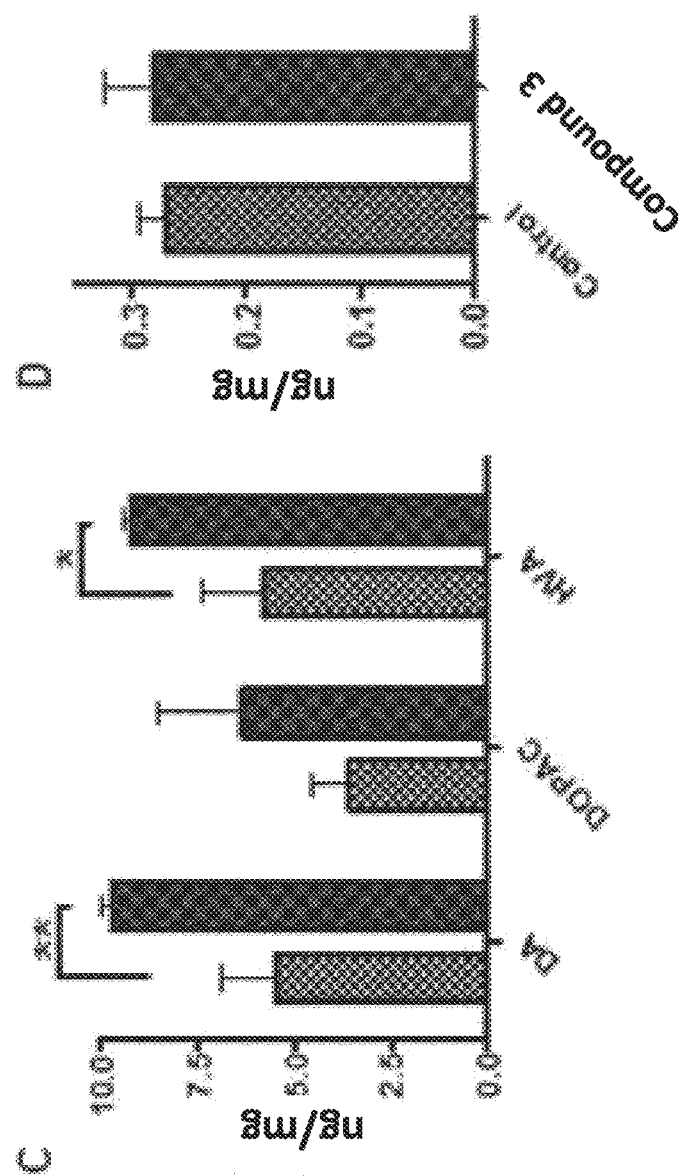
Figure 75:
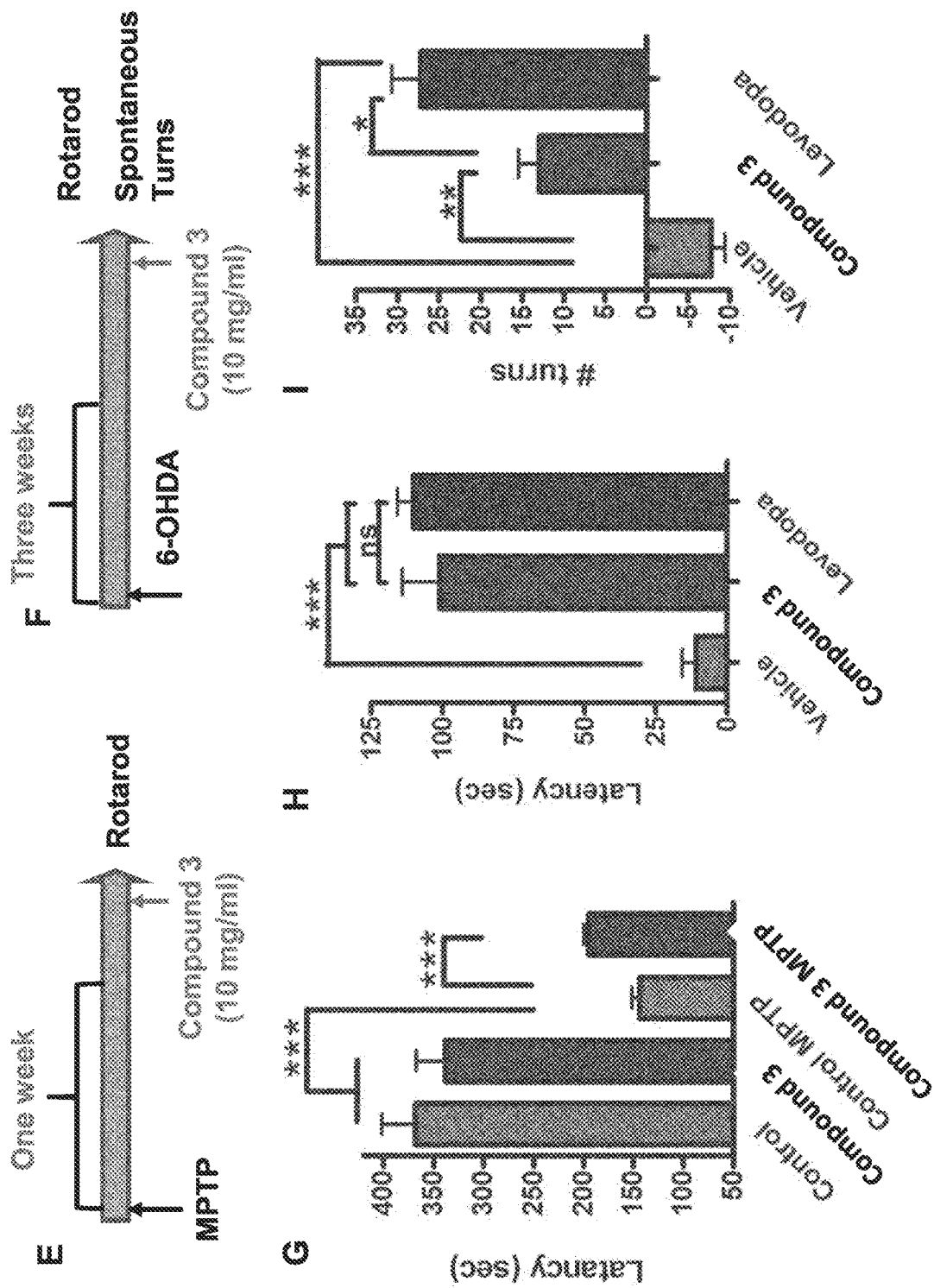
Figure 75:
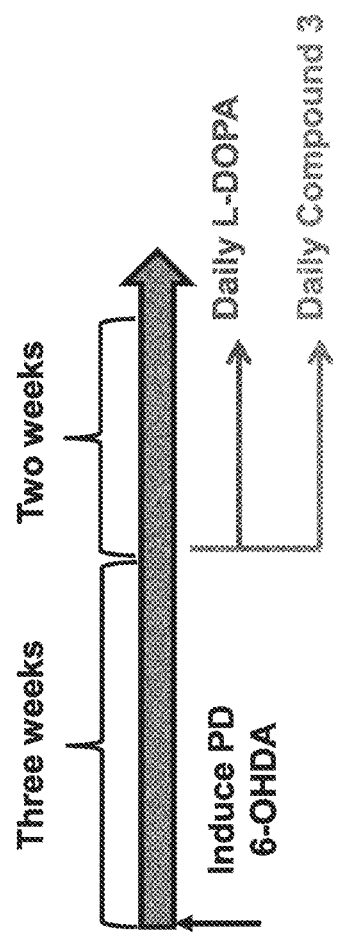

Chronic Daily Treatment with Compound 3 Induces DA Biosynthesis In Vivo and Symptomatic Efficacy without Dyskinesias in Two Post-Neurodegeneration PD Models Given the role of Nurr1:RXRα activation in the transcriptional regulation of DA biosynthesis genes, we tested whether compound 3 could increase DA levels in wt and ASYN transgenic mice (Tofaris et al. J. Neurosci. 26:3942-3950, 2006), which display reduced striatal DA levels after reaching adulthood. A single compound 3 (10 mg/kg) IP injection in wt mice resulted in increased TH gene expression (t test $p=0.0396$) in the midbrain within 4 hours (FIG. 75A). Striatal DA and DA metabolite levels were also increased, and their ratio remained constant, indicating physiological DA catabolism (FIG. 75B). Aiming to model PD based on human genetic data, we also tested whether compound 3 could increase DA levels in ASYN transgenic mice. A single IP injection of compound 3 (10 mg/kg) was able increase striatal DA (t test $p=0.01069$) and DA metabolite levels in ASYN transgenics as well (FIG. 75C) in comparison to mice receiving vehicle. The effect of compound 3 was limited to DA biosynthesis, since noradrenaline levels remained unaffected (FIG. 75D).

We subsequently tested whether the DA increase could be translated in symptomatic relief in post-degeneration PD mouse models based on treatment with MPTP or 6-OHDA (FIGS. 75E-F). A single dose of compound 3 (10 mg/kg) 8 days post-acute MPTP injection or 5-6 weeks post-unilateral 6-OHDA injection, significantly improved temporarily motor coordination in both models (1-way ANOVA, $P=0.01$) (1-way ANOVA, $P=0.0001$) respectively 4 hours, post-dosing (FIGS. 75G-H) and induced contralateral turns in the 6-OHDA model (1-way ANOVA, $P<0.0001$) (FIG. 75I), an effect similar to that of levodopa. Compound 3-induced symptomatic improvement in these models disappeared 8 hours post-dosing. These experiments indicate that Nurr1:

RXRα activation can indeed offer symptomatic relief in rodents, further validating our monotherapy hypothesis.

Significantly, compound 3 was compared to levodopa in causing AIMs. Mice treated daily with levodopa, starting 21 days post-unilateral 6-OHDA injection, displayed severe hyperkinetic dyskinesias/AIMs within 7 days (FIGS. 4C and 75J). In contrast, similar daily compound 3 (10 mg/kg) administration for at least two weeks resulted in consistently improved motor coordination (FIGS. 75H-1) without resulting in dyskinesias/AIMs (2-way ANOVA, p=0.0061, Mann Whitney p=0.0043) (FIG. 4C). These experiments exemplify the simultaneous symptomatic usefulness of Nurr1: RXRα activation devoid of undesirable complications.

REFERENCES

Anderson G, Noorian A R, Taylor G, Anitha M, Bernhard D, Srinivasan S, Greene J G. Loss of enteric dopaminergic neurons and associated changes in colon motility in an MPTP mouse model of Parkinson's disease. Exp Neurol. 2007 September; 207(1):4-12.

Arfaoui A, Lobo M V, Boulbaroud S, Ouichou A, Mesfioui A, Arenas M I. Expression of retinoic acid receptors and retinoid X receptors in normal and vitamin A deficient adult rat brain. Ann Anat. 2012. pii: S0940-9602(12) 00129-X.

Bäckman C, Perlmann T, Wallén A, Hoffer B J, Morales M. A selective group of dopaminergic neurons express Nurr1 in the adult mouse brain. Brain Res. 1999:851(1-2):125-32.

Berrios, G E (1985). "The Psychopathology of Affectivity: Conceptual and Historical Aspects". *Psychological Medicine* 15 (4): 745-758. doi:10.1017/S0033291700004980.PMID 3909185.

Buervenich S, Carmine A, Arvidsson M, Xiang F, Zhang Z, Sydow O, Jönsson E G, Sedvall G C, Leonard S, Ross R G, Freedman R, Chowdari K V, Nimgaonkar V L, Perlmann T, Anvret M, Olson L. NURR1 mutations in cases of schizophrenia and manic-depressive disorder. AJMG. 2000; 96(6):808-13.

Carlson, C. Donald; Heth (2007). *Psychology the science of behavior* (4th ed.). Pearson Education Inc. ISBN 0-205-64524-0

Chaudhuri K R, Schapira A H. Non-motor symptoms of Parkinson's disease: dopaminergic pathophysiology and treatment. Lancet Neurol. 2009; 8(5):464-74.

Chu Y, Kompoliti K, Cochran E J, Mufson E J, Kordower J H. Age-related decreases in Nurr1 immunoreactivity in the human substantia nigra. J Comp Neurol. 2002 Aug. 26; 450(3):203-14.

Chu Y, Kordower J H. Age-associated increases of alpha-synuclein in monkeys and humans are associated with nigrostriatal dopamine depletion: Is this the target for Parkinson's disease? Neurobiol Dis. 2007 January; 25(1):134-49.

Emmanouil D E, Papadopoulou-Daifoti Z, Hagihara P T, Quock D G, Quock R M. A study of the role of serotonin in the anxiolytic effect of nitrous oxide in rodents. Pharmacol Biochem Behav. 2006 June; 84(2):313-20. Epub 2006 Jul. 7

Franklin K B J, Paxinos G. The Mouse Brain in Stereotaxic Coordinates. San Diego: Academic Press; 2001.

Grimes D A, Han F, Panisset M, Racacho L, Xiao F, Zou R, Westaff K, Bulman D E. Translated mutation in the Nurr1 gene as a cause for Parkinson's disease. Mov Disord. 2006 July; 21(7):906-9.

Henchcliffe C, Severt W L. Disease modification in Parkinson's disease. Drugs Aging. 2011 Aug. 1; 28(8):605-15

Hering R, Petrovic S, Mietz E M, Holzmann C, Berg D, Bauer P, Woitalla D, Müller T, Berger K, Krüger R, Riess O. Extended mutation analysis and association studies of Nurr1 (NR4A2) in Parkinson disease. Neurology. 2004 Apr. 13; 62(7):1231-2.

Healy D G, Abou-Sleiman P M, Ahmadi K R, Gandhi S, Muqit M M, Bhatia K P, Quinn N P, Lees A J, Holton J L, Revesz T, Wood N W. NR4A2 genetic variation in sporadic Parkinson's disease: a genewide approach. Mov Disord. 2006 November; 21(11):1960-3.

Hermanson E, Borgius L, Bergsland M, Joodmardi E, Perlmann T. Neuropilin1 is a direct downstream target of Nurr1 in the developing brain stem. J Neurochem. 2006 June; 97(5):1403-11

Jackson-Lewis V, Liberatore G. Effects of a unilateral stereotaxic injection of Tinuvin 123 into the substantia nigra on the nigrostriatal dopaminergic pathway in the rat. Brain Res. 2000 Jun. 2; 866(1-2):197-210.

Jacobsen K X, MacDonald H, Lemonde S, Daigle M, Grimes D A, Bulman D E, Albert P R A Nurr1 point mutant, implicated in Parkinson's disease, uncouples ERK1/2-dependent regulation of tyrosine hydroxylase transcription. Neurobiol Dis. 2008 January; 29(1):117-22.

Le W D, Xu P, Jankovic J, Jiang H, Appel S H, Smith R G, Vassilatis D K. Mutations in NR4A2 associated with familial Parkinson disease. Nat Genet. 2003 January; 33(1):85-9.

Lewis, A J (1934). "Melancholia: A Historical Review.". *Journal of Mental Science* 80(328): 1-42. doi:10.1192/bjp.80.328.1.

Li Z S, Schmauss C, Cuenca A, Ratcliffe E, Gershon M D. Physiological modulation of intestinal motility by enteric dopaminergic neurons and the D2 receptor: analysis of dopamine receptor expression, location, development, and function in wild-type and knock-out mice. J Neurosci. 2006; 26:2798-807.

Luo Y, Henricksen L A, Giuliano R E, Prifti L, Callahan L M, Federoff H J. VIP is a transcriptional target of Nurr1 in dopaminergic cells. Exp Neurol. 2007 January; 203(1):221-32.

McDowell K, Chesselet M F. Animal models of the non-motor features of Parkinson's disease. Neurobiol Dis. 2012 June; 46(3):597-606.

Monaca C, Laloux C, Jacquesson J M, Gelé P, Maréchal X, Bordet R, Destée A, Derambure P. Vigilance states in a parkinsonian model, the MPTP mouse. Eur J Neurosci. 2004; 20(9):2474-8.

Pack A I, Galante R J, Maislin G, Cater J, Metaxas D, Lu S, Zhang L, Von Smith R, Kay T, Lian J, Svenson K, Peters L L. Novel method for high-throughput phenotyping of sleep in mice. Physiol Genomics. 2007; 28(2):232-8.

Prashanth L K, Fox S, Meissner W G. l-Dopa-induced dyskinesia-clinical presentation, genetics, and treatment. Int Rev Neurobiol. 2011; 98:31-54.

Rosland J H, Hunskaar S, Broch O J, Hole K. Acute and long term effects of 1-methyl-4-phenyl-1,2,3,6-tetrahydropyridine (MPTP) in tests of nociception in mice. Pharmacol Toxicol. 1992 January; 70(1):31-7.

Santiago R M, Barbieiro J, Lima M M, Dombrowski P A, Andreatini R, Vital M A. Depressive-like behaviors alterations induced by intranigral MPTP, 6-OHDA, LPS and rotenone models of Parkinson's disease are predominantly associated with serotonin and dopamine. Prog Neuropsychopharmacol Biol Psychiatry. 2010 Aug. 16; 34(6):1104-14

Sleiman P M, Healy D G, Muqit M M, Yang Y X, Van Der Brug M, Holton J L, Revesz T, Quinn N P, Bhatia K, Diss J K, Lees A J, Cookson M R, Latchman D S, Wood N W. Characterisation of a novel NR4A2 mutation in Parkinson's disease brain. Neurosci Lett. 2009 Jun. 26; 457(2):75-9.

Sousa K M, Mira H, Hall A C, Jansson-Sjöstrand L, Kusakabe M, Arenas E. Microarray analyses support a role for Nurr1 in resistance to oxidative stress and neuronal differentiation in neural stem cells. Stem Cells. 2007 February; 25(2):511-9.

Tadaiesky M T, Dombrowski P A, Figueiredo C P, Cargnin-Ferreira E, Da Cunha C, Takahashi R N. Emotional, cognitive and neurochemical alterations in a premotor stage model of Parkinson's disease. Neuroscience. 2008 Oct. 28; 156(4):830-40.

Tofaris G K, Garcia Reitböck P, Humby T, Lambourne S L, O'Connell M, Ghetti B, Gossage H, Emson P C, Wilkinson L S, Goedert M, Spillantini M G. Pathological changes in dopaminergic nerve cells of the substantia nigra and olfactory bulb in mice transgenic for truncated human alpha-synuclein(1-120): implications for Lewy body disorders. J Neurosci. 2006; 26(15):3942-50.

Vila M, Vukosavic S, Jackson-Lewis V, Neystat M, Jakowec M, Przedborski S. Alpha-synuclein up-regulation in substantia nigra dopaminergic neurons following administration of the parkinsonian toxin MPTP J Neurochem. 2000 February; 74(2):721-9.

Volpicelli F, Caiazzo M, Greco D, Consales C, Leone L, Perrone-Capano C, Colucci D'Amato L, di Porzio U. Bdnf gene is a downstream target of Nurr1 transcription factor in rat midbrain neurons in vitro. J Neurochem. 2007 July; 102(2):441-53.

Wallen-Mackenzie A, Mata de Urquiza A, Petersson S, Rodriguez F J, Friling S, Wagner J, Ordentlich P, Lengqvist J, Heyman R A, Arenas E, Perlmann T. Nurr1-RXR heterodimers mediate RXR ligand-induced signaling in neuronal cells. Genes Dev. 2003 Dec. 15; 17(24):3036-47.

Wang Z, Benoit G, Liu J, Prasad S, Aarnisalo P, Liu X, Xu H, Walker N P, Perlmann T. Structure and function of Nurr1 identifies a class of ligand-independent nuclear receptors. Nature. 2003 May 29; 423(6939):555-60.

Xiao Q, Castillo S O, Nikodem V M. Distribution of messenger RNAs for the orphan nuclear receptors Nurr1 and Nur77 in adult rat brain using in situ hybridization. Neuroscience. 1996; 75(1):221-30

Xilouri M, Kyratzi E, Pitychoutis P M, Papadopoulou-Daifoti Z, Perier C, Vila M, Maniati M, Ulusoy A, Kirik D, Park D S, Wada K, Stefanis L. Selective neuroprotective effects of the S18Y polymorphic variant of UCH-L1 in the dopaminergic system. Hum Mol Genet. 2012; 21(4):874-89

Arfaoui A, Lobo M V, Boulbaroud S, Ouichou A, Mesfioui A, Arenas M I. Expression of retinoic acid receptors and retinoid X receptors in normal and vitamin A deficient adult rat brain. Ann Anat. 2012. pii: S0940-9602(12)00129-X.

Bäckman C, Perlmann T, Wallén A, Hoffer B J, Morales M. A selective group of dopaminergic neurons express Nurr1 in the adult mouse brain. Brain Res. 1999:851(1-2):125-32.

Decressac M, Volakakis N, Björklund A, Perlmann T. NURR1 in Parkinson disease—from pathogenesis to therapeutic potential. Nat Rev Neurol. 2013 November; 9(11):629-36.

Franklin K B J, Paxinos G. The Mouse Brain in Stereotaxic Coordinates. San Diego: Academic Press; 2001.

Henchcliffe C, Severt W L. Disease modification in Parkinson's disease. Drugs Aging. 2011 Aug. 1; 28(8):605-15

Overington JP[1], Al-Lazikani B, Hopkins A L. How many drug targets are there? Nat Rev Drug Discov. 2006 December; 5(12):993-6.

Pérez E[1], Bourguet W, Gronemeyer H, de Lera A R. Modulation of RXR function through ligand design. Biochim Biophys Acta. 2012 January; 1821(1):57-69.

Rosland J H, Hunskaar S, Broch O J, Hole K. Acute and long term effects of 1-methyl-4-phenyl-1,2,3,6-tetrahydropyridine (MPTP) in tests of nociception in mice. Pharmacol Toxicol. 1992 January; 70(1):31-7.

Vaz B[1], de Lera Á R. Advances in drug design with RXR modulators. Expert Opin Drug Discov. 2012 November; 7(11):1003-16.

Vila M, Vukosavic S, Jackson-Lewis V, Neystat M, Jakowec M, Przedborski S. Alpha-synuclein up-regulation in substantia nigra dopaminergic neurons following administration of the parkinsonian toxin MPTP J Neurochem. 2000 February; 74(2):721-9.

Wallen-Mackenzie A, Mata de Urquiza A, Petersson S, Rodriguez F J, Friling S, Wagner J, Ordentlich P, Lengqvist J, Heyman R A, Arenas E, Perlmann T. Nurr1-RXR heterodimers mediate RXR ligand-induced signaling in neuronal cells. Genes Dev. 2003 Dec. 15; 17(24):3036-47.

Wang Z, Benoit G, Liu J, Prasad S, Aarnisalo P, Liu X, Xu H, Walker N P, Perlmann T. Structure and function of Nurr1 identifies a class of ligand-independent nuclear receptors. Nature. 2003 May 29; 423(6939):555-60.

The invention claimed is:
1. A compound of formula (I)

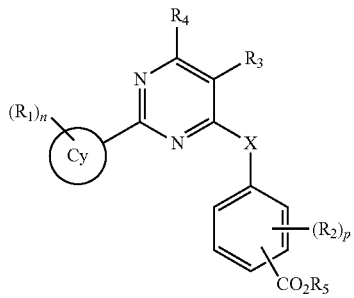

(I)

or a pharmaceutically acceptable salt thereof, wherein n is 0 to 2, p is 0 to 2, X is $N(R_6)$;
Cy is a phenyl ring or a heteroaromatic 6-membered ring containing between 1 and 4 heteroatoms;
each $R_1$ is independently selected from the group consisting of halogen, cyanate, isocyanate, thiocyanate, isothiocyanate, selenocyanate, isoselenocyanate, alkoxy, trifluoromethoxy, azido, cyano, nitro, hydroxy, acyl, mercapto, carboxyl, optionally substituted alkyl, optionally substituted cycloalkyl, optionally substituted heterocyclyl, optionally substituted aryl, optionally substituted heteroaryl, $-OR_7$, $-SR_7$, and $-N(R_8)R_7$;
each $R_2$ is independently selected from the group consisting of halogen, cyanate, isocyanate, thiocyanate, isothiocyanate, selenocyanate, isoselenocyanate, alkoxy, trifluoromethoxy, azido, cyano, nitro, hydroxy, acyl, mercapto, carboxyl, optionally substituted alkyl, optionally substituted cycloalkyl, optionally substituted heterocyclyl, optionally substituted aryl, optionally substituted heteroaryl, $-OR_7$, $-SR_7$, and $-N(R_8)R_7$;
$R_3$ is selected from the group consisting of halogen, cyanate, isocyanate, thiocyanate, isothiocyanate, selenocyanate, isoselenocyanate, alkoxy, trifluoromethoxy, azido, cyano, nitro, hydroxy, acyl, mercapto, optionally substituted alkyl, optionally substituted alkenyl, optionally substituted alkynyl, $OR_7$, $-SR_7$, $-N(R_8)R_7$, optionally substituted aryl, optionally substituted heteroaryl, optionally substituted cycloalkyl and optionally substituted heterocyclyl;
$R_4$ is a haloalkyl;
$R_5$ is selected from the group consisting of hydrogen, optionally substituted alkyl, optionally substituted alkenyl, and optionally substituted aryl;
$R_6$ is selected from the group consisting of hydrogen and optionally substituted alkyl;
each $R_7$ is independently selected from the group consisting of hydrogen, optionally substituted alkyl, optionally substituted alkenyl, optionally substituted aryl, optionally substituted aryl-alkyl, and optionally substituted heterocyclyl; and
each $R_8$ is independently selected from the group consisting of hydrogen and optionally substituted alkyl;
and wherein the compound is not a compound selected from the group consisting of:

i. ethyl 4-(5-allyl-6-methyl-2-phenylpyrimidin-4-ylamino)benzoate;
ii. methyl 4-(5-allyl-6-methyl-2-phenylpyrimidin-4-ylamino)benzoate;
iii. 4-(6-methyl-2-phenyl-5-propylpyrimidin-4-ylamino)benzoic acid;
iv. 4-(5-isopropyl-6-methyl-2-phenylpyrimidin-4-ylamino)benzoic acid;
v. 4-(5-ethyl-6-methyl-2-phenylpyrimidin-4-ylamino)benzoic acid;
vi. 4-(2-(4-chlorophenyl)-5-ethyl-6-methylpyrimidin-4-ylamino)benzoic acid;
vii. 4-(5-ethyl-6-methyl-2-phenylpyrimidin-4-yloxy)benzoic acid;
viii. 4-(2-(4-chlorophenyl)-5-ethyl-6-methylpyrimidin-4-yloxy)benzoic acid; and
ix. 4-(5-allyl-6-methyl-2-phenylpyrimidin-4-ylamino)benzoic acid.

2. The compound of claim 1, wherein n is 0.
3. The compound of claim 1, wherein n is 0 or 1, and wherein p is 0 or 1.
4. The compound of claim 1, wherein $R_4$ is trifluoromethyl.
5. The compound of claim 1 having the formula:

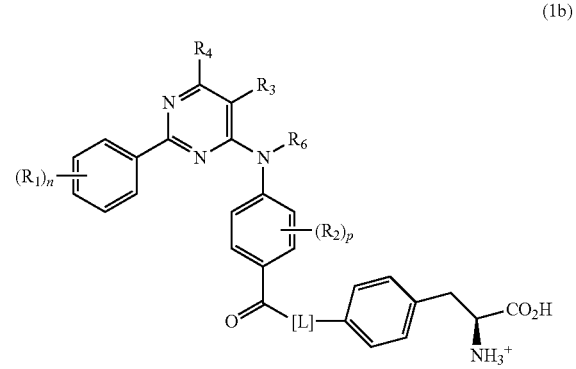

(1b)

or a free base thereof,
wherein L is selected from the group consisting of $-O-$, $-O-R_9-O-$, and $-O-R_9-$, wherein $R_9$ is an optionally substituted alkylene, optionally substituted alkenylene, or optionally substituted alkynylene.
6. The compound of claim 1 having the formula:

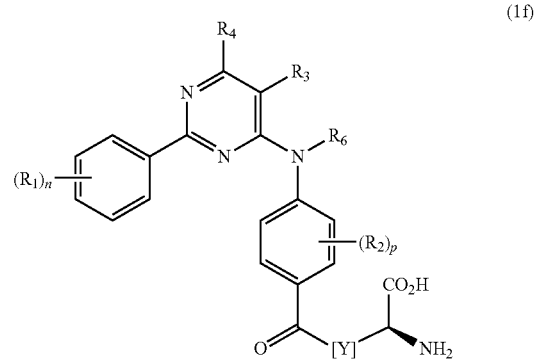

(1f)

or a salt thereof, wherein Y is —O—R₉—, wherein R₉ is an optionally substituted alkylene, optionally substituted alkenylene, or optionally substituted alkynylene chain.

7. The compound of claim 1 having the formula:

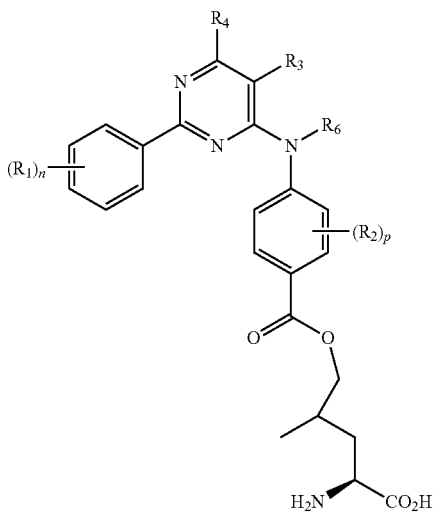

(1g)

or a salt thereof.

8. The compound of claim 1 having the formula:

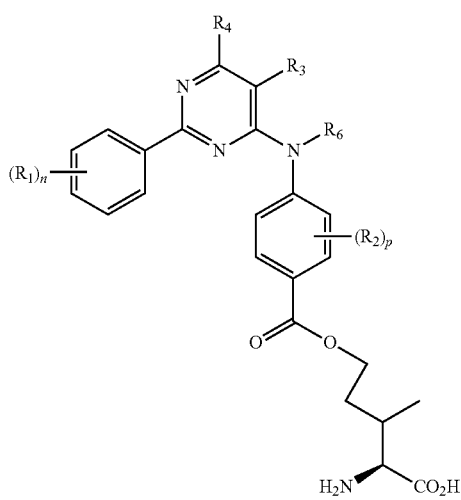

(1h)

or a salt thereof.

9. A compound selected from the group consisting of:
a) 4-((5-allyl-2-phenyl-6-(trifluoromethyl)pyrimidin-4-yl)(methyl)amino)benzoic acid;
b) 3-bromo-4-(4,6-dimethyl-2-phenyl-7H-pyrrolo[2,3-d]pyrimidin-7-yl)benzoic acid;
c) 4-(5-allyl-2-(4-chlorophenyl)-6-methylpyrimidin-4-ylamino)benzoic acid;
d) 4-((5-allyl-6-methyl-2-phenylpyrimidin-4-yl)(methyl)amino)-2-fluorobenzoic acid;
e) 4-(5-allyl-2-(4-chlorophenyl)-6-(trifluoromethyl)pyrimidin-4-ylamino)benzoic acid;
f) (E)-4-(2-(4-chlorophenyl)-5-(prop-1-enyl)-6-(trifluoromethyl)pyrimidin-4-ylamino)benzoic acid;
g) 4-((5-allyl-2-(4-chlorophenyl)-6-methylpyrimidin-4-yl)(methyl)amino)benzoic acid;
h) 4-(5-allyl-2-phenyl-6-(trifluoromethyl)pyrimidin-4-ylamino)benzoic acid;
i) (E)-4-(2-phenyl-5-(prop-1-enyl)-6-(trifluoromethyl)pyrimidin-4-ylamino)benzoic acid;
j) 4-((2-(4-chlorophenyl)-5-ethyl-6-methylpyrimidin-4-yl)(methyl)amino)benzoic acid;
k) pivaloyloxymethyl 4-(5-allyl-6-methyl-2-phenylpyrimidin-4-ylamino)benzoate;
l) 4-((6-methyl-2-phenylpyrimidin-4-yl)(propyl)amino)benzoic acid;
m) (S)-2-(4-(4-(5-allyl-6-methyl-2-phenylpyrimidin-4-ylamino)benzoyloxy)phenyl)-1-carboxyethanaminium chloride; and
n) (S)-2-(4-(3-(4-(5-allyl-6-methyl-2-phenylpyrimidin-4-ylamino)benzoyloxy)propoxy)phenyl)-1-carboxyethanaminium chloride;

or a salt or free base thereof.

10. The compound of claim 1 including a) 4-((5-allyl-2-phenyl-6-(trifluoromethyl)pyrimidin-4-yl)(methyl)amino)benzoic acid, or a salt or free base thereof.

11. A pharmaceutical composition comprising the compound of claim 9 and a pharmaceutically acceptable excipient or in addition with another therapeutically active compound.

12. A method of alleviating or preventing one or more symptoms of Parkinson's disease in a human, said symptom is selected from the group consisting of bradykinesia, dyskinesias, anxiety and depression and said method comprising administering to the human an effective amount of the compound of claim 9 or a pharmaceutical composition in addition with another therapeutically active compound.

13. A method comprising administering to the human an effective amount of the compound of claim 9, wherein the effective amount is sufficient to increase the rate of dopamine biosynthesis or the level of any of the enzymes involved in dopamine biosynthesis.

14. A method comprising administering to the human an effective amount of the compound of claim 9, wherein the effective amount is sufficient to increase the rate of serotonin (5-HT) biosynthesis or the level of any of the enzymes involved in serotonin biosynthesis.

15. A method comprising administering to the human an effective amount of the compound of claim 9, wherein said compound selectively activates a Nurr1:RXRα heterodimer over one or more other RXRα-containing dimers.

* * * * *